United States Patent
Zhong et al.

(10) Patent No.: US 10,954,221 B2
(45) Date of Patent: Mar. 23, 2021

(54) GLP-1R AGONISTS AND USES THEREOF

(71) Applicant: QILU REGOR THERAPEUTICS INC., Shanghai (CN)

(72) Inventors: Wenge Zhong, Thousand Oaks, CA (US); Wei Guo, Shanghai (CN)

(73) Assignee: QILU REGOR THERAPEUTICS INC., Shanghai (CN)

( * ) Notice: Subject to any disclaimer, the term of this patent is extended or adjusted under 35 U.S.C. 154(b) by 0 days.

(21) Appl. No.: 16/902,807

(22) Filed: Jun. 16, 2020

(65) Prior Publication Data

US 2020/0325121 A1 Oct. 15, 2020

Related U.S. Application Data

(63) Continuation of application No. PCT/CN2020/084203, filed on Apr. 10, 2020.

(30) Foreign Application Priority Data

Apr. 12, 2019 (WO) ................ PCT/CN2019/082381

(51) Int. Cl.
*C07D 405/14* (2006.01)
*C07D 417/14* (2006.01)
*C07D 471/04* (2006.01)

(52) U.S. Cl.
CPC ......... *C07D 405/14* (2013.01); *C07D 417/14* (2013.01); *C07D 471/04* (2013.01)

(58) Field of Classification Search
CPC .................................................. C07D 405/14
USPC ....................................................... 514/256
See application file for complete search history.

(56) References Cited

U.S. PATENT DOCUMENTS

| | | | |
|---|---|---|---|
| 10,208,019 B2 | 2/2019 | Aspnes et al. | |
| 2004/0127504 A1 | 7/2004 | Cowart et al. | |
| 2013/0123237 A1 | 5/2013 | Anand et al. | |
| 2020/0071306 A1 | 3/2020 | Esler et al. | |

FOREIGN PATENT DOCUMENTS

| | | |
|---|---|---|
| WO | 2004/099192 A2 | 11/2004 |
| WO | 2006/030925 A1 | 3/2006 |
| WO | 2006/055708 A2 | 5/2006 |
| WO | 2007/082264 A2 | 7/2007 |
| WO | 2011/079315 A1 | 6/2011 |
| WO | 2011/143365 A1 | 11/2011 |
| WO | 2011/156655 A2 | 12/2011 |
| WO | 2012/129562 A2 | 9/2012 |
| WO | 2013/090454 A2 | 6/2013 |
| WO | 2016/109559 A2 | 7/2016 |
| WO | 2017/161028 A1 | 9/2017 |
| WO | 2018/109607 A1 | 6/2018 |
| WO | 2019/239319 A1 | 12/2019 |
| WO | 2019/239371 A1 | 12/2019 |
| WO | 2020/033413 A2 | 2/2020 |

OTHER PUBLICATIONS

Gejl et al., In Alzheimer's disease, 6-month treatment with GLP-1 analog prevents decline of brain glucose metabolism: randomized, placebo-controlled, double-blind clinical trial. Front Aging Neurosci. May 2016;8(Article 108):1-10.
Ishoy et al., GLP-1 receptor agonist treatment in schizophrenia patients with obesity. Schizophr Bull. 2017;43(Suppl 1):S167.
Nylander et al., Liraglutide in polycystic ovary syndrome: a randomized trial, investigating effects on thrombogenic potential. Endocr Connect. Feb. 2017;6(2):89-99.
Prasad-Reddy et al., A clinical review of GLP-1 receptor agonists: efficacy and safety in diabetes and beyond. Drugs Context. Jul. 2015;4:212283. 19 pages.
Suchankova et al., The glucagon-like peptide-1 receptor as a potential treatment target in alcohol use disorder: evidence from human genetic association studies and a mouse model of alcohol dependence. Transl Psychiatry. Jun. 2015;5(6):e583. 11 pages.
International Search Report and Written Opinion for Application No. PCT/CN2018/117047, dated Aug. 21, 2019, 14 pages.
International Search Report and Written Opinion for Application No. PCT/CN2019/082381, dated Jan. 9, 2020, 18 pages.
International Search Report and Written Opinion for Application No. PCT/CN2019/119373, dated Feb. 5, 2020, 16 pages.
U.S. Appl. No. 16/874,908, filed May 15, 2020, Pending.

*Primary Examiner* — Kahsay Habte
(74) *Attorney, Agent, or Firm* — McCarter & English, LLP; Yu Lu; Wei Song

(57) ABSTRACT

The present disclosure provides compounds of Formula (I)

(I)

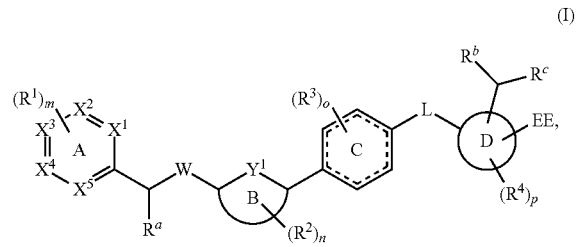

and pharmaceutical compositions thereof, for use in, e.g. treating type 2 diabetes mellitus, pre-diabetes, obesity, non-alcoholic fatty liver disease, non-alcoholic steatohepatitis, and cardiovascular disease.

4 Claims, 6 Drawing Sheets

GLP-1R AGONISTS AND USES THEREOF

CROSS-REFERENCE TO RELATED APPLICATIONS

This application is a continuation application of International Patent Application No. PCT/CN2020/084203, filed on Apr. 10, 2020, which claims the benefit of priority under 35 U.S.C. 365(b) to International Patent Application No. PCT/CN2019/082381, filed on Apr. 12, 2019. The entire contents of the aforementioned applications are incorporated herein by reference.

BACKGROUND OF THE INVENTION

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2. Type 1 diabetes (T1D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (referred to generally as T2DM) usually begins with either insulin resistance or when there is insufficient production of insulin to maintain an acceptable glucose level.

Currently, various pharmacological approaches are available for treating hyperglycemia and subsequently, T2DM (Hampp et al., *Use of Antidiabetic Drugs in the U.S., 2003-2012, Diabetes Care* 37:1367-1374, 2014). These may be grouped into six major classes, each acting through a different primary mechanism.

Insulin secretogogues, including sulphonyl-ureas (e.g., glipizide, glimepiride, glyburide), meglitinides (e.g., nateglidine, repaglinide), dipeptidyl peptidase IV (DPP-IV) inhibitors (e.g., sitagliptin, vildagliptin, alogliptin, dutogliptin, linagliptin, saxogliptin), and glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Sulphonyl-ureas and meglitinides have limited efficacy and tolerability, cause weight gain and often induce hypoglycemia. DPP-IV inhibitors have limited efficacy. Marketed GLP-1R agonists are peptides administered by subcutaneous injection. Liraglutide is additionally approved for the treatment of obesity.

Biguanides (e.g., metformin) are thought to act primarily by decreasing hepatic glucose production. Biguanides often cause gastrointestinal disturbances and lactic acidosis, further limiting their use.

Inhibitors of alpha-glucosidase (e.g., acarbose) decrease intestinal glucose absorption. These agents often cause gastrointestinal disturbances.

Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia.

Insulin is used in more severe cases, either alone or in combination with the above agents, and frequent use may also lead to weight gain and carries a risk of hypoglycemia.

Sodium-glucose linked transporter cotransporter 2 (SGLT2) inhibitors (e.g., dapagliflozin, empagliflozin, canagliflozin, ertugliflozin) inhibit reabsorption of glucose in the kidneys and thereby lower glucose levels in the blood. This emerging class of drugs may be associated with ketoacidosis and urinary tract infections.

However, with the exception of GLP-1R agonists and SGLT2 inhibitors, the drugs have limited efficacy and do not address the most important problems, the declining β-cell function and the associated obesity.

Obesity is a chronic disease that is highly prevalent in modern society and is associated with numerous medical problems including hypertension, hypercholesterolemia, and coronary heart disease. It is further highly correlated with T2DM and insulin resistance, the latter of which is generally accompanied by hyperinsulinemia or hyperglycemia, or both. In addition, T2DM is associated with a two to fourfold increased risk of coronary artery disease. Presently, the only treatment that eliminates obesity with high efficacy is bariatric surgery, but this treatment is costly and risky. Pharmacological intervention is generally less efficacious and associated with side effects.

There is therefore a need for more efficacious pharmacological intervention with fewer side effects and convenient administration.

Although T2DM is most commonly associated with hyperglycemia and insulin resistance, other diseases associated with T2DM include hepatic insulin resistance, impaired glucose tolerance, diabetic neuropathy, diabetic nephropathy, diabetic retinopathy, obesity, dyslipidemia, hypertension, hyperinsulinemia and nonalcoholic fatty liver disease (NAFLD).

NAFLD is the hepatic manifestation of metabolic syndrome, and is a spectrum of hepatic conditions encompassing steatosis, non-alcoholic steatohepatitis (NASH), fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion does.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier et al., *Biodrugs.* 17(2): 93-102, 2013).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll et al., *Diabetes.* 50:609-613, 2001).

Hoist (*Physiol. Rev.* 87:1409, 2007) and Meier (*Nat. Rev. Endocrinol.* 8:728, 2012) describe that GLP-1 receptor agonists, such as GLP-1, liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

There remains a need for an easily-administered prevention and/or treatment for cardiometabolic and associated diseases.

SUMMARY OF THE INVENTION

In one aspect, the present disclosure provides a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof.

In one aspect, the present disclosure provides a pharmaceutical composition comprising a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein, in a mixture with at least one pharmaceutically acceptable excipient.

In another aspect, the present disclosure provides a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein, for use as a medicament.

In another aspect, the present disclosure provides a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein, for use in the prevention and/or treatment of cardiometabolic and associated diseases discussed herein, including T2DM, pre-diabetes, NASH, and cardiovascular disease.

In another aspect, the present disclosure provides a method of treating a disease for which an agonist of GLP-1R is indicated, in a subject in need of such prevention and/or treatment, comprising administering to the subject a therapeutically effective amount of a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein.

In another aspect, the present disclosure provides a use of a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein, for the manufacture of a medicament for treating a disease or condition for which an agonist of the GLP-1R is indicated.

In another aspect, the present disclosure provides a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein, for use in the treatment of a disease or condition for which an agonist of GLP-1R is indicated.

In another aspect, the present disclosure provides a pharmaceutical composition for the treatment of a disease or condition for which an agonist of the GLP-1R is indicated, comprising a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein.

Every Example or pharmaceutically acceptable salt thereof may be claimed individually or grouped together in any combination with any number of each and every embodiment described herein.

The present disclosure also provides a pharmaceutical composition comprising a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein, for use in the treatment and/or prevention of cardiometabolic and associated diseases discussed herein, including T2DM, pre-diabetes, NASH, and cardiovascular disease.

In another aspect, the present disclosure provides a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein, for use in the treatment and/or treatment for cardiometabolic and associated diseases including diabetes (T1D and/or T2DM, including pre-diabetes), idiopathic T1D (Type 1b), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), hyperinsulinemia, NAFLD (including related diseases such as steatosis, NASH, fibrosis, cirrhosis, and hepatocellular carcinoma), cardiovascular disease, atherosclerosis (including coronary artery disease), peripheral vascular disease, hypertension, endothelial dysfunction, impaired vascular compliance, congestive heart failure, myocardial infarction (e.g. necrosis and apoptosis), stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, prevention or treatment of Polycystic Ovary Syndrome and treatment of addiction (e.g., alcohol and/or drug abuse).

In another aspect, the present disclosure provides a method of enhancing or stimulating GLP-1R-mediated cAMP signaling with reduced β-arrestin/arrestin-2 recruitment, comprising administering a compound of any one of the formulae described herein (e.g., Structural Formula (I), (I-1), (I-2), (II), (III), (I-A), (I-B), (I-C), (I-D), (II-A), (II-B), (II-B'), (II-C), or (II-D)), or a pharmaceutically acceptable salt, stereoisomer, solvate, or hydrate thereof, as defined in any one of the embodiments described herein. This is partly based on the surprising finding that the compounds of the present disclosure, while being full agonists of GLP-1R-mediated cAMP signaling, are partial agonists of β-arrestin recruitment to activated GLP-1R, compared to the natural GLP-1R ligand GLP-1, in that maximal β-arrestin recruitment to activated GLP-1R by the compounds of the present disclosure is lower than maximal β-arrestin recruitment by GLP-1. Such partial and/or biased agonists of GLP-1R for cAMP signaling may provide a more sustained cAMP signaling activity for better efficacy and lowered side effects.

Thus, the method of the present disclosure may be advantageously used for the treatment of any of the diseases or conditions described herein, such as type II diabetes (T2D) and related diseases.

In certain embodiments, the treatment elicits a glycemic benefit without concomitant increase, or at least reduced increase, in a GI side effect such as nausea, vomiting, or diarrhea. In certain embodiments, the treatment has greater tolerability compared to a control treatment that has normal or enhanced β-arrestin recruitment (such as β-arrestin recruitment by GLP-1).

BRIEF DESCRIPTION OF THE DRAWINGS

FIG. 1 compares Compounds 74-91, 93-95, 100, and 101 to GLP-1 (7-37).

DETAILED DESCRIPTION OF THE INVENTION

1. Compounds

Figure 1:
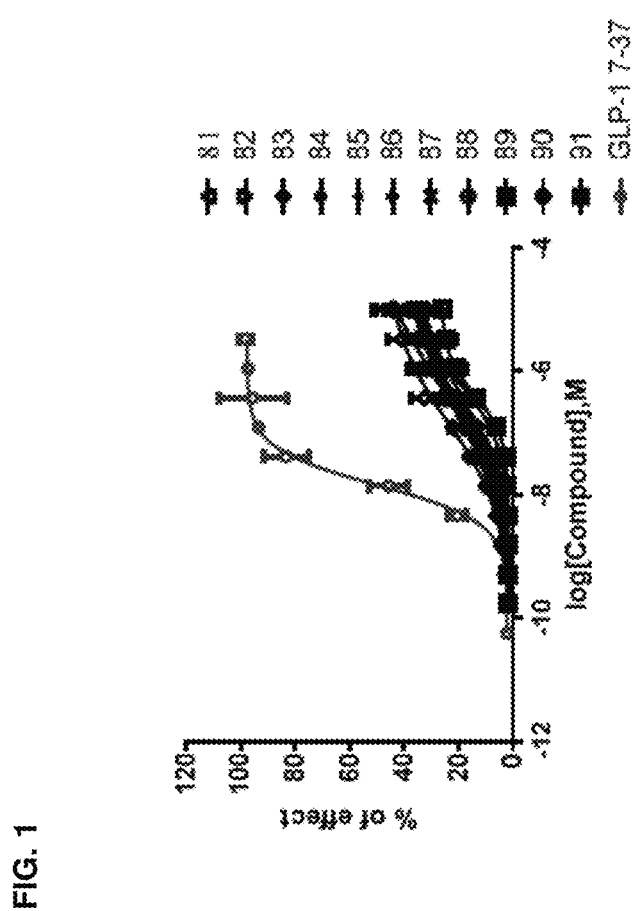
FIG. 1 shows dose-response curves for the GLP-1R/β-Arrestin recruitment assay using certain compounds of the present disclosure and GLP-1 (7-37) as control. The vertical axis represents relative effects of the test compounds normalized to percentage of effect by the natural ligand GLP-1 (7-37).
Figure 1:
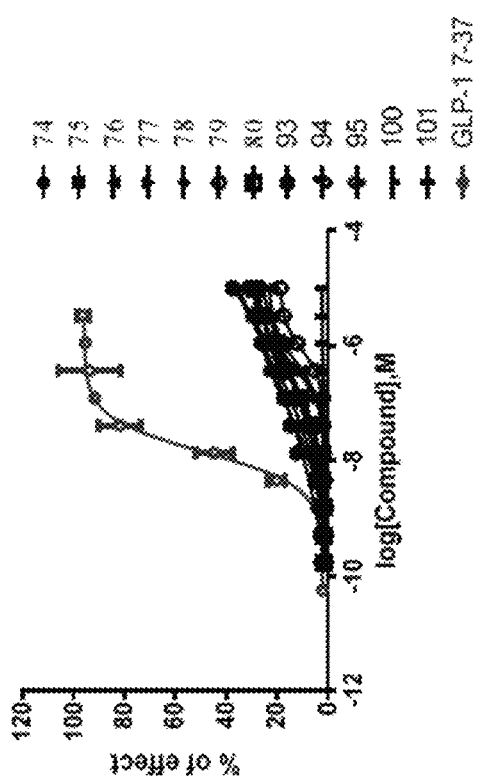

In a first embodiment, the present disclosure provides a compound represented by structural formula (I):

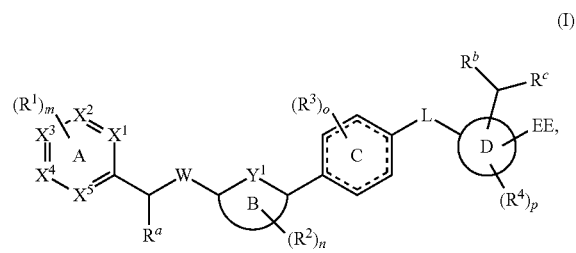

or a pharmaceutically acceptable salt, stereoisomer, solvate, or hydrate thereof, wherein:

----- indicates a single bond or a double bond;

$X^1$, $X^2$, $X^3$, $X^4$, and $X^5$ are each independently selected from N and CH;

W is selected from O, S, $CR^5R^6$, and $NR^{5'}$;

ring B is 6-membered heteroaryl, 6-membered monocyclic heterocyclyl, or phenyl, wherein $Y^1$ is selected from N, NH, CH, and $CH_2$;

ring C is cyclohexyl, phenyl, or pyridyl;

L is $CHR^d$, O, S, or $NR^{5'}$;

ring D is bicyclic heteroaryl;

EE is —COOH or a carboxylic group surrogate, optionally, the carboxylic group surrogate is:

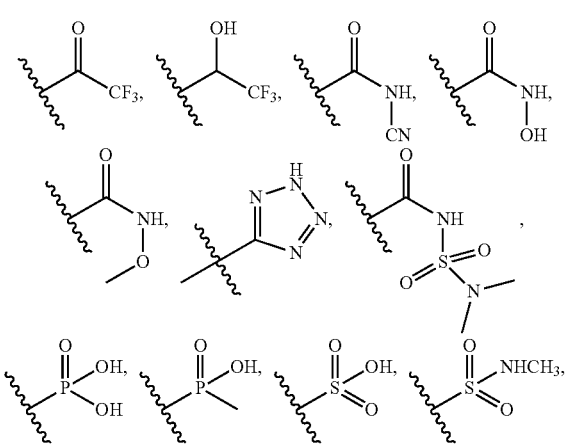

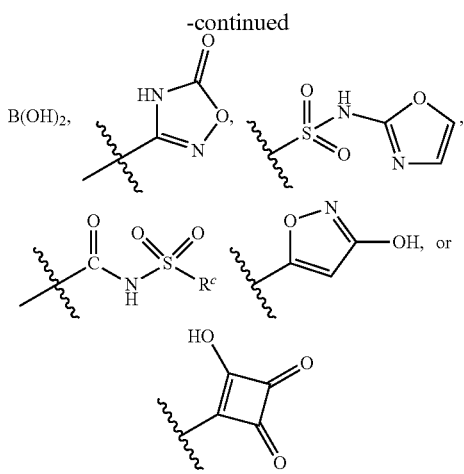

each $R^a$ and $R^b$ are independently selected from hydrogen, deuterium, halogen, —CN, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^a/R^b$ is optionally substituted with one or more groups selected from halogen, oxo, CN, OH, and $C_3$-$C_6$ saturated or partially saturated cycloalkyl; and wherein the aryl, heteroaryl, saturated or partially saturated cycloalkyl, or saturated or partially saturated heterocyclyl represented by $R^a/R^b$ or in the group represented by $R^a/R^b$ is optionally substituted with one or more groups selected from halogen, oxo (as appropriate), CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

each $R^c$ and $R^d$ are independently selected from hydrogen, deuterium, halogen, —CN, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^c/R^d$ is optionally substituted with one or more groups selected from halogen, oxo, CN, OH, and $C_3$-$C_6$ saturated or partially saturated cycloalkyl; and wherein the aryl, heteroaryl, saturated or partially saturated cycloalkyl, or saturated or partially saturated heterocyclyl represented by $R^c/R^d$ or in the group represented by $R^c/R^d$ is optionally substituted with one or more groups selected from halogen, oxo (as appropriate), CN, and $NR^{5'}R^{6'}$;

each $R^1$ is independently selected from H, deuterium, halogen, —CN, OH, $C_1$-$C_6$ alkyl, $C_1$-$C_6$ alkoxy, $C_2$-$C_6$ alkenyl, $C_2$-$C_6$ alkynyl, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl, $C_1$-$C_6$ alkoxy, $C_2$-$C_6$ alkenyl, or $C_2$-$C_6$ alkynyl represented by $R^1$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^1$ or in the group represented by $R^1$ is optionally substituted with one or more groups selected from halogen, oxo (as appropriate), CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$.

each $R^2$ is independently selected from H, deuterium, halogen, —CN, OH, oxo, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^2$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^2$ or in the group represented by $R^2$ is optionally substituted with one or more groups selected from halogen, oxo (as appropriate), CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

each $R^3$ is independently selected from H, deuterium, halogen, —CN, OH, oxo, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^3$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^3$ or in the group represented by $R^3$ is optionally substituted with one or more groups selected from halogen, oxo (as appropriate), CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

each $R^4$ is independently selected from H, deuterium, halogen, OH, —CN, $C_1$-$C_6$ alkyl, $C_1$-$C_6$ alkoxy, and $NR^{5'}R^{6'}$, wherein the $C_1$-$C_6$ alkyl and $C_1$-$C_6$ alkoxy represented by $R^4$ is optionally substituted with one or more groups selected from halogen, oxo, CN, $CF_3$, and saturated or partially saturated $C_3$-$C_6$ cycloalkyl (optionally substituted with one or more groups selected from halogen, oxo, CN, $CF_3$, OH, $OCH_3$, $OCH_2CH_3$);

$R^5$ and $R^6$ are each independently selected from hydrogen, deuterium, halogen, CN, OH, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^5$ or $R^6$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^5$ or $R^6$ or in the group represented by $R^5$ or $R^6$ is optionally substituted with one or more groups selected from halogen, oxo (as appropriate), CN, OH, $C_1$-$C_3$ alkyl (optionally substituted with 1 to 3 groups selected from F, OH, and OCH$_3$), and C$_1$-C$_3$ alkoxy (optionally substituted with 1 to 3 groups selected from F, OH, and OCH$_3$), and NR$^{5'}$R$^{6'}$.

R$^{5'}$ and R$^{6'}$ are each independently selected from hydrogen and C$_1$-C$_6$ alkyl;

wherein optionally two R$^1$; two R$^2$; two R$^3$; two R$^4$; R$^1$ and R$^2$; R$^2$ and R$^3$; R$^a$ and R$^1$; R$^a$ and R$^2$; R$^1$ and any of R$^5$, R$^{5'}$ (in the group represented by W), or R$^6$; R$^a$ and any of R$^5$, R$^{5'}$ (in the group represented by W), or R$^6$; R$^2$ and any of R$^5$, R$^{5'}$ (in the group represented by W), or R$^6$; R$^5$ and R$^6$; any of two groups selected from R$^c$, R$^d$, R$^e$, and R$^f$; or R$^4$ and any one of R$^c$, R$^d$, R$^e$, and R$^f$; taken together with their respective intervening carbon or hetero atom(s), form phenyl, 5-6 membered heteroaryl, 4-8 membered saturated or partially saturated cycloalkyl or 4-8 membered saturated or partially saturated heterocyclyl, and each of which is optionally substituted with one or more groups selected from halogen, —CN, —OH, CF$_3$, C$_1$-C$_6$ alkyl, C$_1$-C$_6$ alkoxy, —NH$_2$, —NHC$_1$-C$_6$ alkyl, —N(C$_1$-C$_6$ alkyl)$_2$, oxo, and saturated or partially saturated C$_3$-C$_6$ cycloalkyl, wherein the C$_1$-C$_6$ alkyl and C$_1$-C$_6$ alkoxy is optionally substituted with one or more groups selected from halogen, oxo, CN, CF$_3$, OH, OCH$_3$, OCH$_2$CH$_3$, and saturated or partially saturated C$_3$-C$_6$ cycloalkyl, wherein the cycloalkyl is optionally substituted with one or more groups selected from halogen, oxo, CN, CF$_3$, OH, OCH$_3$, OCH$_2$CH$_3$;

m is an integer selected from 0, 1, 2, 3, and 4;
n is an integer selected from 0, 1, 2, 3, 4, and 5;
o is an integer selected from 0, 1, 2, 3, and 4; and
p is an integer selected from 0, 1, 2, 3, and 4.

In a second embodiment, the present disclosure provides a compound according to the first embodiment, wherein the compound is represented by structural formula (II):

(II)

or a pharmaceutically acceptable salt, stereoisomer, solvate, or hydrate thereof, wherein:

X$^1$, X$^2$, X$^3$, X$^4$, and X$^5$ are each independently selected from N and CH; wherein no more than three of X$^1$, X$^2$, X$^3$, X$^4$, and X$^5$ are N and wherein ring A does not contain 3 nitrogen ring atoms at 3 contiguous positions;

ring B is 6 membered heteroaryl or phenyl, wherein Y$^1$, Y$^3$, Y$^4$, and Y$^5$ are each independently selected from N or CH; wherein there are no more than 3 nitrogen ring atoms in ring B and ring B does not contain 3 nitrogen ring atoms at 3 contiguous positions;

T$^2$ is selected from N and C;
T$^4$ is selected from N, NR$^4$, O, S, and CR$^4$;
T$^6$, T$^7$, and T$^8$ are each independently selected from N and CR$^4$;

wherein no more than 4 of T$^2$, T$^4$, T$^6$, T$^7$, and T$^8$ are selected from N, O, and S.

In a third embodiment, the present disclosure provides a compound according to the first or second embodiment, or a pharmaceutically acceptable salt, stereoisomer, solvate, or hydrate thereof, wherein W is O, NH or CH$_2$;
R$^a$ is H, CH$_3$, or CF$_3$;
R$^b$ is selected from hydrogen, C$_1$-C$_6$ alkyl, C$_1$-C$_6$ alkoxy, NR$^{5'}$R$^{6'}$, 6-10 membered aryl, 5-6 membered heteroaryl, 3-6 membered saturated or partially saturated cycloalkyl and 3-7 membered saturated or partially saturated heterocyclyl, wherein the C$_1$-C$_6$ alkyl or C$_1$-C$_6$ alkoxy represented by R$^b$ is optionally substituted with one or more groups selected from halogen, oxo, CN, OH, and C$_3$-C$_6$ saturated or partially saturated cycloalkyl; and wherein the aryl, heteroaryl, saturated or partially saturated cycloalkyl, or saturated or partially saturated heterocyclyl represented by R$^b$ or in the group represented by R$^b$ is optionally substituted with one or more groups selected from halogen, oxo (when R$^b$ is non-aromatic), CN, OH, C$_1$-C$_3$ alkyl (optionally substituted with 1 to 3 groups selected from F, OH, and OCH$_3$), and C$_1$-C$_3$ alkoxy (optionally substituted with 1 to 3 groups selected from F, OH, and OCH$_3$), and NR$^{5'}$R$^{6'}$;

R$^c$ is selected from hydrogen, halogen, and C$_1$-C$_4$ alkyl optionally substituted with one or more groups selected from halogen and hydroxy;

R$^d$ is H, F, CH$_3$, or CF$_3$; and each R$^1$ is independently selected from H, deuterium, halogen, —CN, OH, C$_1$-C$_6$ alkyl, C$_1$-C$_6$ alkoxy, C$_2$-C$_6$ alkenyl, C$_2$-C$_6$ alkynyl, NR$^{5'}$R$^{6'}$, 6-10 membered aryl, 5-8 membered heteroaryl, 3-8 membered saturated or partially saturated cycloalkyl and 3-8 membered saturated or partially saturated heterocyclyl, wherein the C$_1$-C$_6$ alkyl, C$_1$-C$_6$ alkoxy, C$_2$-C$_6$ alkenyl, or C$_2$-C$_6$ alkynyl represented by R$^1$ is optionally substituted with one or more groups selected from halogen, oxo, CN, CF$_3$, OH, OCH$_3$, OCH$_2$CH$_3$, and saturated or partially saturated C$_3$-C$_6$ cycloalkyl (optionally substituted with one or more groups selected from halogen, oxo, CN, CF$_3$, OH, OCH$_3$, OCH$_2$CH$_3$); and wherein the aryl, heteroaryl, saturated or partially saturated cycloalkyl, or saturated or partially saturated heterocyclyl represented by R$^1$ or in the group represented by R$^1$ is optionally substituted with one or more groups selected from halogen, oxo (when R$^1$ is non-aromatic), CN, OH, C$_1$-C$_3$ alkyl (optionally substituted with 1 to 3 groups selected from F, OH, and OCH$_3$), and C$_1$-C$_3$ alkoxy (optionally substituted with 1 to 3 groups selected from F, OH, and OCH$_3$), and NR$^{5'}$R$^{6'}$.

each R$^2$ and R$^3$ are independently selected from H, deuterium, halogen, —CN, OH, oxo, C$_1$-C$_6$ alkyl, C$_1$-C$_6$ alkoxy, NR$^{5'}$R$^{6'}$, wherein the C$_1$-C$_6$ alkyl or C$_1$-C$_6$ alkoxy represented by R$^2$ and/or R$^3$ is optionally substituted with one or more groups selected from halogen, oxo, CN, CF$_3$, OH, OCH$_3$, OCH$_2$CH$_3$, and saturated or partially saturated C$_3$-C$_6$ cycloalkyl (optionally substituted with one or more groups selected from halogen, oxo, CN, CF$_3$, OH, OCH$_3$, OCH$_2$CH$_3$);

each R$^4$ is independently selected from H, deuterium, halogen, OH, —CN, C$_1$-C$_6$ alkyl, C$_1$-C$_6$ alkoxy, and NR$^{5'}$R$^{6'}$, wherein the C$_1$-C$_6$ alkyl and C$_1$-C$_6$ alkoxy represented by R$^4$ is optionally substituted with one or more groups selected from halogen, oxo, CN, CF$_3$, and saturated or partially saturated C$_3$-C$_6$ cycloalkyl (optionally substituted with one or more groups selected from halogen, oxo, CN, CF$_3$, OH, OCH$_3$, OCH$_2$CH$_3$); and o is an integer selected from 0, 1, 2, 3, and 4.

In a fourth embodiment, the present disclosure provides a compound according to the first, second, or third embodiment, wherein the compound is represented by the structural formula (III):

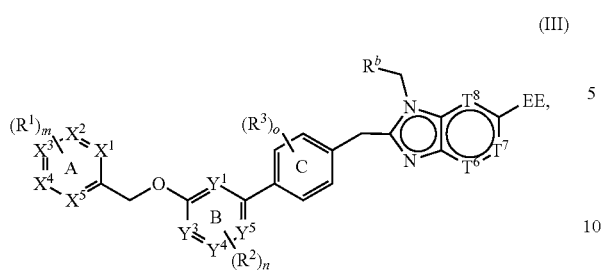
(III)

or a pharmaceutically acceptable salt, stereoisomer, solvate, or hydrate thereof, wherein $R^4$ is H, F, Cl, methyl, or methoxy.

In a fifth embodiment, the present disclosure provides a compound according to the second, third, or fourth embodiment, or a pharmaceutically acceptable salt, stereoisomer, solvate, or hydrate thereof, wherein

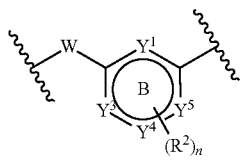

is

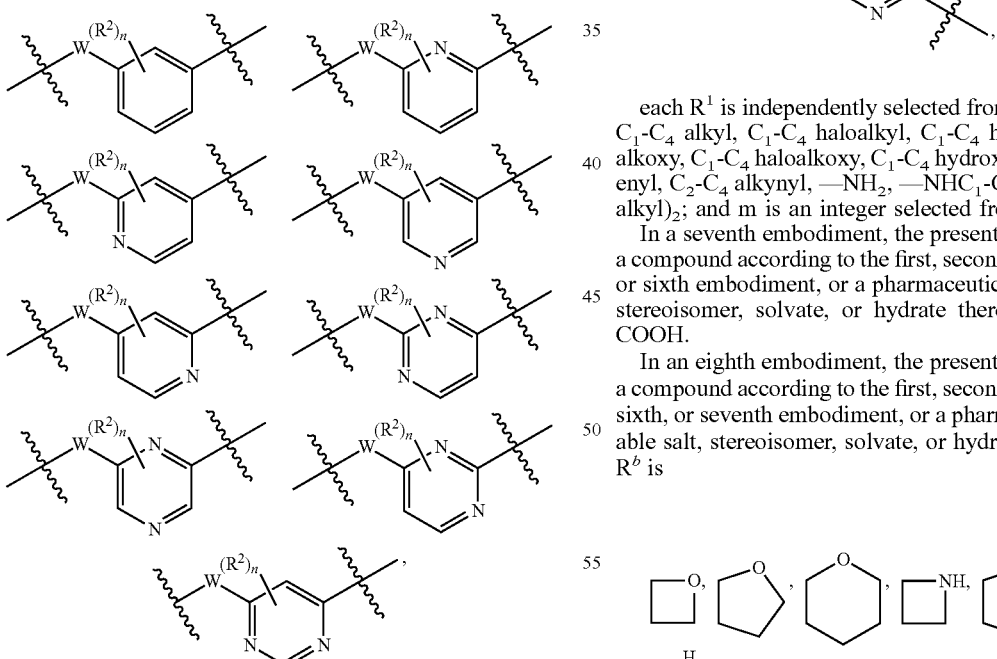

wherein n is an integer selected from 0, 1, 2, 3, and 4, as appropriate.

In a sixth embodiment, the present disclosure provides a compound according to the first, second, third, fourth, or fifth embodiment, or a pharmaceutically acceptable salt, stereoisomer, solvate, or hydrate thereof, wherein ring A is

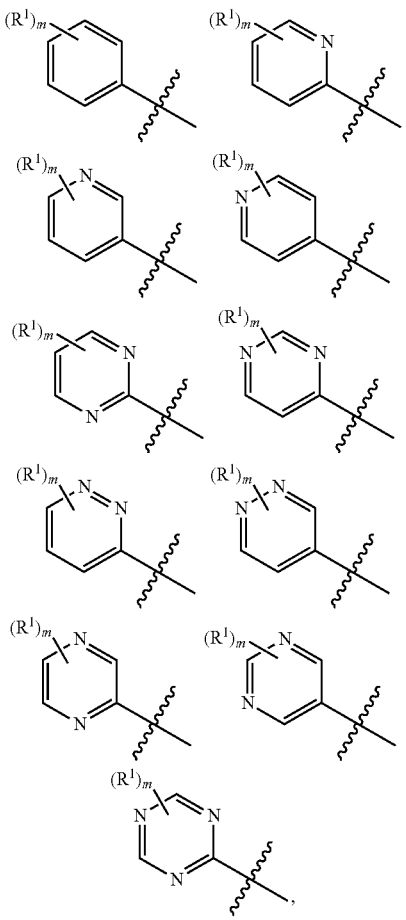

each $R^1$ is independently selected from halogen, OH, CN, $C_1$-$C_4$ alkyl, $C_1$-$C_4$ haloalkyl, $C_1$-$C_4$ hydroxyalkyl, $C_1$-$C_4$ alkoxy, $C_1$-$C_4$ haloalkoxy, $C_1$-$C_4$ hydroxyalkoxy, $C_2$-$C_4$ alkenyl, $C_2$-$C_4$ alkynyl, —$NH_2$, —$NHC_1$-$C_4$ alkyl, —$N(C_1$-$C_4$ alkyl)$_2$; and m is an integer selected from 0, 1, and 2.

In a seventh embodiment, the present disclosure provides a compound according to the first, second, third, fourth, fifth, or sixth embodiment, or a pharmaceutically acceptable salt, stereoisomer, solvate, or hydrate thereof, wherein EE is COOH.

In an eighth embodiment, the present disclosure provides a compound according to the first, second, third, fourth, fifth, sixth, or seventh embodiment, or a pharmaceutically acceptable salt, stereoisomer, solvate, or hydrate thereof, wherein $R^b$ is

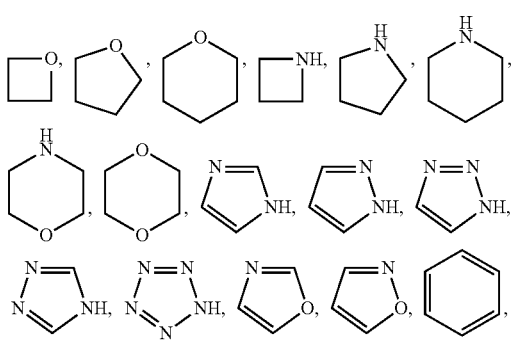

-continued

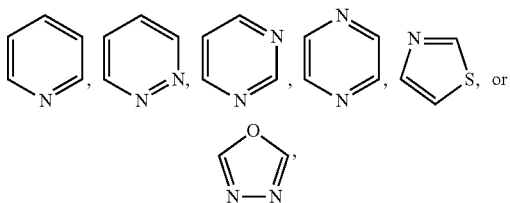

each of which is optionally substituted with 1 or 2 groups selected from halogen, oxo (when $R^b$ is non-aromatic), CN, $NR^{5'}R^{6'}$, $C_1$-$C_4$ alkyl, and $C_1$-$C_4$ alkoxy, wherein the $C_1$-$C_4$ alkyl or $C_1$-$C_4$ alkoxy in the group represented by $R^b$ is optionally substituted with 1 or 2 groups selected from F, OH, and $OCH_3$.

In a ninth embodiment, the present disclosure provides a compound according to the second, third, fourth, fifth, sixth, seventh, or eighth embodiment, or a pharmaceutically acceptable salt, stereoisomer, solvate, or hydrate thereof, wherein

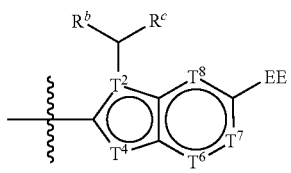

is

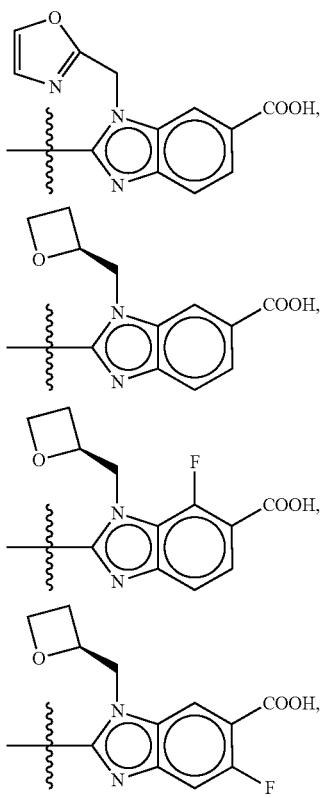

-continued

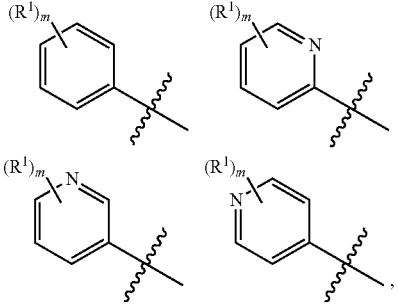

In a tenth embodiment, the present disclosure provides a compound according to the first, second, third, fourth, fifth, sixth, seventh, eighth, or ninth embodiment, or a pharmaceutically acceptable salt, stereoisomer, solvate, or hydrate thereof, wherein $R^3$ is halogen, CN, OH, $C_1$-$C_4$ alkyl, $C_1$-$C_4$ haloalkyl, $C_1$-$C_4$ alkoxy, or $NR^{5'}R^{6'}$; and o is an integer selected from 0, 1, 2, 3, and 4.

In an eleventh embodiment, the present disclosure provides a compound according to the first, second, third, fourth, fifth, sixth, seventh, eighth, ninth, or tenth embodiment, or a pharmaceutically acceptable salt, stereoisomer, solvate, or hydrate thereof, wherein each $R^2$ is independently selected from deuterium, halogen, —CN, OH, $C_1$-$C_2$ alkyl, $C_1$-$C_2$ haloalkyl, and $C_1$-$C_2$ alkoxy; and n is an integer selected from 0, 1, 2, 3, and 4.

In a twelfth embodiment, the present disclosure provides a compound according to the first, second, third, fourth, fifth, sixth, seventh, eighth, ninth, tenth, or eleventh embodiment, or a pharmaceutically acceptable salt, stereoisomer, solvate, or hydrate thereof, wherein ring A is each R is independently selected from halogen, OH, CN, $C_1$-$C_2$ alkyl, $C_1$-$C_2$ haloalkyl, $C_1$-$C_2$ hydroxyalkyl, $C_1$-$C_2$ alkoxy, $C_1$-$C_2$ haloalkoxy, $C_1$-$C_2$ hydroxyalkoxy, and $C_2$-$C_4$ alkynyl; and m is an integer selected from 0, 1, and 2.

In a thirteenth embodiment, the present disclosure provides a compound according to the fourth, fifth, sixth, seventh, eighth, ninth, tenth, eleventh, or twelfth embodiment, or a pharmaceutically acceptable salt, stereoisomer, solvate, or hydrate thereof, wherein

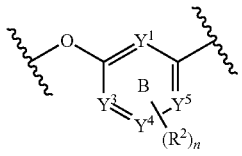

is

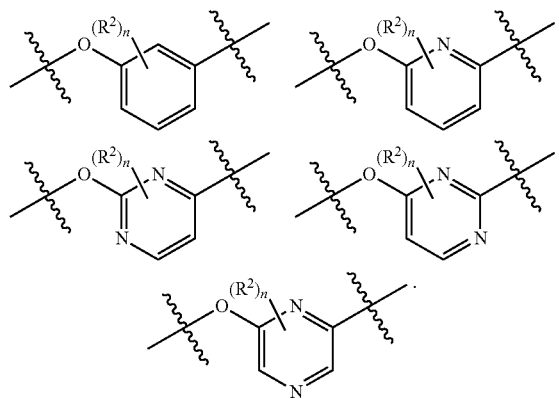

In a fourteenth embodiment, the present disclosure provides a compound according to the second, third, fourth, fifth, sixth, seventh, eighth, ninth, tenth, eleventh, twelfth, or thirteenth embodiment, or a pharmaceutically acceptable salt, stereoisomer, solvate, or hydrate thereof, wherein

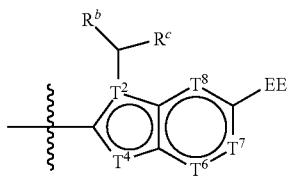

is

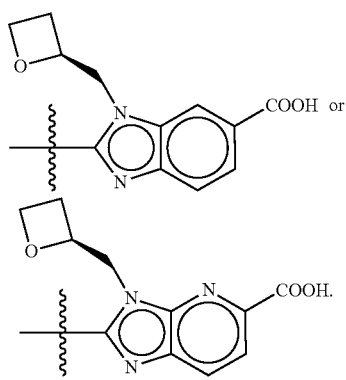

In a fifteenth embodiment, the present disclosure provides a compound according to the first, second, third, fourth, fifth, sixth, seventh, eighth, ninth, tenth, eleventh, twelfth, thirteenth, or fourteenth embodiment, or a pharmaceutically acceptable salt, stereoisomer, solvate, or hydrate thereof, wherein each $R^2$ is independently selected from halogen (e.g., F) or deuterium; and n is an integer selected from 0, 1, and 2, provided that when $R^2$ is deuterium, ring B is fully substituted with deuterium.

In a sixteenth embodiment, the present disclosure provides a compound according to the first, second, third, fourth, fifth, sixth, seventh, eighth, ninth, tenth, eleventh, twelfth, thirteenth, fourteenth, or fifteenth embodiment, or a pharmaceutically acceptable salt, stereoisomer, solvate, or hydrate thereof, wherein each $R^3$ is F, Cl or $CH_3$; and o is 0, 1, or 2.

In a seventeenth embodiment, the present disclosure provides a compound according to the first, second, third, fourth, fifth, sixth, seventh, eighth, ninth, tenth, eleventh, twelfth, thirteenth, fourteenth, fifteenth, or sixteenth embodiment, or a pharmaceutically acceptable salt, stereoisomer, solvate, or hydrate thereof, wherein ring A is

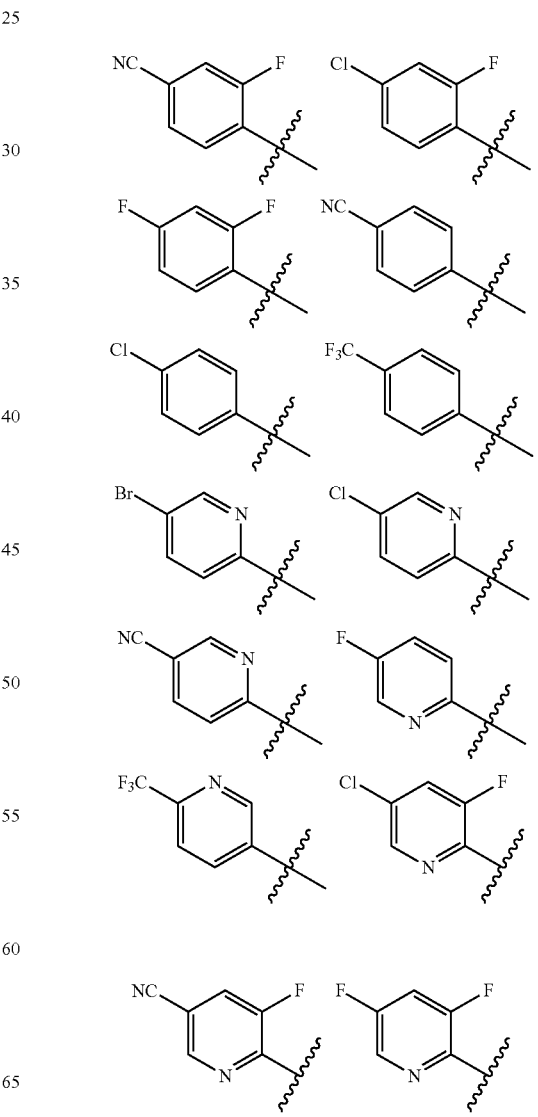

-continued

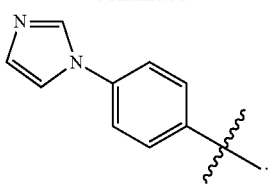

In an eighteenth embodiment, the present disclosure provides a compound according to the first, second, third, fourth, fifth, sixth, seventh, eighth, ninth, tenth, eleventh, twelfth, thirteenth, fourteenth, fifteenth, sixteenth, or seventeenth embodiment, or a pharmaceutically acceptable salt, stereoisomer, solvate, or hydrate thereof, wherein ring A is

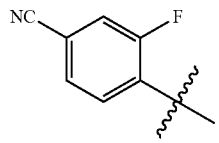 or 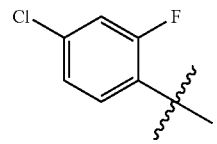.

In a nineteenth embodiment, the present disclosure provides a compound according to the second, third, fourth, fifth, sixth, seventh, eighth, ninth, tenth, eleventh, twelfth, thirteenth, fourteenth, fifteenth, sixteenth, seventeenth, or eighteenth embodiment, or a pharmaceutically acceptable salt, stereoisomer, solvate, or hydrate thereof, wherein

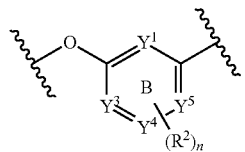

is

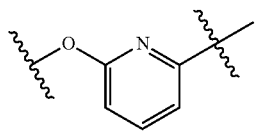

The present disclosure also provides a compound represented by structural formula (I-1) or (I-2):

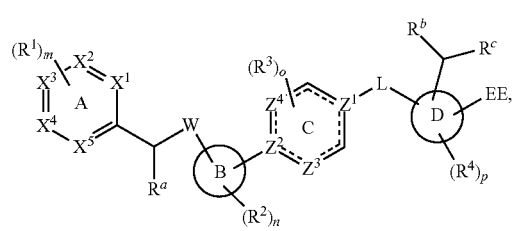

(I-1)

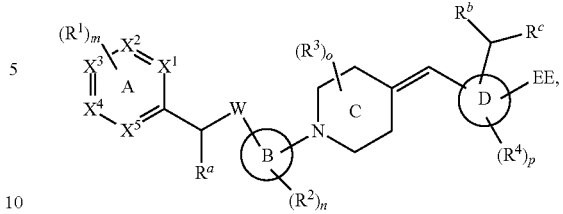

(I-2)

or a pharmaceutically acceptable salt, stereoisomer, solvate, or hydrate thereof, wherein:

᎓᎓᎓᎓᎓ indicates a single bond or a double bond;

$X^1$, $X^2$, $X^3$, $X^4$, and $X^5$ are each independently selected from N and CH; wherein no more than three of $X^1$, $X^2$, $X^3$, $X^4$, and $X^5$ are N and wherein ring A does not contain 3 nitrogen ring atoms at 3 contiguous positions;

W is selected from O, S, $CR^5R^6$, and $NR^{5'}$;

ring B is 5-6 membered heteroaryl, 5-6 membered monocyclic heterocyclyl, or phenyl;

$Z^1$ and $Z^2$ are each independently selected from N, C, and CH; $Z^3$ and $Z^4$ are each independently selected from a bond, CH, $CH_2$, CH=CH, $CH_2CH_2$, $CH_2CH$, and $CHCH_2$; wherein ring C contains no more than two double bonds;

L is $CHR^d$, O, S, or $NR^{5'}$;

ring D is bicyclic heteroaryl;

EE is —COOH or a carboxylic group surrogate, optionally, the carboxylic group surrogate is:

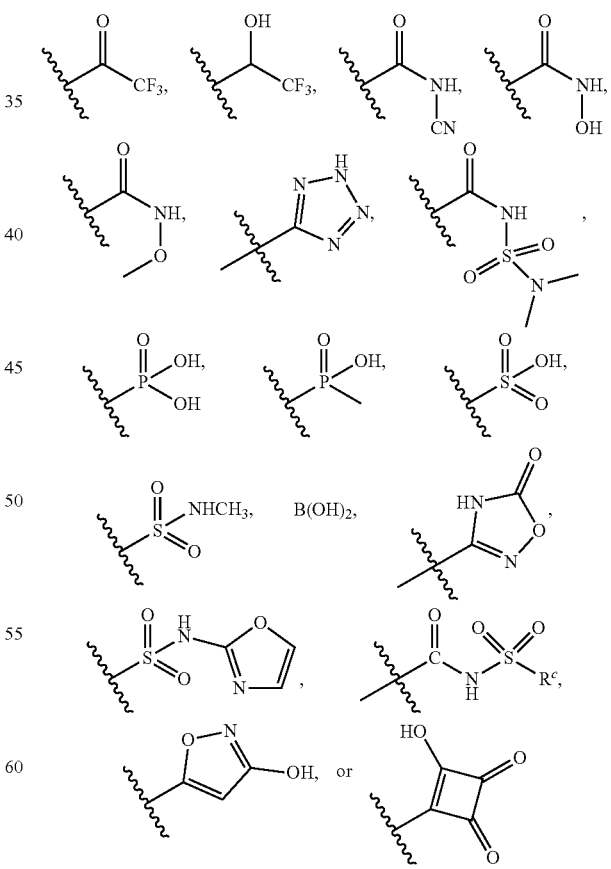

each $R^a$ and $R^b$ are independently selected from hydrogen, deuterium, halogen, —CN, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^a/R^b$ is optionally substituted with one or more groups selected from halogen, oxo, CN, OH, and $C_3$-$C_6$ saturated or partially saturated cycloalkyl; and wherein the aryl, heteroaryl, saturated or partially saturated cycloalkyl, or saturated or partially saturated heterocyclyl represented by $R^a/R^b$ or in the group represented by $R^a/R^b$ is optionally substituted with one or more groups selected from halogen, oxo (as appropriate), CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

each $R^c$ and $R^d$ are independently selected from hydrogen, deuterium, halogen, —CN, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^c/R^d$ is optionally substituted with one or more groups selected from halogen, oxo, CN, OH, and $C_3$-$C_6$ saturated or partially saturated cycloalkyl; and wherein the aryl, heteroaryl, saturated or partially saturated cycloalkyl, or saturated or partially saturated heterocyclyl represented by $R^c/R^d$ or in the group represented by $R^c/R^d$ is optionally substituted with one or more groups selected from halogen, oxo (as appropriate), CN, and $NR^{5'}R^{6'}$;

each $R^1$ is independently selected from H, deuterium, halogen, —CN, OH, $C_1$-$C_6$ alkyl, $C_1$-$C_6$ alkoxy, $C_2$-$C_6$ alkenyl, $C_2$-$C_6$ alkynyl, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl, $C_1$-$C_6$ alkoxy, $C_2$-$C_6$ alkenyl, or $C_2$-$C_6$ alkynyl represented by $R^1$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^1$ or in the group represented by $R^1$ is optionally substituted with one or more groups selected from halogen, oxo (as appropriate), CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$.

each $R^2$ is independently selected from H, deuterium, halogen, —CN, OH, oxo, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^2$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^2$ or in the group represented by $R^2$ is optionally substituted with one or more groups selected from halogen, oxo (as appropriate), CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

each $R^3$ is independently selected from H, deuterium, halogen, —CN, OH, oxo, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^3$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^3$ or in the group represented by $R^3$ is optionally substituted with one or more groups selected from halogen, oxo (as appropriate), CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$;

each $R^4$ is independently selected from H, deuterium, halogen, OH, —CN, $C_1$-$C_6$ alkyl, $C_1$-$C_6$ alkoxy, and $NR^{5'}R^{6'}$, wherein the $C_1$-$C_6$ alkyl and $C_1$-$C_6$ alkoxy represented by $R^4$ is optionally substituted with one or more groups selected from halogen, oxo, CN, $CF_3$, and saturated or partially saturated $C_3$-$C_6$ cycloalkyl (optionally substituted with one or more groups selected from halogen, oxo, CN, $CF_3$, OH, $OCH_3$, $OCH_2CH_3$);

$R^5$ and $R^6$ are each independently selected from hydrogen, deuterium, halogen, CN, OH, $C_1$-$C_6$ alkyl, $C_1$-$C_6$ alkoxy, $NR^{5'}R^{6'}$, 6-10 membered aryl, 5-8 membered heteroaryl, 3-8 membered saturated or partially saturated cycloalkyl and 3-8 membered saturated or partially saturated heterocyclyl, wherein the $C_1$-$C_6$ alkyl or $C_1$-$C_6$ alkoxy represented by $R^5$ or $R^6$ is optionally substituted with one or more groups selected from halogen, oxo, CN, $CF_3$, OH, $OCH_3$, $OCH_2CH_3$, and saturated or partially saturated $C_3$-$C_6$ cycloalkyl (optionally substituted with one or more groups selected from halogen, oxo, CN, $CF_3$, OH, $OCH_3$, $OCH_2CH_3$); and wherein the aryl, heteroaryl, saturated or partially saturated cycloalkyl, or saturated or partially saturated heterocyclyl represented by $R^5$ or $R^6$ or in the group represented by $R^5$ or $R^6$ is optionally substituted with one or more groups selected from halogen, oxo (as appropriate), CN, OH, $C_1$-$C_3$ alkyl (optionally substituted with 1 to 3 groups selected from F, OH, and $OCH_3$), and $C_1$-$C_3$ alkoxy (optionally substituted with 1 to 3 groups selected from F, OH, and $OCH_3$), and $NR^{5'}R^{6'}$.

$R^{5'}$ and $R^{6'}$ are each independently selected from hydrogen, and $C_1$-$C_6$ alkyl;

wherein optionally two $R^1$; two $R^2$; two $R^3$; two $R^4$; $R^1$ and $R^2$; $R^2$ and $R^3$; $R^a$ and $R^1$; $R^a$ and $R^2$; $R^1$ and any of $R^5$, $R^{5'}$ (in the group represented by W), or $R^6$; $R^a$ and any of $R^5$, $R^{5'}$ (in the group represented by W), or $R^6$; $R^2$ and any of $R^5$, $R^{5'}$ (in the group represented by W), or $R^6$; $R^5$ and $R^6$; any of two groups selected from $R^c$, $R^d$, $R^e$, and $R^f$; or R and any one of $R^c$, $R^d$, $R^e$, and $R^f$; taken together with their respective intervening carbon or hetero atom(s), form phenyl, 5-6 membered heteroaryl, 4-8 membered saturated or partially saturated cycloalkyl or 4-8 membered saturated or partially saturated heterocyclyl, or the carbon atom of —C($R^a$)—, W, and $R^2$, taken together with two adjacent carbon atoms of ring B form

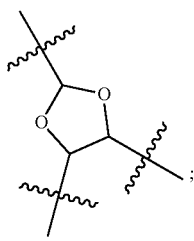 [SMILES: *C1OC(*)C(*)O1]

and each of which is optionally substituted with one or more groups selected from halogen, —CN, —OH, CF$_3$, C$_1$-C$_6$ alkyl, C$_1$-C$_6$ alkoxy, —NH$_2$, —NHC$_1$-C$_6$ alkyl, —N(C$_1$-C$_6$ alkyl)$_2$, oxo, and saturated or partially saturated C$_3$-C$_6$ cycloalkyl, wherein the C$_1$-C$_6$ alkyl and C$_1$-C$_6$ alkoxy is optionally substituted with one or more groups selected from halogen, oxo, CN, CF$_3$, OH, OCH$_3$, OCH$_2$CH$_3$, and saturated or partially saturated C$_3$-C$_6$ cycloalkyl, wherein the cycloalkyl is optionally substituted with one or more groups selected from halogen, oxo, CN, CF$_3$, OH, OCH$_3$, OCH$_2$CH$_3$;

m is an integer selected from 0, 1, 2, 3, and 4;

n is an integer selected from 0, 1, 2, 3, 4, and 5;

o is an integer selected from 0, 1, 2, 3, 4, and 5; and p is an integer selected from 0, 1, 2, 3, and 4.

The present disclosure also provides a compound represented by structural formula (I-A), (I-B), (I-C), or (I-D):

(I-A)

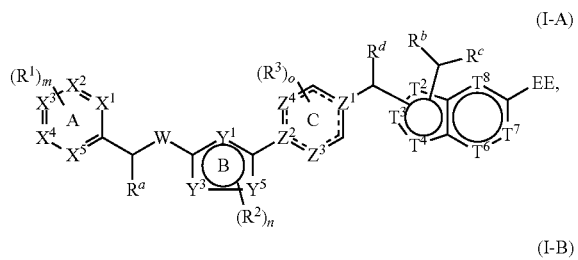

(I-B)

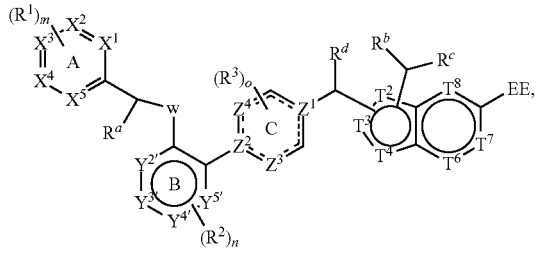

(I-C)

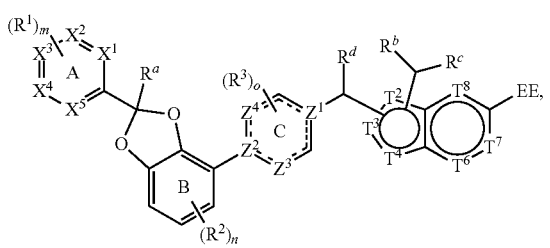

(I-D)

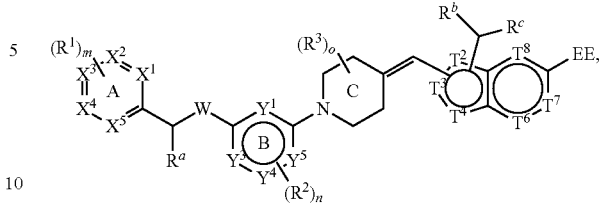

or a pharmaceutically acceptable salt, stereoisomer, solvate, or hydrate thereof, wherein:

===== indicates a single bond or a double bond;

X$^1$, X$^2$, X$^3$, X$^4$, and X$^5$ are each independently selected from N and CH; wherein no more than three of X$^1$, X$^2$, X$^3$, X$^4$, and X$^5$ are N and wherein ring A does not contain 3 nitrogen ring atoms at 3 contiguous positions;

W is selected from O, S, CR$^5$R$^6$, and NR$^{5'}$;

Y$^1$ is N or CH;

Y$^3$ and Y$^5$ are each independently selected from N, CH, O, and S;

Y$^4$ is absent, N or CH;

Y$^{2'}$ are each independently N or CH;

Y$^{3'}$ and Y$^{5'}$ are each independently selected from N, CH, O, and S; and

Y$^{4'}$ is absent, N or CH;

wherein there are no more than 3 hetero ring atoms in ring B and wherein ring B does not contain 3 hetero ring atoms at 3 contiguous positions;

Z$^1$ and Z$^2$ are each independently selected from N, C, and CH; wherein at least one of Z$^1$ and Z$^2$ is N; Z$^3$ and Z$^4$ are each independently selected from a bond, CH, CH$_2$, CH=CH, CH$_2$CH$_2$, CH$_2$CH, and CHCH$_2$; wherein ring C contains no more than two double bonds;

T$^2$, T$^3$, and T$^4$ are each independently selected from N, NR$^4$, O, S, C, and CR$^4$;

T$^6$, T$^7$, and T$^8$ are each independently selected from N and CR$^4$;

wherein no more than 4 of T$^2$, T$^3$, T$^4$, T$^6$, T$^7$, and T$^8$ are selected from N, O, and S;

and the remainder of the variables are as defined in the previous embodiments for the compounds represented by structural formula (I-1) or (I-2).

In some embodiments, the present disclosure provides a compound according to structural formula (I-1), (I-2), (I-A), (I-B), (I-C), or (I-D), wherein the compound is represented by structural formula (II-A), (II-B), (II-B'), (II-C) or (II-D):

(II-A)

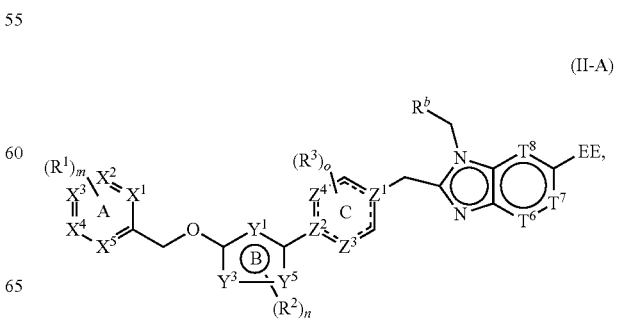

-continued

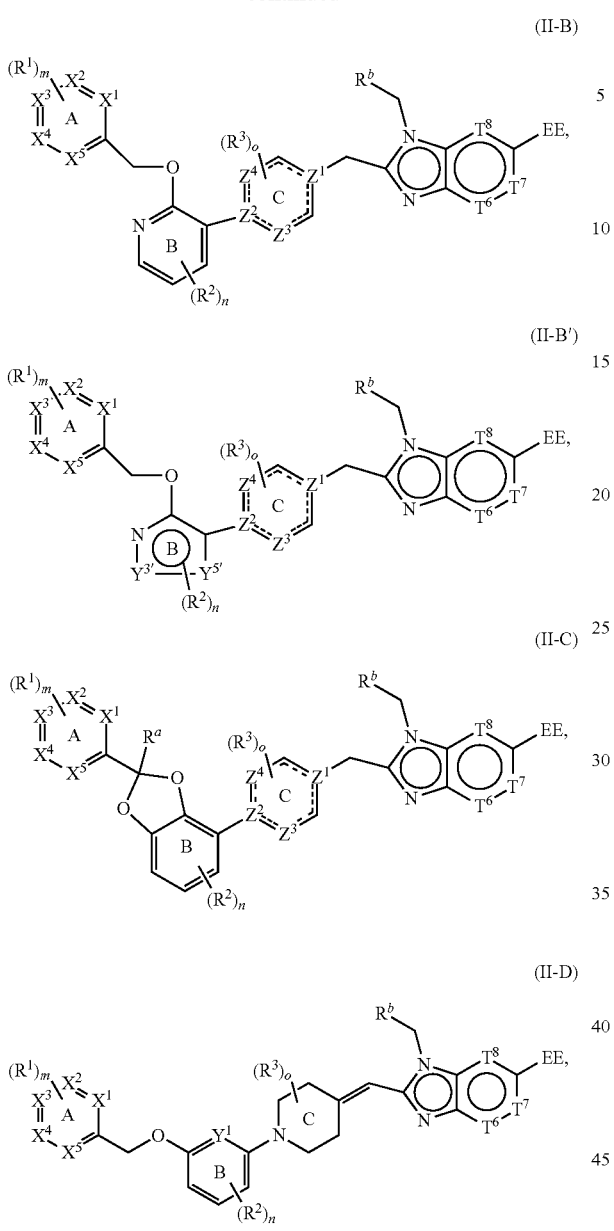

or a pharmaceutically acceptable salt, stereoisomer, solvate, or hydrate thereof, wherein the variables are as defined in the previous embodiments for the compounds represented by structural formula (I-1), (I-2), (I-A), (I-B), (I-C), or (I-D).

In some embodiments, the present disclosure provides a compound according to structural formula (I-1), (I-2), (I-A), (I-B), (I-C), (II-A), (II-B), (II-B'), (II-C), or (II-D) or a pharmaceutically acceptable salt, stereoisomer, solvate, or hydrate thereof, wherein ring A is

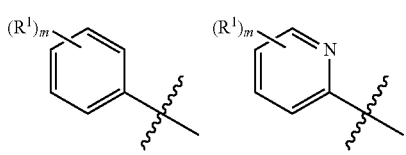

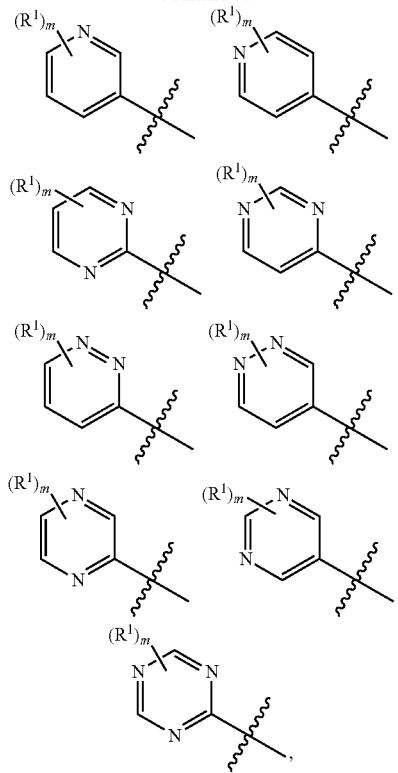

each $R^1$ is independently selected from halogen, OH, CN, $C_1$-$C_4$ alkyl, $C_1$-$C_4$ haloalkyl, $C_1$-$C_4$ hydroxyalkyl, $C_1$-$C_4$ alkoxy, $C_1$-$C_4$ haloalkoxy, $C_1$-$C_4$ hydroxyalkoxy, $C_2$-$C_4$ alkenyl, $C_2$-$C_4$ alkynyl, —$NH_2$, —$NHC_1$-$C_4$ alkyl, —$N(C_1$-$C_4$ alkyl$)_2$; and m is an integer selected from 0, 1, and 2; and the remainder of the variables are as defined in the previous embodiments.

In some embodiments, the present disclosure provides a compound according to structural formula (I-1), (I-2), (I-A), (I-B), (I-C), (II-A), (II-B), (II-B'), (II-C), or (II-D), or a pharmaceutically acceptable salt, stereoisomer, solvate, or hydrate thereof, wherein ring A is

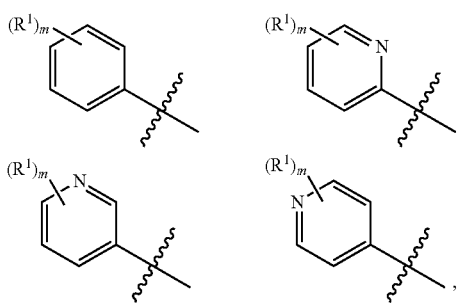

each $R^1$ is independently selected from halogen, OH, CN, $C_1$-$C_2$ alkyl, $C_1$-$C_2$ haloalkyl, $C_1$-$C_2$ hydroxyalkyl, $C_1$-$C_2$ alkoxy, $C_1$-$C_2$ haloalkoxy, $C_1$-$C_2$ hydroxyalkoxy, $C_2$-$C_4$ alkenyl, $C_2$-$C_4$ alkynyl; and m is an integer selected from 0, 1, and 2; and the remainder of the variables are as defined in the previous embodiments. In a specific embodiment, ring A is

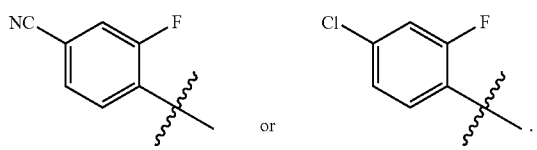 [SMILES: *c1ccc(C#N)cc1F ; *c1ccc(Cl)cc1F] or

In some embodiments, the present disclosure provides a compound according to structural formula (I-1), (I-2), (I-A), (I-B), (I-C), (II-A), (II-B), (II-B'), (II-C), or (II-D), or a pharmaceutically acceptable salt, stereoisomer, solvate, or hydrate thereof, wherein

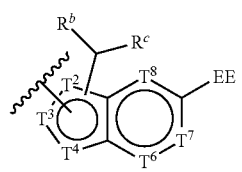

is

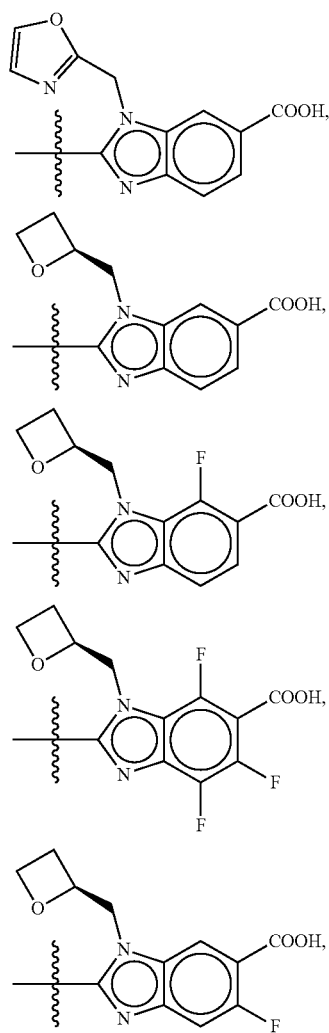

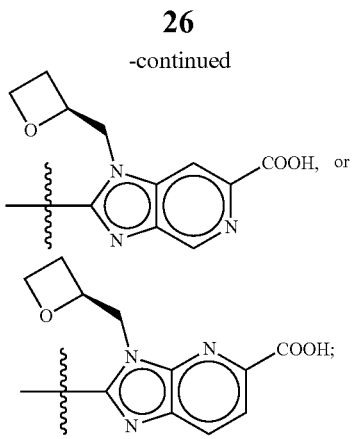

and the remainder of the variables are as defined in the previous embodiments. In a specific embodiment,

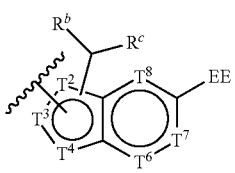

is

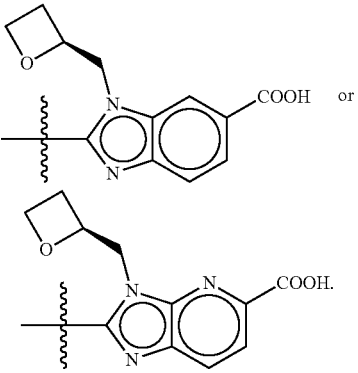

In a more specific embodiment,

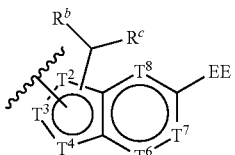

is

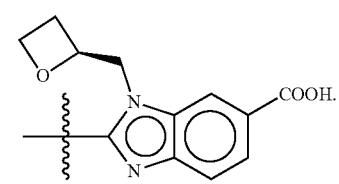

In some embodiments, the present disclosure provides a compound according to structural formula (I-1), (I-2), (I-A), (I-B), (I-C), (II-A), (II-B), (II-B'), or (II-C), or a pharmaceutically acceptable salt, stereoisomer, solvate, or hydrate thereof, wherein

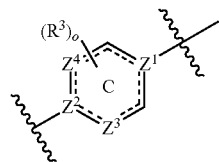

is

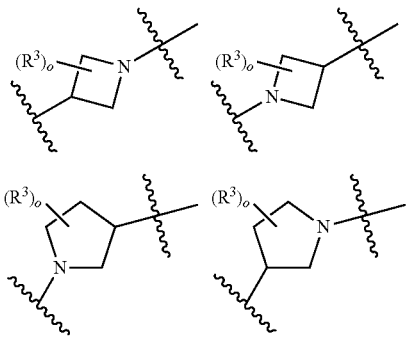

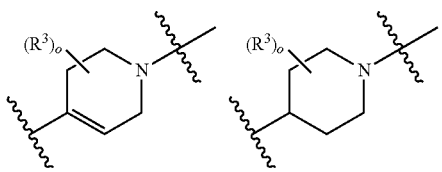

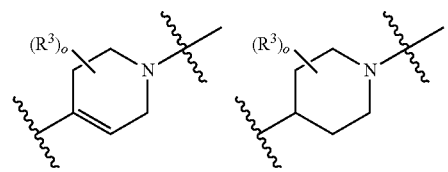

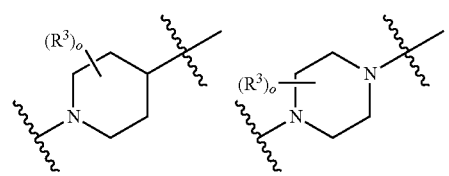

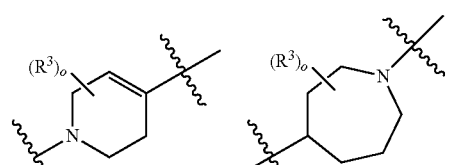

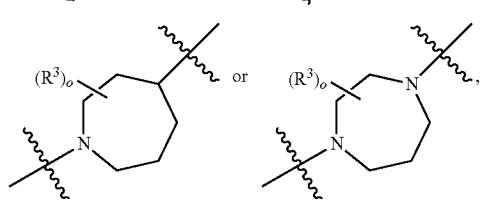

wherein R³ is halogen, CN, OH, oxo, $C_1$-$C_4$ alkyl, $C_1$-$C_4$ haloalkyl, $C_1$-$C_4$ alkoxy, or $NR^{5'}R^{6'}$; and o is an integer selected from 0, 1, 2, and 3; and the remainder of the variables are as defined in the previous embodiments. In a specific embodiment,

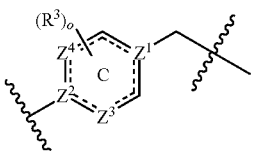

is

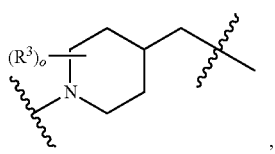, or

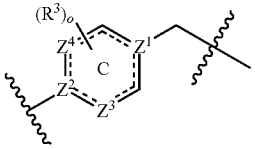, wherein R³ is independently halogen, $C_1$-$C_4$ alkyl, or $C_1$-$C_4$ haloalkyl; and o is 0, 1, or 2. In a more specific embodiment,

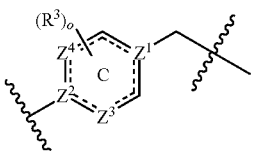

is

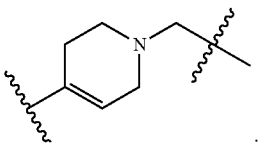 [SMILES: *CN1CC=C(*)CC1]

In some embodiments, the present disclosure provides a compound according to structural formula (II-A) or (II-B'), or a pharmaceutically acceptable salt, stereoisomer, solvate, or hydrate thereof, wherein

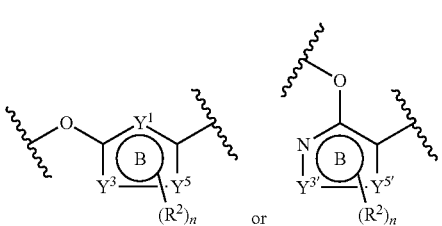

is

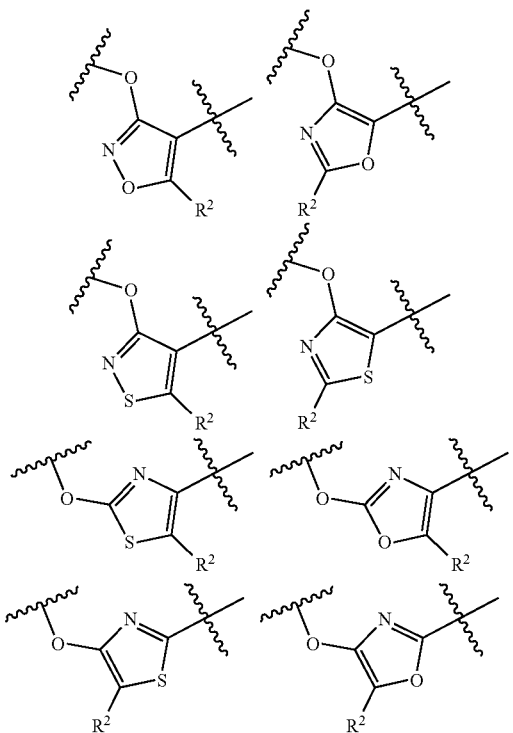

and the remainder of the variables are as defined in the previous embodiments. In a specific embodiment, wherein is

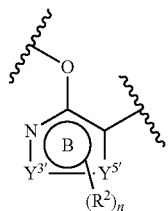

is

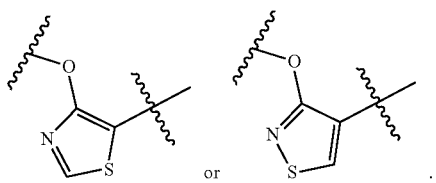 [SMILES: *Oc1ncsc1* ; *Oc1nscc1*]

In a specific embodiment, wherein

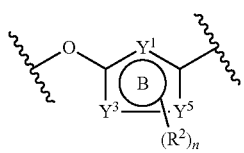

is

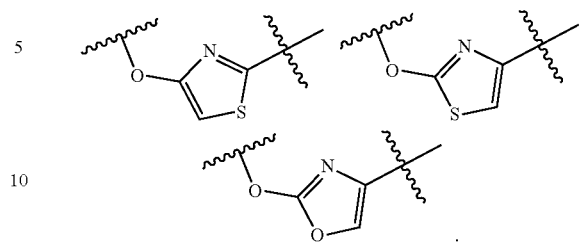

In some embodiments, the present disclosure provides a compound according to structural formula (II-D), or a pharmaceutically acceptable salt, stereoisomer, solvate, or hydrate thereof, wherein

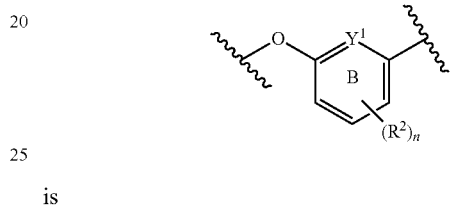

is

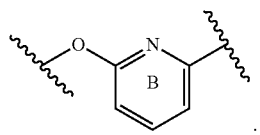

In one embodiment, the compound, or a pharmaceutically acceptable salt, stereoisomer, solvate, or hydrate thereof, is selected from the compounds disclosed in examples and Table 1.

2. Definitions

The term "halogen," as used herein, refers to fluoride, chloride, bromide, or iodide.

The term "alkyl" used alone or as part of a larger moiety, such as "alkoxy" or "haloalkyl" and the like, means saturated aliphatic straight-chain or branched monovalent hydrocarbon radical of formula —$C_nH_{(2n+1)}$). Unless otherwise specified, an alkyl group typically has 1-4 carbon atoms, i.e. ($C_1$-$C_4$)alkyl. As used herein, a "($C_1$-$C_4$)alkyl" group means a radical having from 1 to 4 carbon atoms in a linear or branched arrangement. Examples include methyl, ethyl, n-propyl, iso-propyl, and the like.

The term "alkylene" as used herein, means a straight or branched chain divalent hydrocarbon group of formula —$C_nH_{2n}$—. Non-limiting examples include ethylene, and propylene.

The term "alkenyl" means an alkyl group in which one or more carbon/carbon single bond is replaced by a double bond.

The term "alkynyl" means an alkyl group in which one or more carbon/carbon single bond is replaced by a triple bond.

The term "alkoxy" means an alkyl radical attached through an oxygen linking atom, represented by —O-alkyl. For example, "($C_1$-$C_4$)alkoxy" includes methoxy, ethoxy, propoxy, and butoxy.

The terms "haloalkyl" and "haloalkoxy" means alkyl or alkoxy, as the case may be, substituted with one or more halogen atoms.

The terms "hydroxyalkyl" and "hydroxyalkoxy" means alkyl or alkoxy, as the case may be, substituted with one or more hydroxy groups.

The term "cycloalkyl," as used herein, means a cyclic, hydrocarbon group containing at least three carbon atoms (e.g., $C_3$, $C_4$, $C_5$, $C_6$, $C_7$, $C_8$, or $C_{3-8}$ or $C_{3-6}$). The cycloalkyl may be (fully) saturated or partially saturated (i.e., not aromatic), and may contain one or more carbon-carbon double bond(s).

A fully saturated cycloalkyl has the formula $C_nH_{(2n-1)}$. Non-limiting examples include cyclopropyl, cyclobutyl, cyclopentyl and cyclohexyl.

The term "heterocyclyl" or "heterocyclic" refers to a radical of a 3- to 12-membered non-aromatic ring system having ring carbon atoms and 1 to 4 ring heteroatoms, wherein each heteroatom is independently selected from nitrogen, quaternary nitrogen, oxidized nitrogen (e.g., NO), oxygen, and sulfur, including sulfoxide and sulfone ("3-12 membered heterocyclyl"). In some embodiments, a heterocyclyl group is a 3-8 membered non-aromatic ring system having ring carbon atoms and 1-4 ring heteroatoms, wherein each heteroatom is independently selected from nitrogen, oxygen, and sulfur ("3-8 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a bicyclic system ("bicyclic heterocyclyl") or tricyclic system ("tricyclic heterocyclyl"); polycyclic ring systems include fused, bridged, or spiro ring systems). Exemplary monocyclic heterocyclyl groups include azetidinyl, oxetanyl, thietanyl, tetrahydrofuranyl, pyrrolidinyl, piperidinyl, tetrahydropyranyl, piperazinyl, morpholinyl, azepanyl, oxepanyl, thiepanyl, tetrahydropyridinyl, and the like. Heterocyclyl polycyclic ring systems can include heteroatoms in one or more rings in the polycyclic ring system. Substituents may be present on one or more rings in the polycyclic ring system.

Generally, the cycloalkyl or the heterocyclyl may be unsubstituted, or be substituted with one or more substituents as valency allows, wherein the substituents can be independently selected from a number of groups such as oxo, —CN, halogen, alkyl and alkoxyl, optionally, the alkyl substitution may be further substituted.

The term "heteroaryl," as used herein, refers to a monocyclic or multicyclic aromatic hydrocarbon in which at least one of the ring carbon atoms has been replaced with a heteroatom independently selected from oxygen, nitrogen and sulfur. Preferably, the heteroaryl is based on a $C_{5-8}$ aryl with one or more of its ring carbon atoms replaced by the heteroatom. A heteroaryl group may be attached through a ring carbon atom or, where valency permits, through a ring nitrogen atom. Generally, the heteroaryl may be unsubstituted, or be substituted with one or more substituents as valency allows with the substituents being independently selected from halogen, OH, alkyl, alkoxyl, and amino (e.g., $NH_2$, NHalkyl, $N(alkyl)_2$), optionally, the alkyl may be further substituted.

Certain abbreviations used herein include: Room temperature: RT; Methanol: MeOH; Ethanol: EtOH; Isopropanol: iPrOH; Ethyl acetate: EtOAc; Tetrahydrofuran: THF; Toluene: $PhCH_3$; Cesium carbonate: $Cs_2CO_3$; Lithium bis(trimethylsilyl)amide: LiHMDS; Sodium t-butoxide: NaOtBu; Potassium t-butoxide: KotBu; Lithium diisopropylamide: LDA; Triethylamine: $Et_3N$; N,N-diisopropylethyl amine: DIPEA; Potassium carbonate: $K_2CO_3$; Dimethyl formamide: DMF; Dimethyl acetamide: DMAc; Dimethyl sulfoxide: DMSO; N-Methyl-2-pyrrolidinone: NMP; Sodium hydride: NaH; Trifluoroacetic acid: TFA; Trifluoroacetic anhydride: TFAA; Acetic anhydride: $Ac_2O$; Dichloromethane: DCM; 1,2-Dichloroethane: DCE; Hydrochloric acid: HCl; 1,8-Diazabicyclo[5.4.0]undec-7-ene: DBU; Borane-dimethylsulfide complex: $BH_3$-DMS; Borane-tetrahydrofuran complex: $BH_3$-THF; Lithium aluminum hydride: LAH; Acetic acid: AcOH; Acetonitrile: MeCN; p-Toluenesulfonic acid: pTSA; Dibenzylidine acetone: DBA; 2,2'-Bis(diphenylphosphino)-1,1'-binaphthalene: BINAP; 1,1'-Ferrocenediyl-bis(diphenylphosphine): dppf, 1,3-Bis(diphenylphosphino)propane: DPPP; 3-Chloroperbenzoic acid: m-CPBA; Tert-Butyl methyl ether: MTBE; Methanesulfonyl: Ms; N-Methylpyrrolidinone: NMP; Thin layer chromatography: TLC; Supercritical fluid chromatography: SFC; 4-(Dimethylamino)pyridine: DMAP; Tert-Butyloxycarbonyl: Boc; 1-[Bis(dimethylamino)methylene]-1H-1,2,3-triazolo[4,5-b]pyridinium 3-oxid hexafluoropho- sphate: HATU; Petroleum ether: PE; 2-(1H-Benzotriazole-1-yl)-1,1,3,3-tetramethyluronium hexafluorophosphate: HBTU; and 2-Amino-2-(hydroxymethyl)propane-1,3-diol: tris; tris(dibenzylideneacetone)dipalladium: $Pd_2(dba)_3$ $^1$H Nuclear magnetic resonance (NMR) spectra were in all cases consistent with the proposed structures. Characteristic chemical shifts (δ) are given in parts-per-million relative to the residual proton signal in the deuterated solvent ($CHCl_3$ at 7.27 ppm; $CD_2HOD$ at 3.31 ppm; MeCN at 1.94 ppm; DMSO at 2.50 ppm) and are reported using conventional abbreviations for designation of major peaks: e.g. s, singlet; d, doublet; t, triplet; q, quartet; m, multiplet; br, broad. $^1$H NMR spectra were obtained with field strengths of 400 or 600 MHz if not stated.

As used herein, a wavy line denotes a point of attachment of a substituent to another group.

Pharmaceutically Acceptable Salts

Pharmaceutically acceptable salts of the compounds of any one of the formulae described above include acid addition and base salts.

Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphathalenedisulfonic acid and xinafoate salts.

Suitable base salts are formed from bases which form non-toxic salts. Examples include the aluminium, arginine, benzathine, calcium, choline, diethylamine, bis(2-hydroxyethyl)amine (diolamine), glycine, lysine, magnesium, meglumine, 2-aminoethanol (olamine), potassium, sodium, 2-Amino-2-(hydroxymethyl)propane-1,3-diol (tris or tromethamine) and zinc salts.

Hemisalts of acids and bases may also be formed, for example, hemisulfate and hemicalcium salts. For a review on suitable salts, see *Handbook of Pharmaceutical Salts: Properties, Selection, and Use* by Stahl and Wermuth (Wiley-VCH, 2002). Incorporated herein by reference.

Pharmaceutically acceptable salts of compounds of any one of the formulae described above may be prepared by one or more of three methods:

(i) by reacting the compound of any one of the formulae described above with the desired acid or base;

(ii) by removing an acid- or base-labile protecting group from a suitable precursor of the compound of any one of the formulae described above or by ring-opening a suitable cyclic precursor, for example, a lactone or lactam, using the desired acid or base; or (iii) by converting one salt of the compound of any one of the formulae described above to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of any one of the formulae described above, and pharmaceutically acceptable salts thereof, may exist in unsolvated and solvated forms.

Solvates and Hydrates

The term "solvate" is used herein to describe a molecular complex comprising the compound of any one of the formulae described above, or a pharmaceutically acceptable salt thereof, and one or more pharmaceutically acceptable solvent molecules, for example, ethanol.

The term "hydrate" is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Stereoisomers and Other Variations

The compounds of any one of the formulae described above may exhibit one or more kinds of isomerism (e.g. optical, geometric or tautomeric isomerism). The compounds of any one of the formulae described above may also be isotopically labelled. Such variation is implicit to the compounds of any one of the formulae described above defined as they are by reference to their structural features and therefore within the scope of the present disclosure.

Compounds of any one of the formulae described above containing one or more asymmetric carbon atoms can exist as two or more stereoisomers. Where a compound of any one of the formulae described above contains an alkenyl or alkenylene group, geometric cis/trans (or Z/E) isomers are possible. Where structural isomers are interconvertible via a low energy barrier, tautomeric isomerism ("tautomerism") can occur. This can take the form of proton tautomerism in compounds of any one of the formulae described above containing, for example, an imino, keto, or oxime group, or so-called valence tautomerism in compounds which contain an aromatic moiety. It follows that a single compound may exhibit more than one type of isomerism.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. The term "geometric isomer" refers to compounds having at least one double bond, wherein the double bond(s) may exist in cis (also referred to as syn or entgegen (E)) or trans (also referred to as anti or zusammen (Z)) forms as well as mixtures thereof. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

The pharmaceutically acceptable salts of compounds of any one of the formulae described above may also contain a counterion which is optically active (e.g. d-lactate or l-lysine) or racemic (e.g. dl-tartrate or dl-arginine).

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of any one of the formulae described above contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of any one of the formulae described above (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present disclosure are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein). Columns can be obtained from Chiral Technologies, Inc, West Chester, Pa., USA, a subsidiary of Daicel® Chemical Industries, Ltd., Tokyo, Japan.

It must be emphasized that the compounds of any one of the formulae described above have been drawn herein in a single tautomeric form, all possible tautomeric forms are included within the scope of the present disclosure.

The present disclosure also includes all pharmaceutically acceptable isotopically-labeled compounds of any one of the formulae described above wherein one or more atoms are replaced by atoms having the same atomic number, but an atomic mass or mass number different from the atomic mass or mass number which predominates in nature.

Examples of isotopes suitable for inclusion in the compounds of the present disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of any one of the formulae described above, for example those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of any one of the formulae described above can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the present disclosure include those wherein the solvent of crystallization may be isotopically substituted, e.g., D$_2$O, d$_6$-acetone, d$_6$-DMSO.

Prodrugs

One way of carrying out the present disclosure is to administer a compound of any one of the formulae described above in the form of a prodrug. Thus, certain derivatives of a compound of any one of the formulae described above which may have little or no pharmacological activity themselves can, when administered into or onto the body, be converted into a compound of any one of the formulae described above having the desired activity, for example by hydrolytic cleavage, particularly hydrolytic cleavage promoted by an esterase or peptidase enzyme. Such derivatives are referred to as "prodrugs." Further information on the use of prodrugs may be found in *Pro-drugs as Novel Delivery Systems*, Vol. 14, *ACS Symposium Series* (T. Higuchi and W. Stella) and *Bioreversible Carriers in Drug Design*, Pergamon Press, 1987 (Ed. E. B. Roche, American Pharmaceutical Association). Reference can also be made to *Nature Reviews/Drug Discovery*, 7:355, 2008, and *Current Opinion in Drug Discovery and Development*, 10:550, 2007.

Prodrugs in accordance with the present disclosure can, for example, be produced by replacing appropriate functionalities present in the compounds of any one of the formulae described above with certain moieties known to those skilled in the art as "pro-moieties" as described, for example, in *Design of Prodrugs* by H. Bundgaard (Elsevier, 1985) and Y. M. Choi-Sledeski and C. G. Wermuth, *Designing Prodrugs and Bioprecursors* in Practice of Medicinal Chemistry, (Fourth Edition), Chapter 28, 657-696 (Elsevier, 2015).

Thus, a prodrug in accordance with the present disclosure is (a) an ester or amide derivative of a carboxylic acid in a compound of any one of the formulae described above; (b) an ester, carbonate, carbamate, phosphate or ether derivative of a hydroxyl group in a compound of any one of the formulae described above; (c) an amide, imine, carbamate or amine derivative of an amino group in a compound form any one of the formulae described above; (d) an oxime or imine derivative of a carbonyl group in a compound of any one of the formulae described above; or (e) a methyl, primary alcohol or aldehyde group that can be metabolically oxidized to a carboxylic acid in a compound of any one of the formulae described above.

Some specific examples of prodrugs in accordance with the present disclosure include:

(i) where the compound of any one of the formulae described above contains a carboxylic acid functionality (—COOH), an ester thereof, such as a compound wherein the hydrogen of the carboxylic acid functionality of the compound of any one of the formulae described above is replaced by $C_1$-$C_8$ alkyl (e.g. ethyl) or ($C_1$-$C_8$ alkyl)C(═O)OCH$_2$— (e.g. $^t$BuC(═O)OCH$_2$—);

(ii) where the compound of any one of the formulae described above contains an alcohol functionality (—OH), an ester thereof, such as a compound wherein the hydrogen of the alcohol functionality of the compound of any one of the formulae described above is replaced by —CO($C_1$-$C_8$ alkyl) (e.g. methylcarbonyl) or the alcohol is esterified with an amino acid;

(iii) where the compound of any one of the formulae described above contains an alcohol functionality (—OH), an ether thereof, such as a compound wherein the hydrogen of the alcohol functionality of the compound of any one of the formulae described above is replaced by ($C_1$-$C_8$ alkyl) C(=O)OCH$_2$— or —CH$_2$OP(=O)(OH)$_2$;

(iv) where the compound of any one of the formulae described above contains an alcohol functionality (—OH), a phosphate thereof, such as a compound wherein the hydrogen of the alcohol functionality of the compound of any one of the formulae described above is replaced by —P(=O)(OH)$_2$ or —P(=O)(ONa)$_2$ or —P(=O)(O$^-$)$_2$Ca$^{2+}$;

(v) where the compound of any one of the formulae described above contains a primary or secondary amino functionality (—NH$_2$ or —NHR where R≠H), an amide thereof, for example, a compound wherein, as the case may be, one or both hydrogens of the amino functionality of the compound of any one of the formulae described above is/are replaced by ($C_1$-$C_{10}$)alkanoyl, —COCH$_2$NH$_2$ or the amino group is derivatised with an amino acid;

(vi) where the compound of any one of the formulae described above contains a primary or secondary amino functionality (—NH$_2$ or —NHR where R≠H), an amine thereof, for example, a compound wherein, as the case may be, one or both hydrogens of the amino functionality of the compound of any one of the formulae described above is/are replaced by —CH$_2$OP(=O)(OH)$_2$;

(vii) where the carboxylic acid group within compound of any one of the formulae described above is replaced by a methyl group, a —CH$_2$OH group or an aldehyde group.

Certain compounds of any one of the formulae described above may themselves act as prodrugs of other compounds of any one of the formulae described above. It is also possible for two compounds of any one of the formulae described above to be joined together in the form of a prodrug. In certain circumstances, a prodrug of a compound of any one of the formulae described above may be created by internally linking two functional groups in a compound of any one of the formulae described above, for instance by forming a lactone.

References to compounds of any one of the formulae described above are taken to include the compounds themselves and prodrugs thereof. The present disclosure includes such compounds of any one of the formulae described above as well as pharmaceutically acceptable salts of such compounds and pharmaceutically acceptable solvates of said compounds and salts.

3. Administration and Dosing

Typically, a compound of the present disclosure is administered in an amount effective to treat a condition as described herein. The compounds of the present disclosure can be administered as compound per se, or alternatively, as a pharmaceutically acceptable salt. For administration and dosing purposes, the compound per se or pharmaceutically acceptable salt thereof will simply be referred to as the compounds of the present disclosure.

The compounds of the present disclosure are administered by any suitable route in the form of a pharmaceutical composition adapted to such a route, and in a dose effective for the treatment intended. The compounds of the present disclosure may be administered orally, rectally, vaginally, parenterally, or topically.

The compounds of the present disclosure may be administered orally. Oral administration may involve swallowing, so that the compound enters the gastrointestinal tract, or buccal or sublingual administration may be employed by which the compound enters the bloodstream directly from the mouth.

In another embodiment, the compounds of the present disclosure may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the present disclosure may also be administered topically to the skin or mucosa, that is, dermally or transdermally. In another embodiment, the compounds of the present disclosure can also be administered intranasally or by inhalation. In another embodiment, the compounds of the present disclosure may be administered rectally or vaginally. In another embodiment, the compounds of the present disclosure may also be administered directly to the eye or ear.

The dosage regimen for the compounds of the present disclosure and/or compositions containing said compounds is based on a variety of factors, including the type, age, weight, sex and medical condition of the patient; the severity of the condition; the route of administration; and the activity of the particular compound employed. Thus the dosage regimen may vary widely. In one embodiment, the total daily dose of a compound of the present disclosure is typically from about 0.001 to about 100 mg/kg (i.e., mg compound of the present disclosure per kg body weight) for the treatment of the indicated conditions discussed herein. In another embodiment, total daily dose of the compound of the present disclosure is from about 0.01 to about 30 mg/kg, and in another embodiment, from about 0.03 to about 10 mg/kg, and in yet another embodiment, from about 0.1 to about 3. It is not uncommon that the administration of the compounds of the present disclosure will be repeated a plurality of times in a day (typically no greater than 4 times). Multiple doses per day typically may be used to increase the total daily dose, if desired.

For oral administration, the compositions may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the present disclosure include mammalian subjects, including non-human mammal such as primates, rodents (mice, rats, hamsters, rabbits etc). In one embodiment, humans are suitable subjects. Human subjects may be of either gender and at any stage of development.

4. Pharmaceutical Compositions

In another embodiment, the present disclosure comprises pharmaceutical compositions. Such pharmaceutical compositions comprise a compound of the present disclosure presented with a pharmaceutically acceptable carrier. Other pharmacologically active substances can also be present.

As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of present disclosure may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the present disclosure. In another embodiment, the oral administration may be in a powder or granule form. In another embodiment, the oral dose form is sub-lingual, such as, for example, a lozenge. In such solid dosage forms, the compounds of any one of the formulae described above are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present disclosure comprises a parenteral dose form.

"Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present disclosure comprises a topical dose form.

"Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of present disclosure are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, *J Pharm. Sci.*, 88:955-958, 1999.

Formulations suitable for topical administration to the eye include, for example, eye drops wherein the compound of present disclosure is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the compounds of the present disclosure are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present disclosure comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the present disclosure may be prepared by any of the well-known techniques of pharmacy, such as effective formulation and administration procedures.

The above considerations in regard to effective formulations and administration procedures are well known in the art and are described in standard textbooks. Formulation of drugs is discussed in, for example, Hoover, John E., *Remington's Pharmaceutical Sciences*, Mack Publishing Co., Easton, Pa., 1975; Liberman et al., Eds., *Pharmaceutical Dosage Forms*, Marcel Decker, New York, N.Y., 1980; and Kibbe et al., Eds., *Handbook of Pharmaceutical Excipients* (3$^{rd}$ Ed.), American Pharmaceutical Association, Washington, 1999.

5. Co-Administration

The compounds of the present disclosure can be used alone, or in combination with other therapeutic agents. The present disclosure provides any of the uses, methods or compositions as defined herein wherein the compound of any embodiment of any one of the formulae described above herein, or pharmaceutically acceptable salt thereof, or pharmaceutically acceptable solvate of said compound or salt, is used in combination with one or more other therapeutic agent discussed herein.

The administration of two or more compounds "in combination" means that all of the compounds are administered closely enough in time that each may generate a biological effect in the same time frame. The presence of one agent may alter the biological effects of the other compound(s). The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

The phrases "concurrent administration," "co-administration," "simultaneous administration," and "administered simultaneously" mean that the compounds are administered in combination.

In another embodiment, the present disclosure provides methods of treatment that include administering compounds of the present disclosure in combination with one or more other pharmaceutical agents, wherein the one or more other pharmaceutical agents may be selected from the agents discussed herein.

In one embodiment, the compounds of present disclosure are administered with an antidiabetic agent including but not limited to a biguanide (e.g., metformin), a sulfonylurea (e.g., tolbutamide, glibenclamide, gliclazide, chlorpropamide, tolazamide, acetohexamide, glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In another embodiment, the compounds of present disclosure are administered with an anti-obesity agent including but not limited to peptide YY or an analogue thereof, a neuropeptide Y receptor type 2 (NPYR2) agonist, a NPYR1 or NPYR5 antagonist, a cannabinoid receptor type 1 (CB1R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In another embodiment, the compounds of present disclosure are administered with an agent to treat NASH including but not limited to PF-05221304, an FXR agonist (e.g., obeticholic acid), a PPAR α/δ agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor 21 (FGF21) agonist (e.g., BMS-986036), a leukotriene D4 (LTD4) receptor antagonist (e.g., tipelukast), a niacin analogue (e.g., ARI 3037MO), an ASBT inhibitor (e.g., volixibat), an acetyl-CoA carboxylase (ACC) inhibitor (e.g., NDI 010976), a ketohexokinase (KHK) inhibitor, a diacylglyceryl acyltransferase 2 (DGAT2) inhibitor, a CB1 receptor antagonist, an anti-CB1R antibody, or an apoptosis signal-regulating kinase 1 (ASK1) inhibitor, including the pharmaceutically acceptable salts of the specifically named agents and the pharmaceutically acceptable solvates of said agents and salts.

These agents and compounds of the present disclosure can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; mono-saccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Liposomes containing these agents and/or compounds of the present disclosure are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the present disclosure may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in *Remington, The Science and Practice of Pharmacy*, 20$^{th}$ Ed., Mack Publishing (2000).

Sustained-release preparations may be used. Suitable examples of sustained-release preparations include semi-permeable matrices of solid hydrophobic polymers containing the compound of any one of the formulae described above, which matrices are in the form of shaped articles, e.g., films, or microcapsules. Examples of sustained-release matrices include polyesters, hydrogels (for example, poly (2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the present disclosure are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 m, particularly 0.1 and 0.5 μm, and have a pH in the range of 5.5 to 8.0.

The emulsion compositions can be those prepared by mixing a compound of the present disclosure with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

6. Kits

Another aspect of the present disclosure provides kits comprising the compound of any one of the formulae described above or pharmaceutical compositions comprising the compound of any one of the formulae described above of the present disclosure. A kit may include, in addition to the compound of any one of the formulae described above, of the present disclosure or pharmaceutical composition thereof, diagnostic or therapeutic agents. A kit may also include instructions for use in a diagnostic or therapeutic method. In some embodiments, the kit includes the compound of any one of the formulae described above, or a pharmaceutical composition thereof and a diagnostic agent. In other embodiments, the kit includes the compound of any one of the formulae described above, or a pharmaceutical composition thereof.

In yet another embodiment, the present disclosure comprises kits that are suitable for use in performing the methods of treatment described herein. In one embodiment, the kit contains a first dosage form comprising one or more of the compounds of the present disclosure in quantities sufficient to carry out the methods of the present disclosure. In another embodiment, the kit comprises one or more compounds of the present disclosure in quantities sufficient to carry out the methods of the present disclosure and a container for the dosage and a container for the dosage.

7. Preparation

The compounds of any one of the formulae described above, may be prepared by the general and specific methods described below, using the common general knowledge of one skilled in the art of synthetic organic chemistry. Such common general knowledge can be found in standard reference books such as *Comprehensive Organic Chemistry*, Ed. Barton and Ollis, Elsevier; *Comprehensive Organic Transformations: A Guide to Functional Group Preparations*, Larock, John Wiley and Sons; and *Compendium of*

*Organic Synthetic Methods*, Vol. I-XII (published by Wiley-Interscience). The starting materials used herein are commercially available or may be prepared by routine methods known in the art.

In the preparation of the compounds of any one of the formulae described above, it is noted that some of the preparation methods described herein may require protection of remote functionality (e.g., primary amine, secondary amine, carboxyl in any one of the formulae described above precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxy-carbonyl (Boc), benzyloxycarbonyl (Cbz), and 9-fluorenyl-methylenoxycarbonyl (Fmoc) for amines, and lower alkyl or benzyl esters for carboxylic acids) which are generally not chemically reactive under the reaction conditions described and can typically be removed without chemically altering other functionality in the any one of the formulae described above compounds.

The Schemes described below are intended to provide a general description of the methodology employed in the preparation of the compounds of the present disclosure. Some of the compounds of the present disclosure may contain single or multiple chiral centers with the stereochemical designation (R) or (S). It will be apparent to one skilled in the art that all of the synthetic transformations can be conducted in a similar manner whether the materials are enantioenriched or racemic. Moreover, the resolution to the desired optically active material may take place at any desired point in the sequence using well known methods such as described herein and in the chemistry literature.

Amine compounds prepared via methods described herein can be alkylated with a protected 2-bromoacetate in the presence of a suitable base such as $K_2CO_3$, $Et_3N$, NaH or LiHMDS in a polar aprotic solvent such as but not limited to DMF, DMAc, DMSO or NMP to deliver compounds. Standard ester hydrolysis can be performed to provide acids. If $Pg^2$ is t-butyl, standard acidic deprotection methods such as TFA/DCM, HCl/1,4-dioxane, HCl/EtOAc or other suitable conditions may be used to deliver acids.

EXAMPLES

Activation of a G protein-coupled receptor (GPCR) GLP-1R by its natural ligand GLP-1 causes recruitment of multiple intracellular proteins, each of which can activate distinct signaling pathways, most prominently the activation of downstream G proteins (which can be measured by cAMP production), the recruitment of β-Arrestin, and/or the subsequent internalization of the GPCR (i.e., GLP-1R)—β-Arrestin complex. Unlike the natural ligand GLP-1, certain GLP-1R agonists are so-called "biased agonists," in that they preferentially stimulate subsets among the natural signaling pathways, such as the G protein activation/cAMP production pathway, as compared to the recruitment of β-Arrestin, and/or the subsequent internalization of the GPCR (i.e., GLP-1R)-β-Arrestin complex. The assays below provide means to measure the various downstream signaling pathways upon activation by the subject compounds.

Biological Example 1: GLP-1R/β-Arrestin Assay and Internalization Assay for Demonstrating Small Molecule Compound-Mediated GLP-1R/β-Arrestin Interaction Activation GLP1 plays an important physiological role in maintaining blood glucose homeostasis. GLP-1R is known to be expressed in pancreatic beta cells. GLP-1 mediates its effects via a Gαs-coupled pathway. Activated GLP-1R stimulates the adenylyl cyclase pathway thus increases the intracellular concentration of cAMP, which results in increased insulin synthesis and release of insulin. Consequently GLP-1R has been suggested as a potential target for the treatment of diabetes.

GLP-1R activation following agonist/ligand binding also leads to β-arrestin recruitment to the GLP-1 receptor, which blocks GLP-1R signaling by, for example, occluding the binding site on GLP-1R for heterotrimeric G-protein to prevent its activation (desensitization), and by linking the GLP-1R to elements of the internalization machinery, such as clathrin and clathrin adaptor AP2, which promotes receptor internalization via coated pits and subsequent transport to internal compartments endosomes. Subsequently, the receptor could be either directed to degradation compartments (lysosomes) or recycled back to the plasma membrane where it can again signal. The strength of arrestin-receptor interaction is believed to play a role in this choice: tighter complexes tend to increase the probability of receptor degradation (Class B), whereas more transient complexes favor recycling (Class A), although this "rule" is far from being absolute.

GLP-1R agonist activity with respect to β-arrestin recruitment can be determined with a cell-based functional assay using PathHunter eXpress GLP1R CHO-K1β-Arrestin GPCR Assay kit (DiscoverX Cat #93-0300E2CP0M).

The PathHunter β-Arrestin GPCR assay technology utilizes a β-galactosidase (β-gal) enzyme that is split into two fragments, the smaller Enzyme Donor (ED) and the larger Enzyme Acceptor (EA). These fragments can be fused to two proteins that may interact with each other, such as EA-β-Arrestin and ED-GLP-1R. The fusions can be stably expressed in a test cell line, such as the PathHunter CHO-K1 GLP1R β-Arrestin cells described below.

Independently, these fragment fusions have no β-gal activity; however, in solution or in a living cell, they can be brought together and complement to form an active β-gal enzyme due to the interaction between the fused proteins, thus generating a chemiluminescent signal in the presence of a suitable β-gal substrate.

In this experiment, PathHunter CHO-K1 GLP1R β-Arrestin cells from the assay kit were plated at a density of 1000 or 2000 cells/20 μl/well in a 384-well white/clear bottom plates (Greiner Cat #781098). Frozen cells were quickly thawed and 10 mL of cell plating medium (provided by the kit) was added to thawed cells. Cells were stored in a 37° C. incubator under 5% $CO_2$ and kept for approximately 48 hours until ready to run the assay.

Reference and test compounds were dissolved in 100% DMSO. 5× concentration of an agonist was prepared in serum free DMEM (Thermo Cat #11965). 5 μL of this solution was added to 20 μL cell medium in assay plate for a final top concentration of 10 μM. Plates were then incubated at 37° C. under 5% $CO_2$ for 90 min.

Following 90 min incubation, detection reagents were made up by combining 1 part Galacton Star Substrate with 5 parts Emerald II™ Solution, and 19 parts of PathHunter Cell Assay Buffer, respectively. 12.5 μl detection reagent was added to each well. The plates were then incubated at room temperature in dark for 60 min. Plates were then read on Envision for 0.1 sec/well.

$EC_{50}$ determinations were made from agonist dose-response curves analyzed with a curve fitting program using a 4-parameter logistic dose response equation.

The effect of a small molecule compound, such as one of the instant present disclosure, on the GLP-1R/β-Arrestin interaction activation, or β-Arrestin recruitment, can be demonstrated and measured using the assay and commercial reagents described herein below.

Preparations

Reagents and Consumables:

| Reagent | Vendor | Catalog No. |
| --- | --- | --- |
| PathHunter eXpress GLP1R CHO-K1 β-Arrestin GPCR Assay kit | Discover X | 93-0300E2CP0M |
| 384 well white/clear bottom plates | Greiner | 781098 |

Instruments:

| Instrument | Vendor | Internal Code |
| --- | --- | --- |
| En Vision | PerkinElmer | HD-4HYSG2330 |

Media and Solutions

Prepare detection Working Solution by combining 1 part Galacton Star® Substrate with 5 parts Emerald II™ Solution, and 19 parts of PathHunter Cell Assay Buffer, respectively.

Once prepared, the working solution is stable for at least 24 hours at room temperature with no impact on assay performance. Sufficient reagents are provided in each kit to perform the indicated number of assays.

Procedures

1. Plating Cells

Cells were plated at a density of 1000 or 2000 cells/20 μL/well. Frozen cells were quickly thawed and added to 10 mL of cell plating medium. Cells were stored in a 37 degree incubator under 5% $CO_2$ and left for approximately 48 hours until ready to run the assay 2. Compound Preparation 1) Reference agonist compound GLP1 (7-37): dissolved with DMSO to make 1 mM stock solutions, aliquoted and stored at −80° C.

2) Test compounds (such as the compounds of the present disclosure) came solubilized in 100% DMSO. Prepare 10× concentration of an agonist in serum free DMEM, and add all solutions into the compound plate. 2.5 μL of this solution was added to 20 μL cell medium in assay plate for a final top concentration of 10 μM. Plates were incubated at 37° C. under 5% $CO_2$ for 30 min. An additional 2.5 μL of Buffer was added to the entire plate for agonist mode and incubated at 37° C. for another 90 min.

3. Detection Reagents

Following 90 min incubation, detection reagents were made up as described. 12.5 μL was added to all wells. The plates were then incubated at room temperature in dark for 60 min. Plates were then read on Envision for 0.1 sec/well.

4. β-Arrestin Assay Data Processing

Data analysis: GraphPad Prism 6 was used for establishment of progression curve. $EC_{50}$s or IC50s were determined by 4-parameter logistic dose response equation.

The β-Arrestin recruitment dose-response curves for selected compounds of the present disclosure, as compared to GLP-1(7-37) as a control, were shown in FIG. 1. The tested compounds include Compounds 74-91, 93-95, 100, 101, 257, 263, 266, 267, 271, 276-278, 281, 284, 285, 289-293, 303, 305, 307, 308, 310-312, 323, and 331-334. Note that the partial maximum relative effect $B_{max}$ (at the highest concentration tested in the assays) for the tested compound generally approaches about 20-40% of the $B_{max}$ for the natural ligand GLP-1 (7-37).

β-Arrestin Recruitment as Measured by PathHunter CHO-K1-Based Assay

| Compound No. | β-arrestin recruitment $B_{max}$ (%) |
| --- | --- |
| 74 | 32.1 (n = 1) |
| 75 | 30.4 ± 1.15 (n = 2) |
| 76 | 25.1 (n = 1) |
| 77 | 39.4 (n = 1) |
| 78 | 22.7 (n = 1) |
| 79 | 19.7 (n = 1) |
| 80 | 31.6 (n = 1) |
| 81 | 37.2 (n = 1) |
| 82 | 20.1 (n = 1) |
| 83 | 44.6 (n = 1) |
| 84 | 33.5 (n = 1) |
| 85 | 37.0 (n = 1) |
| 86 | 33.5 (n = 1) |
| 87 | 33.1 (n = 1) |
| 88 | 44.6 (n = 1) |
| 89 | 25.3 (n = 1) |
| 90 | 29.5 ± 3.21 (n = 2) |
| 91 | 35.8 (n = 1) |
| 93 | 41.7 (n = 1) |
| 94 | 33.3 (n = 1) |
| 95 | 29.0 (n = 1) |
| 100 | 0.971 (n = 1) |
| 101 | 1.05 (n = 1) |
| 102 | 28.3 (n = 1) |
| — | — |
| — | — |
| — | — |
| — | — |
| 257 | 31.4 (n = 1) |
| 262 | 47.3 ± 4.55 (n = 3) |
| 263 | 18.9 (n = 1) |
| 266 | 26.7 ± 4.76 (n = 2) |
| 267 | 41.7 ± 3.45 (n = 3) |
| 271 | 28.5 (n = 1) |
| 276 | 35.6 ± 3.90 (n = 2) |
| 277 | 39.3 ± 4.96 (n = 3) |
| 278 | 36.2 ± 5.56 (n = 2) |
| 281 | 48.5 ± 6.64 (n = 2) |
| 284 | 25.5 (n = 1) |
| 285 | 24.0 (n = 1) |
| 289 | 29.6 (n = 1) |
| 290 | 39.9 ± 4.40 (n = 2) |
| 291 | 29.4 ± 6.84 (n = 2) |
| 292 | 42.2 ± 2.68 (n = 2) |
| 293 | 32.0 (n = 1) |
| 303 | 39.2 ± 4.75 (n = 2) |
| 305 | 31.8 (n = 1) |

-continued

| Compound No. | β-arrestin recruitment $B_{max}$ (%) |
|---|---|
| 307 | 46.8 ± 7.21 (n = 3) |
| 308 | 62.8 ± 4.09 (n = 3) |
| 310 | 37.8 (n = 1) |
| 311 | 38.8 ± 7.09 (n = 3) |
| 312 | 33.4 ± 2.13 (n = 2) |
| 323 | 19.4 (n = 1) |
| 331 | 17.9 (n = 1) |
| 332 | 14.5 (n = 1) |
| 333 | 9.75 (n = 1) |
| 334 | 26.6 (n = 1) |

Note that in these tested compounds of the present disclosure, with few exceptions, the partial maximum relative effect $B_{max}$ (at the highest concentration tested in the assays) for the tested compounds generally fall within about 10% to about 40% of the $B_{max}$ for the natural ligand GLP-1 (7-37). See $B_{max}$ values in the table above.

A similar assay can also be used to assess the extent of signal attenuation due to GLP-1R internalization (the Internalization Assay). In this assay, activated GLP1R Internalization cells were engineered to co-express an untagged GLP1R, Enzyme Acceptor (EA) tagged β-Arrestin, and a ProLink™ (PK) tag localized to the endosomes. Activation of the GLP1R induces β-Arrestin recruitment, which leads to internalization of the Receptor/Arrestin-EA complex in PK-tagged endosomes. This forces complementation of the two β-galactosidase enzyme fragments (EA and PK) to form a functional enzyme that hydrolyzes substrate to generate a chemiluminescent signal. These cells have been modified to prevent long term propagation and expansion using a proprietary compound that has no apparent effect on assay performance.

Specifically, PathHunter engineered U2OS cells from the assay kit (Cat #93-0724E3CP0L) were plated at a density of 2000 cells/20 μL/well in a 384-well white/clear bottom plates (Greiner Cat #781098). Frozen cells were quickly thawed and 10 mL of cell plating medium (provided by the kit) was added to thawed cells. Cells were stored in a 37° C. incubator and kept for approximately 48 hours until ready for the assay.

Reference and test compounds were dissolved in 100% DMSO. 5× concentration of an agonist was prepared in serum free DMEM (Thermo Cat #11965). 5 μL of this solution was added to 20 μL cell medium in assay plate for a final top concentration of 10 μM. Plates were incubated at 37° C. for 180 min.

Following 180 min incubation, detection reagents were made up by combining 1 part Galacton Star Substrate with 5 parts Emerald II™ Solution, and 19 parts of PathHunter Cell Assay Buffer, respectively. 12.5 μL detection reagent was added to each well. The plates were then incubated at room temperature for 60 min. Plates were then read on Envision for 0.1 sec/well.

$EC_{50}$ determinations were made from agonist dose-response curves analyzed with a curve fitting program using a 4-parameter logistic dose response equation.

Figure 2:
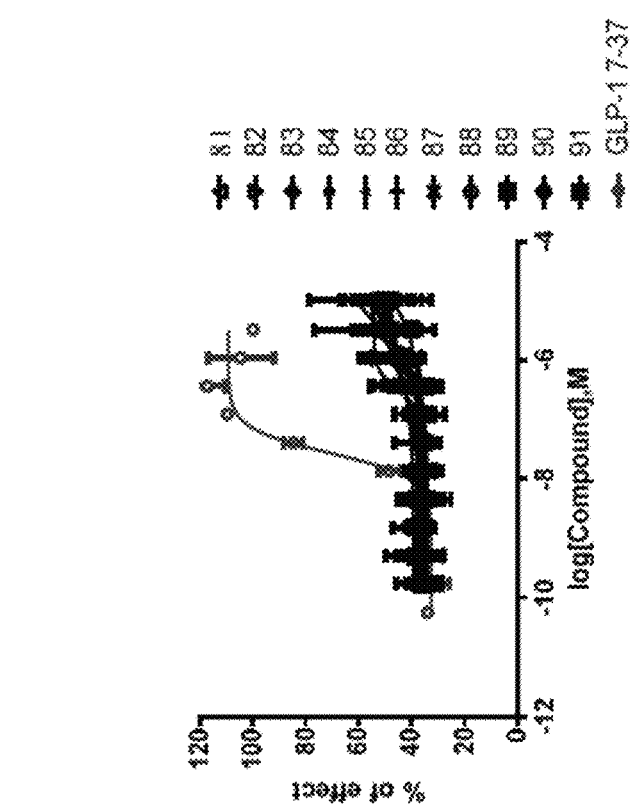
FIG. 2 shows dose-response curves for the GLP-1R/β-Arrestin internalization assay using certain compounds of the present disclosure and GLP-1 (7-37) as control. The vertical axis represents relative effects of the test compounds normalized to percentage of effect by the natural ligand GLP-1 (7-37). The two panels in FIG. 2 compare Compounds 74-80, 93-95, 100, and 101 (left panel), and Compounds 81-91 (right panel), respectively, to GLP-1 (7-37).
Figure 2:
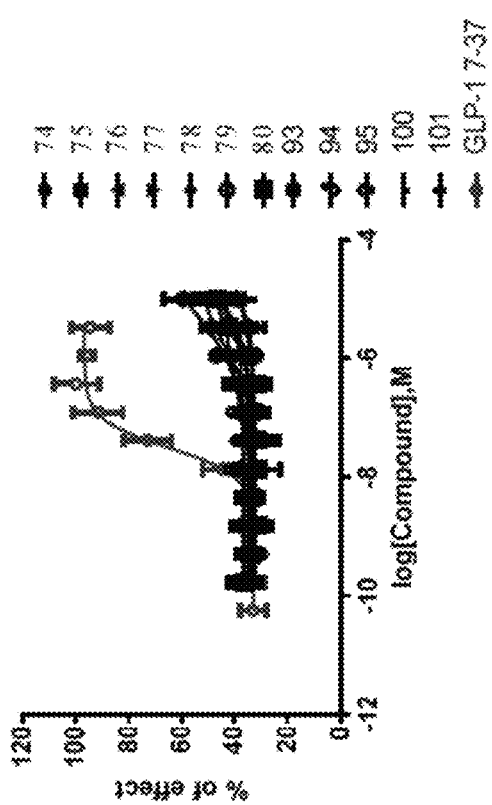

The GLP-1R internalization dose-response curves for selected compounds of the present disclosure, as compared to GLP-1 (7-37) as a control, were shown in FIG. 2. The tested compounds include Compounds 74-80, 93-95,100, and 101 (left panel), and Compounds 81-91 (right panel). Again, the partial maximum relative effect $B_{max}$ (at the highest concentration tested in the assays) for the tested compound generally approaches about 20-30% of the $B_{max}$ for the natural ligand GLP-1 (7-37).

Using this assay system, β-Arrestin-mediated GLP1R internalization was also measured for other selected compounds of the present disclosure, and the results are compiled in the table below.

β-Arrestin Internalization as Measured by PathHunter U2OS Cell-Based Assay

| Compound No. | β-arrestin internalization ~~recruitment~~ $B_{max}$ (POC)* |
|---|---|
| 74 | 17.0 (n = 1) |
| 75 | 20.8 ± 10.2 (n = 2) |
| 76 | 21.6 (n = 1) |
| 77 | 22.5 (n = 1) |
| 78 | 7.49 (n = 1) |
| 79 | 9.25 (n = 1) |
| 80 | 21.2 (n = 1) |
| 81 | 30.6 (n = 1) |
| 82 | 13.8 (n = 1) |
| 83 | 27.8 (n = 1) |
| 84 | 24.7 (n = 1) |
| 85 | 29.5 (n = 1) |
| 86 | 41.8 (n = 1) |
| 87 | 23.9 (n = 1) |
| 88 | 29.2 (n = 1) |
| 89 | 20.0 (n = 1) |
| 90 | 21.6 (n = 1) |
| 91 | 21.6 (n = 1) |
| 93 | 41.0 (n = 1) |
| 94 | 27.3 ± 7.75 (n = 2) |
| 95 | 23.1 (n = 1) |
| 100 | 0.881 (n = 1) |
| 101 | 3.08 (n = 1) |
| 247 | 26.6 (n = 1) |
| 262 | 25.4 ± 1.39 (n = 2) |
| 266 | 19.9 ± 0.122 (n = 2) |
| 267 | 30.2 ± 6.53 (n = 2) |
| 276 | 26.7 (n = 1) |
| 277 | 23.0 (n = 1) |
| 278 | 36.5 (n = 1) |
| 281 | 36.5 (n = 1) |
| 290 | 21.6 ± 3.52 (n = 2) |
| 291 | 22.8 ± 0.142 (n = 2) |
| 292 | 29.6 (n = 1) |
| 303 | 28.4 (n = 1) |
| 307 | 33.8 ± 2.73 (n = 2) |
| 308 | 48.8 ± 6.11 (n = 2) |
| 311 | 26.7 ± 4.53 (n = 2) |
| 312 | 45.2 (n = 1) |

*This value stands for averaged $B_{max}$ where applicable (POC, or Percentage of Control).

Again, note that in each case, with few exceptions, the partial maximum relative effect $B_{max}$ (at the highest concentration tested in the assays) for the tested compounds generally fall within about 10% to about 40% of the $B_{max}$ for the natural ligand GLP-1 (7-37).

Biological Example 2: NanoBit GLP1R/β-Arrestin Interaction Assay for Demonstrating Small Molecule Compounds-Mediated GLP1R and β-Arrestin Interaction Activation GLP-1R-mediated interaction with β-Arrestin by agonist activity is determined with a cell-based functional assay, utilizing a NanoLuc® Binary Technology (NanoBiT) (Promega N2015) designed to detect GLP-1R and β-Arrestin interaction in a living cell. The method is a two-subunit system based on NanoLuc® luciferase that can be used for intracellular detection of protein: protein interactions (PPIs). The two subunits are known as the Large BiT (LgBiT; 17.6 kDa) and the Small BiT (SmBiT; 11 amino acids). These two subunits are fused to two proteins of interest, respectively. When both are expressed, the PPI brings the subunits into close proximity to form a functional enzyme that generates a bright, luminescent signal.

More specifically, the human GLP-1R coding sequence (NCBI Reference Sequence NM_002062) and β-Arrestin2 coding sequence (NCBI Reference Sequence NM_004313.3) were subcloned into transient expression vectors provided in the NanoBiT kit, such that GLP-1R-LgBiT and SmBiT-β-Arrestin2 fusions were generated. A total of 8 combinations were selected using HEK293T-based transfection with activation by the natural ligand GLP-1$_{7-37}$. The combination showed the highest assay window (GLP-1R-LgBiT and SmBiT-β-Arrestin2) was selected for testing the compounds of the present disclosure.

The NanoBit assay was performed as briefly described herein: HEK293T cells (7.5k cells/well) were seeded in 96-well culture plate (Corning Cat #3917) in DMEM (Thermo Cat #11965) with 10% FBS (Biosera Cat #FB-10581) that was heat inactivated, and 25 mM glucose. After 48 hours, cells were transfected with the GLP-1R-LgBiT and SmBiT-β-Arrestin2 constructs using Lipofectamine2000 (Thermo Cat #11668019) following the manufacturer's assay protocol. Briefly, plasmids encoding the GLP-1R-LgBiT and SmBiT-β-Arrestin2 fusions, and transfection reagent were diluted with Opti-MEM (Thermo Cat #31985-070). Then about 50 ng of GLP-1R-LgBiT and 50 ng of SmBiT-β-Arrestin2 plasmid constructs were mixed, and the resulting plasmids mixture was added into diluted transfection reagent. The ratio of plasmid (μg):Lipofectamine2000 (μl) was 1:10. The mixtures were then added into cells after 5 minutes' incubation at room temperature. About 48 hours after transfection, medium was replaced by 65 μl/well fresh Opti-MEM.

Nano-Glo® Live Cell Substrate was then diluted with Nano-Glo® LCS Dilution Buffer at 1:24 ratio. About 25 μl of Nano-Glo® Live Cell Reagent was added into each well. Varying concentrations of each subject compound to be tested (in DMSO) were diluted in Opti-MEM with 0.1% BSA (Sigma Cat #A7409) to make 10× stocks. About 10 μl compound stocks were added into each well using pipette. Luminescence was measured immediately by EnVision for 40, 60, or 120 repeats, with 0.25 seconds per well.

$EC_{50}$ determinations were made from agonist dose-response curves analyzed with a curve fitting program using a 4-parameter logistic dose response equation.

The effect of a small molecule compound, such as one of the instant present disclosure, on the GLP-1R/β-Arrestin interaction activation, or β-Arrestin recruitment, can be demonstrated and measured using the assay and commercial reagents described herein or equivalents thereof. The reagents and detailed experimental protocols used in this example are further described below.

Preparations
Reagents and Consumables:

| Reagent | Vendor | Catalog No. |
| --- | --- | --- |
| NanoBiT ® Protein:Protein Interaction System | Promega | N2015 |
| Opti-MEM ™ I Reduced Serum Medium | Thermo Fisher | 31985-070 |

-continued

| Reagent | Vendor | Catalog No. |
| --- | --- | --- |
| Lipofectamine ™ 2000 Transfection Reagent | Thermo Fisher | 11668019 |
| Human GLP-1-(7-36)-amide | MCE | HY-P0054A |
| 96 well plates, white | Corning | 3917 |
| DMEM | Thermo Fisher | 11965 |
| Fetal Bovine Serum | Biosera | FB-10581/500 |
| DMSO | Sigma | D2650 |

Instruments:

| Instrument | Vendor | Internal Code |
| --- | --- | --- |
| En Vision | PerkinElmer | HD-4HYSG2330 |

Preparation of the Nano-Glo® Live Cell Reagent:
1. Equilibrate Nano-Glo® LCS Dilution Buffer to ambient temperature if using for the first time.
2. Remove the Nano-Glo® Live Cell Substrate from storage and mix.
3. Prepare the desired amount of reconstituted Nano-Glo® Live Cell Reagent by combining 1 volume of Nano-Glo® Live Cell Substrate with 24 volumes of Nano-Glo® LCS Dilution Buffer (a 25-fold dilution), creating a 4× stock to mix with cell culture medium.

Procedures
Compound Preparation:
GLP-1 (7-36) is dissolved in 100% DMSO and the stock concentration is 1 mM.
HPE: 10 μM GLP-1 (7-36)
ZPE: 0.1% DMSO
For test compounds, dilute 1 mM stock to 100 μM using Opti-MEM containing 1% BSA, final top concentration is 10 μM, ¼ log (4-fold) dilution, 8-dilution points, duplicate samples for each dilution. The layout is similar to GLP-1 above.

Assay Procedure:
Cell Culture and Transfection:
1. Seed 7.5 k cells/well 293T cells in 96 well culture plate (Corning #3917) in the DMEM with 10% FBS (heat inactivated and 25 mM glucose).
2. After 48 hours, performance transfection according to protocol of Lipofectamine2000.
3. 50 ng Lg-Bit and 50 ng Sm-Bit/well, the ratio of plasmid (μg):Lipofectamine2000 (μl) is 1:10.
4. 48 hours later after transfection, medium was replaced by fresh 65 μL Opti-MEM/well.

Activation and Luminescence Measurement:
5. Prepare Nano-Glo® Live Cell Reagent, diluted Nano-Glo® Live Cell Substrate with Nano-Glo® LCS Dilution Buffer in 1:24 ratio.
6. Add 25 μL Nano-Glo® Live Cell Reagent into each well.
7. Add 10 μL 10% DMSO or 10×GLP-1 solutions or test compounds into each well.
8. Immediately measure luminescence for 40, 60, or 120 repeats, with 0.25 seconds/well.

Figure 3:
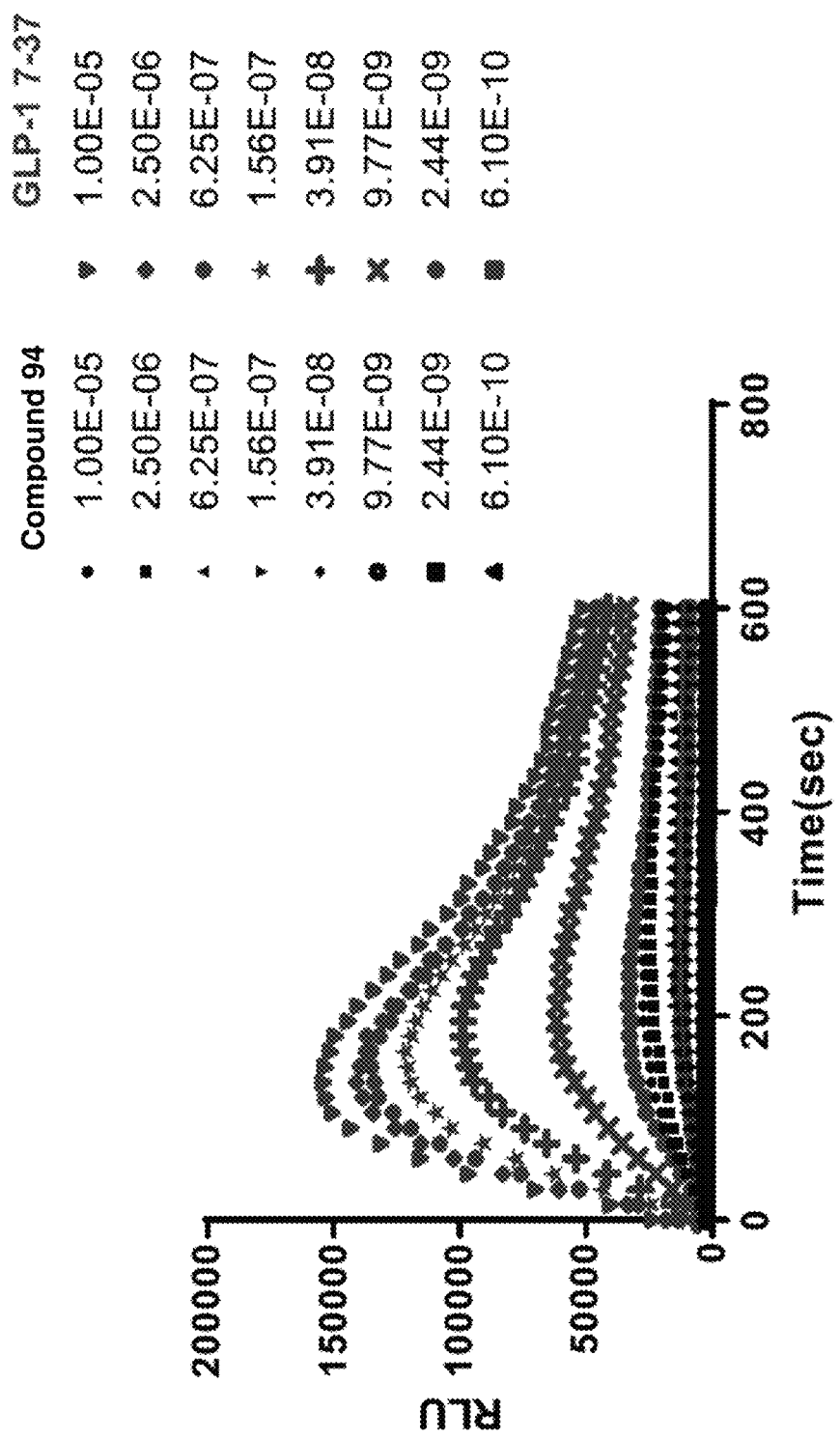
FIG. 3 shows NanoBit assay time course responses for both GLP-1 (7-37) and Compound 94 at different compound concentrations.

As shown in FIG. 3, the NanoBit assay time-course responses at different compound concentrations are plotted for GLP-1 (7-37) and Compound 94 (FIG. 3).

The results clearly show that the time-course profiles are quite different between the natural ligand GLP-1 (7-37) and the tested compounds of the present disclosure.

Figure 4:
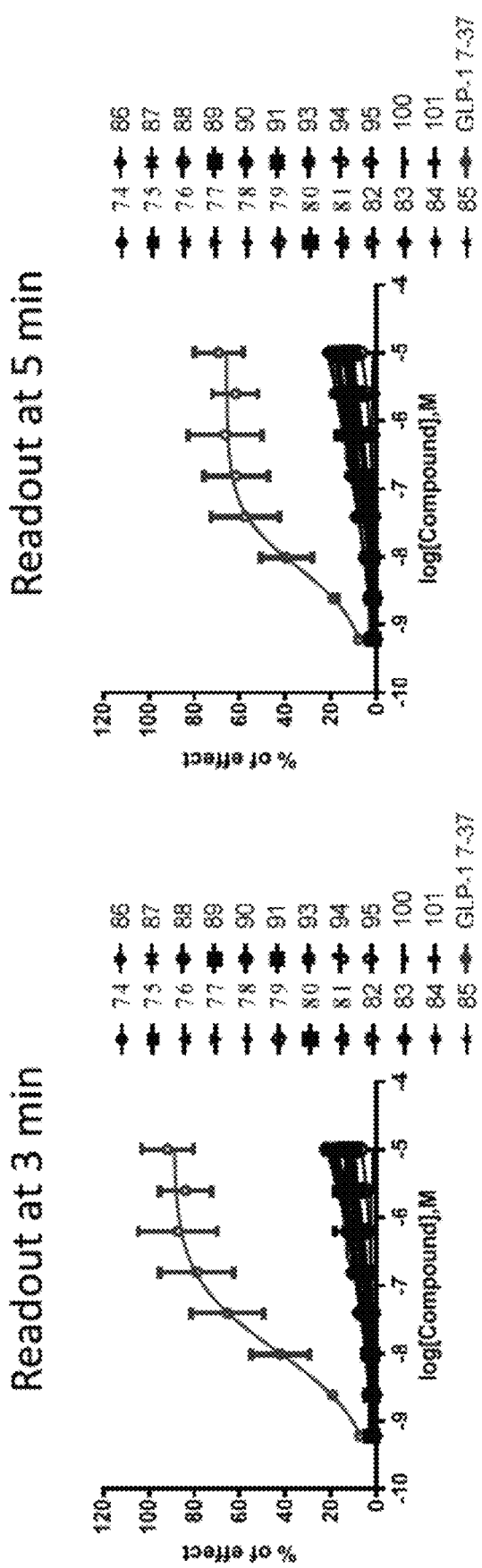
FIG. 4 shows dose-response curves for the GLP-1R/β-Arrestin NanoBit assay using certain compounds of the present disclosure and GLP-1 (7-37) as control. The vertical axis represents relative effects of the test compounds normalized to percentage of effect by the natural ligand GLP-1 (7-37). The two panels in FIG. 4 compare Compounds 74-91, 93-95, 100, and 101 to GLP-1 (7-37), at 3 min. and 5 min. readouts, respectively.

NanoBit assay dose response curves for the 3 min (180 sec) and 5 min (300 sec) time points were also generated for additional test compounds, including Compounds 74-91, 93-95, 100, and 101 (FIG. 4). In each of these figures, the maximum relative effects for the tested compounds $E_{max}$, for the highest concentrations tested, are generally no more than 40% (usually about 20-40%) of that of GLP-1 (7-37).

EC50 values for Compounds 74-91, 93-95, 100 and 101 were determined (data not shown).

As an alternative, data analysis/report to obtain EC50 values can be done when compounds reach maximal signals—such as at 450-500 sec (~8 min).

Biological Example 3 GLP1R cAMP Assay for Demonstrating Small Molecule Compounds-Mediated GLP-1R Activation HEK293/GLP-1R/CRE/Luc, Clone 4—cAMP Assay GLP-1R-mediated agonist activity was determined with a cell-based functional assay utilizing an HTRF (Homogeneous Time-Resolved Fluorescence) cAMP detection kit (cAMP Dynamic 2 Assay Kit; CisBio cat #62AM4PEC) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e., energy transfer) is inversely proportional to the concentration of cAMP in either standard or experimental sample.

The human GLP-1R coding sequence (NCBI Reference Sequence NM_002062) was subcloned into pcDNA3.1+/Hygro vector (Invitrogen) and transfected into HEK293/CRE/Luc parental cell line. A cell line stably expressing the receptor was isolated. Saturation binding analyses (filtration assay procedure) using $^{125}$I-GLP-1$_{7-36}$ (Perkin Elmer) shows that plasma membranes derived from this cell line express a high GLP-1R density ($K_d$: <1 nM, $B_{max}$: >800 fmol/mg protein).

Varying concentrations of each compound to be tested (in DMSO) were diluted in DMSO to obtain 200× compound working solution first and then 50 nl compounds were added to a white 384-well assay plate (Greiner 784075) with ECHO. The final DMSO concentration was 0.5%. The compound concentration range may be adjusted at any time.

Cells were removed from cryopreservation, re-suspended in 5 mL of Dulbecco's Phosphate Buffered Saline (DPBS-Sigma Cat #D8537) and centrifuged at 900×g for 5 min at 22° C. The cell pellet was then re-suspended in 1 mL of assay buffer [DPBS with 500 μM IBMX (Sigma #15879) and 0.1% BSA (Sigma #A1933). IBMX and BSA were freshly added on the day of assay]. A 10 μL sample of the cell suspension was counted on an Invitrogen Countess II to determine cell viability and cell count per mL. The remaining cell suspension was then adjusted with assay buffer to deliver 1000 viable cells per well using a Matrix Combi Multidrop reagent dispenser. 10 μL cell suspensions were added to each well of the assay plate which already contains compound. The plate was sealed and incubated at 37° C. with 5% $CO_2$ for 30 minutes.

Following the 30 minute incubation, 5 μL of labeled d2 cAMP and 5 μL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-1$_{7-37}$ (10 nM) included on each plate. EC$_{50}$ determinations were made from agonist dose-response curves analyzed with a curve fitting program using a 4-parameter logistic dose response equation.

This assay demonstrates that the compounds of the present disclosure activates GLP-1R signaling through the cAMP pathway, thus behave as GLP-1R agonists. The representative commercial reagents/kits that can be (were) used in such assays are described below.

Preparations

Reagents and Consumables:

| Reagent | Vendor | Catalog No. |
| --- | --- | --- |
| HEK/GLP1R/CRE/Luc cell line | HDB | |
| DMEM | Gibco | 12100 |
| Exendin (9-39) | MCE | HY-P0264 |
| Human GLP-1-(7-37)-amide | MCE | HY-P0055 |
| 384 well plates, white | Greiner | 784075 |
| cAMP dynamic 2 | Cisbio | 62AM4PEC |
| Fetal Bovine Serum | Biosera | FB-10581/500 |
| IBMX | Sigma | 15879 |
| BSA | Sigma | A1933-5G |
| DPBS | Sigma | D8537 |

Instruments:

| Instrument | Vendor | Internal Code |
| --- | --- | --- |
| EnVision | PerkinElmer | HD-4HYSG2330 |

Media and Solutions:
1) Assay Buffer
   DPBS with 500 μM IBMX and 0.1% BSA. IBMX and BSA are freshly added on the day of assay.
2) cAMP-d2 Working Solution Preparation
   a) The lyophilisate was reconstituted with an appropriate amount of distilled water according to manufacturer's instructions to make working stock which can be aliquoted and frozen (−20° C.).
   b) The working stock solution was diluted 1:20 in the conjugate and lysis buffer before use.
3) Anti-cAMP Antibody-Cryptate Working Solution Preparation
   c) The lyophilisate was reconstituted with appropriate amount of distilled water according to manufacturer's instruction to make working stock which can be aliquoted and frozen (−20° C.).
   d) The working stock solution was diluted 1:20 in the conjugate and lysis buffer before use.

Procedures

Procedures for Cell Suspension Preparation
1. Frozen cells were thawed very briefly in a 37° C. water bath under sterile conditions until just before ice completely melt (for about 1 minute) with a continuous agitation. Caution was taken because a longer incubation could result in cell death.
2. DMSO was removed from the media by carefully transferring thawed cells to a sterile 15/50 mL tube, filling a tube with 10-50 mL of complete media prewarmed to 37° C., and allowing the cells to sit 5 min before centrifuging at 900 rpm for 5 minutes for cell collection.
3. The cells were resuspended with assay buffer.
4. For stable GLP1-R assay, the optimized cell density is 1000 cells/well. Caution was taken because cell density optimization was crucial and needed to be optimized in different laboratories. The level of cAMP produced by the cells must fall within the linear range of the standard curve.

Procedures for Compound Preparation

1) Reference agonist compound GLP1 (7-37) was dissolved with DMSO to make a 1 mM stock solution, which was then aliquoted and stored at −80° C.
2) Reference antagonist compound Exendin (9-39) was dissolved with DMSO to make a 2 mM stock solution, which was then aliquoted and stored at −80° C.
3) Test compounds were dissolved with DMSO to make stock solutions, aliquoted and stored at −80° C. Serial dilutions of compound solutions were made using DMSO to obtain a 200× compound working solution first and then 50 nL of the working solution to 384-well plate with ECHO. The final DMSO concentration is 0.5%. The compound concentration range may be adjusted at any time.
4) IBMX: 500 mM stock solution dissolved in DMSO, aliquot and stored at −20° C.

Procedures for Agonist Assay

1) Compound preparation: compound addition plates were prepared in advance of the assay. 200× compound working solutions were prepared according to procedures described above.
2) Cell preparation: cell suspensions were prepared according to procedures described above before running the assay.
3) Compound addition: 50 nL/well of 200× compound working solutions were added to low-volume 384 white assay plate with Echo.
4) Cell addition: 10 μL cell suspensions were added to each well of the assay plate which already contained the compound working solution. The plate was sealed and incubated at 37° C. with 5% $CO_2$ for 30 minutes.
5) 5 μL of a cAMP-d2 working solution was added to each well of the assay plate.
6) 5 μL of an anti-cAMP antibody-cryptate working solution was added to each well of the assay plate. The plate was covered with a lid. Incubate at room temperature for 1 hours.
7) The fluorescence was read at 665 and 615 nm with an EnVision plate reader with TRF LASER using the specified settings and the data was saved.

Procedures for Antagonist Blocking Assay

1) Compound preparation: prepare compound addition plates in advance of assay. Prepare 200× concentration of compound working solutions according to procedures described above.
2) Cell preparation: cell suspensions are prepared according to procedures described above before running the assay.
3) Compound addition: add 50 nL/well of working concentration of 200× compound to low-volume 384 white assay plate.
4) Cell addition: Add 5 μL of 2× cell suspensions to each well of the assay plate which already contains compound.
5) Exendin (9-39) Antagonist addition: Add 5 μL of 2× Exendin (9-39) to each well of the assay plate which already contains compound and cells. The final concentration of Exendin (9-39) is IC80. Seal the plate and incubate at 37° C. with 5% CO2 for 30 minutes.
6) Add 5 μL cAMP-d2 working solution to each well of the assay plate.
7) Add 5 μL Anti-cAMP antibody-cryptate working solution to each well of the assay plate. Cover the plate with lid. Incubate at room temperature for 1-4 hours.
8) Read the fluorescence at 665 and 615 nm with EnVision plate reader with TRF LASER using the specified settings and save data.

Setting Up EnVision for HTRF cAMP Measurements

Required Filters and Mirrors

Excitation: TRF LASER
Emission #1: 665 nm (CWL 665 nm BW 7.5 nm)
Emission #2: 615 nm (CWL 615 nm BW 8.5 nm)
Dichroic mirror: DELFIA/LANCE Dual Enh D400/D630

Required Settings:

Delay: 50 μs
Window Time: 300 μs (also called "integration time")
Number of sequence windows: 1
Cycle: Default 2000 μs (also called "time between flashes")
Time between flashes: 2000 μs
number of flashes: 20
number of flashes for 2nd detector: 10
measurement height (mm): 6.5
Z height: Must be optimized (use optimization Wizard, optimize on a well with maximum FRET)
Excitation and Emissions are done on the top of the well cAMP Assay Data Processing Data analysis: GraphPad Prism 5 or IDBS XLfit software is used for establishment of progression curve. $EC_{50}$s or $IC_{50}$s were determined by 4-parameter logistic dose response equation.

Using the assay substantially as described above, dose-response curve for each compound tested below were obtained, and their respective $EC_{50}$ values calculated and tabulated. Here, $EC_{50}$ value for each compound is defined as the compound concentration that yielded 50% of the maximum cAMP level achieved with the same compound.

Final compound concentration is 10, 100, or 300 nM in 0.5% DMSO. A total of 11 data points were generated for each compound serial dilution.

Figure 5:
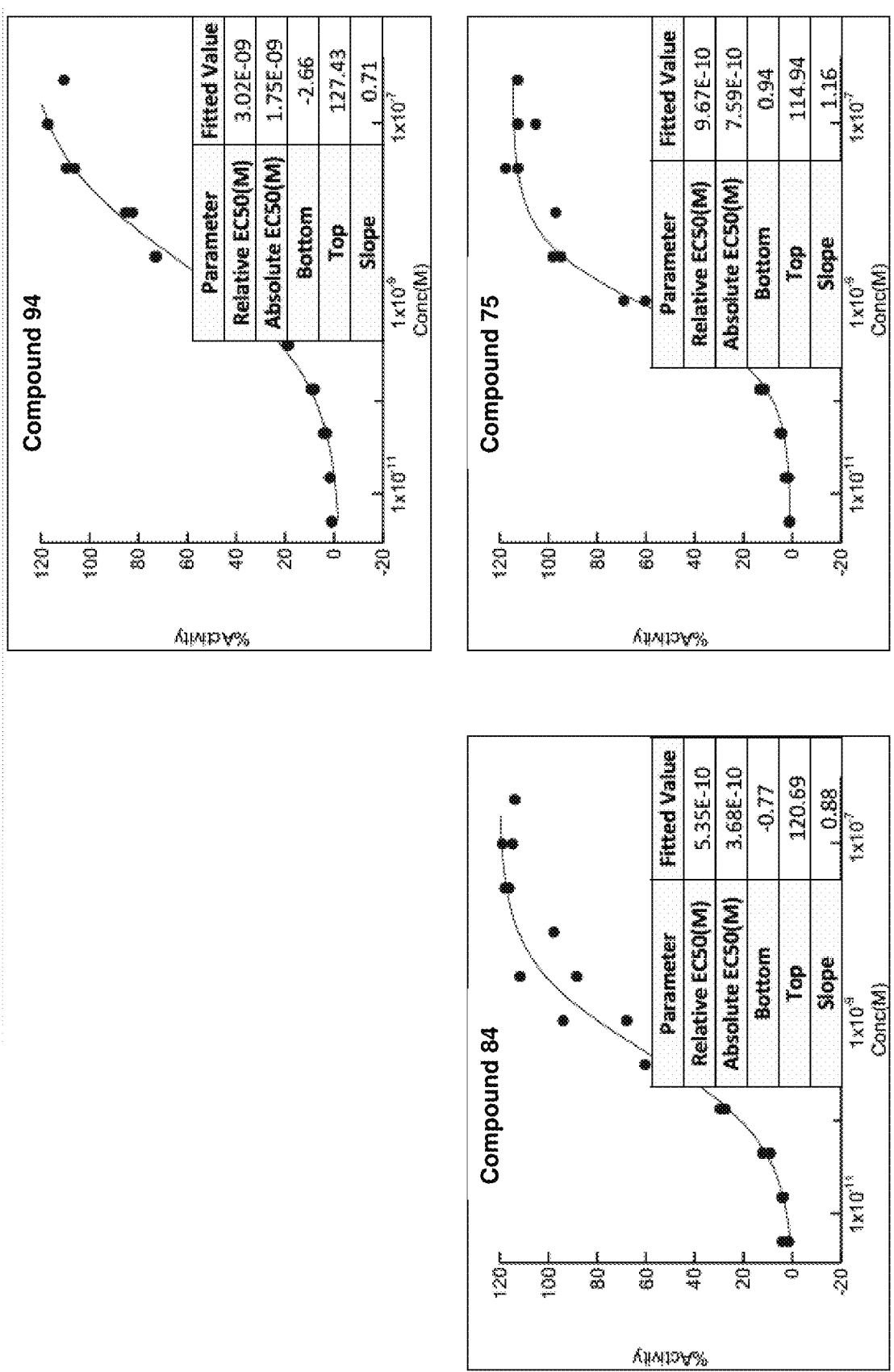
FIG. 5 shows cAMP assay results using a monkey GLP-1R, for selected compounds of the present disclosure (i.e., Compounds 75, 84, 93, and 94) and GLP-1(7-37) as control.
Figure 5:
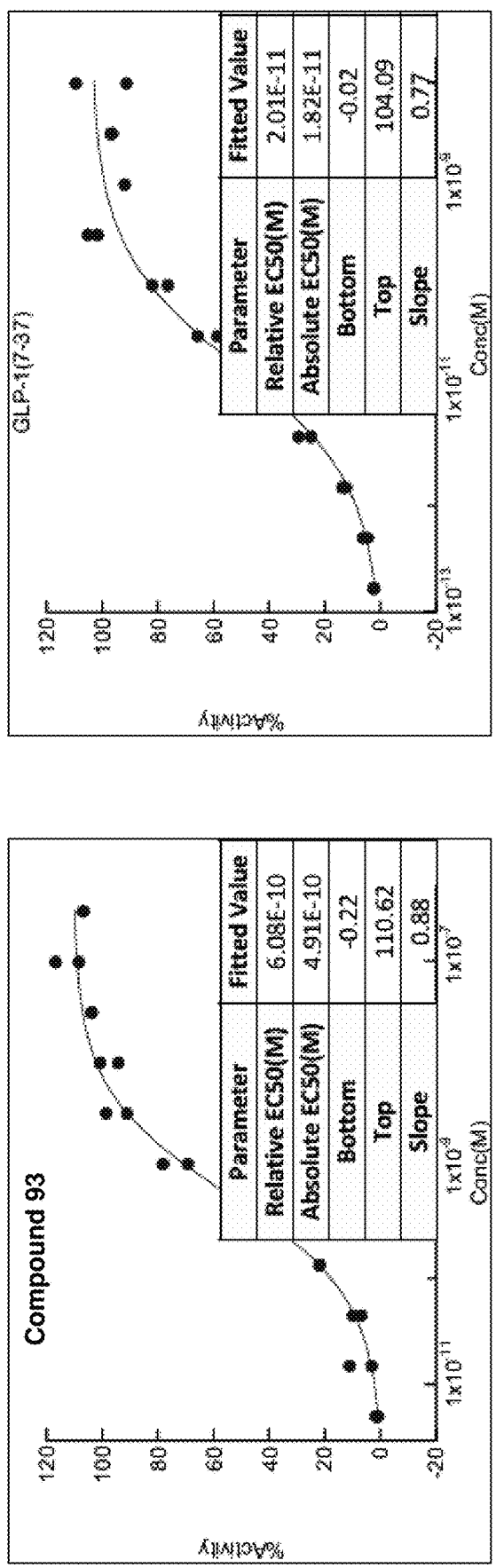

The cAMP assay results for Compounds 75, 84, 93, 94, and GLP-1(7-37) as control, are shown in FIG. 5.

Two different cell types were used for this assay. In one assay, each compound was tested in HEK293T cells. The results are shown below in Table 1. In another assay, selected compounds were also tested in CHO cells that have been stably transfected to express human GLP-1R. The results are shown below in Table 2.

TABLE 1

| Compound # | $EC_{50}$ Values in HEK293T Cells |
|---|---|
| | $EC_{50}$ |
| | A = ≤0.015 μM |
| | B = ≤0.15 μM |
| | C = ≤1 μM |
| | D = >1 μM |
| 74 | A |
| 75 | A |
| 76 | A |
| 77 | A |
| 78 | A |
| 79 | B |

TABLE 1-continued

Compound EC$_{50}$ Values in HEK293T Cells

| Compound # | EC$_{50}$<br>A = ≤0.015 μM<br>B = ≤0.15 μM<br>C = ≤1 μM<br>D = >1 μM |
|---|---|
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | D |
| 101 | D |
| 102 | A |
| 246 | B |
| 247 | A |
| 248 | D |
| 249 | B |
| 250 | B |
| 251 | B |
| 252 | B |
| 253 | B |
| 254 | B |
| 255 | B |
| 256 | B |
| 257 | A |
| 258 | A |
| 259 | A |
| 260 | A |
| 261 | A |
| 262 | A |
| 263 | A |
| 264 | A |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | A |
| 277 | A |
| 278 | A |
| 279 | A |
| 280 | A |
| 281 | A |
| 282 | A |
| 283 | A |
| 284 | A |
| 285 | A |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | B |
| 303 | A |
| 304 | A |
| 305 | A |
| 306 | A |

TABLE 1-continued

Compound $EC_{50}$ Values in HEK293T Cells

| Compound # | $EC_{50}$<br>A = ≤0.015 μM<br>B = ≤0.15 μM<br>C = ≤1 μM<br>D = >1 μM |
|---|---|
| 307 | A |
| 308 | A |
| 309 | A |
| 310 | A |
| 311 | A |
| 312 | A |
| 313 | A |
| 314 | B |
| 315 | C |
| 316 | B |
| 317 | A |
| 318 | B |
| 319 | B |
| 320 | B |
| 321 | B |
| 322 | A |
| 323 | A |
| 324 | B |
| 325 | B |
| 326 | B |
| 327 | B |
| 328 | B |
| 329 | B |
| 330 | A |
| 331 | A |
| 332 | A |
| 333 | B |
| 334 | A |

TABLE 2

Compound $EC_{50}$ Values in CHO Cells Stably Expressing hGLP-1R

| Compound # | CHO cAMP stable $EC_{50}$<br>A = ≤0.015 μM<br>B = ≤0.15 μM<br>C = ≤1 μM<br>D = >1 μM | Compound # | CHO cAMP stable $EC_{50}$<br>A = ≤0.015 μM<br>B = ≤0.15 μM<br>C = ≤1 μM<br>D = >1 μM |
|---|---|---|---|
| 84 | A | 93 | A |
| 263 | A | 266 | A |
| 272 | B | 276 | A |
| 278 | A | 279 | A |
| 280 | B | 287 | B |
| 288 | B | 292 | A |
| 294 | B | 296 | A |
| 298 | B | 300 | B |
| 301 | B | 303 | A |
| 310 | A | 311 | A |
| 312 | A | 322 | B |
| 326 | D | | |

The data shows that, similar to GLP-1(7-37), many tested compounds have nanomolar or sub-nanomolar (<10 nM) $EC_{50}$ values in the cAMP assay. This, coupled with the fact that many tested compounds also have $B_{max}$ values reaching substantially the same level of that for GLP-1(7-37), suggests that many of the tested compounds of the present disclosure are full agonists of the GLP-1R signaling leading to cAMP production.

In contrast, as shown in Examples 1 and 2 above, particularly the data for the compounds listed in the tables, the compounds of the present disclosure generally have $B_{max}$ approaching about 20-40% of that of GLP-1 (7-37) in the β-Arrestin recruitment assay and GLP-1R internalization assay, though a few exceptions exist. Further, the NanoBit time course profiles are different between the compounds of the present disclosure and those of GLP-1(7-37).

Example 4 Compound Synthesis (S)-2-(4-(6-((4-chloro-2-fluorobenzyl)oxy)pyridin-2-yl)-3-fluorobenzyl)-1-(oxetan-2-ylmethyl)-1H-benzo[d]imidazole-6-carboxylic acid (Compound 74)

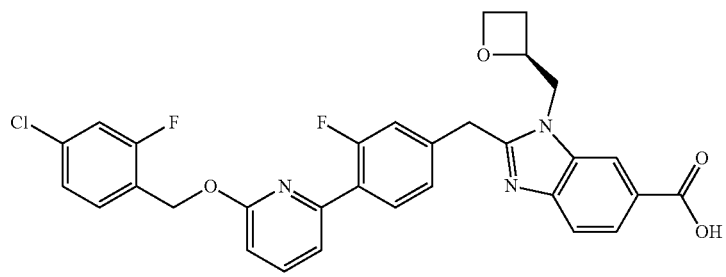 [SMILES: O=C(O)c1ccc2nc(Cc3ccc(-c4cccc(OCc5ccc(Cl)cc5F)n4)c(F)c3)n(C[C@@H]3CCO3)c2c1]

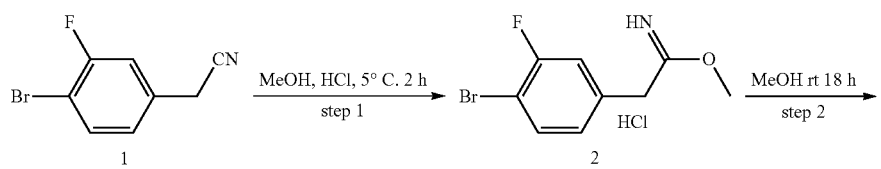

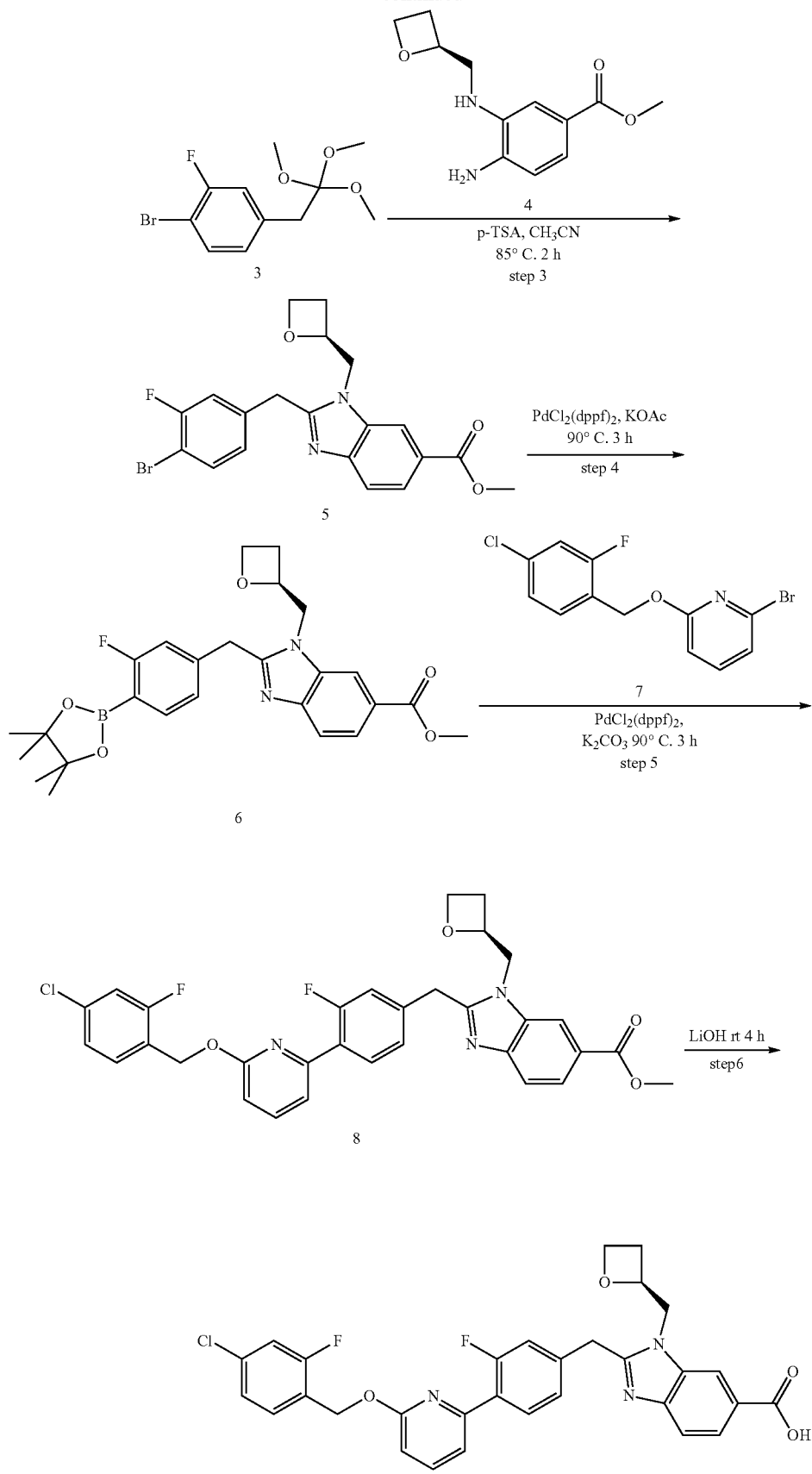

Step 1. Synthesis of methyl 2-(4-bromo-3-fluorophenyl)acetimidate

To a mixture of 1 2-(4-bromo-3-fluoro-phenyl)acetonitrile (4.24 g, 19.8 mmol), methanol (600 mg, 19.8 mmol) and 1,4-dioxane (20 mL) in a Schlenk tube was bubbled HCl gas, until the completion of the reaction. The reaction mixture was filtered to afford the title compound methyl 2-(4-bromo-3-fluorophenyl)acetimidate (2) (4.2 g, 17.1 mmol, 86.2% yield) as a white solid.

Step 2. Synthesis of 1-bromo-2-fluoro-4-(2,2,2-trimethoxyethyl)benzene

A mixture of 2 from above (2.1 g, 8.53 mmol) in methanol (20 mL) was stirred for 18 h in a Schlenk tube under an atmosphere of $N_2$. The reaction was monitored by TLC and LCMS. The reaction mixture was concentrated in vacuo, and then EtOAc was added to reaction mixture until large quantities of solid precipitated out. The solid was filtered out, the filtrate was concentrated to afford the title compound 1-bromo-2-fluoro-4-(2,2,2-trimethoxyethyl) benzene as a crude product (3) (1.8 g, 6.14 mmol, 72% yield) as a colorless oil.

Step 3. Synthesis of methyl (S)-2-(4-bromo-3-fluorobenzyl)-1-(oxetan-2-ylmethyl)-1H-benzo[d]imidazole-6-carboxylate A mixture of 3 from above (297.8 mg, 1.02 mmol), p-TSA (100 mg, 0.63 mmol) and methyl 4-amino-3-[[(2S)-oxetan-2-yl]methylamino]benzoate 4 (150 mg, 0.63 mmol) in acetonitrile (15 mL) was stirred for 2 h in a Schlenk tube under an atmosphere of $N_2$ and then moved to an oil bath at 85° C. and stirred for 3 h, until the reaction was completed as indicated by TLC. The reaction mixture was concentrated in vacuo, purified by SGC (hexanes/EtOAc=5:1-1:1) to give the title compound methyl (S)-2-(4-bromo-3-fluorobenzyl)-1-(oxetan-2-ylmethyl)-1H-benzo[d]imidazole-6-carboxylate (5) (180 mg, 0.42 mmol, 65.4% yield) as a yellow solid.

Step 4. Synthesis of methyl (S)-2-(3-fluoro-4-(4,4,5,5-tetramethyl-1,3,2-dioxaborolan-2-yl)benzyl)-1-(oxetan-2-ylmethyl)-1H-benzo[d]imidazole-6-carboxylate A mixture of 5 from above (220 mg, 0.51 mmol), 4,4,5,5-tetramethyl-2-(4,4,5,5-tetramethyl-1,3,2-dioxaborolan-2-yl)-1,3,2-dioxaborolane (154.7 mg, 0.61 mmol) and KOAc (124.6 mg, 1.27 mmol) and Pd(dppf)Cl$_2$ (37.2 mg, 0.051 mmol) in 1,4-dioxane (5 mL) in a Schlenk tube under an atmosphere of $N_2$. The reaction tube was sealed, moved to an oil bath at 90° C. and stirred for 3 h, the reaction was complete as indicated by TLC and LCMS. The reaction mixture was filtered and the solution of crude product methyl (S)-2-(3-fluoro-4-(4,4,5,5-tetramethyl-1,3,2-dioxaborolan-2-yl)benzyl)-1-(oxetan-2-ylmethyl)-1H-benzo[d]imidazole-6-carboxylate (6) (280 mg, 0.41 mmol, 80.4% yield, 70% purity) was used to next step. LCMS: [M+H]$^+$=480.0.

Step 5. Synthesis of methyl (S)-2-(4-(6-((4-chloro-2-fluorobenzyl)oxy)pyridin-2-yl)-3-fluorobenzyl)-1-(oxetan-2-ylmethyl)-1H-benzo[d]imidazole-6-carboxylate A mixture of 7 (30 mg, 0.095 mmol), Pd(dppf)Cl$_2$ (7.7 mg, 0.0095 mmol) and K$_2$CO$_3$ (39.3 mg, 0.28 mmol) and crude product of 6 from above (68.3 mg, 0.14 mmol) in 1,4-dioxane (3 mL) and water (1 mL) was stirred for 3 h in a Schlenk tube under an atmosphere of $N_2$. The reaction tube was sealed, moved to an oil bath at 100° C. and stirred for 3 h, the reaction was complete as indicated by TLC and LCMS. The reaction mixture was filtered and crude product was purification by TLC to give the title compound methyl (S)-2-(4-(6-((4-chloro-2-fluorobenzyl)oxy)pyridin-2-yl)-3-fluorobenzyl)-1-(oxetan-2-ylmethyl)-1H-benzo[d]imidazole-6-carboxylate (8) (9 mg, 0.015 mmol, 17.9% yield). LCMS: [M+H]$^+$=590.1.

Step 6. Synthesis of (S)-2-(4-(6-((4-chloro-2-fluorobenzyl)oxy)pyridin-2-yl)-3-fluorobenzyl)-1-(oxetan-2-ylmethyl)-1H-benzo[d]imidazole-6-carboxylic acid A mixture of 8 from above (9 mg, 0.015 mmol), LiOH (3.7 mg, 0.15 mmol) in methanol (3 mL) was stirred for 3 h in a Schlenk tube under an atmosphere of $N_2$ at 25° C., the reaction as indicated by TLC and LCMS. The reaction mixture was adjusted with AcOH to pH=7.0. Then the crude product was purified by prep-HPLC to give the title compound (S)-2-(4-(6-((4-chloro-2-fluorobenzyl)oxy)pyridin-2-yl)-3-fluorobenzyl)-1-(oxetan-2-ylmethyl)-1H-benzo[d]imidazole-6-carboxylic acid (3.3 mg, 0.006 mmol, 37.6% yield, 100% purity) as a white solid. LCMS: [M+H]$^+$=576.1.

(S)-2-(4-(6-(4-cyano-2-fluorobenzyloxy)pyridin-2-yl)-3-fluorobenzyl)-1-(oxetan-2-ylmethyl)-1H-benzo[d]imidazole-6-carboxylic acid (Compound 75)

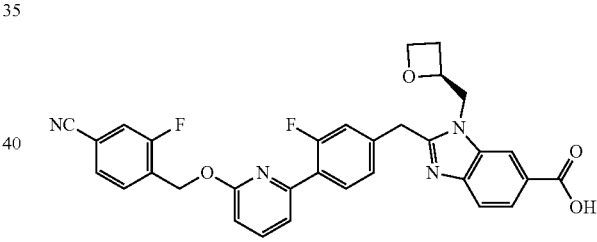

The title compound was prepared analogously as for Compound 74 as a white solid. LCMS: [M+H]$^+$=567.3.

(S)-2-((3'-((4-chloro-2-fluorobenzyl)oxy)-2-fluoro-[1,1'-biphenyl]-4-yl)methyl)-1-(oxetan-2-ylmethyl)-1H-benzo[d]imidazole-6-carboxylic acid (Compound 76)

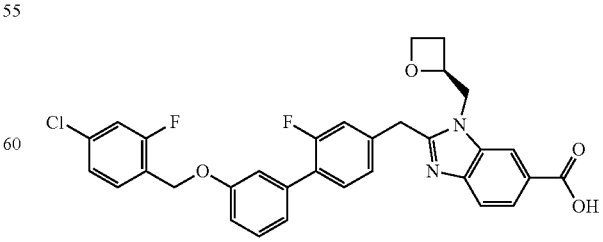

The title compound was prepared analogously as for Compound 74 as a white solid. LCMS [M+H]$^+$=575.2.

(S)-2-(4-(6-((4-chloro-2-fluorobenzyl)oxy)-3,5-difluoropyridin-2-yl)-3-fluorobenzyl)-1-(oxetan-2-ylmethyl)-1H-benzo[d]imidazole-6-carboxylic acid (Compound 77)

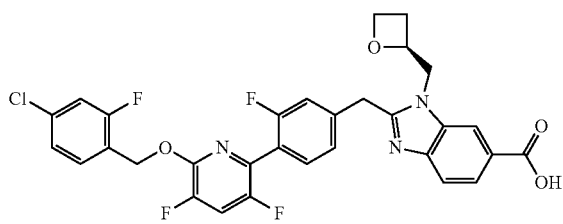 [SMILES: O=C(O)c1ccc2nc(Cc3ccc(-c4nc(OCc5ccc(Cl)cc5F)c(F)cc4F)c(F)c3)n(C[C@@H]3CCO3)c2c1]

The title compound was prepared analogously as for Compound 74 as a white solid. LCMS: [M+H]⁺=611.8.

(S)-2-((3'-((4-chloro-2-fluorobenzyl)oxy)-2,4'-difluoro-[1,1'-biphenyl]-4-yl)methyl)-1-(oxetan-2-ylmethyl)-1H-benzo[d]imidazole-6-carboxylic acid (Compound 78)

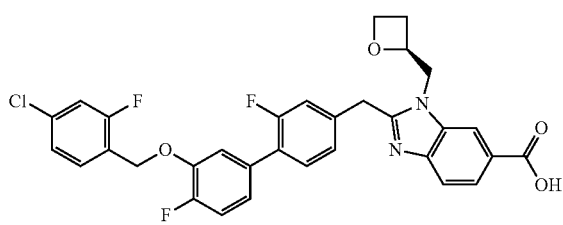 [SMILES: O=C(O)c1ccc2nc(Cc3ccc(-c4ccc(F)c(OCc5ccc(Cl)cc5F)c4)c(F)c3)n(C[C@@H]3CCO3)c2c1]

The title compound was prepared analogously as for Compound 74 as a white solid. LCMS: [M+H]⁺=593.1.

(S)-2-((5'-((4-chloro-2-fluorobenzyl)oxy)-2,2'-difluoro-[1,1'-biphenyl]-4-yl)methyl)-1-(oxetan-2-ylmethyl)-1H-benzo[d]imidazole-6-carboxylic acid (Compound 79)

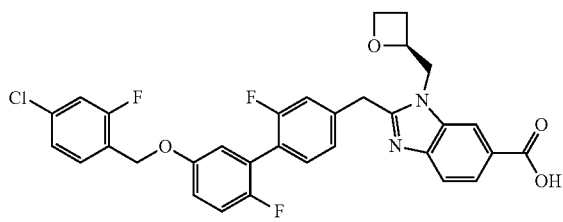 [SMILES: O=C(O)c1ccc2nc(Cc3ccc(-c4cc(OCc5ccc(Cl)cc5F)ccc4F)c(F)c3)n(C[C@@H]3CCO3)c2c1]

The title compound was prepared analogously as for Compound 74 as a white solid. LCMS: [M+H]⁺=593.0.

(S)-2-(4-(2-((4-chloro-2-fluorobenzyl)oxy)pyrimidin-4-yl)-3-fluorobenzyl)-1-(oxetan-2-ylmethyl)-1H-benzo[d]imidazole-6-carboxylic acid (Compound 80)

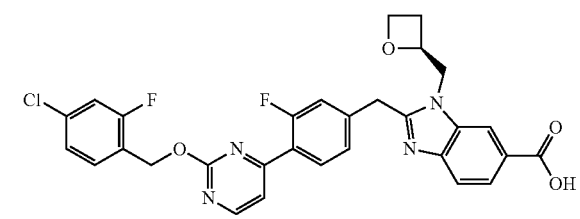 [SMILES: O=C(O)c1ccc2nc(Cc3ccc(-c4ccnc(OCc5ccc(Cl)cc5F)n4)c(F)c3)n(C[C@@H]3CCO3)c2c1]

The title compound was prepared analogously as for Compound 74 as a white solid. LCMS [M+H]⁺=576.1.

(S)-2-(4-(4-(4-chloro-2-fluorobenzyloxy)-5-fluoropyrimidin-2-yl)-3-fluorobenzyl)-1-(oxetan-2-ylmethyl)-1H-benzo[d]imidazole-6-carboxylic acid (Compound 81)

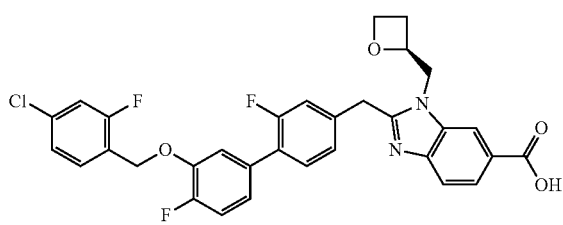 [SMILES: O=C(O)c1ccc2nc(Cc3ccc(-c4ccc(F)c(OCc5ccc(Cl)cc5F)c4)c(F)c3)n(C[C@@H]3CCO3)c2c1]

The title compound was prepared analogously as for Compound 74 as a white solid. LCMS: [M+H]⁺=594.9.

(S)-2-(4-(2-(4-chloro-2-fluorobenzyloxy)-5-fluoropyrimidin-4-yl)-3-fluorobenzyl)-1-(oxetan-2-ylmethyl)-1H-benzo[d]imidazole-6-carboxylic acid (Compound 82)

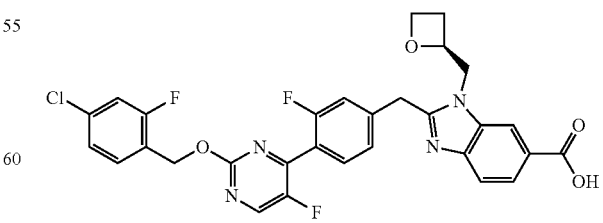

The title compound was prepared analogously as for Compound 74 as a white solid. LCMS [M+H]⁺=595.2.

(S)-2-(4-(6-((4-chloro-2-fluorobenzyl)oxy)-5-fluoro-pyridin-2-yl)-3-fluorobenzyl)-1-(oxetan-2-ylmethyl)-1H-benzo[d]imidazole-6-carboxylic acid (Compound 83)

(S)-2-(4-(4-((4-chloro-2-fluorobenzyl)oxy)pyrimidin-2-yl)-2-fluorobenzyl)-1-(oxetan-2-ylmethyl)-1H-benzo[d]imidazole-6-carboxylic acid (Compound 86)

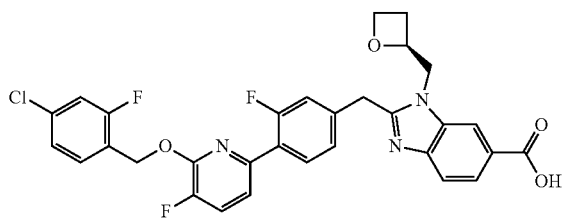 [SMILES: O=C(O)c1ccc2nc(Cc3ccc(-c4ccc(F)c(OCc5ccc(Cl)cc5F)n4)c(F)c3)n(C[C@@H]3CCO3)c2c1]

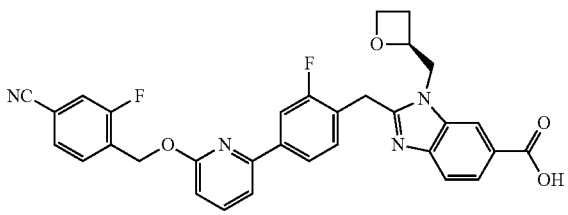

The title compound was prepared analogously as for Compound 74 as a white solid. LCMS: [M+H]$^+$=594.0.

The title compound was prepared analogously as for Compound 74 as a white solid. LCMS [M+H]$^+$=576.9.

(S)-2-(4-(6-((4-cyano-2-fluorobenzyl)oxy)pyridin-2-yl)-2-fluorobenzyl)-1-(oxetan-2-ylmethyl)-1H-benzo[d]imidazole-6-carboxylic acid (Compound 84)

(S)-2-(4-(2-((4-chloro-2-fluorobenzyl)oxy)pyrimidin-4-yl)-2-fluorobenzyl)-1-(oxetan-2-ylmethyl)-1H-benzo[d]imidazole-6-carboxylic acid (Compound 87)

The title compound was prepared analogously as for Compound 74 as a white solid. LCMS: [M+H]$^+$=567.0.

The title compound was prepared analogously as for Compound 74 as a white solid. LCMS [M+H]$^+$=576.9.

(S)-2-((3'-((4-chloro-2-fluorobenzyl)oxy)-3,4'-difluoro-[1,1'-biphenyl]-4-yl)methyl)-1-(oxetan-2-ylmethyl)-1H-benzo[d]imidazole-6-carboxylic acid) (Compound 85)

(S)-2-(4-(6-(4-chloro-2-fluorobenzyloxy)-5-fluoro-pyridin-2-yl)-2-fluorobenzyl)-1-(oxetan-2-ylmethyl)-1H-benzo[d]imidazole-6-carboxylic acid (Compound 88)

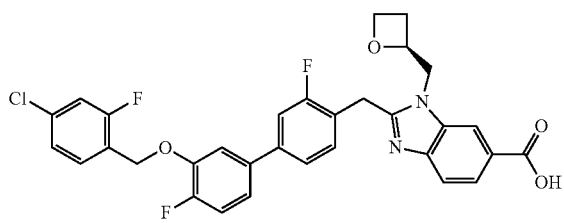 [SMILES: O=C(O)c1ccc2nc(Cc3ccc(-c4ccc(F)c(OCc5ccc(Cl)cc5F)c4)cc3F)n(C[C@@H]3CCO3)c2c1]

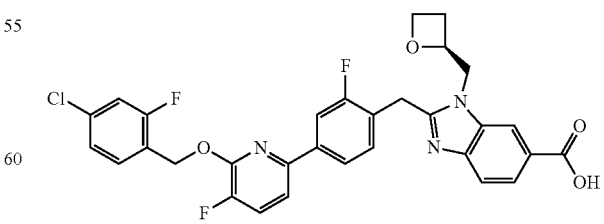

The title compound was prepared analogously as for Compound 74 as a white solid. LCMS: [M+H]$^+$=593.0.

The title compound was prepared analogously as for Compound 74 as a white solid. LCMS [M+H]$^+$=594.1.

(S)-2-((3'-((4-chloro-2-fluorobenzyl)oxy)-3-fluoro-[1,1'-biphenyl]-4-yl)methyl)-1-(oxetan-2-ylmethyl)-1H-benzo[d]imidazole-6-carboxylic acid (Compound 89)

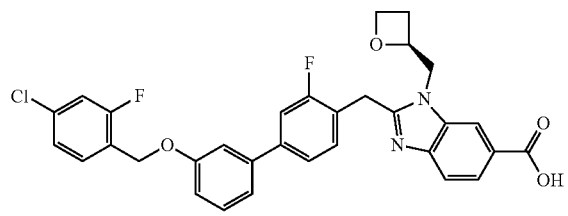 [SMILES: O=C(O)c1ccc2nc(Cc3ccc(-c4cccc(OCc5ccc(Cl)cc5F)c4)cc3F)n(C[C@@H]3CCO3)c2c1]

The title compound was prepared analogously as for Compound 74 as a white solid. LCMS: [M+H]$^+$=575.0.

(S)-2-(4-(4-((4-chloro-2-fluorobenzyl)oxy)-5-fluoro-pyrimidin-2-yl)-2-fluorobenzyl)-1-(oxetan-2-ylmethyl)-1H-benzo[d]imidazole-6-carboxylic acid (Compound 90)

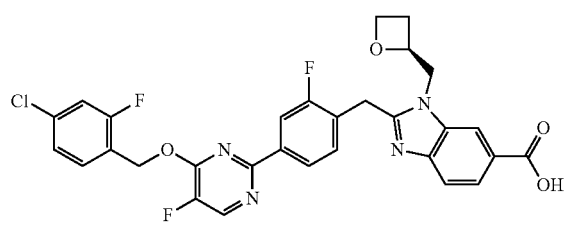 [SMILES: O=C(O)c1ccc2nc(Cc3ccc(-c4ncc(F)c(OCc5ccc(Cl)cc5F)n4)cc3F)n(C[C@@H]3CCO3)c2c1]

The title compound was prepared analogously as for Compound 74 as a white solid. LCMS [M+H]$^+$=594.9.

(S)-2-(4-(2-(4-chloro-2-fluorobenzyloxy)-5-fluoro-pyrimidin-4-yl)-2-fluorobenzyl)-1-(oxetan-2-ylmethyl)-1H-benzo[d]imidazole-6-carboxylic acid (Compound 91)

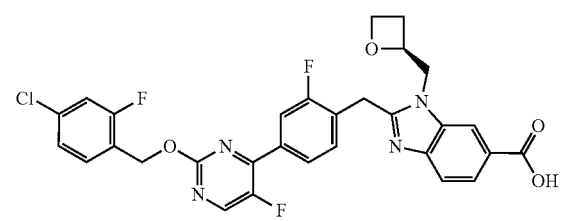 [SMILES: O=C(O)c1ccc2nc(Cc3ccc(-c4nc(OCc5ccc(Cl)cc5F)ncc4F)cc3F)n(C[C@@H]3CCO3)c2c1]

The title compound was prepared analogously as for Compound 74 as a white solid. LCMS: [M+H]$^+$=595.0.

(S)-2-(4-(6-((4-chloro-2-fluorobenzyl)oxy)-3-fluoro-pyridin-2-yl)-2-fluorobenzyl)-1-(oxetan-2-ylmethyl)-1H-benzo[d]imidazole-6-carboxylic acid (Compound 92)

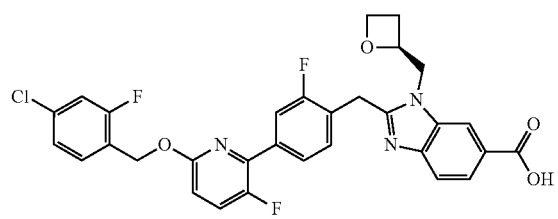 [SMILES: O=C(O)c1ccc2nc(Cc3ccc(-c4nc(OCc5ccc(Cl)cc5F)ccc4F)cc3F)n(C[C@@H]3CCO3)c2c1]

The title compound was prepared analogously as for Compound 74 as a white solid. LCMS: [M+H]$^+$=594.8.

(S)-2-(4-(6-((4-chloro-2-fluorobenzyl)oxy)pyridin-2-yl)-2-fluorobenzyl)-1-(oxetan-2-ylmethyl)-1H-benzo[d]imidazole-6-carboxylic acid (Compound 93)

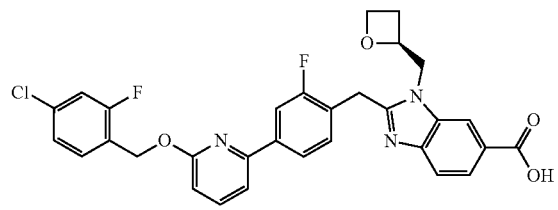 [SMILES: O=C(O)c1ccc2nc(Cc3ccc(-c4cccc(OCc5ccc(Cl)cc5F)n4)cc3F)n(C[C@@H]3CCO3)c2c1]

The title compound was prepared analogously as for Compound 74 as a white solid. LCMS: [M+H]$^+$=576.2.

(S)-2-(4-(6-((4-chloro-2-fluorobenzyl)oxy)pyridin-2-yl)benzyl)-1-(oxetan-2-ylmethyl)-1H-benzo[d]imidazole-6-carboxylic acid (Compound 94)

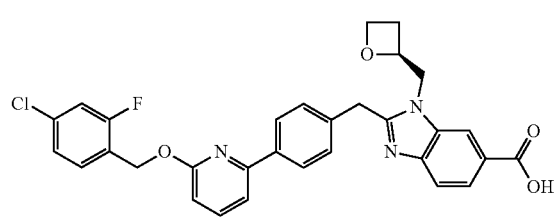 [SMILES: O=C(O)c1ccc2nc(Cc3ccc(-c4cccc(OCc5ccc(Cl)cc5F)n4)cc3)n(C[C@@H]3CCO3)c2c1]

The title compound was prepared analogously as for Compound 74 as a white solid. LCMS: [M+H]$^+$=558.0.

71

(S)-2-(4-(6-((4-cyano-2-fluorobenzyl)oxy)pyridin-2-yl)benzyl)-1-(oxetan-2-ylmethyl)-1H-benzo[d]imidazole-6-carboxylic acid (Compound 95)

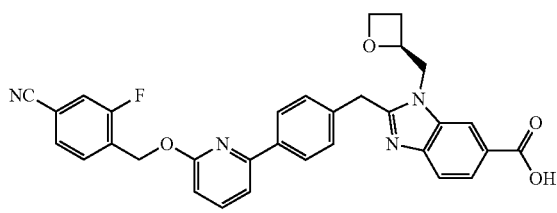 [SMILES: N#Cc1ccc(COc2cccc(-c3ccc(Cc4nc5ccc(C(=O)O)cc5n4C[C@@H]4CCO4)cc3)n2)c(F)c1]

The title compound was prepared analogously as for Compound 74 as a white solid. LCMS: [M+H]⁺=549.2.

(S)-2-(4-(4-((4-chloro-2-fluorobenzyl)oxy)pyrimidin-2-yl)-3-fluorobenzyl)-1-(oxetan-2-ylmethyl)-1H-benzo[d]imidazole-6-carboxylic acid (Compound 96)

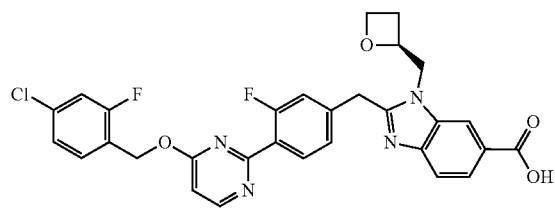 [SMILES: O=C(O)c1ccc2nc(Cc3ccc(-c4nccc(OCc5ccc(Cl)cc5F)n4)c(F)c3)n(C[C@@H]3CCO3)c2c1]

The title compound was prepared analogously as for Compound 74 as a white solid. LCMS [M+H]⁺=577.0.

(S)-2-(4-(6-(4-chloro-2-fluorobenzyloxy)-3-fluoropyridin-2-yl)-3-fluorobenzyl)-1-(oxetan-2-ylmethyl)-1H-benzo[d]imidazole-6-carboxylic acid (Compound 97)

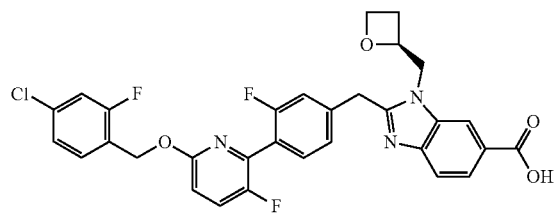 [SMILES: O=C(O)c1ccc2nc(Cc3ccc(-c4nc(OCc5ccc(Cl)cc5F)ccc4F)c(F)c3)n(C[C@@H]3CCO3)c2c1]

72

The title compound was prepared analogously as for Compound 74 as a white solid. LCMS [M+H]⁺=594.1.

(S)-2-(4-(6-(4-chloro-2-fluorobenzyloxy)-3,5-difluoropyridin-2-yl)-2-fluorobenzyl)-3-(oxetan-2-ylmethyl)-3H-benzo[d]imidazole-5-carboxylic acid (Compound 98)

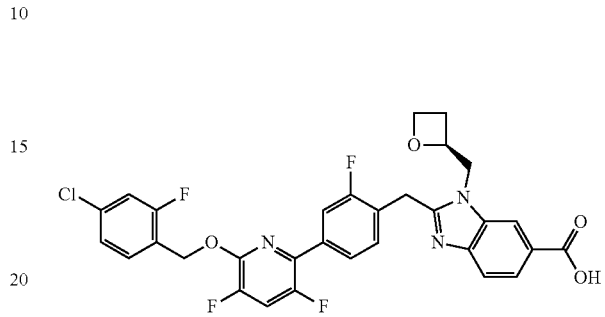

The title compound was prepared analogously as for Compound 74 as a white solid. LCMS: [M+H]⁺=612.0.

(S)-2-(2-chloro-4-(6-((4-chloro-2-fluorobenzyl)oxy)pyridin-2-yl)benzyl)-1-(oxetan-2-ylmethyl)-1H-benzo[d]imidazole-6-carboxylic acid (Compound 99)

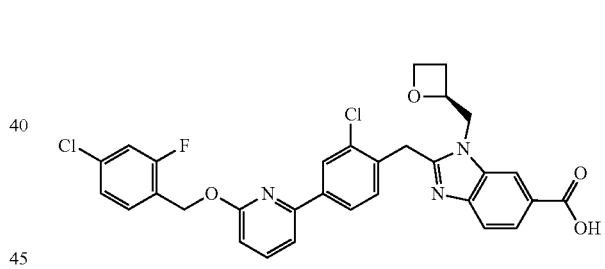

The title compound was prepared analogously as for Compound 74 as a white solid. LCMS: [M+H]⁺=593.1.

(S)-2-((6'-(4-chloro-2-fluorobenzyloxy)-2,2'-bipyridin-5-yl)methyl)-1-(oxetan-2-ylmethyl)-1H-benzo[d]imidazole-6-carboxylic acid (Compound 100)

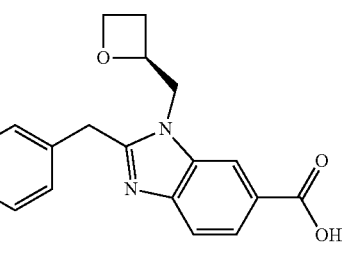

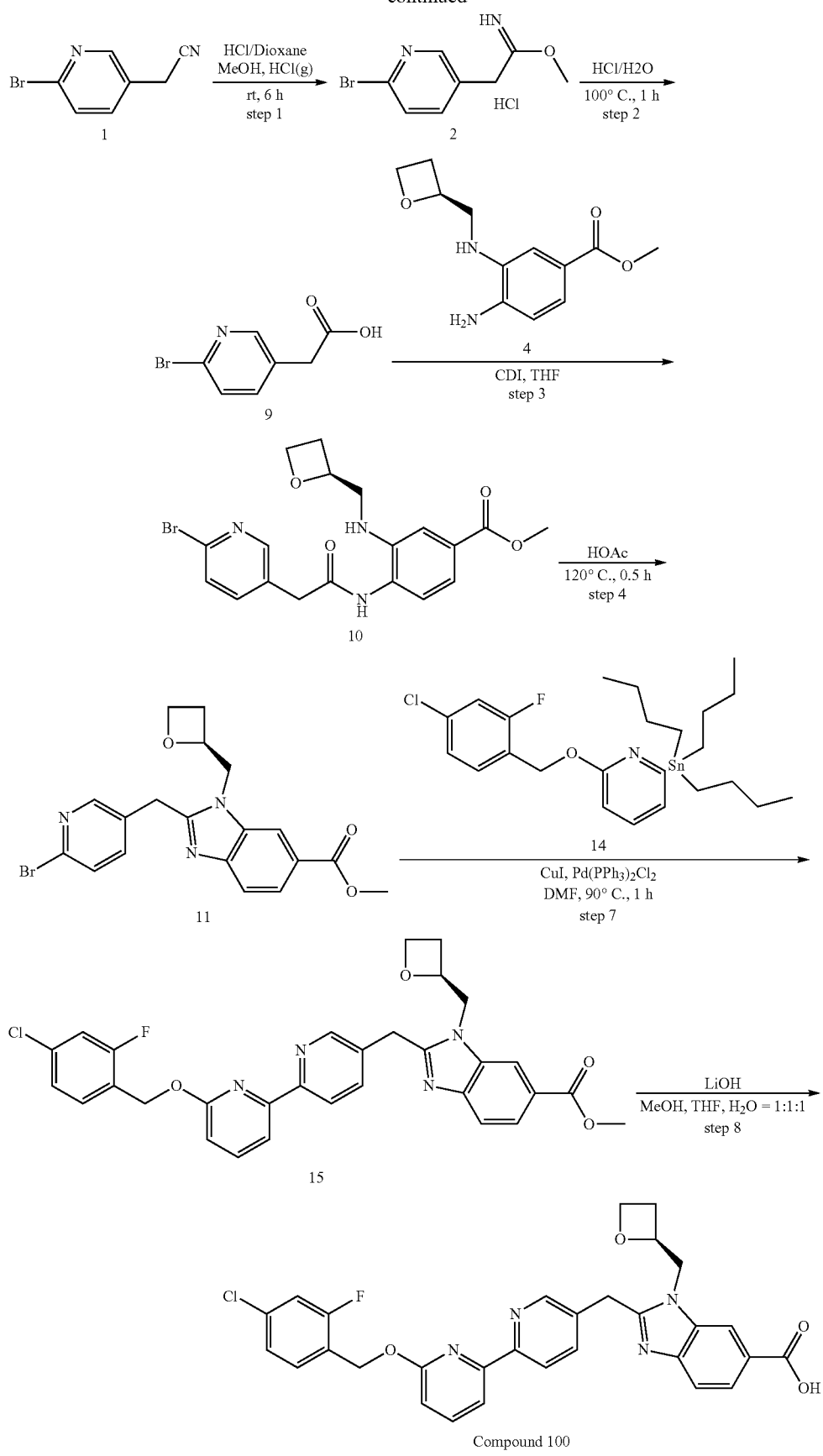

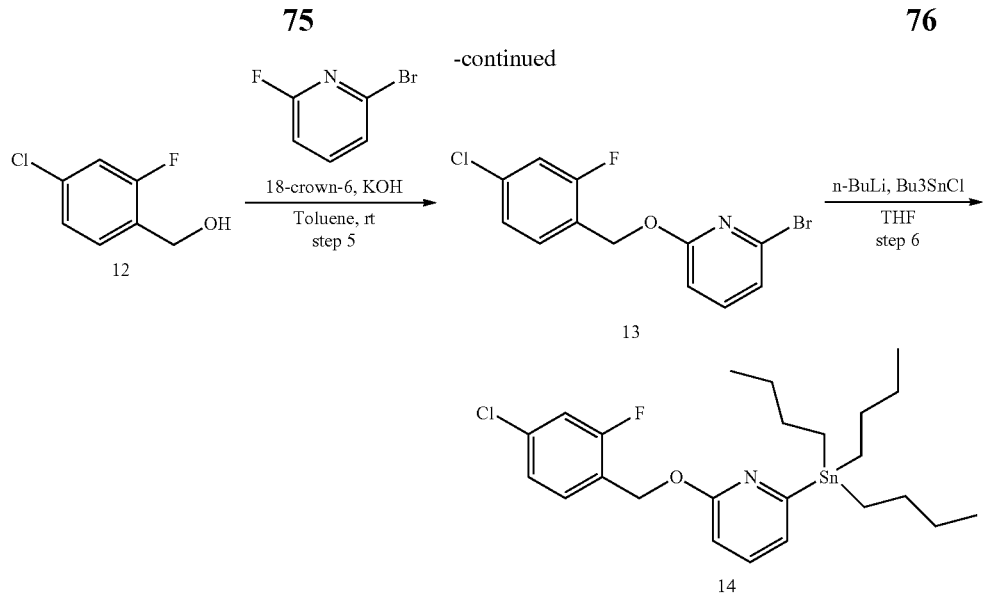

Step 1. Synthesis of methyl 2-(6-bromo-3-pyridyl)ethanimidate

To a mixture of 2-(6-bromo-3-pyridyl)acetonitrile 1 (985 mg, 5.0 mmol), methanol (0.30 mL, 7.5 mmol) in dioxane (20 mL) was bubbled HCl (gas) with stirred for 6 h at rt in a round bottom flask, until the reaction was completed as indicated by LCMS, the reaction mixture was concentrated in vacuo to give the desired product methyl 2-(6-bromo-3-pyridyl)ethanimidate (2) (1.4 g, crude) as white solid. LCMS: $(M+H)^+=230.0$.

Step 2. Synthesis of 2-(6-bromo-3-pyridyl)acetic acid

A mixture of 2 from above (1.2 g, 5.24 mmol), Conc. HCl (10 mL) in Water (10 mL) was stirred for 1 h at 100° C. in a round bottom flask—under $N_2$, until the reaction was completed as indicated by LCMS, the reaction mixture was concentrated in vacuo to give the desired product 2-(6-bromo-3-pyridyl)acetic acid (9) (0.68 g, crude) as pale yellow solid. LCMS: $(M+H)^+=217.9$.

Step 3. Synthesis of methyl methyl (S)-4-(2-(6-bromopyridin-3-yl)acetamido)-3-((oxetan-2-ylmethyl)amino)benzoate A mixture of 9 from above (216 mg, 999.9 umol), di(imidazol-1-yl)methanone (162.1 mg, 1.0 mol) in THF (20 mL) was stirred for 0.5 h at 50° C., then methyl 4-amino-3-[[(2S)-oxetan-2-yl]methylamino]benzoate (4) (236.2 mg, 1.0 mmol) was added to the mixture, it was stirred for another 2.5 h under $N_2$, until the reaction was completed as indicated by LCMS, the reaction mixture was concentrated in vacuo, purified by prep-HPLC to give the desired product methyl methyl (S)-4-(2-(6-bromopyridin-3-yl)acetamido)-3-((oxetan-2-ylmethyl)amino)benzoate (10) (180 mg, 0.42 mol, 41.5% yield) as white solid. LCMS: $(M+H)^+=435.9$.

Step 4. Synthesis of methyl (S)-2-((6-bromopyridin-3-yl)methyl)-1-(oxetan-2-ylmethyl)-1H-benzo[d]imidazole-6-carboxylate A mixture of 10 from above (180 mg, 0.41 mmol) in acetic acid (10 mL) was stirred for 0.5 h at 120° C. in a round bottom flask under $N_2$, until the reaction was completed as indicated by LCMS, the reaction mixture was concentrated in vacuo, dried in vacuo to give the desired product methyl (S)-2-((6-bromopyridin-3-yl)methyl)-1-(oxetan-2-ylmethyl)-1H-benzo[d]imidazole-6-carboxylate (11) (170 mg, crude) as pale yellow solid. LCMS: $(M+H)^+=416.0$.

Step 5. Synthesis of 2-bromo-6-((4-chloro-2-fluorobenzyl)oxy)pyridine

A mixture of (4-chloro-2-fluoro-phenyl)methanol 12 (8.0 g, 49.8 mmol), 2-bromo-6-fluoro-pyridine (8.77 g, 49.8 mmol, 5.13 mL), 1,4,7,10,13,16-hexaoxacyclooctadecane (658.4 mg, 2.5 mmol, 0.56 mL), KOH (4.19 g, 74.7 mmol) in Toluene (100 mL) was stirred for 18 h at rt in a round bottom flask under $N_2$, until the reaction was completed as indicated by LCMS, the reaction mixture was extracted with 50 mL of EtOAc 3 times, the combined organic layers were washed by brine, dried over $Na_2SO_4$, and concentrated in vacuo, purified by silica gel chromatography (Hexanes/EtOAc=20:1) to give the desired product 2-bromo-6-((4-chloro-2-fluorobenzyl)oxy)pyridine (13) (15 g, 47.4 mmol, 95.1% yield) as white solid. LCMS: $(M+H)^+=316.0$.

Step 6. Synthesis of 2-((4-chloro-2-fluorobenzyl)oxy)-6-(tributylstannyl)pyridine To the mixture of 13 from above (1.58 g, 4.99 mmol) in THF (20 mL) was added n-butyllithium (383.7 mg, 5.99 mmol, 2.4 mL) stirred for 3 h at −70° C. in a round bottom flask under $N_2$, then $Bu_3SnCl$ (2.44 g, 7.49 mmol, 2.03 mL) was added to the mixture, after addition the mixture was allowed to warm to rt for another 2 h, the reaction was completed as indicated by LCMS, the reaction mixture was quenched with saturated $NH_4Cl$ in an ice bath, dried over $Na_2SO_4$, the organics were concentrated in vacuo to give the desired product 2-((4-chloro-2-fluorobenzyl)oxy)-6-(tributylstannyl)pyridine (14) (3.5 g, crude) as pale yellow liquid, which was directly use to the next step.

Step 7. Synthesis of methyl (S)-2-((6'-((4-chloro-2-fluorobenzyl)oxy)-[2,2'-bipyridin]-5-yl)methyl)-1-(oxetan-2-ylmethyl)-1H-benzo[d]imidazole-6-carboxylate A mixture of 11 (150 mg, 0.35 mmol), 14 (189.8 mg, 0.36 mmol), $Pd(PPh_3)_2Cl_2$ (34 mg, 0.029 mol), CuI (34 mg, 0.178 mol, 6.05 uL) in DMF (5 mL) was stirred for 1 h at 90° C. in a RBF under N₂, until the reaction was completed as indicated by LCMS, the reaction mixture was filtered and purified by prep-HPLC to give the desired product methyl (S)-2-((6'-((4-chloro-2-fluorobenzyl)oxy)-[2,2'-bipyridin]-5-yl)methyl)-1-(oxetan-2-ylmethyl)-1H-benzo[d]imidazole-6-carboxylate (15) (40.0 mg, 0.070 mmol, 19.4% yield) as pale yellow solid. LCMS: (M+H)⁺=573.0.

Step 8. Synthesis of (S)-2-((6'-((4-chloro-2-fluorobenzyl)oxy)-[2,2'-bipyridin]-5-yl)methyl)-1-(oxetan-2-ylmethyl)-1H-benzo[d]imidazole-6-carboxylic acid A mixture of 15 from above (40.0 mg, 0.070 mmol) and LiOH (117.2 mg, 2.79 mmol, 77.6 uL) in methanol (1 mL), Water (1 mL), THF (1 mL) was stirred for 1 h at rt in a RBF under N₂, until the reaction was completed as indicated by LCMS, the reaction mixture was adjusted pH=7 by HOAc, the mixture was purified by prep-HPLC to give the title compound (S)-2-((6'-((4-chloro-2-fluorobenzyl)oxy)-[2,2'-bipyridin]-5-yl)methyl)-1-(oxetan-2-ylmethyl)-1H-benzo[d]imidazole-6-carboxylic acid (6.9 mg, 0.012 mmol, 17.7% yield) as white solid. LCMS: (M+H)⁺=558.9.

(S)-2-((6-((4-chloro-2-fluorobenzyl)oxy)-[2,3'-bipyridin]-6'-yl)methyl)-1-(oxetan-2-ylmethyl)-1H-benzo[d]imidazole-6-carboxylicacid (Compound 101)

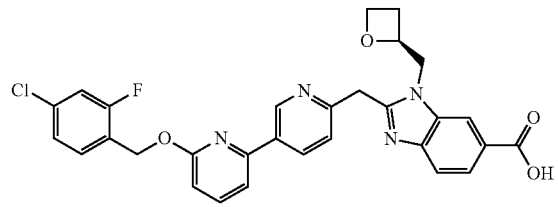 [SMILES: O=C(O)c1ccc2nc(Cc3ccc(-c4cccc(OCc5ccc(Cl)cc5F)n4)cn3)n(C[C@@H]3CCO3)c2c1]

The title compound was prepared in analogous manner as for Compound 100 as a white solid.
LCMS: (M+H)⁺=558.9.

(S)-2-(4-(6-((4-chloro-2-fluorobenzyl)oxy)pyridin-2-yl)-3-fluorobenzyl)-3-(oxetan-2-ylmethyl)-3H-imidazo[4,5-b]pyridine-5-carboxylic acid (Compound 102)

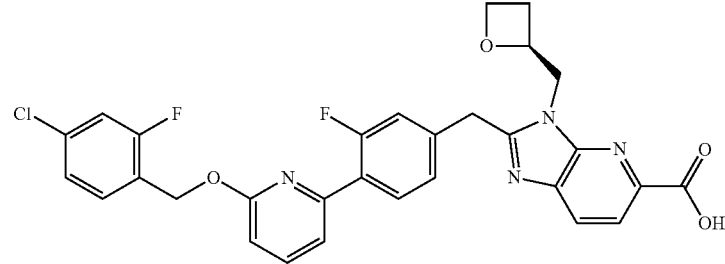

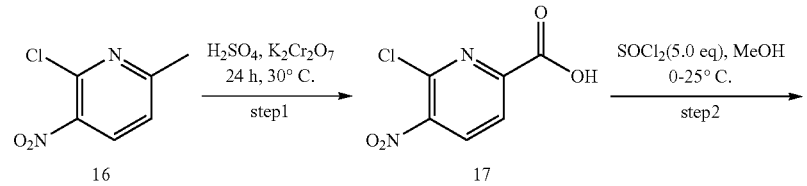

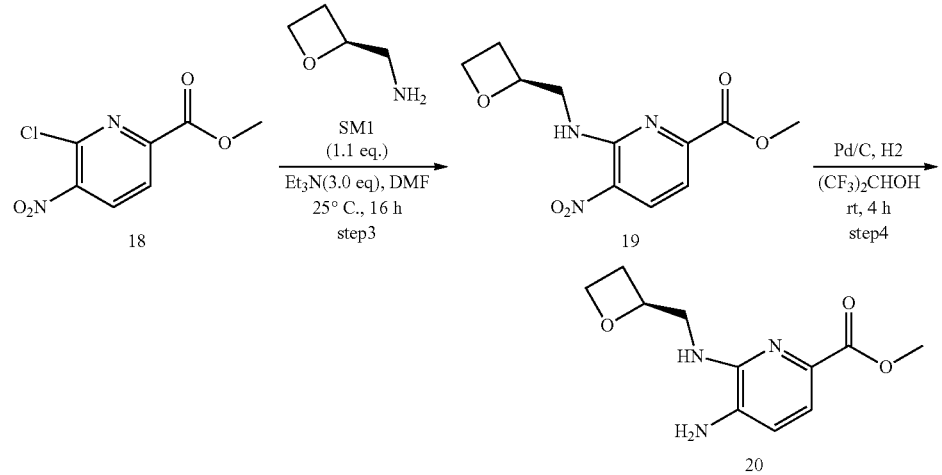

-continued
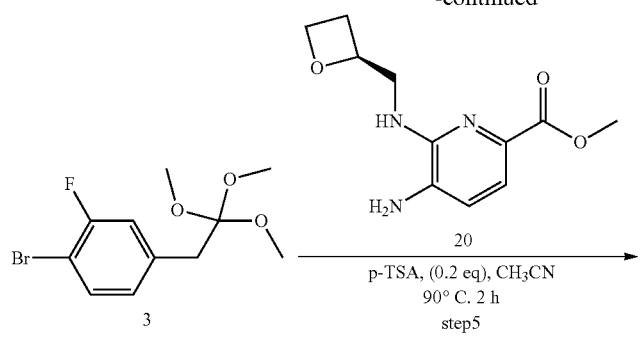
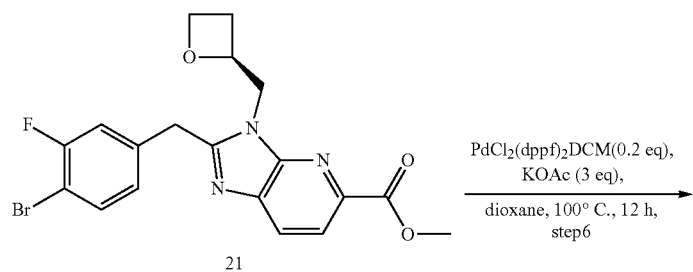
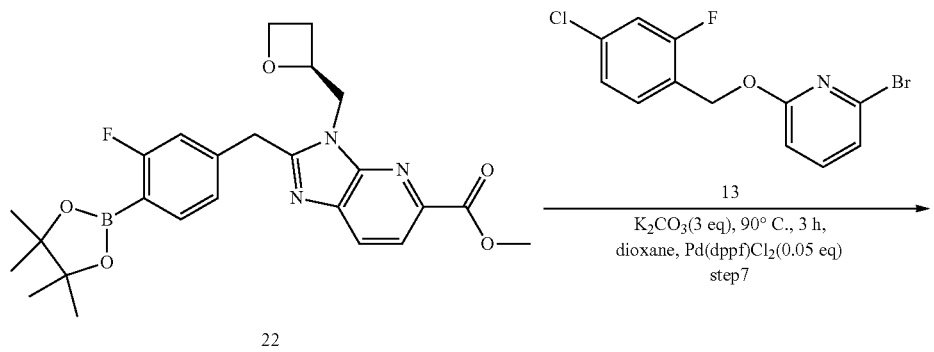
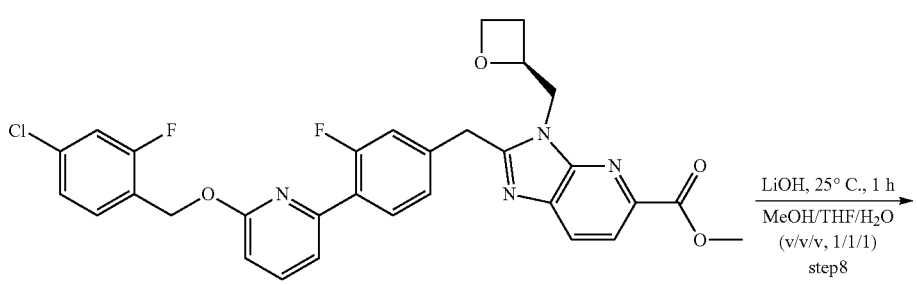
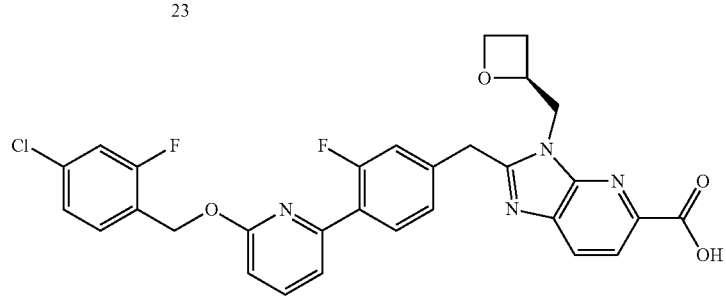

Step 1. Synthesis of 6-chloro-5-nitropicolinic acid

To a stirred solution of 2-chloro-6-methyl-3-nitro-pyridine 16 (4.0 g, 23.2 mmol) in sulfuric acid (16 mL) at room temperature was added $K_2Cr_2O_7$ (10.2 g, 34.8 mmol). The reaction mixture was stirred at 30° C. for 24 h and upon completion of the reaction, as judged by LCMS, the mixture was diluted with Water (200 mL) under ice bath, The resultant precipitates were filtered and washed with water (20 mL) and dried under reduced pressure to afford 6-chloro-5-nitropicolinic acid 17 (3.9 g, 19.3 mmol, 83.3% yield, 100% purity) as a light-yellow solid. LCMS: $[M+H]^+=203$.

Step 2. Synthesis of methyl 6-chloro-5-nitropicolinate

To a suspension of 17 from above (3.9 g, 19.3 mmol) in Dichloromethane (40 mL) was added oxalyl dichloride (4.9 g, 38.5 mmol, 3.35 ml) and N,N-dimethylformamide (0.23 ml) at 0° C. The reaction mixture was stirred at 25° C. for 1 h. Methanol (2.37 g, 74.1 mmol, 3 mL) was added to the reaction mixture at 25° C. The solution was stirred at 25° C. for an additional 60 min. The mixture was concentrated in vacuo to give the residue, which was purified by flash chromatography (Biotage, 80 g silica gel column at 100 mL/min, eluting with 0-60% ethyl acetate in petroleum ether for 30 min) to afford methyl 6-chloro-5-nitropicolinate 18 (2.63 g, 12.1 mmol, 63.1% yield, 100% purity) as a white solid. LCMS $[M+H]^+=217$.

Step 3. Synthesis of methyl (S)-5-nitro-6-((oxetan-2-ylmethyl)amino)picolinate To a stirred solution of [(2S)-oxetan-2-yl]methanamine (663.7 mg, 7.6 mmol) and 18 from above (1.50 g, 6.9 mmol) in DMF (23 ml) at 25° C. was added N-ethyl-N-isopropylpropan-2-amine (2.69 g, 20.8 mmol, 3.62 ml). The reaction mixture was stirred at 25° C. for 16 h and upon completion of the reaction, as judged by LCMS, the mixture was diluted with EtOAc (100 mL) and warmed to room temperature. The layers were separated, and the aqueous layer was extracted with EtOAc (2×100 ml). The combined organic phase was washed with brine (100 ml) and dried over anhydrous $Na_2SO_4$, filtered and concentrated in vacuo. The crude product was purified by flash column chromatography ($SiO_2$, Petroleum ether/ethyl acetate=0~40%) to afford methyl (S)-5-nitro-6-((oxetan-2-ylmethyl)amino)picolinate 19 (1.80 g, 6.5 mmol, 93.3% yield, 96% purity) as a yellow solid. LCMS: $[M+H]^+=267$.

Step 4. Synthesis of methyl (S)-5-amino-6-((oxetan-2-ylmethyl)amino)picolinate To a stirred solution of 19 from above (1.8 g, 6.7 mmol) in Hexafluoroisopropanol (25 mL) at 25° C. was added 10% Pd/C (304 mg). The reaction mixture was stirred at 25° C. for 4 h under hydrogen and upon completion of the reaction, as judged by LCMS, the mixture was diluted with EtOAc (100 mL), filtered and the filtrate cake was washed with EtOAc (2×100 mL). The combined organic phase concentrated in vacuo to afford methyl (S)-5-amino-6-((oxetan-2-ylmethyl)amino)picolinate 20 (1.6 g, 6.1 mmol, 91.1% yield, 91% purity) as a yellow solid. LCMS: $[M+H]^+=238$.

Step 5. Synthesis of methyl (S)-2-(4-bromo-3-fluorobenzyl)-3-(oxetan-2-ylmethyl)-3H-imidazo[4,5-b]pyridine-5-carboxylate To a stirred solution of 20 (260 mg, 1.10 mmol) in $CH_3CN$ (8 mL) at room temperature was added 4-methylbenzenesulfonic acid (41.9 mg, 0.22 mmol) and 1-bromo-2-fluoro-4-(2,2,2-trimethoxyethyl)benzene (483.7 mg, 1.7 mmol). The reaction mixture was stirred at 90° C. for 2 h and upon completion of the reaction, as judged by LCMS, the mixture was diluted with EtOAc (100 mL) and cooled to room temperature. The layers were separated, and the aqueous layer was extracted with EtOAc (2×150 mL). The combined organic phase was washed with brine (100 mL) and dried over anhydrous $Na_2SO_4$, filtered and concentrated in vacuo. The crude product was purified by flash column chromatography (SiO2, petroleum ether/ethyl acetate 5:1) to afford methyl (S)-2-(4-bromo-3-fluorobenzyl)-3-(oxetan-2-ylmethyl)-3H-imidazo[4,5-b]pyridine-5-carboxylate 21 (180 mg, 0.41 mmol, 37.7% yield) as a white solid. LCMS: $[M+H]^+=434$.

Step 6. Synthesis of methyl (S)-2-(3-fluoro-4-(4,4,5,5-tetramethyl-1,3,2-dioxaborolan-2-yl)benzyl)-3-(oxetan-2-ylmethyl)-3H-imidazo[4,5-b]pyridine-5-carboxylate To a stirred solution of 21 from above (20.0 mg, 0.046 mmol) and 4,4,5,5-tetramethyl-2-(4,4,5,5-tetramethyl-1,3,2-dioxaborolan-2-yl)-1,3,2-dioxaborolane (14.0 mg, 55.3 mmol) in 1,4-Dioxane (1 mL) at 100° C. was added $PdCl_2$ (dppf) (5.1 mg) and potassium acetate (13.6 mg). The reaction mixture was stirred at 100° C. for 12 h and upon completion of the reaction, as judged by LCMS, the mixture was diluted with EtOAc (100 mL) and warmed to room temperature to concentrated in vacuo to afford crude methyl (S)-2-(3-fluoro-4-(4,4,5,5-tetramethyl-1,3,2-dioxaborolan-2-yl)benzyl)-3-(oxetan-2-ylmethyl)-3H-imidazo[4,5-b]pyridine-5-carboxylate 22 (22 mg, 0.046 mmol, 99.2% yield) as a yellow solid, which was used for the next step without purification.

Step 7. Synthesis of methyl (S)-2-(4-(6-((4-chloro-2-fluorobenzyl)oxy)pyridin-2-yl)-3-fluorobenzyl)-3-(oxetan-2-ylmethyl)-3H-imidazo[4,5-b]pyridine-5-carboxylate To a stirred solution of 22 from above (22.0 mg, 0.046 mmol) and 13 (17.4 mg, 0.055 mmol) in 1,4-dioxane (2 mL) at 25° C. was added $PdCl_2$(dppf) (1.7 mg, 0.002 mmol) and potassium carbonate (19.0 mg, 0.14 mmol). The reaction mixture was stirred at 90° C. for 3 hand upon completion of the reaction, as judged by LCMS, the mixture was diluted with EtOAc (100 mL) and warmed to room temperature to concentrated in vacuo, which was purified by flash column chromatography (silica gel, Petroleum ether/ethyl acetate=0~40%) to afford methyl (S)-2-(4-(6-((4-chloro-2-fluorobenzyl)oxy)pyridin-2-yl)-3-fluorobenzyl)-3-(oxetan-2-ylmethyl)-3H-imidazo[4,5-b]pyridine-5-carboxylate 23 (20.0 mg, 0.034 mmol, 74.0% yield) as a yellow solid. LCMS: $[M+H]^+=591$.

Step 8. Synthesis of (S)-2-(4-(6-((4-chloro-2-fluorobenzyl)oxy)pyridin-2-yl)-3-fluorobenzyl)-3-(oxetan-2-ylmethyl)-3H-imidazo[4,5-b]pyridine-5-carboxylic acid To a stirred solution of 23 from above (20.0 mg, 0.034 mmol) in Water (1 ml), THF (1 mL) and methanol (1 mL) at 25° C. was added Lithium hydroxide monohydrate (2.8 mg, 0.068 mmol). The reaction mixture was stirred at 25° C. for 1 h and upon completion of the reaction, as judged by LCMS, the mixture was acidified with AcOH until pH~6 and diluted with DMF (3 mL) and purified by reverse phase-HPLC (Instrument: Gilson 281(PHG012); Column: Xtimate C18 10 um, 21.2×250 mm; Mobile phase: A: water (10 mM NH$_4$HCO$_3$, 0.025% NH$_3$.H$_2$O), B: Acetonitrile; Gradient: 30% B for 1 min, then 45% B in 7 min, stop at 15 min; Flow rate: 30 mL/min; Detective wavelength: 214/254 nm; Retention time: 8.0 min; Injection number: 3), the corresponding fractions were combined, concentrated under reduced pressure to remove most of the organic solvent, and the aqueous residue was lyophilized to afford the title compound (S)-2-(4-(6-((4-chloro-2-fluorobenzyl)oxy)pyridin-2-yl)-3-fluorobenzyl)-3-(oxetan-2-ylmethyl)-3H-imidazo[4,5-b]pyridine-5-carboxylic acid as a white solid (7.0 mg, 0.012 mmol, 35.9% yield). LCMS: [M+H]$^+$=577.

(S)-2-((4-(4-((4-chloro-2-fluorobenzyl)oxy)thiazol-2-yl)-3,6-dihydropyridin-1(2H)-yl)methyl)-1-(oxetan-2-ylmethyl)-1H-benzo[d]imidazole-6-carboxylic acid (Compound 246)

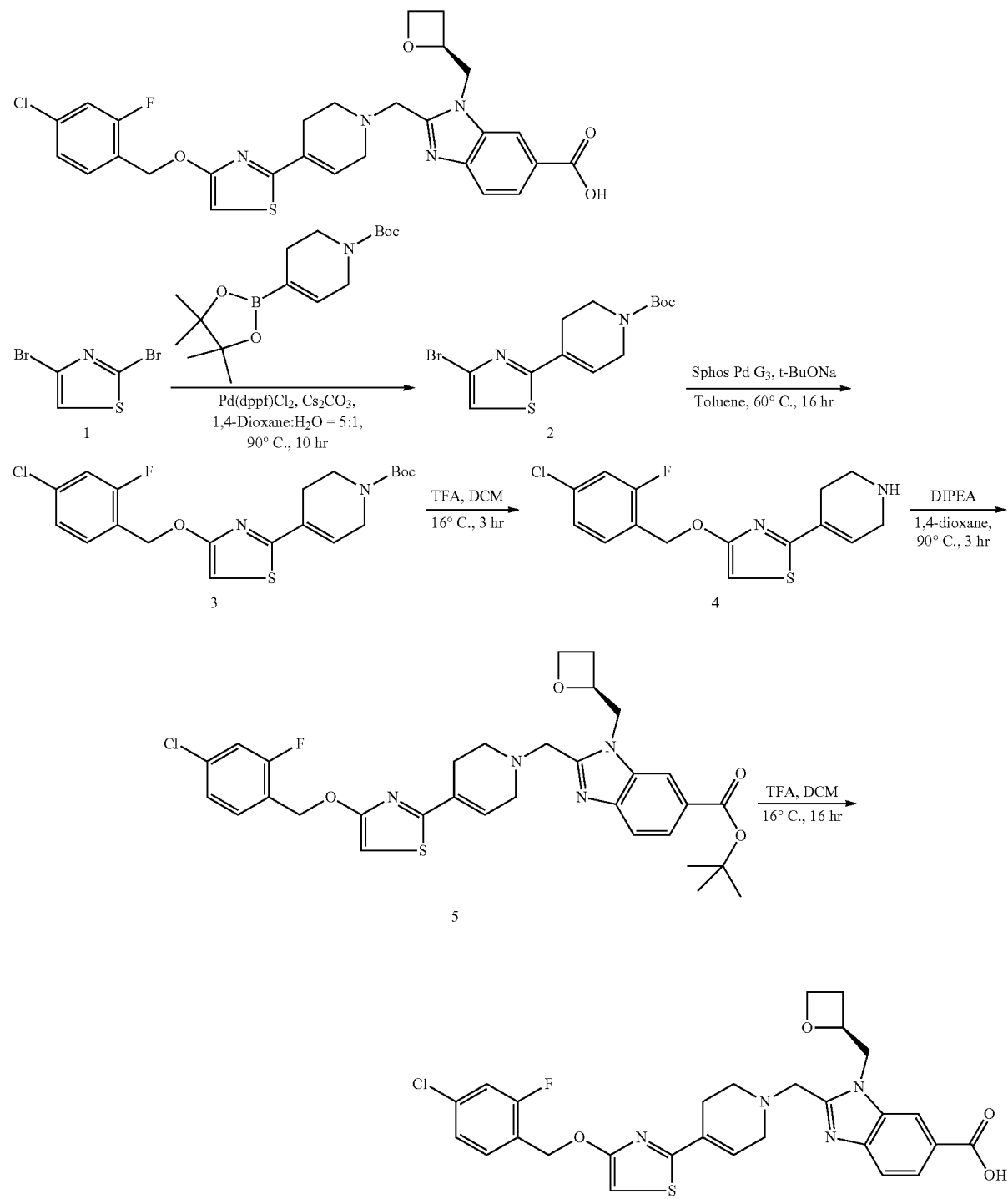

Step 1

A mixture of 2,4-dibromothiazole (2.0 g, 8.23 mmol), tert-butyl 4-(4,4,5,5-tetramethyl-1,3,2-dioxaborolan-2-yl)-3,6-dihydro-2H-pyridine-1-carboxylate (2.55 g, 8.23 mmol) and Pd(dppf)Cl$_2$ (602.42 mg, 823.32 µmol), Cs$_2$CO$_3$ (5.37 g, 16.47 in mol) in 1,4-Dioxane (40 mL) was stirred for 10 h at 90° C. in a RBF under N$_2$, until the reaction was completed as indicated by LCMS, the reaction mixture was concentrated in vacuo, purified by silica gel chromatography (Hexanes/EtOAc=10:1, R$_f$=0.4) to give the desired product tert-butyl 4-(4-bromothiazol-2-yl)-3,6-dihydro-2H-pyridine-1-carboxylate (2.2 g, 6.37 mmol, 77.4 yield, 100% purity) as a light yellow solid. LCMS: [M+H]$^+$=291.0; Retention time (10 mM NH$_4$HCO$_3$)=1.79 m.

Step 2

A mixture of tert-butyl 4-(4-bromothiazol-2-yl)-3,6-dihydro-2H-pyridine-1-carboxylate (1.0 g, 2.90 mmol), (4-chloro-2-fluoro-phenyl)methanol (697.6 mg, 4.34 mmol) and Sphos-Pd G$_3$ (225.92 mg, 289.64 µmol), t-BuONa (835.1 mg, 8.69 mmol) in toluene (5 mL) was stirred for 16 hr at 60° C. in a RBF under N$_2$, until the reaction was completed as indicated by LCMS, the reaction mixture was filtered through a pad of Celite with EtOAc, and the combined organics were concentrated in vacuo, purified by prep-HPLC to give the desired product tert-butyl 4-[4-[(4-chloro-2-fluoro-phenyl)methoxy]thiazol-2-yl]-3,6-dihydro-2H-pyridine-1-carboxylate (30 mg, 70.60 µmol, 2.400 yield) as yellow oil. LCMS: [M+H]$^+$=425.2; Retention time (0.01% TFA)=2.49 min.

Step 3

A mixture of tert-butyl 4-[4-[(4-chloro-2-fluoro-phenyl)methoxy]thiazol-2-yl]-3,6-dihydro-2H-pyridine-1-carboxylate (26 mg, 61.19 µmol) and 2,2,2-trifluoroacetic acid (1.48 g, 12.98 mmol, 1 mL) in dichloromethane (3 mL) was stirred for 3 hr at 16° C., until the reaction was completed as indicated by LCMS, the reaction mixture was concentrated in vacuo to give the desired product 4-[(4-chloro-2-fluoro-phenyl)methoxy]-2-(1,2,3,6-tetrahydropyridin-4-yl)thiazole (20 mg, crude) as a yellow solid. LCMS: [M+H]$^+$=325.0; Retention time (10 mM NH$_4$HCO$_3$)=1.58 min.

Step 4

A mixture of 4-[(4-chloro-2-fluoro-phenyl)methoxy]-2-(1,2,3,6-tetrahydropyridin-4-yl)thiazole (15 mg, 46.18 µmol), tert-butyl 2-(chloromethyl)-3-[[(2S)-oxetan-2-yl]methyl]benzimidazole-5-carboxylate (15.55 mg, 46.18 µmol) and N-ethyl-N-isopropyl-propan-2-amine (29.84 mg, 230.91 µmol, 40.22 µL) in N,N-dimethylformamide (3 mL) was stirred for 4 hr at 50° C. in a RBF under N$_2$, until the reaction was completed as indicated by LCMS, the reaction mixture concentrated in vacuo to yield a residue which was purified by prep-HPLC to give the desired product tert-butyl 2-[[4-[4-[(4-chloro-2-fluoro-phenyl)methoxy]thiazol-2-yl]-3,6-dihydro-2H-pyridin-1-yl]methyl]-3-[[(2S)-oxetan-2-yl]methyl]benzimidazole-5-carboxylate (3 mg, 4.80 µmol, 10.39% yield, 100% purity) as a yellow solid. LCMS: [M+H]$^+$=625.3; Retention time (10 mM NH$_4$HCO$_3$)=1.84 min.

Step 5

A mixture of tert-butyl 2-[[4-[4-[(4-chloro-2-fluoro-phenyl)methoxy]thiazol-2-yl]-3,6-dihydro-2H-pyridin-1-yl]methyl]-3-[[(2S)-oxetan-2-yl]methyl]benzimidazole-5-carboxylate (3 mg, 4.80 µmol) and 2,2,2-trifluoroacetic acid (1.48 g, 12.98 mmol, 1 mL) in dichloromethane (4 mL) was stirred for 1 h at 16° C. in a RBF under N$_2$, until the reaction was complete as indicated by LCMS, the reaction mixture was concentrated in vacuo to give a residue which was purified by prep-HPLC to give the desired product 2-[[4-[4-[(4-chloro-2-fluoro-phenyl)methoxy]thiazol-2-yl]-3,6-dihydro-2H-pyridin-1-yl]methyl]-3-[[(2S)-oxetan-2-yl]methyl]benzimidazole-5-carboxylic acid (0.8 mg, 1.41 µmol, 29.3% yield, 100% purity) as a white solid. LCMS: [M+H]$^+$=569.2; Retention time (10 mM NH$_4$HCO$_3$)=1.46 min; Purity: 100% (254 nm).

$^1$H NMR (400 MHz, CD$_3$OD) δ 8.20 (s, 1H), 7.97 (dd, J=8.5, 1.2 Hz, 1H), 7.65-7.52 (m, 2H), 7.30-7.22 (m, 2H), 6.61-6.60 (brs, 1H), 6.39-6.38 (brs, 1H), 5.24 (s, 2H), 4.71-4.63 (m, 3H), 4.43 (s, 2H), 4.15 (d, J=13.6 Hz, 1H), 4.05 (d, J=13.6 Hz, 1H), 3.25-3.24 (m, 2H), 2.86-2.80 (m, 2H), 2.80-2.73 (m, 1H), 2.65-2.63 (brs, 2H), 2.52-2.50 (m, 1H).

(S)-2-((4-(2-((4-chloro-2-fluorobenzyl)oxy)thiazol-4-yl)-3,6-dihydropyridin-1(2H)-yl)methyl)-1-(oxetan-2-ylmethyl)-1H-benzo[d]imidazole-6-carboxylic acid (Compound 247)

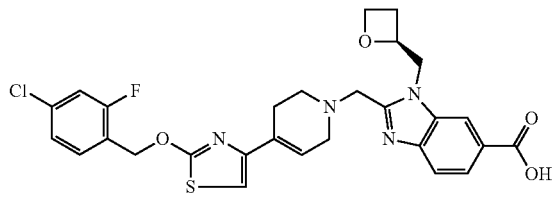 [SMILES: O=C(O)c1ccc2nc(CN3CC=C(c4coc(OCc5ccc(Cl)cc5F)n4)CC3)n(C[C@@H]3CCO3)c2c1]

Prepared in analogous manner as for Compound 250. LCMS: [M+H]$^+$=568.9; Retention time (10 mM NH$_4$HCO$_3$)=1.41 min.

$^1$H NMR (400 MHz, CD$_3$OD) δ 8.37 (d, J=0.9 Hz, 1H), 8.07 (dd, J=8.5, 1.5 Hz, 1H), 7.84 (d, J=8.5 Hz, 1H), 7.58 (t, J=8.0 Hz, 1H), 7.33-7.23 (m, 2H), 6.93 (s, 1H), 6.60 (s, 1H), 5.54 (s, 2H), 5.28-5.14 (m, 1H), 5.11-4.90 (m, 2H), 4.79 (dd, J=15.8, 6.9 Hz, 1H), 4.67 (dt, J=13.8, 5.4 Hz, 2H), 4.42 (dt, J=9.3, 5.9 Hz, 1H), 4.23 (s, 2H), 3.80 (d, J=5.4 Hz, 2H), 3.00-2.72 (m, 3H), 2.51 (dq, J=11.3, 7.4 Hz, 1H).

(S)-2-((4-(2-((4-chloro-2-fluorobenzyl)oxy)oxazol-4-yl)-5,6-dihydropyridin-1(2H)-yl)methyl)-1-(oxetan-2-ylmethyl)-1H-benzo[d]imidazole-6-carboxylic acid (Compound 248)

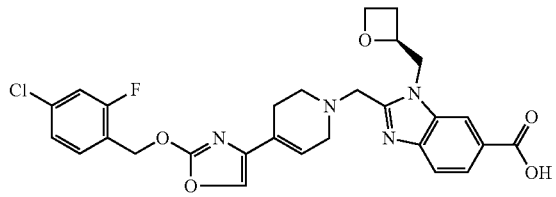

Prepared in analogous manner as for Compound 250. LCMS: [M+H]$^+$=553.2; Retention time (0.01% TFA)=1.50 min.

$^1$H NMR (400 MHz, CDCl$_3$) δ 7.73 (brs, 3H), 7.46 (t, J=8.0 Hz, 1H), 7.16 (t, J=9.3 Hz, 3H), 6.39 (s, 1H), 5.44 (s, 2H), 5.15 (s, 1H), 4.59 (d, J=5.6 Hz, 3H), 4.34 (s, 2H), 2.70 (s, 3H), 2.41 (s, 3H), 2.06 (d, J=14.3 Hz, 5H).

(S)-2-((4-(2-((4-(cyclopropylethynyl)-2-fluorobenzyl)oxy)thiazol-4-yl)-3,6-dihydropyridin-1(2H)-yl)methyl)-1-(oxetan-2-ylmethyl)-1H-benzo[d]imidazole-6-carboxylic acid (Compound 249)

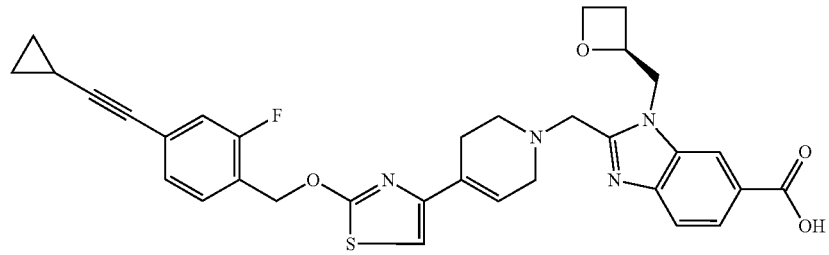 [SMILES: O=C(O)c1ccc2nc(CN3CC=C(c4csc(OCc5ccc(C#CC6CC6)cc5F)n4)CC3)n(C[C@@H]3CCO3)c2c1]

Prepared in analogous manner as for Compound 250. LCMS: [M+H]$^+$=599.0; Retention time (10 mM NH$_4$HCO$_3$)=1.68 min.

$^1$H NMR (400 MHz, DMSO-D6-d6) δ 8.23-8.18 (brs, 1H), 7.80 (dd, J=8.4, 1.4 Hz, 1H), 7.60 (d, J=8.4 Hz, 1H), 7.53 (t, J=7.9 Hz, 1H), 7.26 (dd, J=10.8, 1.2 Hz, 1H), 7.22 (dd, J=7.9, 1.4 Hz, 1H), 6.87-6.82 (brs, 1H), 6.47-6.42 (m, 1H), 5.46 (s, 2H), 5.09-5.02 (m, 1H), 4.78 (dd, J=15.2, 7.2 Hz, 1H), 4.62 (dd, J=15.1, 2.6 Hz, 1H), 4.47 (dd, J=13.7, 7.6 Hz, 1H), 4.36 (dt, J=9.0, 5.9 Hz, 1H), 4.04 (d, J=13.4 Hz, 1H), 3.89 (d, J=13.4 Hz, 1H), 3.21-3.11 (m, 2H), 2.73-2.62 (m, 3H), 2.42-3.32 (m, 3H), 1.60-1.50 (m, 1H), 0.94-0.87 (m, 2H), 0.77-0.72 (m, 2H).

(S)-2-((4-(2-((5-chloropyridin-2-yl)methoxy)thiazol-4-yl)-3,6-dihydropyridin-1(2H)-yl)methyl)-1-(oxetan-2-ylmethyl)-1H-benzo[d]imidazole-6-carboxylic acid (Compound 250)

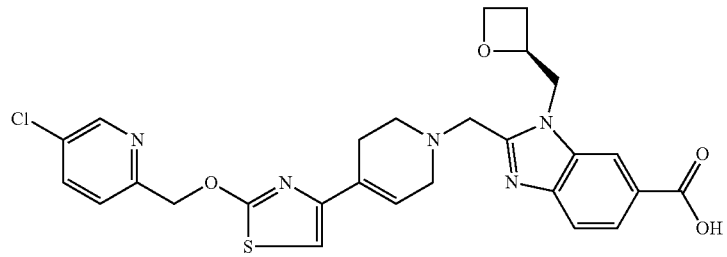

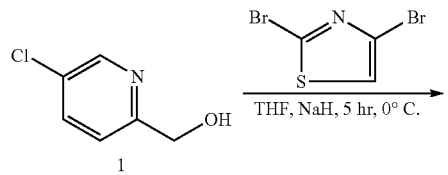

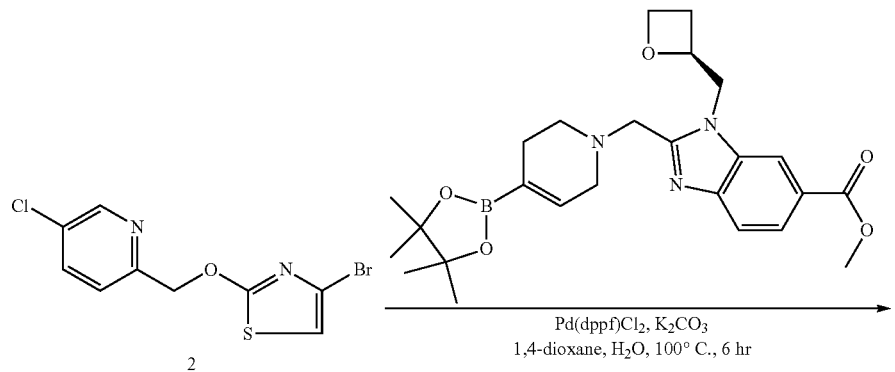

-continued

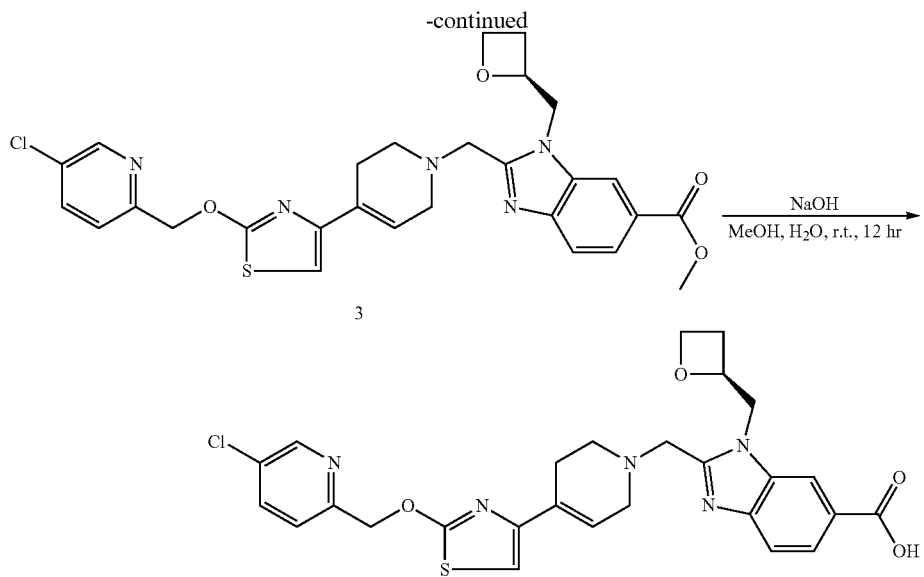

Step 1

To a suspension of (5-chloro-2-pyridyl)methanol (100 mg, 696.5 µmol) in THF (4 mL) was added sodium hydride (33.4 mg, 1.39 mmol) at 0° C. and stirred for 30 min. Then 2,4-dibromothiazole (169.2 mg, 696.5 µmol) was added and stirred for 5 h at 0° C. After completion of the reaction as judged by LCMS, reaction mixture was quenched with ice-cold water (20 mL) and extracted with EtOAc (3×20 mL). The organic phase was washed with brine (50 mL) and dried over anhydrous $Na_2SO_4$, filtered and concentrated in vacuo. The crude product was purified by flash chromatography ($SiO_2$, hexane/ethyl acetate 20:1) to afford 4-bromo-2-[(5-chloro-2-pyridyl)methoxy]thiazole (78 mg, 232.4 µmol, yield 33.4%), as colorless oil. LCMS: $[M+H]^+$=304.9; Retention time (0.01% TFA)=2.02 min.

Step 2

To a suspension of 4-bromo-2-[(5-chloro-2-pyridyl)methoxy]thiazole (78 mg, 255.25 µmol) in 1,4-dioxane (3 mL) was added methyl 3-[[(2S)-oxetan-2-yl]methyl]-2-[[4-(4,4,5,5-tetramethyl-1,3,2-dioxaborolan-2-yl)-3,6-dihydro-2H-pyridin-1-yl]methyl]benzimidazole-5-carboxylate (119.3 mg, 255.3 µmol), $Pd(dppf)Cl_2$ (37.35 mg, 51.1 µmol), $K_2CO_3$ (105.8 mg, 765.8 µmol, 46.22 µL) and water (0.3 mL) at 100° C. and stirred for 6 h under $N_2$. After completion of the reaction as judged by LCMS, reaction mixture was quenched with ice-cold water (20 mL) and extracted with EtOAc (3×20 mL). The organic phase was washed with brine (50 mL) and dried over anhydrous $Na_2SO_4$, filtered and concentrated in vacuo. The crude product was purified by prep-TLC (Dichloromethane/methanol 25:1) to afford methyl (S)-2-((4-(2-((5-chloropyridin-2-yl)methoxy)thiazol-4-yl)-3,6-dihydropyridin-1(2H)-yl)methyl)-1-(oxetan-2-ylmethyl)-1H-benzo[d]imidazole-6-carboxylate (100 mg, 139.3 µmol, 54.6% yield, 78.9% purity) as a yellow oil.

LCMS: $[M+H]^+$=566.1; Retention time (0.01% TFA)= 1.48 min.

Step 3

To a suspension of methyl methyl (S)-2-((4-(2-((5-chloropyridin-2-yl)methoxy)thiazol-4-yl)-3,6-dihydropyridin-1(2H)-yl)methyl)-1-(oxetan-2-ylmethyl)-1H-benzo[d]imidazole-6-carboxylate (100 mg, 176.7 µmol) in MeOH (3 mL) was added sodium hydroxide (80 mg, 2.00 mmol, 37.6 µL) in water (1 mL) at r.t and stirred for 12 h After completion of the reaction as judged by LCMS, reaction mixture was quenched with ice-cold water (10 mL) and extracted with EtOAc (3×10 mL). The organic phase was washed with brine (20 mL) and dried over anhydrous $Na_2SO_4$, filtered and concentrated in vacuo. The crude product was purified by prep-HPLC to afford (S)-2-((4-(2-((5-chloropyridin-2-yl)methoxy)thiazol-4-yl)-3,6-dihydropyridin-1(2H)-yl)methyl)-1-(oxetan-2-ylmethyl)-1H-benzo[d]imidazole-6-carboxylic acid (39.1 mg, 70.8 µmol, 40.1% yield) as a yellow solid. LCMS: $[M+H]^+$=552.0; Retention time (0.01% TFA)= 1.45 min.

$^1$H NMR (400 MHz, DMSO-D6) δ 8.64 (d, J=2.1 Hz, 1H), 8.25 (t, J=3.2 Hz, 1H), 7.99 (dd, J=8.4, 2.5 Hz, 1H), 7.81 (dd, J=8.4, 1.5 Hz, 1H), 7.65 (d, J=8.4 Hz, 1H), 7.59 (t, J=8.4 Hz, 1H), 6.86-6.85 (brs, 1H), 6.39 (s, 1H), 5.51 (s, 2H), 5.05 (qd, J=7.4, 2.8 Hz, 1H), 4.79 (dd, J=15.2, 7.4 Hz, 1H), 4.64 (dd, J=15.2, 2.6 Hz, 1H), 4.47 (dd, J=14.2, 7.0 Hz, 1H), 4.36 (dt, J=9.0, 5.9 Hz, 1H), 4.05 (d, J=13.5 Hz, 1H), 3.89 (d, J=13.5 Hz, 1H), 3.21-3.11 (m, 2H), 2.66 (dd, J=16.2, 11.1, 7.2 Hz, 3H), 2.46-2.31 (m, 3H).

(S)-1-(oxetan-2-ylmethyl)-2-((4-(2-((4-(trifluoromethoxy)benzyl)oxy)thiazol-4-yl)-3,6-dihydropyridin-1(2H)-yl)methyl)-1H-benzo[d]imidazole-6-carboxylic acid (Compound 251)

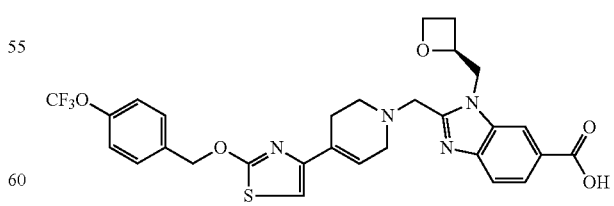

Prepared in analogous manner as for Compound 250. LCMS: $[M+H]^+$=601.0; Retention time (10 mM $NH_4$ $HCO_3$)=1.63 min.

$^1$H NMR (400 MHz, DMSO-D6) δ 8.24 (s, 1H), 7.83-7.79 (m, 1H), 7.66-7.61 (m, 3H), 7.43-7.38 (m, 2H), 6.85 (s, 1H), 6.48-6.44 (m, 1H), 5.48 (s, 2H), 5.10-5.02 (m, 1H), 4.84-4.75 (m, 1H), 4.68-4.61 (m, 1H), 4.51-4.44 (m, 1H), 4.40-4.33 (m, 1H), 4.09-3.87 (dd, J=63.2, 13.4 Hz, 2H), 3.22-3.15 (m, 2H), 2.75-2.64 (m, 3H), 2.42-2.35 (m, 3H).

(S)-2-((4-(2-((2,4-difluorobenzyl)oxy)thiazol-4-yl)-3,6-dihydropyridin-1(2H)-yl)methyl)-1-(oxetan-2-ylmethyl)-1H-benzo[d]imidazole-6-carboxylic acid (Compound 252)

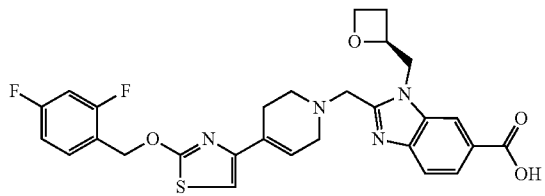 [SMILES: O=C(O)c1ccc2nc(CN3CC=C(c4csc(OCc5ccc(F)cc5F)n4)CC3)n(C[C@@H]3CCO3)c2c1]

Prepared in analogous manner as for Compound 250. LCMS: [M+H]$^+$=553.0; Retention time (10 mM NH$_4$HCO$_3$)=1.54 min.

$^1$H NMR (400 MHz, DMSO-D6) δ 8.24 (s, 1H), 7.80 (dd, J=1.2 Hz, J=8.4 Hz, 1H), 7.70-7.62 (m, 2H), 7.35-7.29 (m, 1H), 7.16-7.11 (m, 1H), 6.84 (s, 1H), 6.46 (s, 1H), 5.45 (s, 2H), 5.06-5.04 (m, 1H), 4.81-4.76 (m, 1H), 4.66-4.61 (dd, J=2.4 Hz, J=15.2 Hz, 1H), 4.46 (t, J=6 Hz, 1H), 4.39-4.35 (m, 1H), 4.05 (d, J=13.6 Hz, 1H), 3.89 (d, J=13.6 Hz, 1H), 3.18 (d, J=9.6 Hz, 2H), 2.72-2.63 (m, 3H), 2.46-2.32 (m, 3H).

(S)-2-((4-(2-((5-bromopyridin-2-yl)methoxy)thiazol-4-yl)-3,6-dihydropyridin-1(2H)-yl)methyl)-1-(oxetan-2-ylmethyl)-1H-benzo[d]imidazole-6-carboxylic acid (Compound 253)

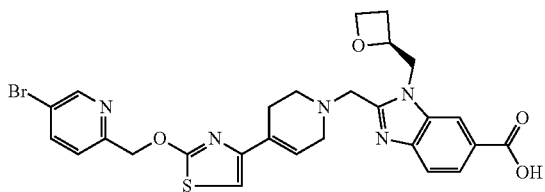 [SMILES: O=C(O)c1ccc2nc(CN3CC=C(c4csc(OCc5ccc(Br)cn5)n4)CC3)n(C[C@@H]3CCO3)c2c1]

Prepared in analogous manner as for Compound 250. LCMS: [M+H]$^+$=596.0; Retention time (10 mM NH$_4$HCO$_3$)=1.47 min.

$^1$H NMR (400 MHz, DMSO-D6) δ 8.72 (d, J=1.9 Hz, 1H), 8.25 (d, J=1.0 Hz, 1H), 8.11 (dd, J=8.3, 2.4 Hz, 1H), 7.81 (dd, J=8.4, 1.5 Hz, 1H), 7.64 (d, J=8.4 Hz, 1H), 7.51 (d, J=8.3 Hz, 1H), 6.86 (s, 1H), 6.39 (s, 1H), 5.48 (s, 2H), 5.13-4.99 (m, 1H), 4.79 (dd, J=15.2, 7.3 Hz, 1H), 4.64 (dd, J=15.2, 2.6 Hz, 1H), 4.46 (dd, J=14.2, 7.1 Hz, 1H), 4.36 (dt, J=8.9, 5.9 Hz, 1H), 4.05 (d, J=13.5 Hz, 1H), 3.89 (d, J=13.5 Hz, 1H), 3.24-3.09 (m, 2H), 2.77-2.59 (m, 3H), 2.40 (dd, J=18.2, 9.4 Hz, 3H).

(S)-2-((4-(2-((2-chloro-4-fluorobenzyl)oxy)thiazol-4-yl)-3,6-dihydropyridin-1(2H)-yl)methyl)-1-(oxetan-2-ylmethyl)-1H-benzo[d]imidazole-6-carboxylic acid (Compound 254)

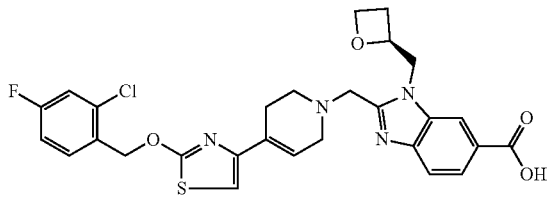 [SMILES: O=C(O)c1ccc2nc(CN3CC=C(c4csc(OCc5ccc(F)cc5Cl)n4)CC3)n(C[C@@H]3CCO3)c2c1]

Prepared in analogous manner as for Compound 250. LCMS: [M+H]$^+$=569.0; Retention time (10 mM NH$_4$HCO$_3$)=1.59 min.

$^1$H NMR (400 MHz, CD$_3$OD) δ 8.31 (s, 1H), 8.00-7.97 (m, 1H), 7.69-7.67 (m, 1H), 7.64-7.62 (m, 1H), 7.31-7.29 (m, 1H), 7.15-7.10 (m, 1H), 6.67 (s, 1H), 6.55-6.52 (m, 1H), 5.54 (s, 2H), 5.28-5.22 (m, 1H), 4.88-4.86 (m, 1H), 4.74-4.70 (m, 1H), 4.66-4.60 (m, 1H), 4.50-4.45 (m, 1H), 4.12 (dd, J=13.6 Hz, 2H), 3.28-3.22 (m, 2H), 2.84-2.79 (m, 2H), 2.77-2.73 (m, 1H), 2.56-2.48 (m, 3H).

(S)-1-(oxetan-2-ylmethyl)-2-((4-(2-((6-(trifluoromethyl)pyridin-3-yl)methoxy)thiazol-4-yl)-3,6-dihydropyridin-1(2H)-yl)methyl)-1H-benzo[d]imidazole-6-carboxylic acid (Compound 255)

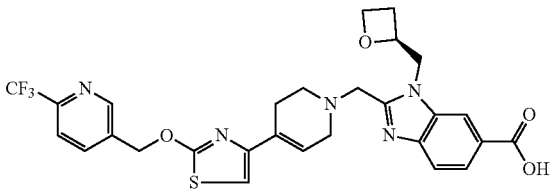 [SMILES: O=C(O)c1ccc2nc(CN3CC=C(c4csc(OCc5ccc(C(F)(F)F)nc5)n4)CC3)n(C[C@@H]3CCO3)c2c1]

Prepared in analogous manner as for Compound 250. LCMS: [M+H]$^+$=586.3; Retention time (10 mM NH$_4$HCO$_3$)=1.50 min, Purity: 100% (254 nm).

$^1$H NMR (400 MHz, DMSO-D6) δ 8.90 (s, 1H), 8.27-8.18 (m, 2H), 7.96 (d, J=8.1 Hz, 1H), 7.80 (dd, J=8.4, 1.5 Hz, 1H), 7.63 (d, J=8.4 Hz, 1H), 6.87 (s, 1H), 6.45 (s, 1H), 5.61 (brs, 2H), 5.09-5.01 (m, 1H), 4.79 (dd, J=15.1, 7.2 Hz, 1H), 4.63 (dd, J=15.2, 2.6 Hz, 1H), 4.47 (dd, J=13.6, 7.7 Hz, 1H), 4.36 (dt, J=8.9, 5.9 Hz, 1H), 4.05 (d, J=13.5 Hz, 1H), 3.89 (d, J=13.5 Hz, 1H), 3.18 (d, J=9.3 Hz, 2H), 2.75-2.60 (m, 3H), 2.43-2.32 (m, 3H).

(S)-1-(oxetan-2-ylmethyl)-2-((4-(2-((4-(trifluoromethyl)benzyl)oxy)thiazol-4-yl)-3,6-dihydropyridin-1(2H)-yl)methyl)-1H-benzo[d]imidazole-6-carboxylic acid (Compound 256)

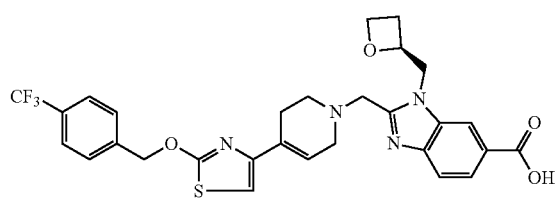 [SMILES: O=C(O)c1ccc2nc(CN3CC=C(c4csc(OCc5ccc(C(F)(F)F)cc5)n4)CC3)n(C[C@@H]3CCO3)c2c1]

Prepared in analogous manner as for Compound 250. LCMS: [M+H]⁺=585.0; Retention time (10 mM NH₄HCO₃)= 1.61 min ¹H NMR (400 MHz, DMSO-D6) δ 8.23 (s, 1H), 7.81-7.76 (m, 3H), 7.70 (d, J=8 Hz, 2H), 7.62 (d, J=8.8 Hz, 1H), 6.85 (s, 1H), 6.43 (s, 1H), 5.55 (s, 2H), 5.05 (t, J=4.4 Hz, 1H), 4.81-4.75 (m, 1H), 4.63 (dd, J=3.2 Hz, J=15.6 Hz, 1H), 4.45 (t, J=5.6 Hz, 1H), 4.38-4.33 (m, 1H), 4.05 (d, J=13.6 Hz, 1H), 3.88 (d, J=13.6 Hz, 1H), 3.19-3.12 (m, 2H), 2.70-2.63 (m, 3H), 2.43-2.32 (m, 3H).

(S)-2-(4-(6-((4-chloro-2-fluorobenzyl)oxy)pyridin-2-yl)-2,5-difluorobenzyl)-1-(oxetan-2-ylmethyl)-1H-benzo[d]imidazole-6-carboxylic acid (Compound 257)

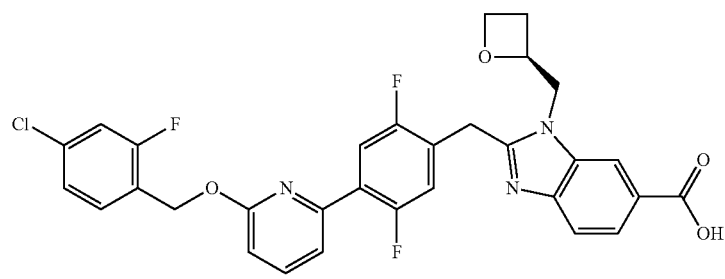 [SMILES: O=C(O)c1ccc2nc(Cc3cc(F)c(-c4cccc(OCc5ccc(Cl)cc5F)n4)cc3F)n(C[C@@H]3CCO3)c2c1]

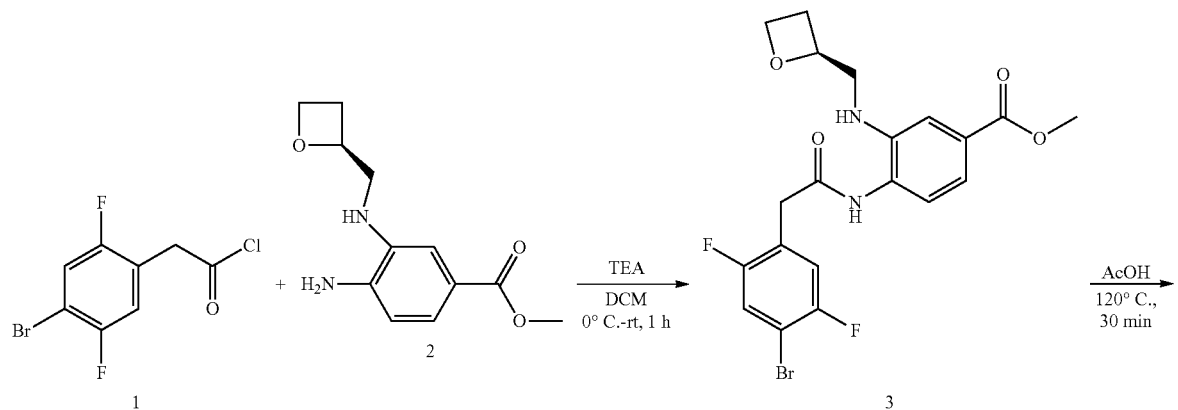

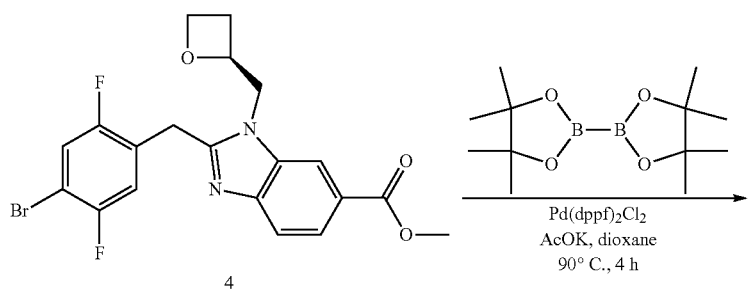

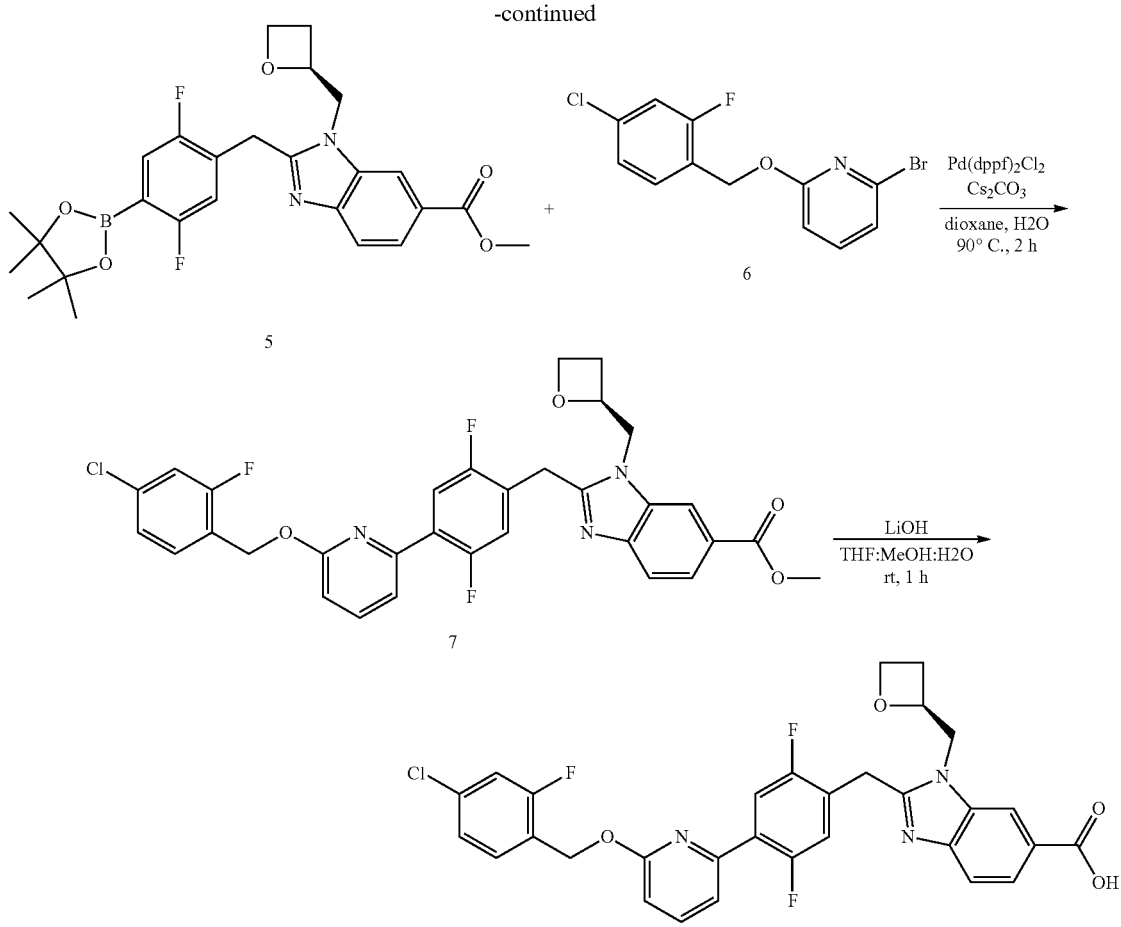

Step 1

To a mixture of methyl 4-amino-3-[[(2S)-oxetan-2-yl]methylamino] benzoate (100 mg, 423 μmol) in DCM (20 mL) was added slowly 2-(4-bromo-2, 5-difluoro-phenyl) acetyl chloride (228 mg, 847 mol) in DCM (20 mL) at ice-bath, and stirred for 1 h at rt, until the reaction was complete as indicated by LCMS, the reaction mixture was concentrated in vacuo, purified by prep-TLC (Hexanes/EtOAc=1:2) to give the desired product methyl 4-[[2-(4-bromo-2, 5-difluoro-phenyl) acetyl] amino]-3-[[(2S)-oxetan-2-yl] methylamino] benzoate (71 mg, 151 μmol, 35.9% yield) as a pale yellow solid. LCMS: [M+H]$^+$=469.0; Retention time=1.57 min.

Step 2

A mixture of methyl 4-[[2-(4-bromo-2, 5-difluoro-phenyl) acetyl] amino]-3-[[(2S)-oxetan-2-yl]methylamino] benzoate (71 mg, 151 μmol) in AcOH (5 mL) was stirred for 30 min at 120° C., until the reaction was complete as indicated by LCMS, the reaction mixture was concentrated in vacuo, purified by silica gel chromatography (Hexanes/EtOAc=20:1) to give the desired product methyl (S)-2-(4-bromo-2,5-difluorobenzyl)-1-(oxetan-2-ylmethyl)-1H-benzo[d]imidazole-6-carboxylate (40 mg, 89 μmol, 58.6% yield) as pale yellow solid. LCMS: [M+H]$^+$=451.1; Retention time (0.01% TFA)=1.49 min.

Step 3

A mixture of (S)-2-(4-bromo-2,5-difluorobenzyl)-1-(oxetan-2-ylmethyl)-1H-benzo[d]imidazole-6-carboxylate (40 mg, 89 μmol), 4, 4, 5, 5-tetramethyl-2-(4, 4, 5, 5-tetramethyl-1, 3, 2-dioxaborolan-2-yl)-1, 3, 2-dioxaborolane (29 mg, 115 μmol), Pd(dppf)Cl$_2$ (8 mg, 11 μmol) and KOAc (13 mg, 133 μmol) in dioxane (10 mL) was stirred for 2 h at 90° C. under Argon, until the reaction was complete as indicated by LCMS, the reaction mixture was filtered through a pad of Celite with EtOAc, and the combined organics were concentrated in vacuo to give the desired product methyl (S)-2-(2,5-difluoro-4-(4,4,5,5-tetramethyl-1,3,2-dioxaborolan-2-yl)benzyl)-1-(oxetan-2-ylmethyl)-1H-benzo[d]imidazole-6-carboxylate (42 mg, 33.0% yield) as a pale yellow solid. The crude was directly used in next step without further purification.

LCMS: [M+H]$^+$=452.9; Retention time=1.83 min.

Step 4

A mixture of methyl (S)-2-(2,5-difluoro-4-(4,4,5,5-tetramethyl-1,3,2-dioxaborolan-2-yl)benzyl)-1-(oxetan-2-ylmethyl)-1H-benzo[d]imidazole-6-carboxylate (42 mg, 84 μmol), 2-bromo-6-[(4-chloro-2-fluoro-phenyl) methoxy] pyridine (32 mg, 101 μmol), Pd(dppf)Cl$_2$ (6 mg, 8 μmol) and K$_2$CO$_3$ (15 mg, 110 μmol) in dioxane (5 mL) and H$_2$O (1 mL) was stirred for 1 h at 90° C. under Argon, until the reaction was complete as indicated by LCMS, the reaction mixture was filtered through a pad of Celite with EtOAc, and the combined organics were concentrated in vacuo, purified by silica gel chromatography (Hexanes/EtOAc=20:1) to give the desired product methyl (S)-2-(4-(6-((4-chloro-2-fluorobenzyl)oxy)pyridin-2-yl)-2,5-difluorobenzyl)-1-(oxetan-2-ylmethyl)-1H-benzo[d]imidazole-6-carboxylate (12 mg, 20 μmol, 24.0% yield) as pale yellow solid. LCMS: [M+H]$^+$=608.0; Retention time=2.28 min.

Step 5

To a mixture of methyl (S)-2-(4-(6-((4-chloro-2-fluorobenzyl)oxy)pyridin-2-yl)-2,5-difluorobenzyl)-1-(oxetan-2-ylmethyl)-1H-benzo[d]imidazole-6-carboxylate (13 mg, 21 μmol) in THF:MeOH:H₂O (3 mL:3 mL:1 mL) was added LiOH (5 mg, 107 μmol), and stirred for 1 h at rt, until the reaction was complete as indicated by LCMS, the reaction mixture was concentrated in vacuo, adjusted pH=7 with aqueous acetic acid (50%), purified by prep-HPLC to give the desired product (S)-2-(4-(6-((4-chloro-2-fluorobenzyl)oxy)pyridin-2-yl)-2,5-difluorobenzyl)-1-(oxetan-2-ylmethyl)-1H-benzo[d]imidazole-6-carboxylic acid (10.1 mg, 17 μmol, 79.5% yield) as a white solid. LCMS: [M+H]⁺=594.1; Retention time=1.44 min.

¹H NMR (400 MHz, DMSO-D6) δ 8.24 (brs, 1H), 7.89 (t, J=7.6, 8 Hz, 1H), 7.83 (t, J=6.4, 4.4 Hz, 1H), 7.79 (t, J=7.2, 1.2 Hz, 1H), 7.62-7.58 (m, 2H), 7.52-7.48 (m, 2H), 7.41 (dd, J=6.4, 5.2 Hz, 1H), 7.34 (dd, J=6.4, 1.6 Hz, 1H), 6.95 (d, J=8.4 Hz, 1H), 5.50 (s, 2H), 5.08-5.04 (m, 1H), 4.78 (dd, J=7.2, 8 Hz, 1H), 4.64 (dd, J=2, 13.2 Hz, 1H), 4.54-4.49 (m, 2H), 4.47-4.42 (m, 1H), 4.38-4.33 (m, 1H), 2.74-2.67 (m, 1H), 2.45-2.33 (m, 1H).

(S)-2-(2-chloro-4-(6-((4-chloro-2-fluorobenzyl)oxy)pyridin-2-yl)benzyl)-1-(oxetan-2-ylmethyl)-1H-benzo[d]imidazole-6-carboxylic acid (Compound 258)

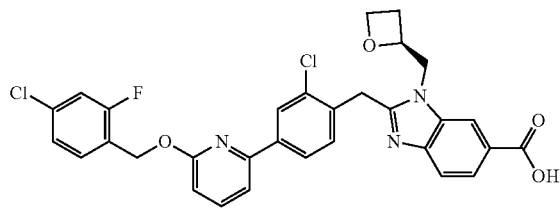 [SMILES: O=C(O)c1ccc2nc(Cc3ccc(-c4cccc(OCc5ccc(Cl)cc5F)n4)cc3Cl)n(C[C@@H]3CCO3)c2c1]

Prepared in analogous manner as for Compound 257. LCMS: [M+H]⁺=593.1; Retention time=1.55 min.

¹H NMR (400 MHz, DMSO-D6) δ 8.25 (s, 1H), 8.15-8.14 (m, 1H), 8.03-8.00 (dd, J=8.1, 1.8 Hz, 1H), 7.88-7.82 (m, 1H), 7.80-7.77 (m, 1H), 7.68-7.55 (m, 3H), 7.52-7.48 (dd, J=10.0, 2.0 Hz, 1H), 7.46-7.43 (m, 1H), 7.34-7.31 (dd, J=8.2, 1.9 Hz, 1H), 6.91-6.88 (m, 1H), 5.52 (s, 2H), 5.10-5.04 (m, 1H), 4.75-4.69 (m, 1H), 4.63-4.56 (m, 2H), 4.52-4.47 (m, 2H), 4.40-4.35 (m, 1H), 2.74-2.67 (m, 1H), 2.43-2.39 (m, 1H).

(S)-2-(4-(4-((4-chloro-2-fluorobenzyl)oxy)pyrimidin-2-yl)-3-fluorobenzyl)-1-(oxetan-2-ylmethyl)-1H-benzo[d]imidazole-6-carboxylic acid (Compound 259)

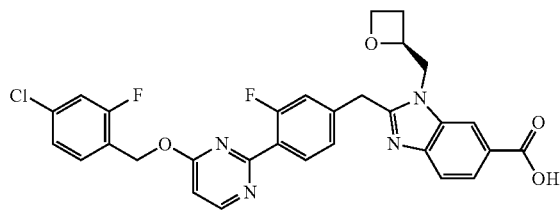 [SMILES: O=C(O)c1ccc2nc(Cc3ccc(-c4nccc(OCc5ccc(Cl)cc5F)n4)c(F)c3)n(C[C@@H]3CCO3)c2c1]

Prepared in analogous manner as for Compound 257. LCMS: [M+H]⁺=577.0; Retention time=1.54 min.

¹H NMR (400 MHz, MeOD) δ 8.61 (dd, J=23.8, 5.1 Hz, 1H), 8.30 (s, 1H), 8.17-7.99 (m, 2H), 7.70 (dd, J=8.5, 4.7 Hz, 1H), 7.62-7.57 (m, 1H), 7.34-7.20 (m, 4H), 6.88 (d, J=5.9 Hz, 1H), 5.59 (s, 2H), 5.16-5.11 (m, 1H), 4.71-4.62 (m, 2H), 4.60 (d, J=5.2 Hz, 2H), 4.52 (d, J=15.6 Hz, 1H), 4.47-4.41 (m, 1H), 2.76 (d, J=8.3 Hz, 1H), 2.49-2.44 (m, 1H).

(S)-2-(4-(6-(4-chloro-2-fluorobenzyloxy-3,5-difluoropyridin-2-yl)-2-fluorobenzyl)-1-(oxetan-2-ylmethyl)-1H-benzo[d]imidazole-6-carboxylic acid (Compound 260)

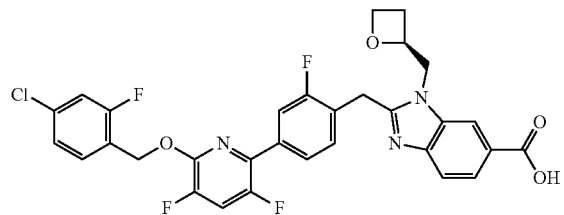 [SMILES: O=C(O)c1ccc2nc(Cc3ccc(-c4nc(OCc5ccc(Cl)cc5F)c(F)cc4F)cc3F)n(C[C@@H]3CCO3)c2c1]

Prepared in analogous manner as for Compound 257. LCMS: [M+H]⁺=612.0; Retention time=1.65 min.

¹H NMR (400 MHz, DMSO-D6) δ 8.22 (d, J=0.9 Hz, 1H), 8.14 (t, J=9.9 Hz, 1H), 7.78 (dd, J=8.4, 1.5 Hz, 1H), 7.72 (t, J=8.7 Hz, 2H), 7.62 (t, J=8.2 Hz, 1H), 7.58-7.44 (m, 3H), 7.35 (dd, J=8.2, 1.8 Hz, 1H), 5.57 (s, 2H), 5.10-4.98 (m, 1H), 4.72 (dd, J=15.6, 7.1 Hz, 1H), 4.63-4.29 (m, 5H), 2.75-2.64 (m, 1H), 2.38 (dt, J=11.1, 7.1 Hz, 1H).

(S)-2-(4-(6-(4-chloro-2-fluorobenzyloxy)-3-fluoropyridin-2-yl)-3-fluorobenzyl)-1-(oxetan-2-ylmethyl)-1H-benzo[d]imidazole-6-carboxylic acid (Compound 261)

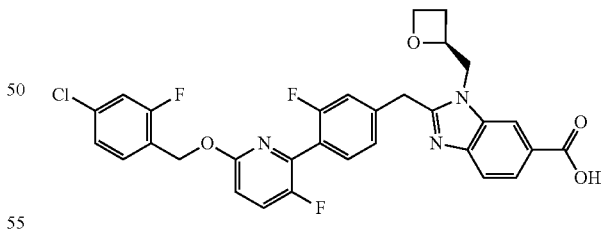

Prepared in analogous manner as for Compound 257. LCMS: [M+H]⁺=594.1; Retention time (10 mM NH₄HCO₃)=1.53 min.

¹H NMR (400 MHz, DMSO-D6) δ 8.20 (s, 1H), 7.80-7.86 (m, 2H), 7.55-7.61 (m, 3H), 7.48 (dd, J=2.0, 10.0 Hz, 1H), 7.32-7.36 (m, 3H), 7.02 (dd, J=3.2 Hz, 9.2 Hz, 1H), 5.38 (s, 2H), 4.97-5.03 (m, 1H), 4.68-4.72 (m, 1H), 4.44-4.58 (m, 4H), 4.34-4.39 (m, 1H), 2.66-2.70 (m, 1H), 2.33-2.42 (m, 1H).

(S)-2-(4-(6-(4-chloro-2-fluorobenzyloxy)pyridin-2-yl)-2,3-difluorobenzyl)-1-(oxetan-2-ylmethyl)-1H-benzo[d]imidazole-6-carboxylic acid (Compound 262)

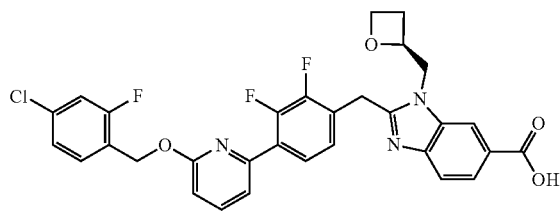 [SMILES: O=C(O)c1ccc2nc(Cc3ccc(-c4cccc(OCc5ccc(Cl)cc5F)n4)c(F)c3F)n(C[C@@H]3CCO3)c2c1]

Prepared in analogous manner as for Compound 257. LCMS: [M+H]⁺=594.0; Retention time (0.01% TFA)=1.67 min.

¹H NMR (400 MHz, DMSO-D6) δ 8.20 (s, 1H), 7.92-7.86 (m, 1H), 7.82-7.73 (m, 2H), 7.61 (t, J=8.2 Hz, 1H), 7.56-7.47 (m, 3H), 7.36-7.26 (m, 2H), 6.95 (d, J=8.2 Hz, 1H), 5.48 (s, 2H), 5.12-5.04 (m, 1H), 4.77-4.68 (m, 1H), 4.64-4.55 (m, 2H), 4.54-4.46 (m, 2H), 4.40-4.32 (m, 1H), 2.77-2.66 (m, 1H), 2.45-2.32 (m, 1H).

(S)-2-(4-(4-(4-cyano-2-fluorobenzyloxy)-5-fluoropyrimidin-2-yl)-2-fluorobenzyl)-3-(oxetan-2-ylmethyl)-3H-imidazo[4,5-b]pyridine-5-carboxylic acid (Compound 263)

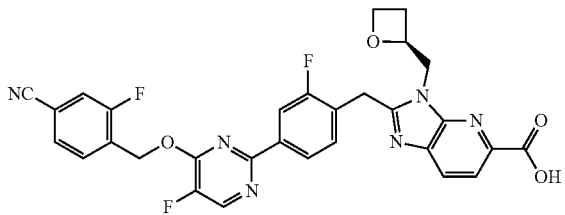 [SMILES: N#Cc1ccc(COc2nc(-c3ccc(Cc4nc5ccc(C(=O)O)nc5n4C[C@@H]4CCO4)c(F)c3)ncc2F)c(F)c1]

Prepared in analogous manner as for Compound 257. LCMS: [M+H]⁺=587.0; Retention time=1.50 min.

¹H NMR (400 MHz, DMSO-D6) δ 8.79 (d, J=2.8 Hz, 1H), 8.12 (dd, J=8.0 Hz, 1.6 Hz, 1H), 8.08-8.02 (m, 2H), 7.99-7.93 (m, 2H), 7.84 (t, J=7.5 Hz, 1H), 7.82 (dd, J=8.0 Hz, 1.6 Hz, 1H), 7.51 (t, J=7.8 Hz, 1H), 5.81 (s, 2H), 5.18-5.10 (m, 1H), 4.72 (dd, J=15.1, 6.4 Hz, 1H), 4.68-4.54 (m, 3H), 4.53-4.49 (m, 1H), 4.38-4.32 (m, 1H), 2.69-2.65 (m, 1H), 2.39-2.31 (m, 1H).

(S)-2-(4-(6-((4-cyano-2-fluorobenzyl)oxy)-5-fluoropyridin-2-yl)-2-fluorobenzyl)-1-(oxetan-2-ylmethyl)-1H-benzo[d]imidazole-6-carboxylic acid (Compound 264)

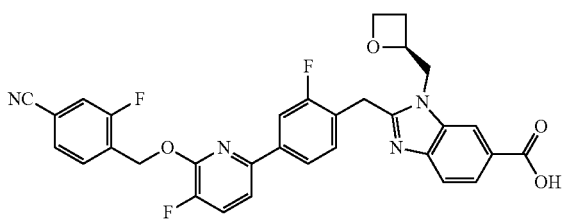 [SMILES: N#Cc1ccc(COc2nc(-c3ccc(Cc4nc5ccc(C(=O)O)cc5n4C[C@@H]4CCO4)c(F)c3)ccc2F)c(F)c1]

Prepared in analogous manner as for Compound 257. LCMS: [M+H]⁺=585.1; Retention time=1.43 min.

¹H NMR (400 MHz, DMSO-D6) δ 8.24 (s, 1H), 7.94 (d, J=8.7 Hz, 1H), 7.87-7.79 (m, 4H), 7.76 (dd, J=13.3, 8.0 Hz, 3H), 7.69 (d, J=8.3, 2.7 Hz, 1H), 7.58 (d, J=8.4 Hz, 1H), 5.71 (s, 2H), 5.05-4.98 (m, 1H), 4.72 (dd, J=15.6, 7.2 Hz, 1H), 4.62-4.47 (m, 3H), 4.44-4.31 (m, 2H), 2.74-2.66 (m, 1H), 2.42-2.36 (m, 1H).

(S)-2-(4-(6-((4-chloro-2-fluorobenzyl)oxy)pyrazin-2-yl)-2-fluorobenzyl)-1-(oxetan-2-ylmethyl)-1H-benzo[d]imidazole-6-carboxylic acid (Compound 265)

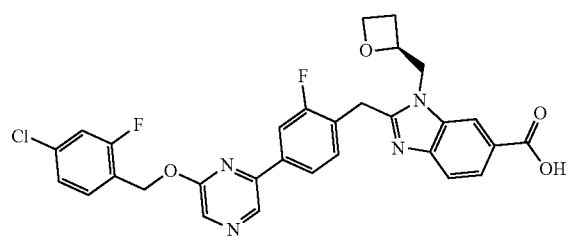 [SMILES: O=C(O)c1ccc2nc(Cc3ccc(-c4cncc(OCc5ccc(Cl)cc5F)n4)cc3F)n(C[C@@H]3CCO3)c2c1]

Prepared in analogous manner as for Compound 257. LCMS: [M+H]⁺=577.7; Retention time (10 mM NH₄HCO₃)=1.55 min.

¹H NMR (400 MHz, DMSO-D6) δ 8.92 (s, 1H), 8.36 (s, 1H), 8.25 (s, 1H), 7.98 (dd, J=16.0, 8.0 Hz, 2H), 7.78 (dd, J=8.0, 4.0 Hz, 1H), 7.66 (t, J=8.2 Hz, 1H), 7.58 (d, J=8.4 Hz, 1H), 7.55-7.46 (m, 2H), 7.35 (dd, J=8.2, 1.8 Hz, 1H), 5.57 (s, 2H), 5.11-4.99 (m, 1H), 4.72 (d, J=7.0 Hz, 1H), 4.65-4.54 (m, 1H), 4.54-4.41 (m, 3H), 4.36 (dd, J=5.9, 3.1 Hz, 1H), 2.77-2.63 (m, 1H), 2.44-2.31 (m, 1H).

(S)-2-(4-(4-((4-cyano-2-fluorobenzyl)oxy)-5-fluoropyrimidin-2-yl)-2-fluorobenzyl)-1-(oxetan-2-ylmethyl)-1H-benzo[d]imidazole-6-carboxylic acid (Compound 266)

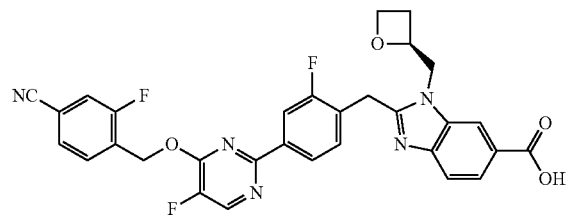 [SMILES: N#Cc1ccc(COc2nc(-c3ccc(Cc4nc5ccc(C(=O)O)cc5n4C[C@@H]4CCO4)c(F)c3)ncc2F)c(F)c1]

Prepared in analogous manner as for Compound 257. LCMS: [M+H]⁺=586.3; Retention time=1.51 min ¹H NMR (400 MHz, DMSO-D6): δ 8.78 (d, J=3.2 Hz, 1H), 8.24 (s, 1H), 8.11 (dd, J=1.6, 8.4 Hz, 1H), 8.04 (dd, J=1.6, 11.6 Hz, 1H), 7.97 (dd, J=1.2, 10 Hz, 1H), 8.45 (t, J=7.6 Hz, 1H), 7.79-7.76 (m, 2H), 7.57 (t, J=8.8 Hz, 1H), 7.48 (t, J=7.6 Hz, 1H), 5.80 (s, 2H), 5.05-5.03 (m, 1H), 4.75-4.69 (m, 1H), 4.59 (dd, J=2, 15.2 Hz, 1H), 4.52-4.43 (m, 3H), 4.37-4.32 (m, 1H), 2.71-2.67 (m, 1H), 2.39-2.32 (m, 1H).

(S)-2-(4-(6-(2,4-difluorobenzyloxy)-5-fluoropyridin-2-yl)-3-fluorobenzyl)-3-(oxetan-2-ylmethyl)-3H-imidazo[4,5-b]pyridine-5-carboxylic acid (Compound 267)

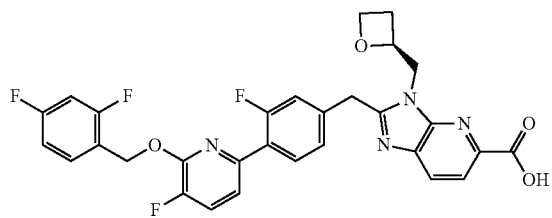 [SMILES: O=C(O)c1ccc2nc(Cc3ccc(-c4ccc(F)c(OCc5ccc(F)cc5F)n4)c(F)c3)n(C[C@@H]3CCO3)c2n1]

Prepared in analogous manner as for Compound 257. LCMS: [M+H]⁺=579.1; Retention time (10 mM NH₄HCO₃)=1.45 min.

¹H NMR (400 MHz, DMSO-D6) δ 8.05 (d, J=8.4 Hz, 1H), 7.97-7.93 (m, 2H), 7.81 (dd, J=8.4 Hz, 10.4 Hz, 1H), 7.70-7.64 (m, 1H), 7.48-7.46 (m, 1H), 7.36-7.31 (m, 3H), 7.17-7.12 (m, 1H), 5.55 (s, 2H), 5.15-5.09 (m, 1H), 4.73-4.67 (m, 1H), 4.60-4.47 (m, 4H), 4.40-4.35 (m, 1H), 2.72-2.68 (m, 1H), 2.47-2.42 (m, 1H).

(S)-2-(4-(6-((4-cyano-2-fluorobenzyl)oxy)-3-fluoropyridin-2-yl)-2-fluorobenzyl)-1-(oxetan-2-ylmethyl)-1H-benzo[d]imidazole-6-carboxylic acid (Compound 268)

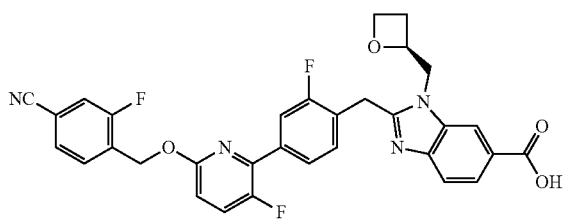 [SMILES: N#Cc1ccc(COc2ccc(F)c(-c3ccc(Cc4nc5ccc(C(=O)O)cc5n4C[C@@H]4CCO4)c(F)c3)n2)c(F)c1]

Prepared in analogous manner as for Compound 257. LCMS: [M+H]⁺=585.0; Retention time=1.55 min.

¹H NMR (400 MHz, DMSO-D6) δ 8.20 (s, 1H), 7.93 (d, J=10.2 Hz, 1H), 7.86 (dd, J=10.4, 9.0 Hz, 1H), 7.74 (dt, J=15.8, 10.3 Hz, 5H), 7.54 (d, J=8.4 Hz, 1H), 7.47 (t, J=7.9 Hz, 1H), 7.02 (dd, J=8.9, 2.6 Hz, 1H), 5.57 (s, 2H), 5.05 (d, J=4.6 Hz, 1H), 4.71 (dd, J=15.5, 7.0 Hz, 1H), 4.61-4.55 (m, 1H), 4.54-4.30 (m, 4H), 2.75-2.65 (m, 1H), 2.42-2.34 (m, 1H).

(S)-2-(4-(6-((5-chloropyridin-2-yl)methoxy)pyridin-2-yl)-2,5-difluorobenzyl)-1-(oxetan-2-ylmethyl)-1H-benzo[d]imidazole-6-carboxylic acid (Compound 269)

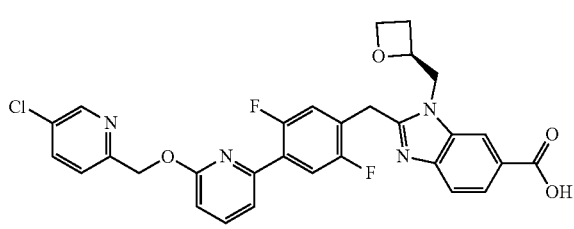 [SMILES: O=C(O)c1ccc2nc(Cc3cc(F)c(-c4cccc(OCc5ccc(Cl)cn5)n4)cc3F)n(C[C@@H]3CCO3)c2c1]

Prepared in analogous manner as for Compound 257. LCMS: [M+H]⁺=576.9; Retention time=1.52 min.

¹H NMR (400 MHz, DMSO-D6) δ 8.63-8.62 (m 1H), 8.24 (s, 1H), 7.97-7.87 (m, 2H), 7.79-7.77 (m, 1H), 7.66-7.62 (m, 1H), 7.59-7.51 (m, 3H), 7.38-7.34 (m, 1H), 7.02 (d, J=8.2 Hz, 1H), 5.54 (s, 2H), 5.09-5.06 (m, 1H), 4.77-4.71 (m, 1H), 4.63-4.58 (m, 1H), 4.53-4.44 (m, 3H), 4.40-4.33 (m, 1H), 2.73-2.67 (m, 1H), 2.42-2.34 (m, 1H).

(S)-2-(4-(6-((4-chloro-2-fluorobenzyl)oxy)pyridin-2-yl)-3-methylbenzyl)-1-(oxetan-2-ylmethyl)-1H-benzo[d]imidazole-6-carboxylic acid (Compound 270)

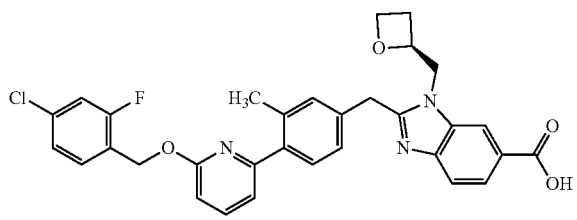 [SMILES: Cc1cc(Cc2nc3ccc(C(=O)O)cc3n2C[C@@H]2CCO2)ccc1-c1cccc(OCc2ccc(Cl)cc2F)n1]

Prepared in analogous manner as for Compound 257. LCMS: [M+H]⁺=572.0; Retention time=1.65 min.

¹H NMR (400 MHz, DMSO-D6): δ 8.22 (brs, 1H), 7.83-7.82 (m, 2H), 7.62 (d, J=8.4 Hz, 1H), 7.55 (t, J=8.4 Hz, 1H), 7.47 (dd, J=2 Hz, J=8 Hz, 1H), 7.36 (d, J=8 Hz, 1H), 7.31 (dd, J=8 Hz, J=6.4 Hz, 1H), 7.24-7.20 (m, 2H), 7.14 (d, J=8 Hz, 1H), 6.85 (d, J=8.4 Hz, 1H), 5.39 (s, 2H), 4.966-4.93 (m, 1H), 4.69-4.63 (m, 1H), 4.55-4.44 (m, 2H), 4.40-4.33 (m, 3H), 2.67-2.63 (m, 1H), 2.39-2.29 (m, 4H).

(S)-2-(4-(6-((4-cyano-2-fluorobenzyl)oxy)pyridin-2-yl)-2,5-difluorobenzyl)-1-(oxetan-2-ylmethyl)-1H-benzo[d]imidazole-6-carboxylic acid (Compound 271)

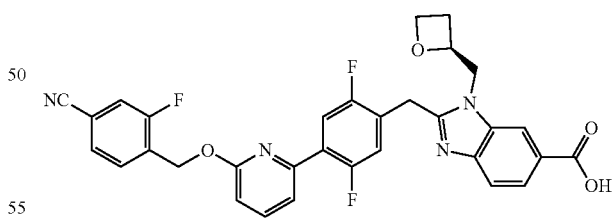

Prepared in analogous manner as for Compound 257. LCMS: [M+H]⁺=585.1; Retention time=1.36 min.

¹H NMR (400 MHz, DMSO-D6-d6) δ 8.24 (brs, 1H), 7.93-7.87 (m, 2H), 7.79-7.71 (m, 4H), 7.59 (d, J=8.4 Hz, 1H), 7.53 (dd, J=1.2, 6.4 Hz, 1H), 7.40 (dd, J=6.4, 5.2 Hz, 1H), 7.00 (d, J=8.4 Hz, 1H), 5.59 (s, 2H), 5.08 (qd, J=2.8, 7.8 Hz, 1H), 4.77 (dd, J=7.2, 8.4 Hz, 1H), 4.63 (dd, J=2.4, 13.2 Hz, 1H), 4.54-4.49 (m, 2H), 4.46 (d, J=6 Hz, 1H), 4.36-4.33 (m, 1H), 2.70-2.67 (m, 1H), 2.37-2.32 (m, 1H).

(S)-2-(4-(4-((5-chloro-3-fluoropyridin-2-yl)methoxy)-5-fluoropyrimidin-2-yl)-2,5-difluorobenzyl)-1-(oxetan-2-ylmethyl)-1H-benzo[d]imidazole-6-carboxylic acid (Compound 272)

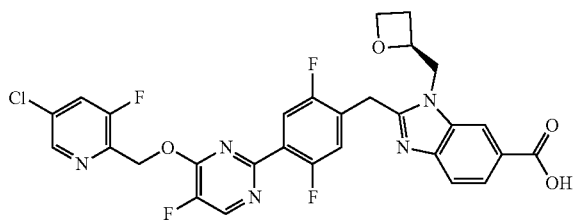 [SMILES: O=C(O)c1ccc2nc(Cc3cc(F)c(-c4ncc(F)c(OCc5ncc(Cl)cc5F)n4)cc3F)n(C[C@@H]3CCO3)c2c1]

Prepared in analogous manner as for Compound 257. LCMS: [M+H]⁺=614.0; Retention time=1.48 min.
¹H NMR (400 MHz, DMSO-D6) δ 8.83 (d, J=2.9 Hz, 1H), 8.54 (d, J=1.4 Hz, 1H), 8.27-8.15 (m, 2H), 7.78 (td, J=8.8, 3.9 Hz, 2H), 7.59 (d, J=8.4 Hz, 1H), 7.37 (dd, J=11.1, 6.0 Hz, 1H), 5.78 (d, J=1.6 Hz, 2H), 5.13-5.02 (m, 1H), 4.74 (dd, J=15.5, 7.0 Hz, 1H), 4.64-4.58 (m, 1H), 4.56-4.41 (m, 3H), 4.35 (dt, J=9.0, 5.9 Hz, 1H), 2.75-2.65 (m, 1H), 2.38 (dt, J=11.3, 7.1 Hz, 1H).

(S)-2-(4-(4-((5-chloro-3-fluoropyridin-2-yl)methoxy)-5-fluoropyrimidin-2-yl)-2,5-difluorobenzyl)-3-(oxetan-2-ylmethyl)-3H-imidazo[4,5-b]pyridine-5-carboxylic acid (Compound 273)

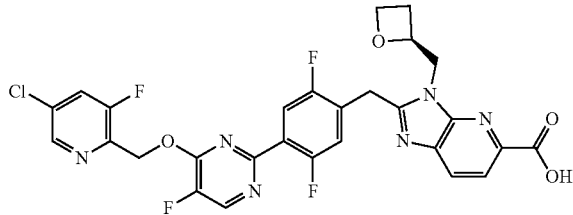

Prepared in analogous manner as for Compound 257. LCMS: [M+H]⁺=615.0; Retention time=1.37 min.
¹H NMR (400 MHz, DMSO-D6) δ 8.83 (d, J=2.9 Hz, 1H), 8.54 (d, J=1.3 Hz, 1H), 8.20 (dd, J=9.7, 2.0 Hz, 1H), 8.04 (d, J=8.2 Hz, 1H), 7.94 (d, J=8.2 Hz, 1H), 7.78 (dd, J=10.2, 6.3 Hz, 1H), 7.40 (dd, J=11.0, 6.0 Hz, 1H), 5.77 (d, J=1.6 Hz, 2H), 5.18-5.12 (m, 1H), 4.74 (dd, J=15.2, 6.2 Hz, 1H), 4.63 (dd, J=10.3, 6.8 Hz, 2H), 4.56-4.48 (m, 2H), 4.37-4.31 (m, 1H), 2.74-2.68 (m, 1H), 2.45-2.40 (m, 1H).

(S)-2-(4-(6-((2,4-difluorobenzyl)oxy)pyridin-2-yl)-2-fluorobenzyl)-1-(oxetan-2-ylmethyl)-1H-benzo[d]imidazole-6-carboxylic acid (Compound 274)

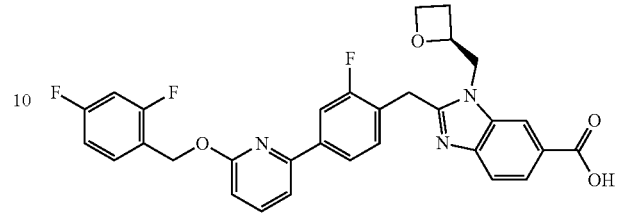

Prepared in analogous manner as for Compound 257. LCMS: [M+H]⁺=560.0; Retention time=1.59 min.
¹H NMR (400 MHz, DMSO-D6-d6) δ 8.23 (brs, 1H), 7.94 (t, J=10, 6.4 Hz, 2H), 7.85 (t, J=8, 8 Hz, 1H), 7.79 (dd, J=1.2, 7.2 Hz, 1H), 7.68 (q, J=8.8, 8 Hz, 2H), 7.58 (d, J=8.4 Hz, 1H), 7.45 (t, J=7.6, 8.4 Hz, 1H), 7.33 (dt, J=2.4, 8 Hz, 1H), 7.14 (dt, J=2.4, 6.4 Hz, 1H), 6.87 (d, J=8 Hz, 1H), 5.50 (s, 2H), 5.06-5.02 (m, 1H), 4.75 (dd, J=7.2, 8.4 Hz, 1H), 4.60 (dd, J=2.4, 13.6 Hz, 1H), 4.54-4.48 (m, 2H), 4.46-4.40 (m, 1H), 4.38-4.32 (m, 1H), 2.74-2.67 (m, 1H), 2.42-2.33 (m, 1H).

(S)-2-(4-(4-((5-cyanopyridin-2-yl)methoxy)-5-fluoropyrimidin-2-yl)-2,5-difluorobenzyl)-1-(oxetan-2-ylmethyl)-1H-benzo[d]imidazole-6-carboxylic acid (Compound 275)

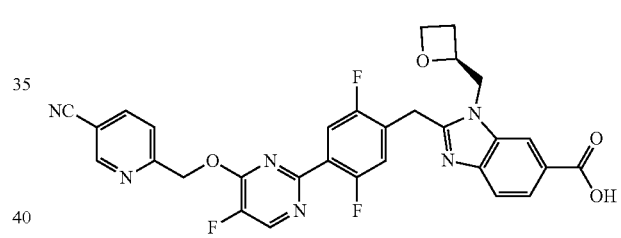

Prepared in analogous manner as for Compound 257. LCMS: [M+H]⁺=587.2; Retention time=1.41 min.
¹H NMR (400 MHz, DMSO-D6) δ 9.03 (d, J=1.4 Hz, 1H), 8.85 (d, J=2.8 Hz, 1H), 8.36 (dd, J=8.2, 2.1 Hz, 1H), 8.24 (s, 1H), 7.83-7.65 (m, 3H), 7.58 (d, J=8.4 Hz, 1H), 7.36 (dd, J=11.1, 6.1 Hz, 1H), 5.79 (s, 2H), 5.06 (d, J=7.0 Hz, 1H), 4.81-4.68 (m, 1H), 4.51 (ddd, J=34.3, 30.6, 14.9 Hz, 4H), 4.34 (dd, J=6.0, 3.0 Hz, 1H), 2.69 (d, J=8.3 Hz, 1H), 2.38 (s, 1H).

(S)-2-(4-(6-((5-chloro-3-fluoropyridin-2-yl)methoxy)pyridin-2-yl)-2,5-difluorobenzyl)-3-(oxetan-2-ylmethyl)-3H-imidazo[4,5-b]pyridine-5-carboxylic acid (Compound 276)

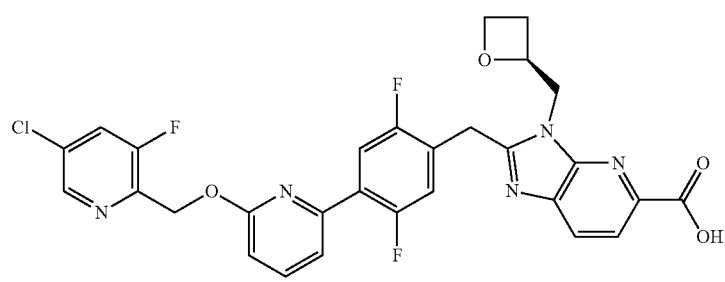

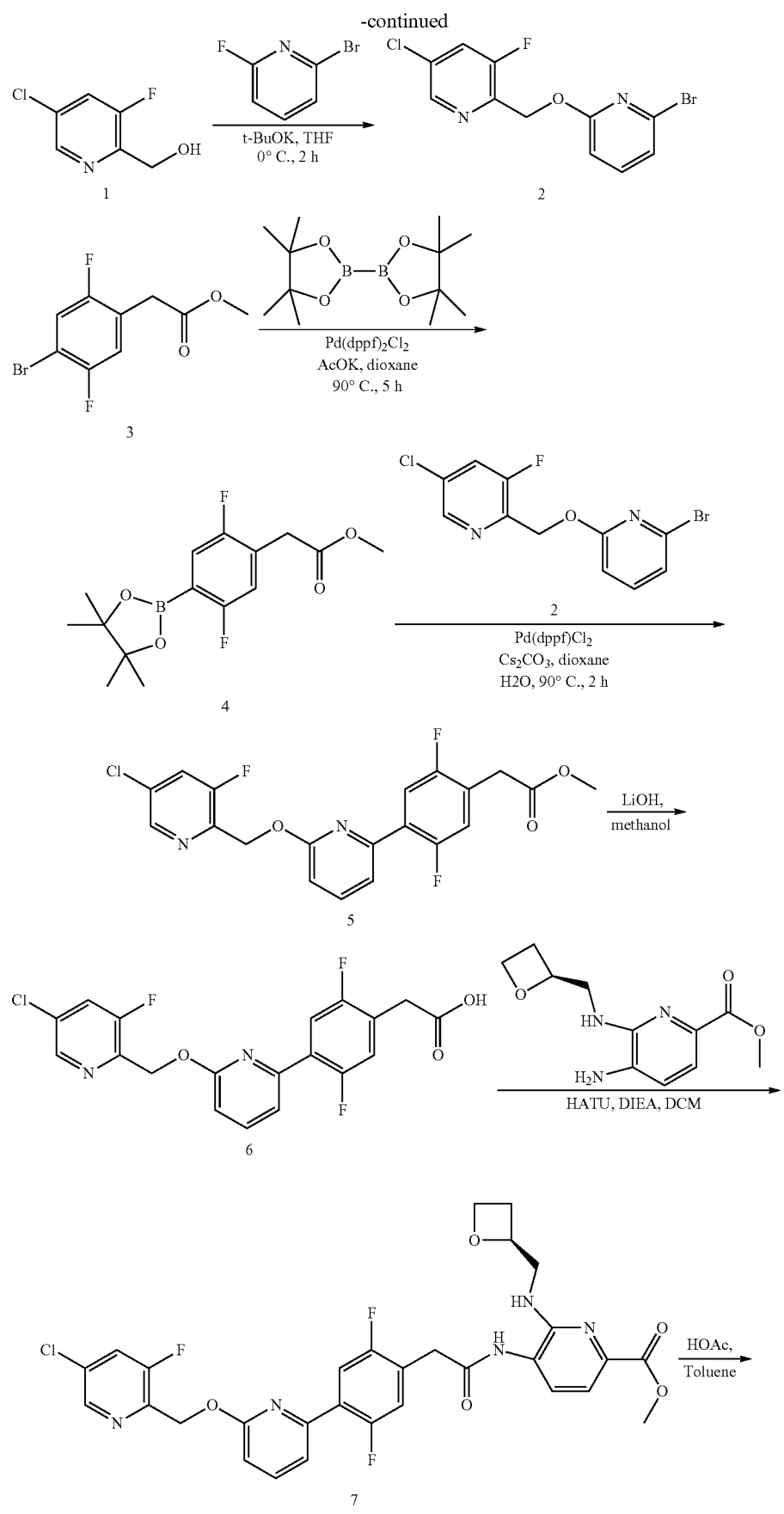

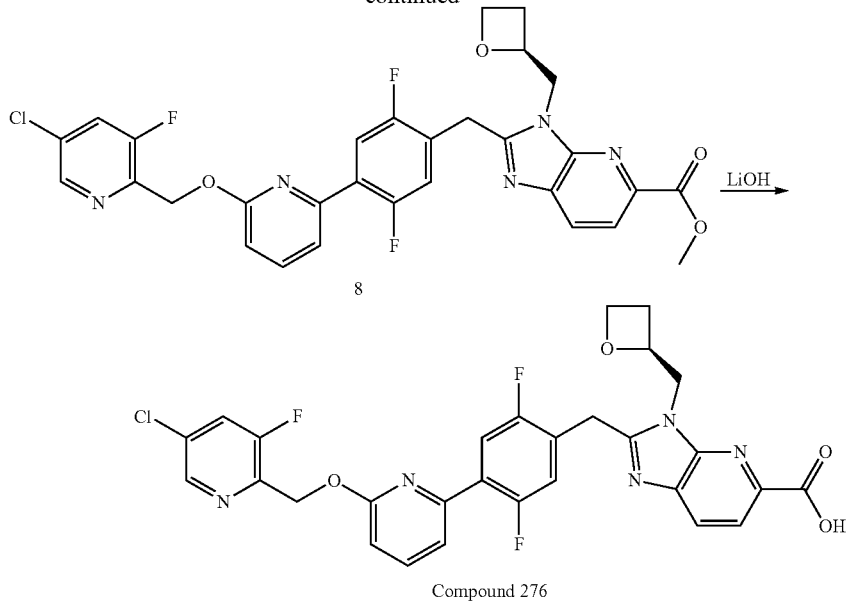

Compound 276

Step 1

To a suspension of (5-chloro-3-fluoro-2-pyridyl)methanol (100 mg, 619 µmol) and 2-bromo-6-fluoro-pyridine (114.4 mg, 650 µmol) in THF (5 mL) was added slowly t-BuOK (76.4 mg, 681 µmol) at 0° C. and stirred for 2 h under $N_2$. After completion of the reaction as judged by LCMS, reaction mixture was quenched with ice-cold water (20 mL) and extracted with EtOAc (3×40 mL). The organic phase was washed with brine (50 mL) and dried over anhydrous $Na_2SO_4$, filtered and concentrated in vacuo. The crude product was purified by flash chromatography ($SiO_2$, hexane/ethyl acetate 10:1) to afford 2-[(6-bromo-2-pyridyl)oxymethyl]-5-chloro-3-fluoro-pyridine (115 mg, 362 µmol) as a white solid.

LCMS: $[M+H]^+$=317.0; Retention time (0.01% TFA)=2.12 min.

Step 2

A mixture of methyl 2-(4-bromo-2,5-difluoro-phenyl)acetate (400 mg, 1.51 mmol), 4,4,5,5-tetramethyl-2-(4,4,5,5-tetramethyl-1,3,2-dioxaborolan-2-yl)-1,3,2-dioxaborolane (459.9 mg, 1.81 mmol), KOAc (296.22 mg, 3.02 mmol) and Pd(dppf)Cl$_2$ (110.4 mg, 151 µmol) in dioxane (8 mL) was stirred for 2 h at 95° C. under $N_2$, until the reaction was complete as indicated by LCMS, the reaction mixture was used in the next run without further purification.

LCMS: $[M+H]^+$=231.1; Retention time (0.01% TFA)=1.53 min.

Step 3

A mixture of 2-[(6-bromo-2-pyridyl)oxymethyl]-5-chloro-3-fluoro-pyridine (110 mg, 346 µmol), methyl 2-[2,5-difluoro-4-(4,4,5,5-tetramethyl-1,3,2-dioxaborolan-2-yl)phenyl]acetate (129.7 mg, 416 µmol), Pd(dppf)Cl$_2$ (50.7 mg, 69 µmol) and Cs$_2$CO3 (225.74 mg, 693 µmol) in dioxane (8 mL) and water (1.5 mL) was stirred for 2 h at 100° C. under $N_2$, until the reaction was complete as indicated by LCMS, the reaction mixture was filtered through a pad of Celite with EtOAc, and the combined organics were concentrated in vacuo, purified by silica gel chromatography (Hexanes/EtOAc=10:1) to give the desired product methyl 2-[4-[6-[(5-chloro-3-fluoro-2-pyridyl)methoxy]-2-pyridyl]-2,5-difluoro-phenyl]acetate (110 mg, 260 µmol) as white solid.

LCMS: $[M+H]^+$=423.0; Retention time (0.01% TFA)=2.22 min.

Step 4

A mixture of methyl 2-[4-[6-[(5-chloro-3-fluoro-2-pyridyl)methoxy]-2-pyridyl]-2,5-difluoro-phenyl]acetate (100 mg, 237 µmol), LiOH (16.99 mg, 710 µmol) and water (0.5 mL) in methanol (3 mL) was stirred for 12 h at 20° C. under $N_2$, until the reaction was complete as indicated by LCMS, HOAc was added to quench the reaction, and the combined organics were concentrated in vacuo, purified by HPLC to give the desired product 2-[4-[6-[(5-chloro-3-fluoro-2-pyridyl)methoxy]-2-pyridyl]-2,5-difluoro-phenyl]acetic acid (90 mg, 220 µmol, 93.1% yield) as white solid.

LCMS: $[M+H]^+$=409.1; Retention time (0.01% TFA)=1.99 min.

Step 5

A mixture of 2-[4-[6-[(5-chloro-3-fluoro-2-pyridyl)methoxy]-2-pyridyl]-2,5-difluoro-phenyl]acetic acid (90 mg, 220 µmol), methyl 5-amino-6-[[(2S)-oxetan-2-yl]methylamino]pyridine-2-carboxylate (94.03 mg, 396 µmol), HATU (125.6 mg, 330 µmol) and DIEA (85.4 mg, 661 µmol) in DCM (8 mL) was stirred for 2 h at 20° C. under $N_2$, until the reaction was complete as indicated by LCMS, water was added to quench the reaction, and the combined organics were concentrated in vacuo, purified by silica gel chromatography (Hexanes/EtOAc=1:1) to give the desired product methyl 5-[[2-[4-[6-[(5-chloro-3-fluoro-2-pyridyl)methoxy]-2-pyridyl]-2,5-difluoro-phenyl]acetyl]amino]-6-[[(2S)-oxetan-2-yl]methylamino]pyridine-2-carboxylate (120 mg, 191 µmol, 86.8% yield) as pale yellow solid.

LCMS: $[M+H]^+$=628.1; Retention time (0.01% TFA)=1.77 min.

Step 6

A mixture of methyl 5-[[2-[4-[6-[(5-chloro-3-fluoro-2-pyridyl)methoxy]-2-pyridyl]-2,5-difluoro-phenyl]acetyl]amino]-6-[[(2S)-oxetan-2-yl]methylamino]pyridine-2-carboxylate (90 mg, 143 µmol) and HOAc (20 drops) in toluene (10 mL) was stirred for 2 h at 60° C. under $N_2$. Water was added to quench the reaction. The reaction mixture was extracted with EtOAc (3×20 mL). The organic phase was washed with brine (50 mL) and dried over anhydrous Na₂SO₄, filtered and concentrated in vacuo. The crude product was purified by flash chromatography (SiO₂, dichloromethane/methanol 15:1) to afford methyl 2-[[4-[6-[(5-chloro-3-fluoro-2-pyridyl)methoxy]-2-pyridyl]-2,5-difluoro-phenyl]methyl]-3-[[(2S)-oxetan-2-yl]methyl]imidazo[4,5-b]pyridine-5-carboxylate (74 mg, 121 μmol, 84.7% yield) as a yellow oil. LCMS: [M+H]⁺=610.2; Retention time (0.01% TFA)=2.07 min.

Step 7

A mixture of methyl 2-[[4-[6-[(5-chloro-3-fluoro-2-pyridyl)methoxy]-2-pyridyl]-2,5-difluoro-phenyl]methyl]-3-[[(2S)-oxetan-2-yl]methyl]imidazo[4,5-b]pyridine-5-carboxylate (40 mg, 66 μmol), LiOH (4.7 mg, 197 μmol) and water (0.5 mL) in methanol (3 mL) was stirred for 3 h at 20° C. under N₂, until the reaction was complete as indicated by LCMS, HOAc was added to quench the reaction, and the combined organics were concentrated in vacuo, purified by HPLC to give the desired product 2-[[4-[6-[(5-chloro-3-fluoro-2-pyridyl)methoxy]-2-pyridyl]-2,5-difluoro-phenyl]methyl]-3-[[(2S)-oxetan-2-yl]methyl]imidazo[4,5-b]pyridine-5-carboxylic acid (22 mg, 37 μmol, 56.3% yield) as white solid. LCMS: [M+H]⁺=596.0; Retention time (0.01% TFA)=1.90 min.

¹H NMR (400 MHz, DMSO-D6) δ 8.53 (d, J=1.2 Hz, 1H), 8.18-8.15 (m, 1H), 8.08 (d, J=8.4 Hz, 1H), 7.97 (dd, J=8.0 Hz, 1H), 7.90-7.86 (m, 1H), 7.72 (dd, J=6.4 Hz, 10.4 Hz, 1H), 7.52 (d, J=6.0 Hz, 1H), 7.41 (dd, J=6.0 Hz, 11.6 Hz, 1H), 6.96 (d, J=8.4 Hz, 1H), 5.59 (d, J=1.6 Hz, 2H), 5.17-5.15 (m, 1H), 4.79-4.73 (m, 1H), 4.65-4.61 (m, 2H), 4.55-4.49 (m, 2H), 4.39-4.33 (m, 1H), 2.76-2.71 (m, 1H), 2.47-2.42 (m, 1H).

(S)-2-(4-(6-(2,4-difluorobenzyloxy)-5-fluoropyridin-2-yl)-2-fluorobenzyl)-3-(oxetan-2-ylmethyl)-3H-imidazo[4,5-b]pyridine-5-carboxylic acid (Compound 277)

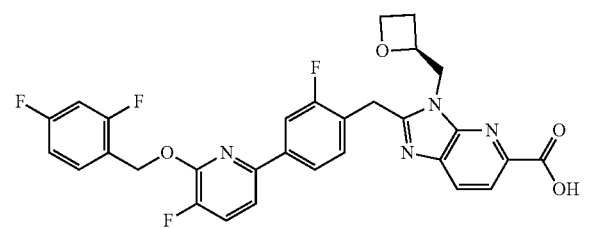 [SMILES: O=C(O)c1ccc2nc(Cc3ccc(-c4ccc(F)c(OCc5ccc(F)cc5F)n4)cc3F)n(C[C@@H]3CCO3)c2n1]

Prepared in analogous manner as for Compound 276. LCMS: [M+H]⁺=579.1; Retention time (10 mM NH₄HCO₃)= 1.46 min.

¹H NMR (400 MHz, DMSO-D6) δ 8.02-7.80 (m, 5H), 7.71-7.65 (m, 2H), 7.48-7.44 (m, 1H), 7.36-7.31 (m, 1H), 7.17-7.12 (m, 1H), 5.60 (s, 2H), 5.17-5.11 (m, 1H), 4.75-4.69 (m, 1H), 4.64-4.59 (m, 2H), 4.53-4.49 (m, 2H), 4.38-4.33 (m, 1H), 2.75-2.67 (m, 1H), 2.48-2.41 (m, 1H).

(S)-2-(4-(6-((5-cyano-3-fluoropyridin-2-yl)methoxy)pyridin-2-yl)-2,5-difluorobenzyl)-3-(oxetan-2-ylmethyl)-3H-imidazo[4,5-b]pyridine-5-carboxylic acid (Compound 278)

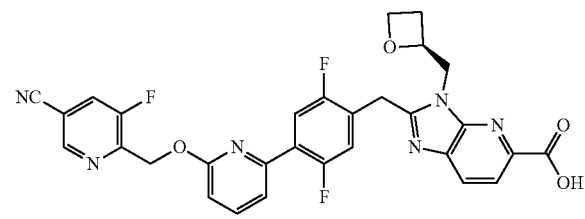 [SMILES: N#Cc1cnc(COc2cccc(-c3cc(F)c(Cc4nc5ccc(C(=O)O)nc5n4C[C@@H]4CCO4)cc3F)n2)c(F)c1]

Prepared in analogous manner as for Compound 276. LCMS: [M+H]⁺=587.1; Retention time (10 mM NH₄HCO₃)= 1.35 min.

¹H NMR (400 MHz, DMSO-D6) δ 8.89 (s, 1H), 8.48 (dd, J=1.6 Hz, 9.6 Hz, 1H), 8.07 (d, J=8.4 Hz, 1H), 7.96 (d, J=8.4 Hz, 1H), 7.90-7.87 (m, 1H), 7.61-7.57 (m, 1H), 7.51 (d, J=6.0 Hz, 1H), 7.39 (dd, J=6.4 Hz, 11.2 Hz, 1H), 6.99 (d, J=8.4 Hz, 1H), 5.69 (d, J=1.2 Hz, 2H), 5.19-5.13 (m, 1H), 4.78-4.73 (m, 1H), 4.65-4.60 (m, 2H), 4.54-4.48 (m, 2H), 4.38-4.33 (m, 1H), 2.75-2.69 (m, 1H), 2.47-2.40 (m, 1H).

(S)-2-(4-(6-((5-cyanopyridin-2-yl)methoxy)pyridin-2-yl)-2,5-difluorobenzyl)-3-(oxetan-2-ylmethyl)-3H-imidazo[4,5-b]pyridine-5-carboxylic acid (Compound 279)

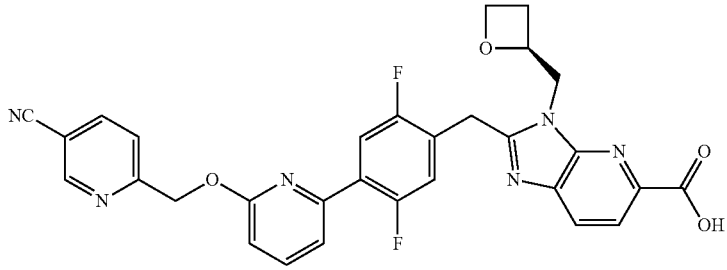

-continued
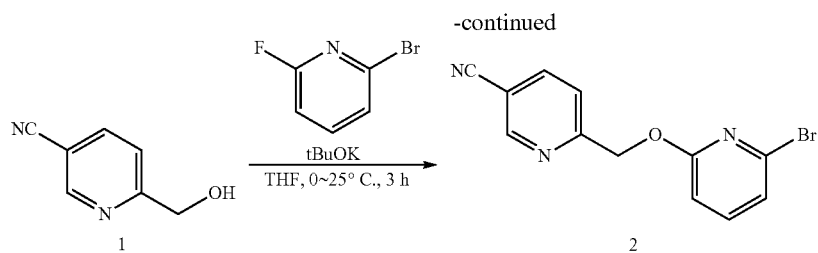
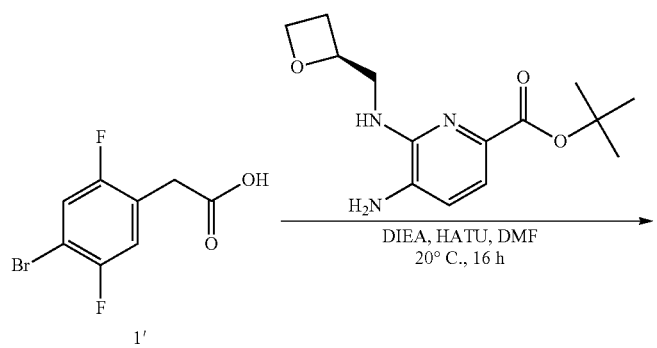
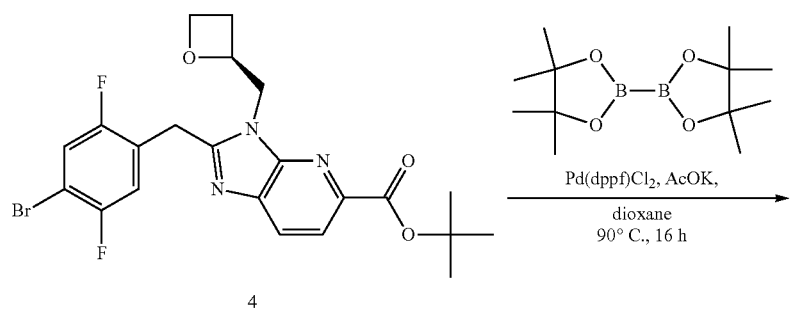
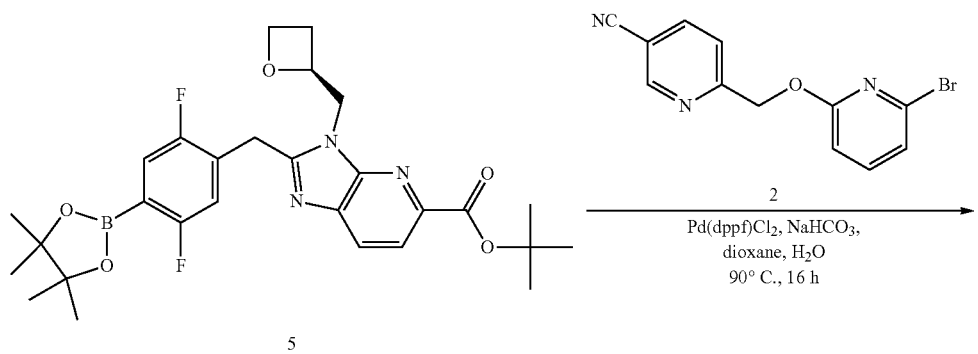

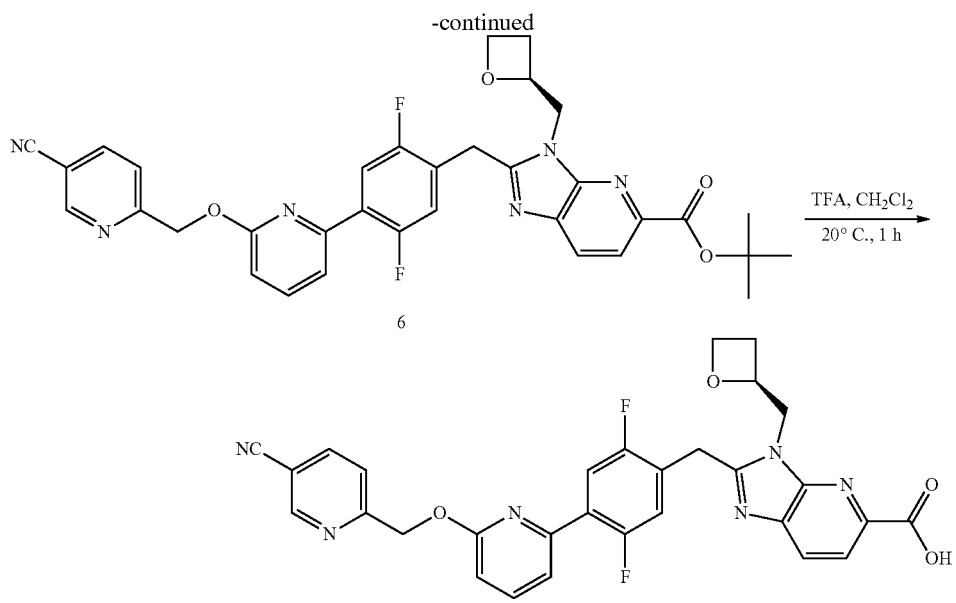

Step 1

A mixture of 6-(hydroxymethyl)pyridine-3-carbonitrile (33 mg, 246 µmol), 2-bromo-6-fluoro-pyridine (43.3 mg, 246 µmol) and sodium hydride (5.7 mg, 246 µmol) in THF (3 mL) was stirred for 2 h at 20° C. under $N_2$, until the reaction was complete as indicated by LCMS, the reaction mixture was filtered through a pad of Celite with EtOAc, and the combined organics were concentrated in vacuum, purified by silica gel chromatography (Hexanes/EtOAc=20:1) to give the desired product 6-[(6-bromo-2-pyridyl)oxymethyl]pyridine-3-carbonitrile (30 mg, 103 µmol, 42.0% yield) as pale yellow solid. LCMS: $[M+H]^+$=290; Retention time (0.01% TFA)=1.86 min.

Step 2

A mixture of tert-butyl 5-amino-6-[[(2S)-oxetan-2-yl]methylamino]pyridine-2-carboxylate (1.39 g, 4.98 mmol) 2-(4-bromo-2, 5-difluoro-phenyl)acetic acid (1.25 g, 4.98 mmol) N-ethyl-N-isopropyl-propan-2-amine (643.6 mg, 4.98 mmol) and [dimethylamino(triazolo[4,5-b]pyridin-3-yloxy)methylene]-dimethyl-ammonium, hexafluorophosphate (1.89 g, 4.98 mmol) in DMF (20 mL) was stirred for 1 h at 20° C. under N2, until the reaction was complete as indicated by LCMS, the reaction mixture was poured into water and extracted with EtOAc, and the combined organics were concentrated in vacuum, purified by silica gel chromatography (Hexanes/EtOAc=2:1) to give the desired product tert-butyl 5-[[2-(4-bromo-2,5-difluoro-phenyl)acetyl]amino]-6-[[(2S)-oxetan-2-yl]methylamino]pyridine-2-carboxylate (1.0 g, 1.95 mmol, 39.2% yield) as pale yellow solid. LCMS: $[M+H]^+$=512; Retention time=1.92 min.

Step 3

A mixture of tert-butyl 5-[[2-(4-bromo-2,5-difluoro-phenyl)acetyl]amino]-6-[[(2S)-oxetan-2-yl]methylamino]pyridine-2-carboxylate (1.0 g, 1.95 mmol) in toluene (10 mL) was stirred for 2 h at 120° C. under N2, until the reaction was complete as indicated by LCMS, the reaction mixture was filtered through a pad of Celite with EtOAc, and the combined organics were concentrated in vacuum, purified by silica gel chromatography (Hexanes/EtOAc=2:1) to give the desired product tert-butyl 2-[(4-bromo-2,5-difluoro-phenyl)methyl]-3-[[(2S)-oxetan-2-yl]methyl]imidazo[4,5-b]pyridine-5-carboxylate (430 mg, 870 µmol, 44.6% yield) as pale yellow solid. LCMS: $[M+H]^+$=494; Retention time (0.01% TFA)=2.02 min.

Step 4

A mixture of tert-butyl 2-[(4-bromo-2,5-difluoro-phenyl)methyl]-3-[[(2S)-oxetan-2-yl]methyl]imidazo[4,5-b]pyridine-5-carboxylate (180 mg, 364 µmol), 4,4,5,5-tetramethyl-2-(4,4,5,5-tetramethyl-1,3,2-dioxaborolan-2-yl)-1,3,2-dioxaborolane (184.93 mg, 728 µmol), and potassium acetate (143.0 mg, 1.46 mmol) in dioxane (20 mL) was stirred for 16 h at 90° C. under $N_2$, until the reaction was complete as indicated by LCMS, the reaction mixture was filtered through a pad of Celite with EtOAc, used for next step, directly.

Step 5

A mixture of 6-[(6-bromo-2-pyridyl)oxymethyl]pyridine-3-carbonitrile (60 mg, 207 µmol), tert-butyl 2-[[2,5-difluoro-4-(4,4,5,5-tetramethyl-1,3,2-dioxaborolan-2-yl)phenyl]methyl]-3-[[(2S)-oxetan-2-yl]methyl]imidazo[4,5-b]pyridine-5-carboxylate (112.0 mg, 207 µmol) and sodium hydrogen carbonate (86.87 mg, 1.03 mmol) in was stirred for 16 h at 110° C. under $N_2$, until the reaction was complete as indicated by LCMS, the reaction mixture was poured into water and extracted with EtOAc, and the combined organics were concentrated in vacuum, purified by silica gel chromatography (Hexanes/EtOAc=5:1) to give the desired product tert-butyl 2-[[4-[6-[(5-cyano-2-pyridyl)methoxy]-2-pyridyl]-2,5-difluoro-phenyl]methyl]-3-[[(2S)-oxetan-2-yl]methyl]imidazo[4,5-b]pyridine-5-carboxylate (80 mg, 61.9% yield) as pale yellow oil. LCMS: $[M+H]^+$=625; Retention time=1.77 min.

Step 6

A mixture of tert-butyl 2-[[4-[6-[(5-cyano-2-pyridyl)methoxy]-2-pyridyl]-2,5-difluoro-phenyl]methyl]-3-[[(2S)-oxetan-2-yl]methyl]imidazo[4,5-b]pyridine-5-carboxylate (80 mg, 128 µmol), 2,2,2-trifluoroacetic acid (23.68 g, 207.68 mmol, 16.00 mL) in $CH_2C_2$ (2 mL) was stirred for 1 h at 30° C. under N2, until the reaction was complete as indicated by LCMS, the reaction mixture were concentrated in vacuum and further purified with PREP-HPLC to give the desired product 2-[[4-[6-[(5-cyano-2-pyridyl)methoxy]-2-pyridyl]-2,5-difluoro-phenyl]methyl]-3-[[(2S)-oxetan-2-yl]

methyl]imidazo[4,5-b]pyridine-5-carboxylic acid (38.3 mg, 51.0% yield) as pale yellow solid. LCMS: [M+H]⁺=569.2; Retention time=1.42 min.

¹H NMR (400 MHz, DMSO-D6) δ 9.03 (d, J=1.4 Hz, 1H), 8.33 (dd, J=8.2, 2.1 Hz, 1H), 8.08 (d, J=8.2 Hz, 1H), 8.02-7.85 (m, 2H), 7.68 (d, J=8.2 Hz, 1H), 7.54 (dd, J=10.9, 6.7 Hz, 2H), 7.39 (dd, J=11.5, 6.0 Hz, 1H), 7.06 (d, J=8.3 Hz, 1H), 5.64 (s, 2H), 5.15 (dd, J=7.1, 3.3 Hz, 1H), 4.75 (dd, J=15.1, 6.4 Hz, 1H), 4.68-4.56 (m, 2H), 4.50 (dd, J=15.5, 5.9 Hz, 2H), 4.35 (dd, J=6.0, 2.9 Hz, 1H), 2.73 (d, J=3.3 Hz, 1H), 2.45 (d, J=9.0 Hz, 1H).

(S)-2-(4-(4-((5-cyanopyridin-2-yl)methoxy)-5-fluoropyrimidin-2-yl)-2,5-difluorobenzyl)-3-(oxetan-2-ylmethyl)-3H-imidazo[4,5-b]pyridine-5-carboxylic acid (Compound 280)

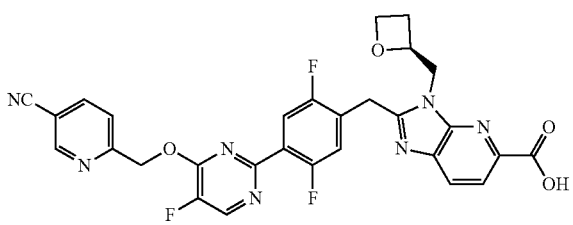 [SMILES: N#Cc1ccc(COc2nc(-c3cc(F)c(Cc4nc5ccc(C(=O)O)nc5n4C[C@@H]4CCO4)cc3F)ncc2F)nc1]

Prepared in analogous manner as for Compound 279. LCMS: [M+H]⁺=588.0; Retention time=1.17 min.

¹H NMR (400 MHz, DMSO-D6) δ 9.04 (d, J=1.4 Hz, 1H), 8.86 (d, J=2.8 Hz, 1H), 8.37 (dd, J=8.2, 2.1 Hz, 1H), 8.03 (d, J=8.2 Hz, 1H), 7.94 (d, J=8.2 Hz, 1H), 7.84-7.63 (m, 2H), 7.39 (dd, J=11.1, 6.1 Hz, 1H), 5.80 (s, 2H), 5.15 (s, 1H), 4.81-4.41 (m, 6H), 4.41-4.23 (m, 1H), 2.70 (dd, J=16.4, 8.3 Hz, 2H).

2-[[4-[6-[(4-chloro-2-fluoro-phenyl)methoxy]-2-pyridyl]-2-fluoro-phenyl]methyl]-3-[[(2S)-oxetan-2-yl]methyl]imidazo[4,5-b]pyridine-5-carboxylic acid (Compound 281)

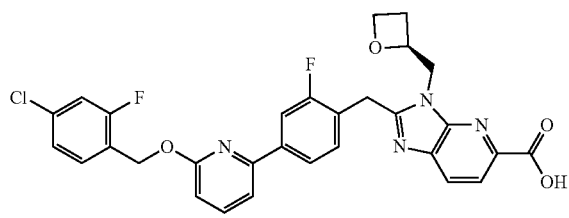

Prepared in analogous manner as for Compound 279. LCMS: [M+H]⁺=577.9; Retention time (10 mM NH₄HCO₃) =2.94 min.

¹H NMR (400 MHz, DMSO-D6) δ 8.06 (d, J=8.2 Hz, 1H), 7.97 (d, J=8.2 Hz, 1H), 7.91 (dd, J=9.1, 5.2 Hz, 2H), 7.84 (t, J=7.8 Hz, 1H), 7.66 (d, J=7.4 Hz, 1H), 7.62 (t, J=8.2 Hz, 1H), 7.54-7.42 (m, 2H), 7.33 (d, J=8.2 Hz, 1H), 6.89 (d, J=8.2 Hz, 1H), 5.52 (s, 2H), 5.15 (s, 1H), 4.73 (dd, J=15.1, 6.2 Hz, 1H), 4.63 (dd, J=10.3, 6.8 Hz, 2H), 4.51 (dd, J=15.3, 9.1 Hz, 2H), 4.36 (dt, J=12.0, 5.9 Hz, 1H), 2.71 (dd, J=17.0, 9.0 Hz, 1H), 2.42 (d, J=18.0 Hz, 1H).

(S)-2-(4-(6-((4-cyano-2-fluorobenzyl)oxy)pyridin-2-yl)-2-fluorobenzyl)-3-(oxetan-2-ylmethyl)-3H-imidazo[4,5-b]pyridine-5-carboxylic acid (Compound 282)

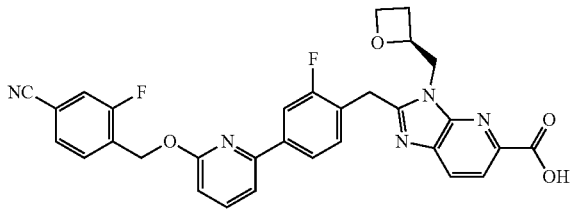 [SMILES: N#Cc1ccc(COc2cccc(-c3ccc(Cc4nc5ccc(C(=O)O)nc5n4C[C@@H]4CCO4)c(F)c3)n2)c(F)c1]

Prepared in analogous manner as for Compound 279. LCMS: [M+H]⁺=568.2; Retention time=1.32 min.

¹H NMR (400 MHz, DMSO-D6) δ 7.99 (d, J=8.4 Hz, 1H), 7.96-7.90 (m, 4.0 Hz, 2H), 7.90-7.84 (m, J=7.8 Hz, 3H), 7.79-7.71 (m, 2H), 7.67 (d, J=7.4 Hz, 1H), 7.44 (t, J=8.1 Hz, 1H), 6.93 (d, J=8.1 Hz, 1H), 5.62 (s, 2H), 5.14 (s, 1H), 4.71 (dd, J=15.3, 6.5 Hz, 1H), 4.60 (d, J=17.0 Hz, 2H), 4.54-4.45 (m, 2H), 4.40-4.31 (m, 1H), 2.76-2.68 (m, 1H), 2.43-2.34 (m, 1H).

(S)-2-(4-(6-(4-chloro-2-fluorobenzyloxy)-5-fluoropyridin-2-yl)-2-fluorobenzyl)-3-(oxetan-2-ylmethyl)-3H-imidazo[4,5-b]pyridine-5-carboxylic acid (Compound 283)

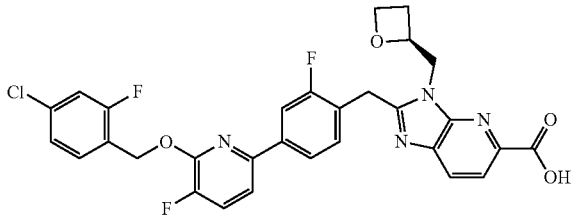 [SMILES: O=C(O)c1ccc2nc(Cc3ccc(-c4ccc(F)c(OCc5ccc(Cl)cc5F)n4)cc3F)n(C[C@@H]3CCO3)c2n1]

Prepared in analogous manner as for Compound 279. LCMS: [M+H]⁺=595.2; Retention time=1.42 min.

¹H NMR (400 MHz, DMSO-D6) δ 8.02 (d, J=8.0 Hz, 1H), 7.94 (d, J=8.4 Hz, 1H), 7.91-7.79 (m, 3H), 7.69 (dd, J=8.4, 2.8 Hz, 1H), 7.64 (t, J=8.2 Hz, 1H), 7.52 (dd, J=10.0, 2.0 Hz, 1H), 7.45 (t, J=8.1 Hz, 1H), 7.36-7.34 (m, 1H), 5.61 (s, 2H), 5.18-5.10 (m, 1H), 4.72 (dd, J=15.0, 6.4 Hz, 1H), 4.65-4.61 (m, 1H), 4.60-4.57 (m, 1H), 4.54-4.47 (m, 2H), 4.39-4.32 (m, 1H), 2.69-2.66 (m, 1H), 2.34-2.32 (m, 1H).

(S)-2-(4-(6-(4-cyano-2-fluorobenzyloxy)-5-fluoropyridin-2-yl)-2-fluorobenzyl)-3-(oxetan-2-ylmethyl)-3H-imidazo[4,5-b]pyridine-5-carboxylic acid (Compound 284)

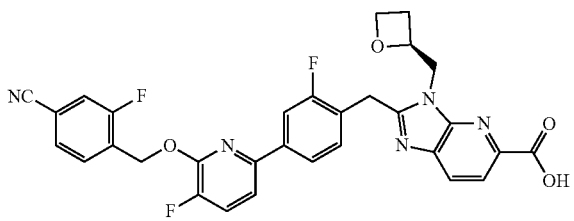 [SMILES: N#Cc1ccc(COc2nc(-c3ccc(Cc4nc5ccc(C(=O)O)nc5n4C[C@@H]4CCO4)c(F)c3)ccc2F)c(F)c1]

Prepared in analogous manner as for Compound 279. LCMS: [M+H]⁺=586.0; Retention time=1.51 min.

$^1$H NMR (400 MHz, DMSO-D6) δ 8.04 (d, J=8.0 Hz, 1H), 7.97-7.92 (m, 2H), 7.87-7.82 (m, 3H), 7.80-7.73 (m, 2H), 7.70 (dd, J=8.4, 2.8 Hz, 1H), 7.45 (t, J=8.0 Hz, 1H), 5.71 (s, 2H), 5.18-5.11 (m, 1H), 4.73 (dd, J=15.2, 6.4 Hz, 1H), 4.65-4.61 (m, 1H), 4.60-4.57 (m, 1H), 4.54-4.46 (m, 2H), 4.36 (dt, J=9.0, 6.0 Hz, 1H), 2.72-2.66 (m, 1H), 2.40-2.30 (m, 1H).

(S)-2-(4-(4-((2,4-difluorobenzyl)oxy)-5-fluoropyrimidin-2-yl)-2-fluorobenzyl)-3-(oxetan-2-ylmethyl)-3H-imidazo[4,5-b]pyridine-5-carboxylic acid (Compound 285)

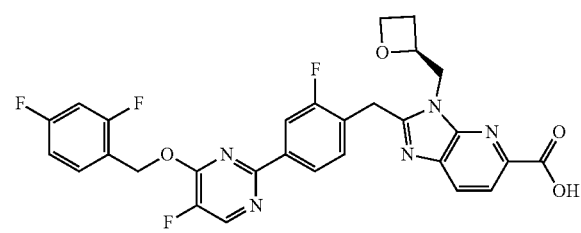

Prepared in analogous manner as for Compound 279. LCMS: [M+H]⁺=580.0; Retention time=1.53 min.

$^1$H NMR (400 MHz, DMSO-D6) δ 8.82-8.76 (m, 1H), 8.19-8.15 (m, 1H), 8.13-8.03 (m, 2H), 7.99-7.94 (m, 1H), 7.78-7.70 (m, 1H), 7.56-7.50 (m, 1H), 7.41-7.32 (m, 1H), 7.22-7.14 (m, 1H), 5.72 (s, 2H), 5.19-5.11 (m, 1H), 4.77-4.49 (m, 5H), 4.39-4.33 (m, 1H), 2.75-2.67 (m, 1H), 2.47-2.40 (m, 1H).

(S)-2-(4-(6-((2,4-difluorobenzyl)oxy)pyridin-2-yl)-2-fluorobenzyl)-3-(oxetan-2-ylmethyl)-3H-imidazo[4,5-b]pyridine-5-carboxylic acid (Compound 286)

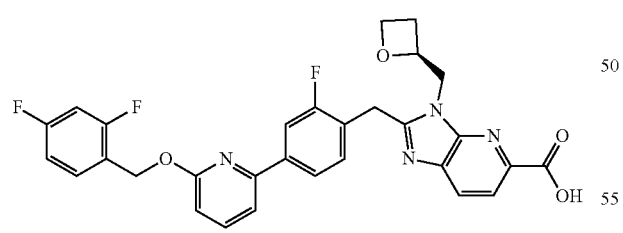

Prepared in analogous manner as for Compound 279. LCMS: [M+H]⁺=561.0; Retention time=1.57 min.

$^1$H NMR (400 MHz, DMSO-D6) δ 7.96-7.89 (m, 4H), 7.88-7.82 (m, 1H), 7.70-7.62 (m, 2H), 7.48-7.42 (m, 1H), 7.35-7.28 (m, 1H), 7.17-7.08 (m, 1H), 6.90-6.85 (m, 1H), 5.51 (s, 2H), 5.18-5.10 (m, 1H), 4.74-4.67 (m, 1H), 4.62-4.47 (m, 4H), 4.39-4.33 (m, 1H), 2.76-2.65 (m, 1H), 2.45-2.40 (m, 1H).

(S)-2-(4-(6-((4-chloro-2-fluorobenzyl)oxy)pyridin-2-yl)-2-fluorobenzyl)-3-(oxetan-2-ylmethyl)-3H-imidazo[4,5-b]pyridine-5-carboxylic acid (Compound 287)

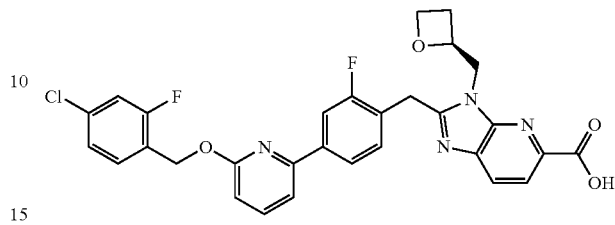

Prepared in analogous manner as for Compound 279. LCMS: [M+H]⁺=576.3; Retention time=2.13 min.

$^1$H NMR (400 MHz, DMSO-D6) δ 7.95-7.89 (m, 2H), 7.65-7.61 (m, 2H), 7.56-7.54 (m, 2H) 7.42-7.31 (m, 5H), 7.06 (d, 1H), 5.23 (s, 2H), 5.00 (m, 1H), 4.67-4.66 (m, 1H), 4.57-4.55 (m, 2H), 4.47-4.43 (m, 2H), 4.34 (m, 1H), 2.51 (m, 1H), 2.32 (m, 1H)

(S)-2-(4-(6-((5-cyanopyridin-2-yl)methoxy)pyridin-2-yl)-2-fluorobenzyl)-3-(oxetan-2-ylmethyl)-3H-imidazo[4,5-b]pyridine-5-carboxylic acid (Compound 288)

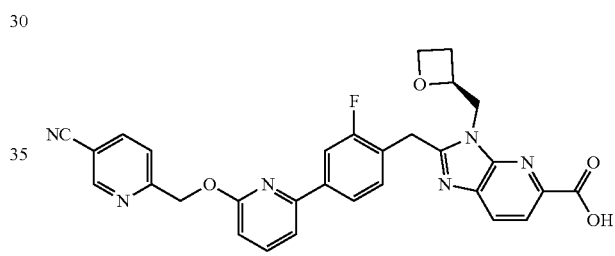

Prepared in analogous manner as for Compound 279. LCMS: [M+H]⁺=550.7; Retention time=1.98 min.

$^1$H NMR (400 MHz, DMSO-D6) δ 9.03 (s, 1H), 8.32 (d, 1H), 7.78 (d, 1H), 7.77 (d, 1H), 7.76 (d, 1H), 7.64-7.63 (m, 4H), 7.39 (t, 1H), 7.00 (d, 1H), 5.64 (s, 2H), 4.51 (m, 1H), 4.46-4.341 (m, 4H), 4.31 (m, 1H), 2.71-2.67 (m, 1H), 2.45-2.43 (m, 1H)

(S)-2-(4-(6-((4-cyano-2-fluorobenzyl)oxy)-5-fluoropyridin-2-yl)-3-fluorobenzyl)-3-(oxetan-2-ylmethyl)-3H-imidazo[4,5-b]pyridine-5-carboxylic acid (Compound 289)

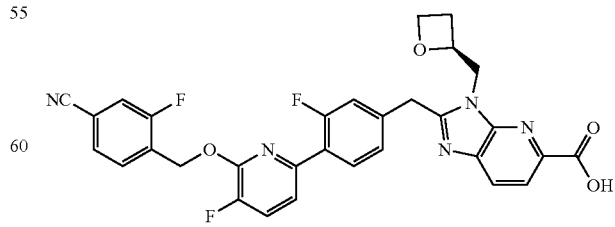

Prepared in analogous manner as for Compound 279. LCMS: [M+H]⁺=586.2; Retention time (0.01% TFA)=1.85 min.

¹H NMR (400 MHz, CDCl₃) δ 8.25-8.22 (m, 2H), 7.93-7.87 (m, 1H), 7.73-7.67 (m, 1H), 7.50-7.37 (m, 4H), 7.21-7.16 (m, 1H), 7.12-7.08 (m, 1H), 5.64 (s, 2H), 5.25-5.19 (m, 1H), 4.71-4.60 (m, 3H), 4.57-4.49 (m, 1H), 4.48-4.37 (m, 2H), 2.82-2.75 (m, 1H), 2.46-2.37 (m, 1H).

(S)-2-(4-(6-((2,4-difluorobenzyl)oxy)pyridin-2-yl)-3-fluorobenzyl)-3-(oxetan-2-ylmethyl)-3H-imidazo[4,5-b]pyridine-5-carboxylic acid (Compound 290)

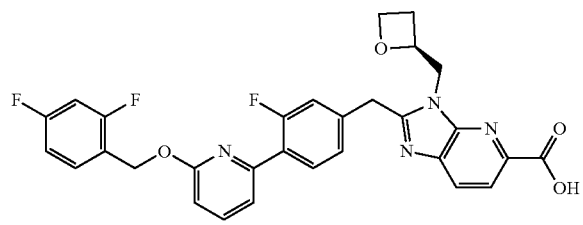 [SMILES: O=C(O)c1ccc2nc(Cc3ccc(-c4cccc(OCc5ccc(F)cc5F)n4)c(F)c3)n(C[C@@H]3CCO3)c2n1]

Prepared in analogous manner as for Compound 279. LCMS: [M+H]⁺=561.0; Retention time=1.57 min.

¹H NMR (400 MHz, DMSO-D6) δ 8.15-8.09 (d, J=8.2 Hz, 1H), 8.02-7.95 (m, 2H), 7.87-7.81 (m, 1H), 7.69-7.60 (dd, J=15.3, 8.5 Hz, 1H), 7.47-7.43 (m, 1H), 7.37-7.27 (m, 3H), 7.15-7.09 (m, 1H), 6.91-6.87 (d, J=8.2 Hz, 1H), 5.46 (s, 2H), 5.17-5.09 (m, 1H), 4.76-4.68 (m, 1H), 4.65-4.46 (m, 4H), 4.42-4.35 (m, 1H), 2.76-2.64 (m, 1H), 2.47-2.41 (m, 1H).

(S)-2-(4-(2-((4-cyano-2-fluorobenzyl)oxy)-5-fluoro-pyrimidin-4-yl)-2-fluorobenzyl)-3-(oxetan-2-ylmethyl)-3H-imidazo[4,5-b]pyridine-5-carboxylic acid (Compound 291)

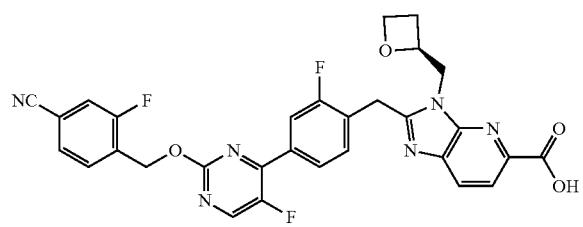 [SMILES: N#Cc1ccc(COc2ncc(F)c(-c3ccc(Cc4nc5ccc(C(=O)O)nc5n4C[C@@H]4CCO4)c(F)c3)n2)c(F)c1]

Prepared in analogous manner as for Compound 279. LCMS: [M+H]⁺=587.0; Retention time=1.43 min.

¹H NMR (400 MHz, DMSO-D6): δ 8.84 (d, J=3.2 Hz, 1H), 8.04 (d, J=4 Hz, 1H), 7.94 (d, J=8.4 Hz, 2H), 7.87 (t, J=8 Hz, 2H), 7.80-7.74 (m, 2H), 7.58 (t, J=8 Hz, 1H), 5.60 (s, 2H), 5.16-5.14 (m, 1H), 4.76-4.69 (m, 1H), 4.64 (t, J=4 Hz, 2H, 1H), 4.60 (d, J=6.4 Hz, 1H), 4.54-4.47 (m, 1H), 4.37-4.32 (m, 1H), 2.74-2.67 (m, 1H), 2.46-2.41 (m, 2H).

(S)-2-(4-(6-((4-cyano-2-fluorobenzyl)oxy)pyridin-2-yl)-2,5-difluorobenzyl)-3-(oxetan-2-ylmethyl)-3H-imidazo[4,5-b]pyridine-5-carboxylic acid (Compound 292)

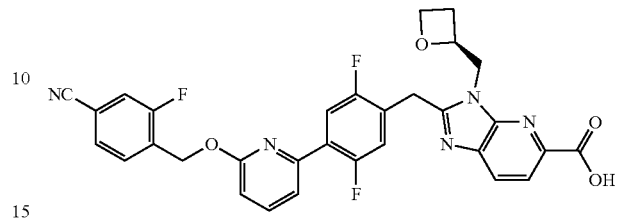

Prepared in analogous manner as for Compound 279. LCMS: [M+H]⁺=586.2; Retention time=1.57 min.

¹H NMR (400 MHz, CD₃OD) δ 8.20-8.16 (m, 1H), 8.12-8.08 (m, 1H), 7.90-7.87 (m, 1H), 7.86-7.77 (m, 2H), 7.70-7.66 (m, 1H), 7.65-7.60 (m, 2H), 7.30-7.24 (m, 1H), 7.00-6.96 (m, 1H), 5.70 (s, 2H), 5.36-5.34 (m, 1H), 4.90-4.86 (m, 1H), 4.82-4.79 (m, 1H), 4.73-4.65 (m, 3H), 4.53-4.48 (m, 1H), 2.93-2.93 (m, 1H), 2.61-2.56 (m, 1H).

(S)-2-(4-(6-((4-cyano-2-fluorobenzyl)oxy)pyridin-2-yl)-3-fluorobenzyl)-3-(oxetan-2-ylmethyl)-3H-imidazo[4,5-b]pyridine-5-carboxylic acid (Compound 293)

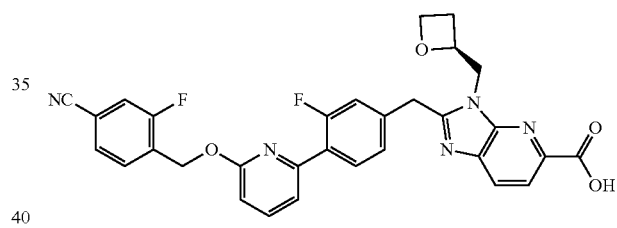

Prepared in analogous manner as for Compound 279. LCMS: [M+H]⁺=568.0; Retention time=1.50 min.

¹H NMR (400 MHz, DMSO-D6): δ 8.76 (d, J=8.4 Hz, 1H), 7.95-7.84 (m, 4H), 7.77-7.71 (m, 2H), 7.46 (dd, J=1.6 Hz, J=7.6 Hz, 1H), 7.30 (t, J=11.2 Hz, 2H), 6.94 (d, J=8 Hz, 1H), 5.56 (s, 2H), 5.12-5.09 (m, 1H), 4.70-4.65 (m, 1H), 4.58-4.46 (m, 4H), 4.38-4.33 (m, 1H), 2.70-2.66 (m, 1H), 2.47-2.40 (m, 1H).

(S)-2-(4-(4-((5-chloro-3-fluoropyridin-2-yl)methoxy)-5-fluoropyrimidin-2-yl)-2-fluorobenzyl)-3-(oxetan-2-ylmethyl)-3H-imidazo[4,5-b]pyridine-5-carboxylic acid (Compound 294)

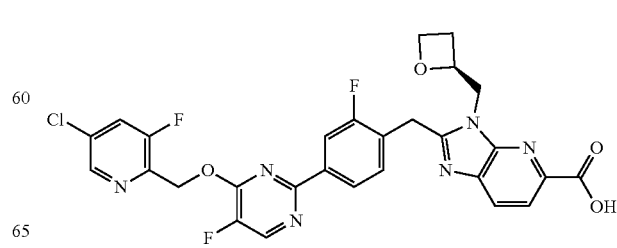

121

Prepared in analogous manner as for Compound 279. LCMS: [M+H]⁺=597.1; Retention time=1.28 min.

¹H NMR (400 MHz, DMSO-D6) δ 8.77 (d, J=2.8 Hz, 1H), 8.56 (d, J=1.4 Hz, 1H), 8.22 (dd, J=9.7, 1.9 Hz, 1H), 8.10-7.90 (m, 4H), 7.49 (t, J=7.9 Hz, 1H), 5.82 (d, J=1.4 Hz, 2H), 5.14 (d, J=7.1 Hz, 1H), 4.78-4.45 (m, 5H), 4.35 (dt, J=9.0, 6.0 Hz, 1H), 2.70 (dd, J=17.0, 8.8 Hz, 1H), 2.44 (d, J=8.8 Hz, 1H).

(S)-2-(4-(6-((4-chloro-2-fluorobenzyl)oxy)pyridin-2-yl)-2-methylbenzyl)-1-(oxetan-2-ylmethyl)-1H-benzo[d]imidazole-6-carboxylic acid (Compound 295)

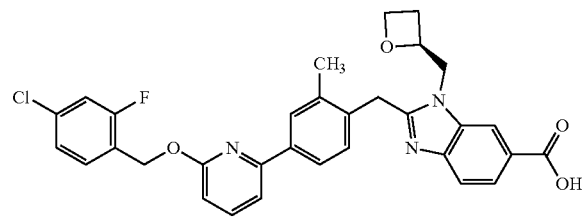 [SMILES: Cc1cc(-c2cccc(OCc3ccc(Cl)cc3F)n2)ccc1Cc1nc2ccc(C(=O)O)cc2n1C[C@@H]1CCO1]

Prepared in analogous manner as for Compound 279. LCMS: [M+H]⁺=572.1; Retention time=1.52 min.

¹H NMR (400 MHz, DMSO-D6): δ 8.22 (brs, 1H), 7.90 (brs, 1H), 7.84-7.76 (m, 3H), 7.62-7.56 (m, 3H), 7.50 (dd, J=2 Hz, J=10 Hz, 1H), 7.32 (dd, J=1.6 Hz, J=8.4 Hz, 1H), 7.16 (d, J=8 Hz, 1H), 6.82 (d, J=8.4 Hz, 1H), 5.51 (s, 2H), 5.03-5.00 (m, 1H), 4.69-4.63 (m, 1H), 4.56-4.46 (m, 2H), 4.43-4.38 (m, 2H), 4.37-4.35 (m, 1H), 2.69-2.65 (m, 1H), 2.42-2.34 (m, 4H).

(S)-2-(4-(6-((5-chloropyridin-2-yl)methoxy)pyridin-2-yl)-2,5-difluorobenzyl)-3-(oxetan-2-ylmethyl)-3H-imidazo[4,5-b]pyridine-5-carboxylic acid (Compound 296)

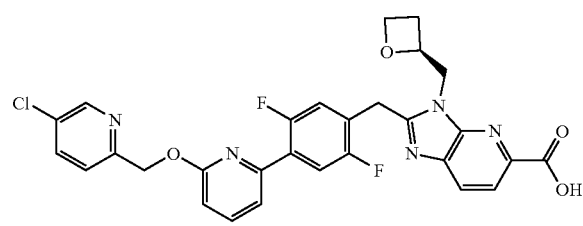

Prepared in analogous manner as for Compound 279. LCMS: [M+H]⁺=578.2; Retention time=1.32 min.

¹H NMR (400 MHz, DMSO-D6) δ 8.63 (d, J=2.4 Hz, 1H), 8.09 (d, J=8.2 Hz, 1H), 7.98-7.94 (m, 2H), 7.91-7.87 (m, 1H), 7.67-7.62 (m, 1H), 7.55-7.51 (m, 2H), 7.42-7.37 (m, 1H), 7.02 (d, J=8.3 Hz, 1H), 5.54 (s, 2H), 5.18-5.14 (m, 1H), 4.78-4.72 (m, 1H), 4.65-4.60 (m, 2H), 4.53-4.48 (m, 2H), 4.38-4.32 (m, 1H), 2.76-2.70 (m, 1H), 2.46-2.43 (m, 1H).

122

(S)-2-(4-(6-((3,5-difluoropyridin-2-yl)methoxy)pyridin-2-yl)-2,5-difluorobenzyl)-3-(oxetan-2-ylmethyl)-3H-imidazo[4,5-b]pyridine-5-carboxylic acid (Compound 297)

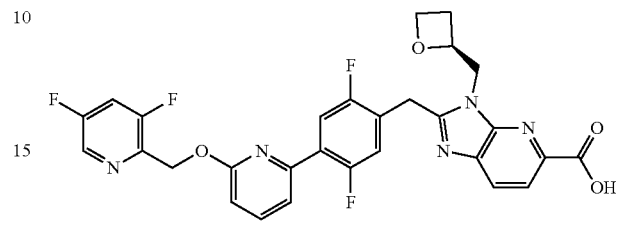

Prepared in analogous manner as for Compound 279. LCMS: [M+H]⁺=580.0; Retention time=1.48 min.

¹H NMR (400 MHz, DMSO-D6): δ 8.52 (d, J=2.4 Hz, 1H), 8.08-7.84 (m, 4H), 7.79-7.75 (m, 1H), 7.52-7.49 (m, 1H), 7.42-7.38 (m, 1H), 6.95-6.92 (m, 1H), 5.58 (d, J=1.6 Hz, 2H), 5.18-4.90 (m, 1H), 4.78-4.32 (m, 5H), 2.74-2.66 (m, 1H), 2.46-2.39 (m, 2H).

(S)-2-(2,5-difluoro-4-(6-((5-fluoropyridin-2-yl)methoxy)pyridin-2-yl)benzyl)-3-(oxetan-2-ylmethy)-3H-imidazo[4,5-b]pyridine-5-carboxylic acid (Compound 298)

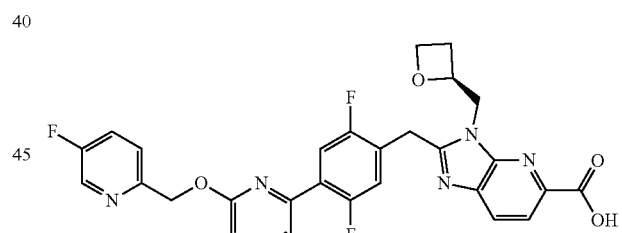

Prepared in analogous manner as for Compound 279. LCMS: [M+H]⁺=562.0; Retention time=1.40 min.

¹H NMR (400 MHz, DMSO-D6) δ 8.58 (d, J=2.9 Hz, 1H), 8.06 (d, J=8.2 Hz, 1H), 7.96 (d, J=8.2 Hz, 1H), 7.92-7.86 (m, 1H), 7.76 (td, J=8.8, 3.0 Hz, 1H), 7.69 (dd, J=10.5, 6.5 Hz, 1H), 7.59 (dd, J=8.7, 4.5 Hz, 1H), 7.51 (d, J=6.2 Hz, 1H), 7.40 (dd, J=11.5, 6.1 Hz, 1H), 7.00 (d, J=8.2 Hz, 1H), 5.53 (s, 2H), 5.19-5.11 (m, 1H), 4.75 (dd, J=15.1, 6.3 Hz, 1H), 4.66-4.58 (m, 2H), 4.50 (dd, J=15.4, 6.9 Hz, 2H), 4.35 (dt, J=9.0, 6.0 Hz, 1H), 2.77-2.67 (m, 1H), 2.47-2.42 (m, 1H).

(S)-2-(4-(6-(4-chloro-2-fluorobenzyloxy)-3,5-difluoropyridin-2-yl)-2-fluorobenzyl)-3-(oxetan-2-ylmethyl)-3H-imidazo [4,5-b]pyridine-S-carboxylic acid (Compound 299)

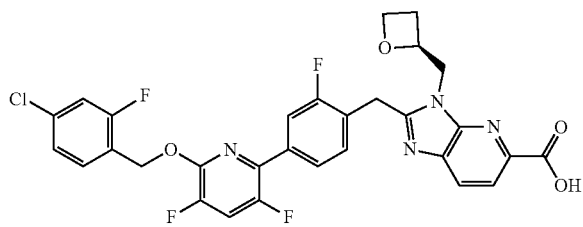 [SMILES: O=C(O)c1ccc2nc(Cc3ccc(-c4nc(OCc5ccc(Cl)cc5F)c(F)cc4F)cc3F)n(C[C@@H]3CCO3)c2n1]

Prepared in analogous manner as for Compound 279. LCMS: [M+H]⁺=612.9; Retention time=1.66 min.

¹H NMR (400 MHz, DMSO-D6) δ 8.15 (t, J=10 Hz, 1H), 8.00 (d, J=8 Hz, 1H), 7.93 (d, J=8.4 Hz, 1H), 7.74 (t, J=6.8 Hz, 1H), 7.64 (t, J=8 Hz, 1H), 7.53-7.48 (m, 2H), 7.36 (dd, J=1.6, 6.4 Hz, 1H), 5.57 (s, 2H), 5.15-5.13 (m, 1H), 4.74 (dd, J=6.4, 8.8 Hz, 1H), 4.65-4.58 (m, 2H), 4.54-4.47 (m, 2H), 4.37-4.32 (m, 1H), 2.73-2.67 (m, 1H), 2.46-2.39 (m, 1H).

(S)-2-(4-(4-((5-chloropyridin-2-yl)methoxy)-5-fluoropyrimidin-2-yl)-2,5-difluorobenzyl)-3-(oxetan-2-ylmethyl)-3H-imidazo[4,5-b]pyridine-5-carboxylic acid (Compound 300)

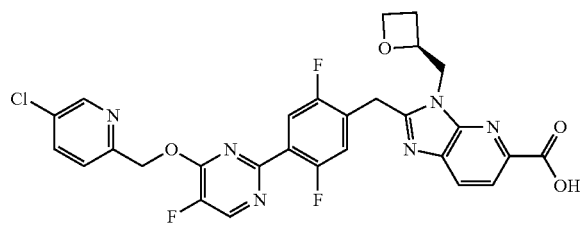 [SMILES: O=C(O)c1ccc2nc(Cc3cc(F)c(-c4ncc(F)c(OCc5ccc(Cl)cn5)n4)cc3F)n(C[C@@H]3CCO3)c2n1]

Prepared in analogous manner as for Compound 279. LCMS: [M+H]⁺=597.1; Retention time=1.24 min.

¹H NMR (400 MHz, DMSO-D6) δ 8.84 (d, J=2.9 Hz, 1H), 8.65 (d, J=2.1 Hz, 1H), 8.05 (d, J=8.2 Hz, 1H), 8.00 (dd, J=8.4, 2.5 Hz, 1H), 7.95 (d, J=8.2 Hz, 1H), 7.76 (dd, J=10.0, 6.4 Hz, 1H), 7.61 (d, J=8.5 Hz, 1H), 7.41 (dd, J=11.1, 6.1 Hz, 1H), 5.70 (s, 2H), 5.18-5.10 (m, 1H), 4.74 (dd, J=15.4, 6.8 Hz, 1H), 4.63 (d, J=16.8 Hz, 2H), 4.52 (dd, J=15.1, 6.2 Hz, 2H), 4.37-4.31 (dd, J=14.9, 5.9 Hz, 1H), 2.75-2.67 (m, 1H), 2.43-2.34 (m, 1H).

(S)-2-(4-(4-((5-cyano-3-fluoropyridin-2-yl)methoxy)-5-fluoropyrimidin-2-yl)-2-fluorobenzyl)-3-(oxetan-2-ylmethyl)-3H-imidazo[4,5-b]pyridine-5-carboxylic acid (Compound 301)

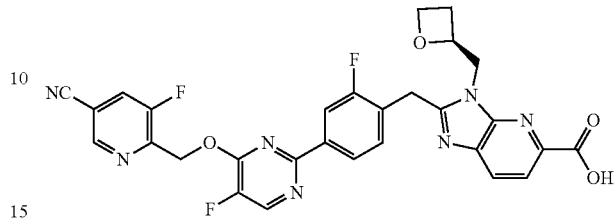

Prepared in analogous manner as for Compound 279. LCMS: [M+H]⁺=588.0; Retention time=1.41 min.

¹H NMR (400 MHz, CDCl₃) δ 8.70 (s, 1H), 8.45 (t, J=11.9 Hz, 1H), 8.18 (dt, J=21.0, 10.4 Hz, 2H), 8.07-7.94 (m, 2H), 7.75 (dd, J=8.7, 1.4 Hz, 1H), 7.39 (t, J=7.7 Hz, 1H), 5.84 (t, J=7.0 Hz, 2H), 5.21 (s, 1H), 4.60 (ddd, J=29.6, 16.5, 8.5 Hz, 4H), 4.39 (dd, J=34.6, 28.6 Hz, 2H), 2.79 (d, J=8.4 Hz, 1H), 2.44 (s, 1H).

(S)-2-(4-(4-((5-cyano-3-fluoropyridin-2-yl)methoxy)-5-fluoropyrimidin-2-yl)-3-fluorobenzyl)-3-(oxetan-2-ylmethyl)-3H-imidazo[4,5-b]pyridine-5-carboxylic acid (Compound 302)

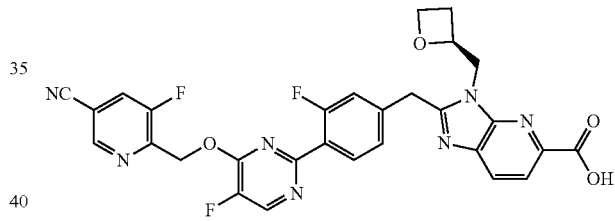

Prepared in analogous manner as for Compound 279. LCMS: [M+H]⁺=587.9; Retention time=1.36 min.

¹H NMR (400 MHz, CD₃OD): δ 8.61 (brs, 1H), 8.46 (d, J=2.8 Hz, 1H), 8.05-8.00 (m, 2H), 7.95 (d, J=8.4 Hz, 1H), 7.84 (t, J=8 Hz, 1H), 7.12-7.05 (m, 2H), 5.75 (d, J=1.6 Hz, 2H), 5.16-5.12 (m, 1H), 4.65-4.56 (m, 2H), 4.54-4.46 (m, 3H), 4.34-4.29 (m, 1H), 2.68-2.64 (m, 1H), 2.41-2.38 (m, 1H).

(S)-2-(4-(6-(4-(1H-imidazol-1-yl)benzyloxy)pyridin-2-yl)-2,5-difluorobenzyl)-3-(oxetan-2-ylmethyl)-3H-imidazo[4,5-b]pyridine-5-carboxylic acid (Compound 303)

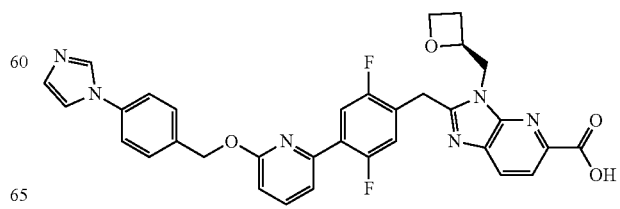

Prepared in analogous manner as for Compound 279. LCMS: [M+H]⁺=609.0; Retention time=1.69 min.

¹H NMR (400 MHz, DMSO-D6) δ 8.28-8.26 (brs, 1H), 8.08 (d, J=8.2 Hz, 1H), 7.97 (d, J=8.2 Hz, 1H), 7.90-7.86 (m, 1H), 7.85-7.81 (m, 1H), 7.76-7.74 (m, 1H), 7.69-7.62 (m, 4H), 7.51 (d, J=6.0 Hz, 1H), 7.42 (dd, J=11.4, 6.1 Hz, 1H), 7.11-7.09 (m, 1H), 6.96 (d, J=8.2 Hz, 1H), 5.52 (s, 2H), 5.18-5.13 (m, 1H), 4.76 (dd, J=15.1, 6.4 Hz, 1H), 4.67-4.61 (m, 2H), 4.56-4.49 (m, 2H), 4.35 (dt, J=9.0, 6.1 Hz, 1H), 2.75-2.68 (m, 1H), 2.43-2.40 (m, 1H).

(S)-2-(4-(6-((4-(1H-imidazol-1-yl)benzyl)oxy)pyridin-2-yl)-2-fluorobenzyl)-3-(oxetan-2-ylmethyl)-3H-imidazo[4,5-b]pyridine-5-carboxylic acid (Compound 304)

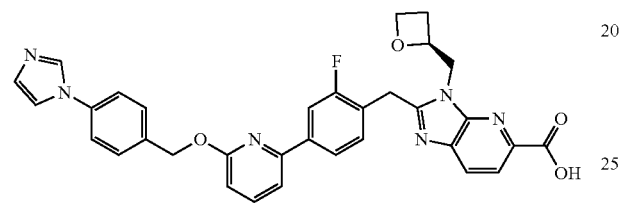

Prepared in analogous manner as for Compound 279. LCMS: [M+H]⁺=591.1; Retention time=1.36 min.

¹H NMR (400 MHz, DMSO-D6) δ 8.25-8.24 (brs, 1H), 8.06 (d, J=8.2 Hz, 1H), 7.99-7.89 (m, 3H), 7.88-7.80 (m, 1H), 7.74 (t, J=1.3 Hz, 1H), 7.70-7.61 (m, 5H), 7.46 (t, J=8.1 Hz, 1H), 7.10-7.09 (brs, 1H), 6.90 (d, J=8.2 Hz, 1H), 5.54 (s, 2H), 5.14 (d, J=7.1 Hz, 1H), 4.73 (dd, J=15.1, 6.4 Hz, 1H), 4.68-4.58 (m, 2H), 4.51 (dd, J=14.9, 10.2 Hz, 2H), 4.36 (dt, J=8.8, 5.9 Hz, 1H), 2.78-2.65 (m, 1H), 2.41-2.35 (m, 1H).

(S)-2-(4-(6-((4-chloro-2-fluorobenzyl)oxy)-5-fluoropyridin-2-yl)-3-fluorobenzyl)-3-(oxetan-2-ylmethyl)-3H-imidazo[4,5-b]pyridine-5-carboxylic acid (Compound 305)

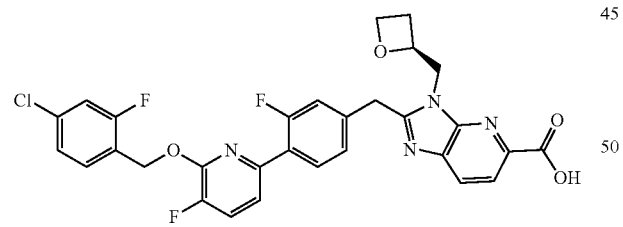

Prepared in analogous manner as for Compound 279. LCMS: [M+H]⁺=595.1; Retention time=1.93 min.

¹H NMR (400 MHz, DMSO-D6) δ 8.07 (d, J=8.2 Hz, 1H), 8.02-7.87 (m, 2H), 7.81 (dd, J=10.3, 8.3 Hz, 1H), 7.62 (t, J=8.2 Hz, 1H), 7.55-7.42 (m, 2H), 7.39-7.26 (m, 3H), 5.55 (s, 2H), 5.11 (d, J=6.7 Hz, 1H), 4.69 (dd, J=15.0, 6.3 Hz, 1H), 4.53 (ddd, J=21.4, 18.2, 7.7 Hz, 4H), 4.35 (dd, J=14.9, 6.0 Hz, 1H), 2.67 (s, 1H), 2.44 (d, J=8.6 Hz, 1H).

(S)-2-(4-(6-((4-chloro-2-fluorobenzyl)oxy)-3,5-difluoropyridin-2-yl)-3-fluorobenzyl)-3-(oxetan-2-ylmethyl)-3H-imidazo[4,5-b]pyridine-5-carboxylic acid (Compound 306)

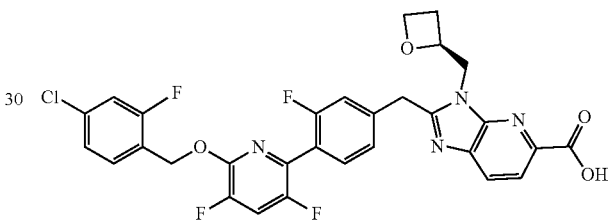

Prepared in analogous manner as for Compound 279. LCMS: [M+H]⁺=613.0; Retention time=1.93 min.

¹H NMR (400 MHz, DMSO-D6) δ 8.20-8.06 (m, 2H), 7.97 (d, J=8.2 Hz, 1H), 7.65-7.48 (m, 3H), 7.36 (t, J=9.5 Hz, 3H), 5.47 (s, 2H), 5.14 (s, 1H), 4.72 (dd, J=15.0, 6.5 Hz, 1H), 4.55 (m, J=21.6, 15.3, 5.2 Hz, 4H), 4.37 (dd, J=14.9, 6.0 Hz, 1H), 2.69 (d, J=7.7 Hz, 1H), 2.45 (s, 1H).

(S)-2-(4-(6-((4-cyano-2-fluorobenzyl)oxy)pyridin-2-yl)-3-fluorobenzyl)-7-fluoro-1-(oxetan-2-ylmethyl)-1H-benzo[d]imidazole-6-carboxylic acid (Compound 307)

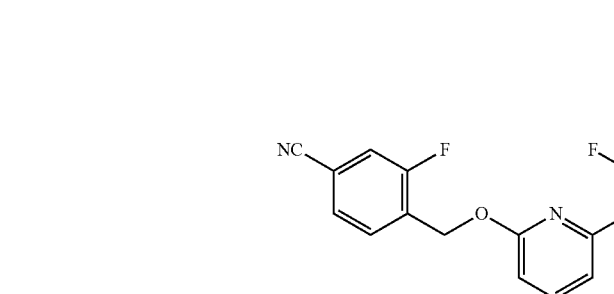

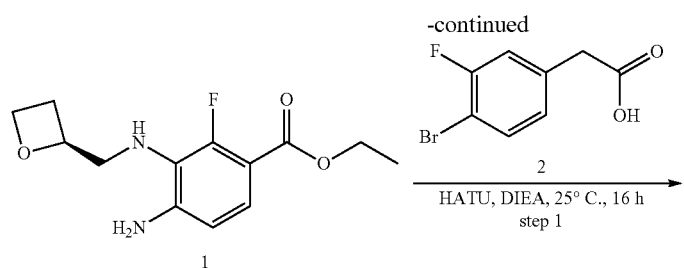
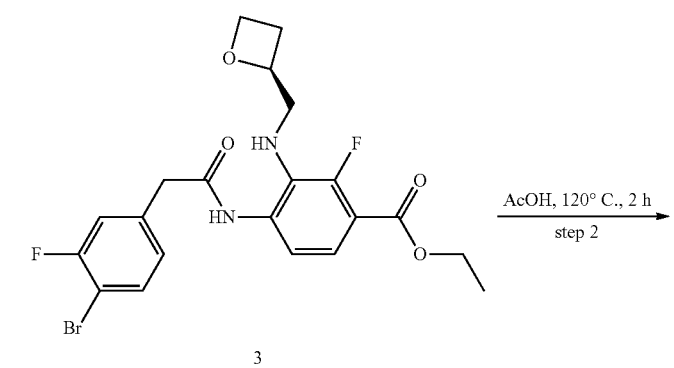
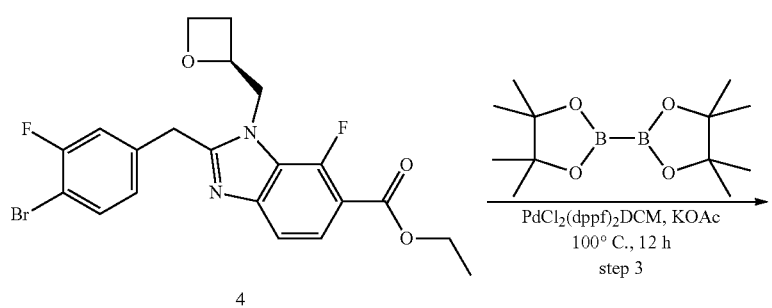
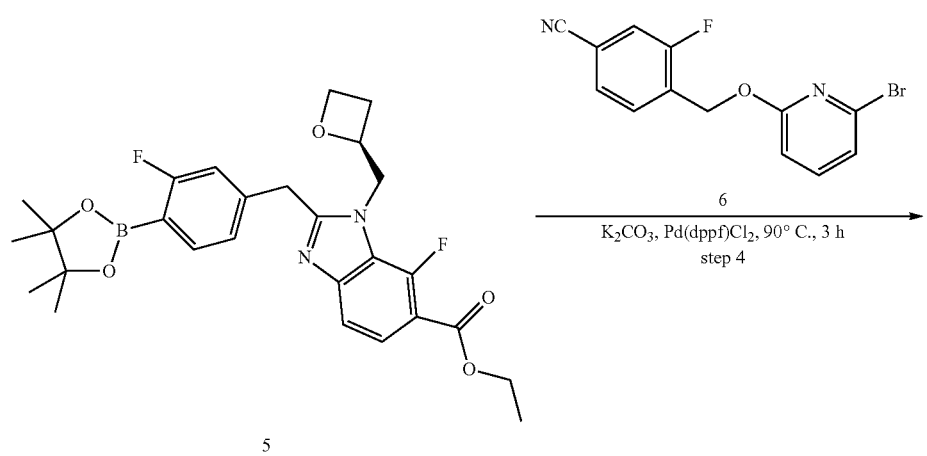

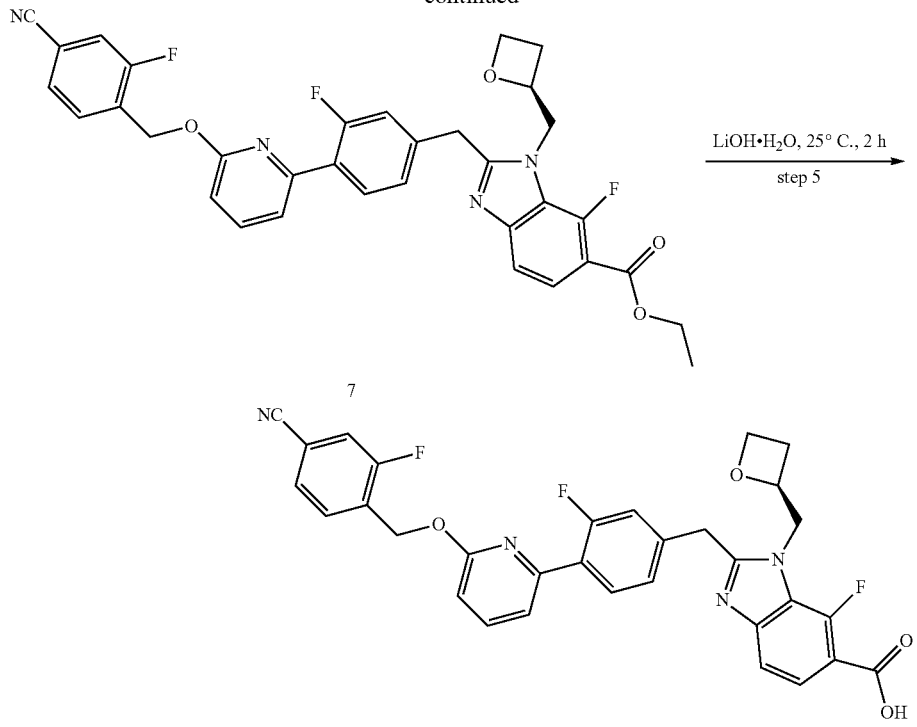

Step 1

A solution of 2-(4-bromo-3-fluoro-phenyl)acetic acid (220.7 mg, 947 μmol), ethyl 4-amino-2-fluoro-3-[[(2S)-oxetan-2-yl]methylamino]benzoate (231 mg, 861 μmol), EDCI (494.3 mg, 2.58 mmol), DIEA (669.90 mg, 5.18 mmol) was stirred at 25° C. for 16 h. The resulting mixture was poured into water and extracted with ethyl acetate (3×20 mL). The combined organic layers were washed with brine (2×30 mL), dried over anhydrous sodium sulfate, concentrated and purified by silica gel chromatography (eluting with ethyl acetate/petroleum ether, v/v, 1/1) to afford ethyl 4-[[2-(4-bromo-3-fluoro-phenyl)acetyl]amino]-2-fluoro-3-[[(2S)-oxetan-2-yl]methylamino]benzoate (82 mg, 15.2% yield) as a yellow solid. LCMS: [M+H]+=483.0, Retention time=2.27 min.

Step 2

A solution of ethyl 4-[[2-(4-bromo-3-fluoro-phenyl)acetyl]amino]-2-fluoro-3-[[(2S)-oxetan-2-yl]methylamino]benzoate (82 mg, 170 μmol) in AcOH (1 mL) was stirred at 120° C. for 2 h. The resulting mixture was concentrated to remove most solvents and adjusted pH of the solution to 7-8 with saturated sodium bicarbonate, extracted with ethyl acetate (3×10 mL), concentrated and purified by silica gel chromatography (eluting with ethyl acetate/petroleum ether, v/v, 1/1) to afford ethyl (S)-2-(4-bromo-3-fluorobenzyl)-7-fluoro-1-(oxetan-2-ylmethyl)-1H-benzo[d]imidazole-6-carboxylate (60 mg, 68.4% yield) as a yellow solid. LCMS: [M+H]+=465.1, Retention time (0.01% TFA)=2.07 min.

Step 3

A mixture of ethyl (S)-2-(4-bromo-3-fluorobenzyl)-7-fluoro-1-(oxetan-2-ylmethyl)-1H-benzo[d]imidazole-6-carboxylate (105 mg, 226 μmol), 4,4,5,5-tetramethyl-2-(4,4,5,5-tetramethyl-1,3,2-dioxaborolan-2-yl)-1,3,2-dioxaborolane (63.0 mg, 248 μmol), PdCl2(dppf)2 (36.9 mg, 45 μmol) and KOAc (66.4 mg, 677 μmol) in dioxane (2 mL) was stirred at 100° C. for 16 h under nitrogen. The resulting mixture was filtered and washed with ethyl acetate, concentrated to obtain ethyl (S)-7-fluoro-2-(3-fluoro-4-(4,4,5,5-tetramethyl-1,3,2-dioxaborolan-2-yl)benzyl)-1-(oxetan-2-ylmethyl)-1H-benzo[d]imidazole-6-carboxylate (227 mg, 204 μmol, 90.31% yield) as a brown solid and used directly for the next stop. LCMS: [M+H]+=513.3, Retention time (0.01% TFA)= 2.10 min.

Step 4

A mixture of ethyl (S)-7-fluoro-2-(3-fluoro-4-(4,4,5,5-tetramethyl-1,3,2-dioxaborolan-2-yl)benzyl)-1-(oxetan-2-ylmethyl)-1H-benzo[d]imidazole-6-carboxylate (110 mg, 215 μmol), 4-[(6-bromo-2-pyridyl)oxymethyl]-3-fluoro-benzonitrile (65.9 mg, 215 μmol), K2CO3 (88.9 mg, 644 μmol) and Pd(dppf)Cl2 (17.5 mg, 21 μmol) in dioxane (2 mL) was stirred at 90° C. for 3 h under nitrogen. The resulting mixture was concentrated and purified by silica gel chromatography (eluting with ethyl acetate/petroleum ether, v/v, 1/1) to afford ethyl (S)-2-(4-(6-((4-cyano-2-fluorobenzyl)oxy)pyridin-2-yl)-3-fluorobenzyl)-7-fluoro-1-(oxetan-2-ylmethyl)-1H-benzo[d]imidazole-6-carboxylate (30 mg, 22.8% yield) as a yellow solid. LCMS: [M+H]+=613.0; Retention time=2.33 min.

Step 5

A solution of ethyl (S)-2-(4-(6-((4-cyano-2-fluorobenzyl)oxy)pyridin-2-yl)-3-fluorobenzyl)-7-fluoro-1-(oxetan-2-ylmethyl)-1H-benzo[d]imidazole-6-carboxylate (90 mg, 147 μmol), 0.5 N LiOH (2 mL) in THF (7 mL) was stirred at 25° C. for 16 h, the mixture was neutralized with acetic acid to pH=5, The resulting mixture was extracted with DCM/MeOH (v/v=10/1, 3×10 mL). The combined organic layers were concentrated and purified by prep-HPLC (Column: Xtimate C18 21.2*250 mm, 10 μm; Mobile Phase: A:water (10 mMNH4HCO3&0.025% NH3.H2O), B: ACN; Gradient: 5% B for 3 min, then 50-50% B in 10 min, stop at 18 min; Flow Rate (ml/min): 30.00; Detective Wavelength (nm): 214 nm) to give (S)-2-(4-(6-((4-cyano-2-fluorobenzyl)oxy)pyridin-2-yl)-3-fluorobenzyl)-7-fluoro-1-(oxetan-2-ylmethyl)-1H-benzo[d]imidazole-6-carboxylic acid (17.3 mg, 20.14% yield) as a white solid. LCMS: [M+H]⁺=585.1; Retention time=1.82 min.

¹H NMR (400 MHz, DMSO-D6) δ 7.97-7.82 (m, 3H), 7.80-7.67 (m, 2H), 7.62-7.50 (m, 1H), 7.46 (d, J=5.9 Hz, 1H), 7.30 (dd, J=17.4, 7.5 Hz, 3H), 6.94 (d, J=8.2 Hz, 1H), 5.57 (s, 2H), 5.04 (d, J=4.9 Hz, 1H), 4.71 (dd, J=15.6, 7.2 Hz, 1H), 4.61-4.31 (m, 5H), 2.72 (dt, J=16.4, 8.3 Hz, 1H), 2.42 (dd, J=21.2, 12.5 Hz, 1H).

(S)-2-(4-(6-((4-chloro-2-fluorobenzyl)oxy)pyridin-2-yl)-3-fluorobenzyl)-7-fluoro-1-(oxetan-2-ylmethyl)-1H-benzo[d]imidazole-6-carboxylic acid (Compound 308)

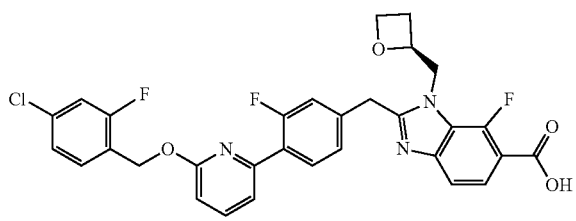 [SMILES: O=C(O)c1ccc2nc(Cc3ccc(-c4cccc(OCc5ccc(Cl)cc5F)n4)c(F)c3)n(C[C@@H]3CCO3)c2c1F]

Prepared in analogous manner as for Compound 307. LCMS: [M+H]⁺=594.0; Retention time=1.93 min.

¹H NMR (400 MHz, DMSO-D6) δ 7.95 (t, J=8.4 Hz, 1H), 7.84 (t, J=7.9 Hz, 1H), 7.61 (dd, J=16.3, 8.2 Hz, 2H), 7.46 (ddd, J=22.7, 13.4, 5.1 Hz, 3H), 7.31 (dd, J=10.0, 5.9 Hz, 3H), 6.89 (d, J=8.2 Hz, 1H), 5.47 (s, 2H), 5.04 (d, J=6.6 Hz, 1H), 4.75 (dd, J=15.5, 7.4 Hz, 1H), 4.65-4.32 (m, 5H), 2.78-2.67 (m, 1H), 2.43 (d, J=8.4 Hz, 1H).

(S)-2-(4-(6-((4-chloro-2-fluorobenzyl)oxy)pyridin-2-yl)-2-fluorobenzyl)-7-fluoro-1-(oxetan-2-ylmethyl)-1H-benzo[d]imidazole-6-carboxylic acid (Compound 309)

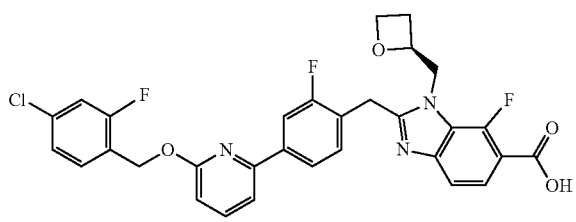 [SMILES: O=C(O)c1ccc2nc(Cc3ccc(-c4cccc(OCc5ccc(Cl)cc5F)n4)cc3F)n(C[C@@H]3CCO3)c2c1F]

Prepared in analogous manner as for Compound 307. LCMS: [M+H]⁺=594.0; Retention time=1.96 min.

¹H NMR (400 MHz, MeOD) δ 7.74 (dd, J=11.5, 9.2 Hz, 2H), 7.69-7.57 (m, 2H), 7.48-7.36 (m, 2H), 7.35-7.18 (m, 2H), 7.10 (dd, J=14.0, 4.9 Hz, 2H), 6.70 (d, J=8.2 Hz, 1H), 5.43 (s, 2H), 5.12 (d, J=5.5 Hz, 1H), 4.66 (dd, J=15.4, 7.2 Hz, 1H), 4.61-4.54 (m, 1H), 4.54-4.44 (m, 2H), 4.42-4.25 (m, 2H), 3.55 (d, J=3.1 Hz, 2H), 2.80-2.64 (m, 1H), 2.49-2.36 (m, 1H).

(S)-2-(4-(6-((4-cyano-2-fluorobenzyl)oxy)pyridin-2-yl)-2-fluorobenzyl)-7-fluoro-1-(oxetan-2-ylmethyl)-1H-benzo[d]imidazole-6-carboxylic acid (Compound 310)

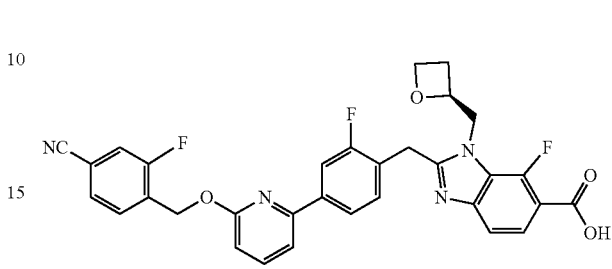

Prepared in analogous manner as for Compound 307. LCMS: [M+H]⁺=585.1; Retention time=1.85 min.

¹H NMR (400 MHz, DMSO-D6) δ 7.89 (dd, J=22.8, 9.2 Hz, 4H), 7.75 (d, J=11.0 Hz, 2H), 7.64 (dd, J=16.6, 7.0 Hz, 2H), 7.50-7.26 (m, 2H), 6.93 (d, J=8.2 Hz, 1H), 5.62 (s, 2H), 5.10 (s, 1H), 4.76 (s, 1H), 4.66-4.29 (m, 5H), 2.75 (s, 1H), 2.43 (s, 1H).

(S)-2-(4-(4-((4-chloro-2-fluorobenzyl)oxy)pyrimidin-2-yl)-2-fluorobenzyl)-7-fluoro-1-(oxetan-2-ylmethyl)-1H-benzo[d]imidazole-6-carboxylic acid (Compound 311)

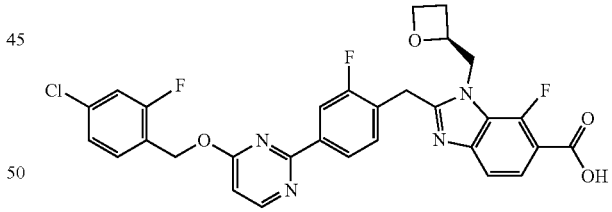

Prepared in analogous manner as for Compound 307. LCMS: [M+H]⁺=595.2; Retention time (0.01% TFA)=1.64 min.

¹H NMR (400 MHz, DMSO-D6) δ 8.73 (d, J=5.2 Hz, 1H), 8.09-7.98 (m, 2H), 7.82 (d, J=5.2 Hz, 1H), 7.63 (dd, J=16.6, 8.4 Hz, 2H), 7.56-7.46 (m, 2H), 7.43-7.28 (m, 2H), 5.53 (s, 2H), 5.09 (d, J=7.0 Hz, 1H), 4.78 (dd, J=15.6, 7.2 Hz, 1H), 4.67-4.28 (m, 5H), 2.80-2.70 (m, 1H), 2.44 (d, J=8.9 Hz, 1H).

133

(S)-2-(4-(4-((4-cyano-2-fluorobenzyl)oxy)-5-fluoropyrimidin-2-yl)-2-fluorobenzyl)-7-fluoro-1-(oxetan-2-ylmethyl)-1H-benzo[d]imidazole-6-carboxylic acid (Compound 312)

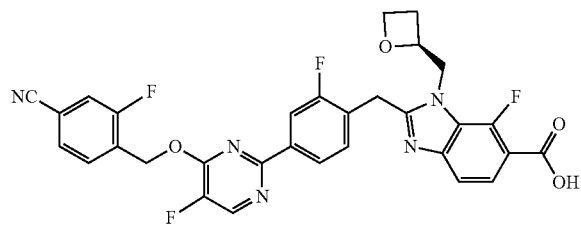 [SMILES: N#Cc1ccc(COc2nc(-c3ccc(Cc4nc5ccc(C(=O)O)c(F)c5n4C[C@@H]4CCO4)c(F)c3)ncc2F)c(F)c1]

Prepared in analogous manner as for Compound 307. LCMS: [M+H]$^+$=603.9; Retention time=1.53 min $^1$H NMR (400 MHz, CDCl$_3$) δ 8.44-8.43 (d, J=2.4 Hz, 1H), 8.11-8.05 (m, 2H), 7.93-7.89 (t, J=8.0 Hz, 1H), 7.70-7.66 (t, J=7.6 Hz, 1H), 7.63-7.61 (d, J=8.0 Hz, 1H), 7.51-7.47 (t, J=8.0 Hz, 2H), 7.45-7.42 (d, J=9.2 Hz, 1H), 5.71 (s, 2H), 5.22-5.20 (d, J=6.8 Hz, 1H), 4.71-4.47 (m, 6H), 2.82 (s, 1H), 2.47 (s, 1H).

134

(S)-2-(4-(4-((5-cyanopyridin-2-yl)methoxy)-5-fluoropyrimidin-2-yl)-2,5-difluorobenzyl)-7-fluoro-1-(oxetan-2-ylmethyl)-1H-benzo[d]imidazole-6-carboxylic acid (Compound 313)

Prepared in analogous manner as for Compound 307. LCMS: [M+H]$^+$=605.2; Retention time (10 mM NH$_4$HCO$_3$)=1.18 min.

(S)-2-((1-(6-(4-cyano-2-fluorobenzyloxy) pyridin-2-yl) piperidin-4-ylidene) methyl)-3-(oxetan-2-ylmethyl)-3H-imidazo [4, 5-b] pyridine-S-carboxylic acid (Compound 314)

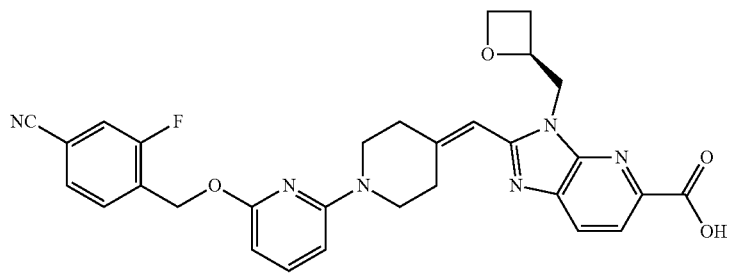

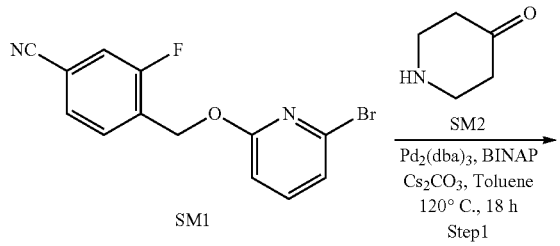

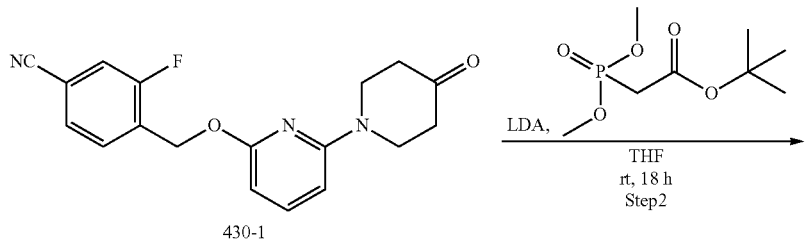

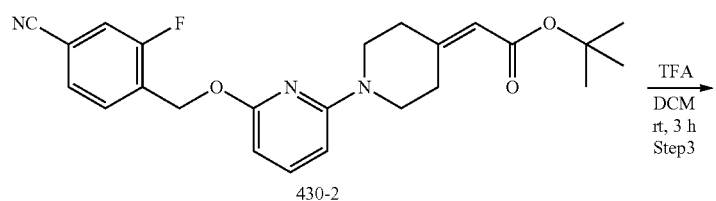

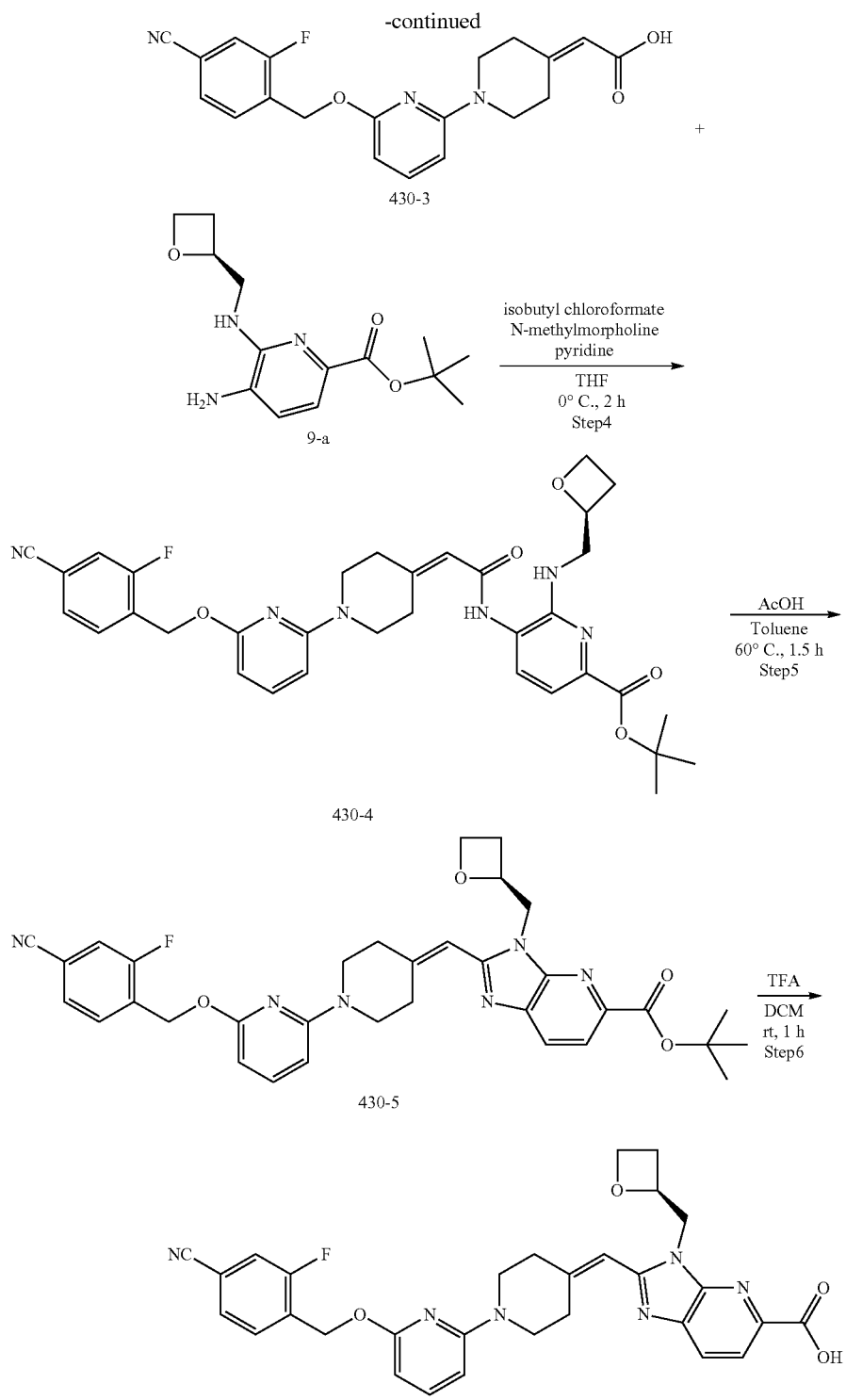

Step 1

A mixture of 4-[(6-bromo-2-pyridyl)oxymethyl]-3-fluoro-benzonitrile (10 g, 30.93 mmol), piperidin-4-one (3.99 g, 40.21 mmol), Pd₂(dba)₃ (1.13 g, 1.55 mmol), BINAP (1.93 g, 3.09 mmol) and Cs2CO3 (15.08 g, 46.40 mmol) in Toluene (80 mL) was stirred for 18 h at 110° C. under Argon, until the reaction was complete as indicated by LCMS, the reaction mixture was filtered through a pad of Celite with EtOAc, and the combined organics were concentrated in vacuo, purified by silica gel chromatography (Hexanes/EtOAc=77:23) to give the desired product 3-fluoro-4-[[6-(4-oxo-1-piperidyl)-2-pyridyl] oxymethyl] benzonitrile (5.25 g, 52.2% yield) as a pale yellow solid. LCMS: [M+H]⁺=326.2; Retention time=1.63 min.

¹H NMR (400 MHz, CDCl₃) δ 7.62 (t, J=7.6 Hz, 1H), 7.50-7.42 (m, 2H), 7.37 (dd, J=1.2, 8 Hz, 1H), 6.32 (d, J=8 Hz, 1H), 6.23 (d, J=7.6 Hz, 1H), 5.44 (s, 2H), 3.85 (t, J=6 Hz, 4H), 2.46 (t, J=6 Hz, 4H).

Step 2

To a suspension of tert-butyl 2-dimethoxyphosphorylacetate (7.13 g, 31.81 mmol) in THF (60 mL) was added slowly LDA (3.98 g, 37.12 mmol, 19 mL) at rt and stirred for 10 min under Ar. A solution of 3-fluoro-4-[[6-(4-oxo-1-piperidyl)-2-pyridyl] oxymethyl] benzonitrile (3.45 g, 10.60 mmol) in THF (15 mL) was added drop-wise at rt. After completion of the reaction as judged by LCMS, the reaction mixture was quenched with water (10 mL) and extracted with EtOAc (3×20 mL). The organic phase was washed with brine (50 mL) and dried over anhydrous Na$_2$SO$_4$, filtered and concentrated in vacuo. The crude product was purified by flash chromatography (SiO$_2$, hexane/ethyl acetate 10:1) to afford tert-butyl 2-[1-[6-[(4-cyano-2-fluoro-phenyl) methoxy]-2-pyridyl]-4-piperidylidene] acetate (2.2 g, 36.1% yield) as a colorless liquid. LCMS: [M+H]$^+$=424.2; Retention time=1.98 min.

Step 3

A mixture of tert-butyl 2-[1-[6-[(4-cyano-2-fluoro-phenyl) methoxy]-2-pyridyl]-4-piperidylidene]acetate (2.2 g, 5.20 mmol) in DCM (21 mL) was added TFA (10.36 g, 90.86 mmol, 7 mL), and stirred for 1 h at rt, until the reaction was complete as indicated by LCMS, the reaction mixture was added DCM (160 mL), washed with Aqueous Sat. NaHCO$_3$ (2×30 mL), dried and evaporated, purified by flash chromatography on silica gel (PE:EA/0%-66%) to give the desired product 2-[1-[6-[(4-cyano-2-fluoro-phenyl) methoxy]-2-pyridyl]-4-piperidylidene] acetic acid (1.78 g, 4.44 mmol, 85.5% yield) as a pale white solid. LCMS: [M+H]$^+$=368.1; Retention time=1.25 min.

Step 4

A mixture of 2-[1-[6-[(4-cyano-2-fluoro-phenyl) methoxy]-2-pyridyl]-4-piperidylidene] acetic acid (723 mg, 1.97 mmol) in THF (30 mL) was stirred and cooled on salt-ice bath. Then isobutyl chloroformate (525.00 mg, 3.84 mmol) and N-methylmorpholine (598 mg, 5.91 mmol, 0.65 mL) were added, and the reaction was stirred at salt-ice bath for 20 min. Tert-butyl 5-amino-6-[[(2S)-oxetan-2-yl] methylamino] pyridine-2-carboxylate (500 mg, 1.79 mmol) was dissolved in pyridine (6.85 g, 86.55 mmol, 7 mL) and N-methylmorpholine (598 mg, 5.91 mmol, 0.65 mL) were added to the reaction mixture on an ice-bath with stirring 1 h at 0° C. After reaction completion, the solvent was evaporated in vacuo and the remaining residue was partitioned with DCM (50 mL) and water (20 mL). The DCM layer was washed once with brine, dried over anhydrous Na$_2$SO$_4$, filtered and evaporated in vacuo to give a crude product. The crude was purified by silica gel chromatography (Hexanes/EtOAc=20:1) to give the desired product tert-butyl 5-[[2-[1-[6-[(4-cyano-2-fluoro-phenyl) methoxy]-2-pyridyl]-4-piperidylidene] acetyl] amino]-6-[[(2S)-oxetan-2-yl] methylamino] pyridine-2-carboxylate (168 mg, 13.35% yield) as a pale yellow solid. LCMS: [M+H]$^+$=629.1; Retention time=2.12 min.

Step 5

A mixture of tert-butyl 5-[[2-[1-[6-[(4-cyano-2-fluoro-phenyl) methoxy]-2-pyridyl]-4-piperidylidene]acetyl] amino]-6-[[(2S)-oxetan-2-yl] methylamino] pyridine-2-carboxylate (64 mg, 102 µmol) and AcOH (102 µmol) in Toluene (4 mL) was stirred for 1.5 h at 60° C., until the reaction was complete as indicated by LCMS, the reaction mixture was concentrated in vacuo, purified by prep-TLC (PE:EA/1:1.5) to give the desired product tert-butyl 2-[[1-[6-[(4-cyano-2-fluoro-phenyl) methoxy]-2-pyridyl]-4-piperidylidene] methyl]-3-[[(2S)-oxetan-2-yl] methyl] imidazo [4, 5-b] pyridine-5-carboxylate (5 mg, 8.0% yield) as a pale yellow oil. LCMS: [M+H]$^+$=612.3; Retention time (0.01% TFA)=2.04 min.

Step 6

A mixture of tert-butyl 2-[[1-[6-[(4-cyano-2-fluoro-phenyl) methoxy]-2-pyridyl]-4-piperidylidene]methyl]-3-[[(2S)-oxetan-2-yl] methyl] imidazo [4, 5-b] pyridine-5-carboxylate (5 mg, 8 µmol) in DCM (4 mL) was added TFA (1.48 g, 13.0 mmol, 1 mL), and stirred for 1 h at rt, until the reaction was complete as indicated by LCMS, the reaction mixture was were concentrated in vacuo, dissolved in THF (1.5 mL), purified by prep-HPLC to give the desired product 2-[[1-[6-[(4-cyano-2-fluoro-phenyl) methoxy]-2-pyridyl]-4-piperidylidene] methyl]-3-[[(2S)-oxetan-2-yl] methyl] imidazo [4, 5-b] pyridine-5-carboxylic acid (1.1 mg, 23.3% yield) as a white solid. LCMS: [M+H]$^+$=555.0; Retention time=1.51 min.

$^1$H NMR (400 MHz, DMSO-D6-d6) δ 8.16-8.09 (m, 1H), 7.68 (t, J=8 Hz, 1H), 7.62-7.55 (m, 2H), 7.52 (t, J=8 Hz, 1H), 6.70 (s, 1H), 6.41 (d, J=8.4 Hz, 1H), 6.18 (d, J=8 Hz, 1H), 5.49 (s, 2H), 5.28 (dd, J=2.8, 2.4 Hz, 1H), 4.82-4.80 (m, 1H), 4.74-4.68 (m, 1H), 4.63-4.60 (m, 1H), 4.46-4.41 (m, 1H), 3.74 (dd, J=4.4, 2 Hz, 2H), 3.68 (t, J=5.6 Hz, 2H), 2.95 (t, J=5.6 Hz, 2H), 2.81-2.76 (m, 1H), 2.56-2.54 (m, 1H), 2.50 (t, J=5.2 Hz, 2H).

(S)-2-((1-(6-(2,4-difluorobenzyloxy)pyridin-2-yl) piperidin-4-ylidene)methyl)-3-(oxetan-2-ylmethyl)-3H-imidazo[4,5-b]pyridine-5-carboxylic acid (Compound 315)

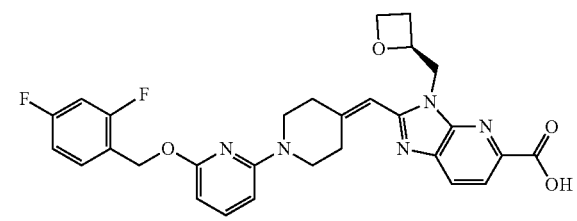 [SMILES: O=C(O)c1ccc2nc(C=C3CCN(c4cccc(OCc5ccc(F)cc5F)n4)CC3)n(C[C@@H]3CCO3)c2n1]

Prepared in analogous manner as for Compound 314. LCMS: [M+H]$^+$=548.0; Retention time (0.01% TFA)=1.97 min $^1$H NMR (400 MHz, MeOD) δ 8.15 (d, J=16.0 Hz, 2H), 7.48-7.47 (brs, 2H), 6.97 (d, J=8.2 Hz, 2H), 6.70-6.69 (brs, 1H), 6.41-6.40 (brs, 1H), 6.13-6.12 (brs, 1H), 5.38 (s, 2H), 5.33-5.28 (m, 1H), 4.77-4.76 (brs, 1H), 4.64-4.63 (brs, 1H), 3.79-3.78 (brs, 1H), 3.73-3.72 (brs, 1H), 3.02-3.01 (brs, 2H), 2.78-2.77 (brs, 1H), 2.56-2.55 (brs, 3H), 2.06-2.05 (brs, 2H), 0.92-0.91 (brs, 2H).

139

(S)-2-((1-(6-((5-cyanopyridin-2-yl)methoxy)pyridin-2-yl)piperidin-4-ylidene)methyl)-3-(oxetan-2-ylmethyl)-3H-imidazo[4,5-b]pyridine-5-carboxylic acid (Compound 316)

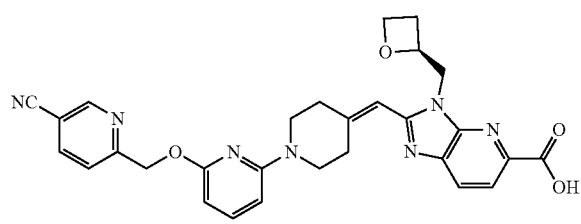 [SMILES: N#Cc1ccc(COc2cccc(N3CCC(=Cc4nc5ccc(C(=O)O)nc5n4C[C@@H]4CCO4)CC3)n2)nc1]

Prepared in analogous manner as for Compound 314. LCMS: [M+H]$^+$=538.2; Retention time (0.01% TFA)=1.74 min.

$^1$H NMR (400 MHz, CDCl$_3$) δ 8.85-8.83 (m, 1H), 8.26-8.18 (m, 2H), 7.95-7.91 (m, 1H), 7.60-7.54 (m, 1H), 7.48-7.44 (m, 1H), 6.22-6.20 (m, 1H), 6.17-6.14 (m, 1H), 5.57-5.54 (m, 1H), 5.52 (s, 2H), 5.20-5.18 (m, 1H), 4.67-4.58 (m, 3H), 4.41-4.35 (m, 1H), 3.95-3.83 (m, 4H), 3.69-3.58 (m, 2H), 2.81-2.79 (m, 1H), 2.47-2.42 (m, 1H), 2.21-2.20 (m, 2H).

140

(S)-2-((1-(6-((4-cyano-2-fluorobenzyl)oxy)pyridin-2-yl)piperidin-4-ylidene)methyl)-1-(oxetan-2-ylmethyl)-1H-benzo[d]imidazole-6-carboxylic acid (Compound 317)

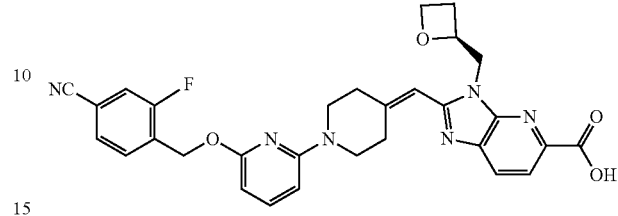

Prepared in analogous manner as for Compound 314. LCMS: [M+H]$^+$=554.0; Retention time=1.31 min.

$^1$H NMR δ 8.18 (s, 1H), 7.88 (d, J=9.8 Hz, 1H), 7.79 (d, J=8.4 Hz, 1H), 7.70-7.66 (m, 2H), 7.58 (d, J=8.4 Hz, 1H), 7.50-7.45 (m, 1H), 6.29 (d, J=8.2 Hz, 1H), 6.10 (d, J=7.8 Hz, 1H), 5.57-5.53 (brs, 1H), 5.42 (s, 2H), 5.02-4.96 (m, 1H), 4.62-4.57 (m, 1H), 4.51-4.43 (m, 2H), 4.35-4.30 (m, 1H), 3.91-3.84 (m, 2H), 3.82-3.71 (m, 2H), 3.65-3.58 (m, 3H), 2.68-2.64 (m, 1H), 2.19-2.12 (m, 2H).

(S)-2-((1-(6-((5-cyanopyridin-2-yl)methoxy)pyridin-2-yl)piperidin-4-ylidene)methyl)-7-fluoro-1-(oxetan-2-ylmethyl)-1H-benzo[d]imidazole-6-carboxylic acid (Compound 318)

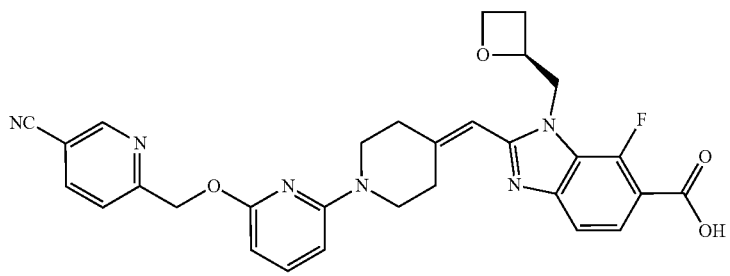 [SMILES: N#Cc1ccc(COc2cccc(N3CCC(=Cc4nc5ccc(C(=O)O)c(F)c5n4C[C@@H]4CCO4)CC3)n2)nc1]

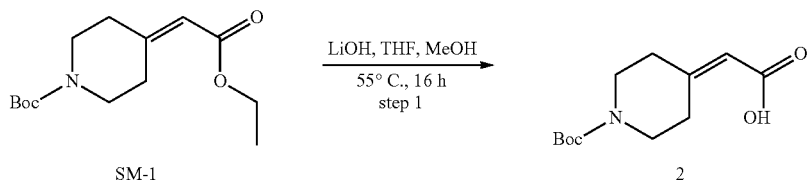

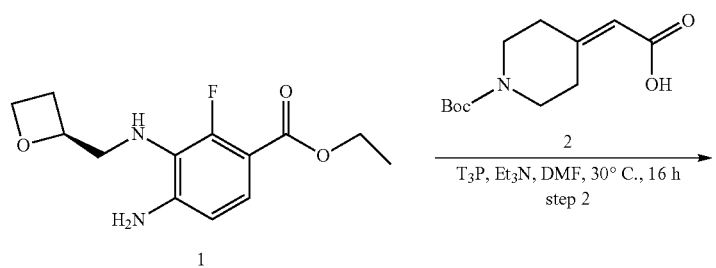

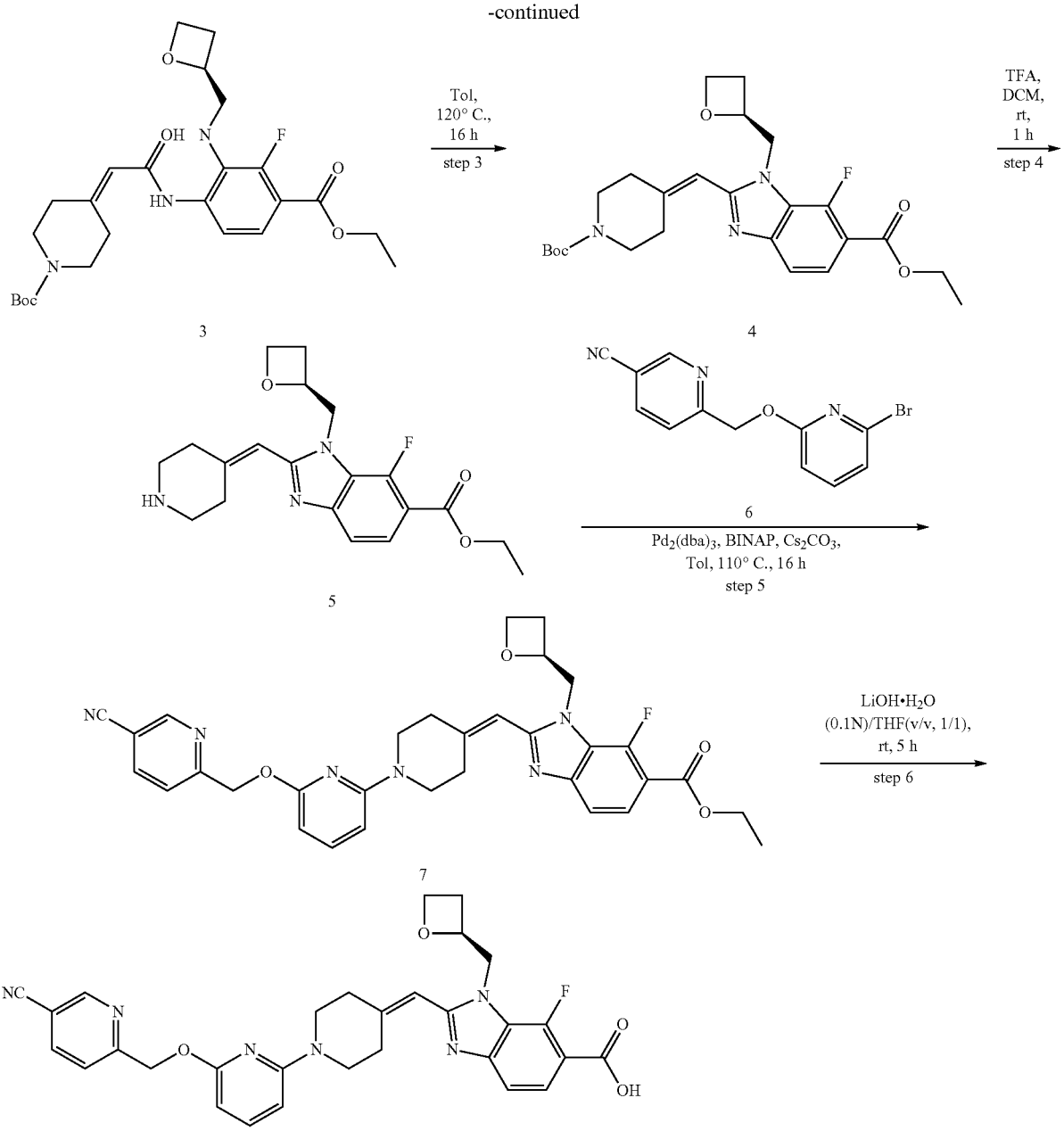

Step 1

A solution of tert-butyl 4-(2-ethoxy-2-oxo-ethylidene)piperidine-1-carboxylate (1.0 g, 3.71 mmol) in THF (10 mL) and Ethanol (8 mL). Lithium hydroxide hydrate (779 mg, 18.56 mmol) in Water (7 mL) was added. The mixture was stirred at 50° C. for 16 h, the mixture was neutralized with acetic acid to pH=5 and the resulting mixture was extracted with EtOAc (2×50 mL). The combined organic layers were concentrated to give 2-(1-tert-butoxycarbonyl-4-piperidylidene)acetic acid (0.9 g, 3.54 mmol, 95.4% yield). LCMS: [M+Na]+=264.1, Retention time (0.01% TFA)=1.75 min.

Step 2

A solution of ethyl 4-amino-2-fluoro-3-[[(2S)-oxetan-2-yl]methylamino]benzoate (207 mg, 772 mol), 2-(1-tert-butoxycarbonyl-4-piperidylidene)acetic acid (204.79 mg, 889 μmol), T₃P (736.08 mg, 2.31 mmol) and Et₃N (311.72 mg, 3.09 mmol) in DMF (5 mL), the mixture was stirred at 30° C. for 16 h. The resulting mixture was poured into water and extracted with ethyl acetate (3×20 mL). The combined organic layers were washed with brine (2×50 mL), dried over anhydrous sodium sulfate, concentrated and purified by silica gel chromatography (eluting with ethyl acetate/petroleum ether, v/v, 3/2) to afford tert-butyl (S)-4-(2-((4-(ethoxycarbonyl)-3-fluoro-2-((oxetan-2-ylmethyl)amino)phenyl)amino)-2-oxoethylidene)piperidine-1-carboxylate (135 mg, 27.4% yield) as a yellow oil. LCMS: [M+H]+=492.3, Retention time (0.01% TFA)=2.07 min.

Step 3

A solution of tert-butyl 4-[2-[4-ethoxycarbonyl-3-fluoro-2-[[(2S)-oxetan-2-yl]methylamino]anilino]-2-oxo-ethylidene]piperidine-1-carboxylate (64 mg, 130 μmol) in Toluene (2 mL) was stirred at 120° C. for 16 h. The resulting mixture was concentrated and purified by silica gel chromatography (eluting with ethyl acetate/petroleum ether, v/v, 4/1) to afford ethyl (S)-2-((1-(tert-butoxycarbonyl)piperidin-4-ylidene)methyl)-7-fluoro-1-(oxetan-2-ylmethyl)-1H-benzo[d]imidazole-6-carboxylate (46 mg, 74.6% yield) as a yellow oil. LCMS: [M+H]$^+$=474.3, Retention time (0.01% TFA)=1.97 min.

Step 4

To a solution of ethyl (S)-2-((1-(tert-butoxycarbonyl)piperidin-4-ylidene)methyl)-7-fluoro-1-(oxetan-2-ylmethyl)-1H-benzo[d]imidazole-6-carboxylate (20 mg, 41 μmol) in DCM (5 mL) was added TFA (8.5 mg, 75 μmol). The mixture was stirred at rt for 2 h. The resulting mixture was concentrated and adjusted to pH~8 with sat. sodium bicarbonate, extracted with dichloromethane, dried over anhydrous sodium sulfate and concentrated to afford ethyl (S)-7-fluoro-1-(oxetan-2-ylmethyl)-2-(piperidin-4-ylidenemethyl)-1H-benzo[d]imidazole-6-carboxylate (10 mg, 27 μmol, 65.8% yield) as a yellow oil. LCMS: [M+H]$^+$=374.2; Retention time (0.1% TFA)=0.89 min.

Step 5

A solution of ethyl (S)-7-fluoro-1-(oxetan-2-ylmethyl)-2-(piperidin-4-ylidenemethyl)-1H-benzo[d]imidazole-6-carboxylate (40 mg, 107 μmol), 6-[(6-bromo-2-pyridyl)oxymethyl]pyridine-3-carbonitrile (31.08 mg, 107 μmol), Pd$_2$(dba)$_3$ (9.8 mg, 11 μmol), BINAP (13.3 mg, 21 μmol) and Cs$_2$CO$_3$ (104.8 mg, 321 μmol) in Toluene (2 mL) in glove box was stirred at 110° C. for 16 h. The resulting solution was filtered and purified by silica gel chromatography (eluting with ethyl acetate/petroleum ether, v/v, 4/1) to afford ethyl (S)-2-((1-(6-((5-cyanopyridin-2-yl)methoxy)pyridin-2-yl)piperidin-4-ylidene)methyl)-7-fluoro-1-(oxetan-2-ylmethyl)-1H-benzo[d]imidazole-6-carboxylate (63 mg, 66.6% yield) as a yellow oil. LCMS: [M+H]$^+$=583.3; Retention time (0.1% TFA)=1.36 min.

Step 6

A solution of ethyl (S)-2-((1-(6-((5-cyanopyridin-2-yl)methoxy)pyridin-2-yl)piperidin-4-ylidene)methyl)-7-fluoro-1-(oxetan-2-ylmethyl)-1H-benzo[d]imidazole-6-carboxylate (60 mg, 103 mol) and LiOH (0.1N) (86.5 mg, 2.06 mmol) in THF (10 mL) was stirred at rt for 6 h. The resulting mixture was neutralized with acetic acid to pH=5 and extracted with DCM/MeOH (v/v=10/1, 3×10 mL). The combined organic layers were concentrated and purified by prep-HPLC to give (S)-2-((1-(6-((5-cyanopyridin-2-yl)methoxy)pyridin-2-yl)piperidin-4-ylidene)methyl)-7-fluoro-1-(oxetan-2-ylmethyl)-1H-benzo[d]imidazole-6-carboxylic acid (3.7 mg, 6.5% yield) as a white solid. LCMS: [M+H]$^+$=555.2; Retention time (0.1% FA)=1.88 min.

$^1$H NMR (400 MHz, DMSO-D6) δ 8.98 (d, J=1.3 Hz, 1H), 8.26 (dd, J=8.2, 2.1 Hz, 1H), 7.90-7.71 (m, 1H), 7.57 (t, J=7.9 Hz, 2H), 7.48 (t, J=8.0 Hz, 1H), 7.35 (d, J=8.4 Hz, 1H), 6.27 (d, J=8.2 Hz, 1H), 6.16 (d, J=7.7 Hz, 1H), 5.51 (s, 1H), 5.43 (s, 2H), 5.00 (s, 1H), 4.62 (dd, J=15.5, 7.4 Hz, 1H), 4.54-4.39 (m, 2H), 4.34 (dt, J=8.8, 6.0 Hz, 1H), 3.73 (dd, J=25.8, 15.9 Hz, 3H), 2.68 (d, J=6.8 Hz, 2H), 2.39 (dd, J=22.8, 14.1 Hz, 2H), 2.10 (s, 2H).

(S)-2-((4-(6-((4-chloro-2-fluorobenzyl)oxy)pyridin-2-yl)cyclohexyl)methyl)-1-(oxetan-2-ylmethyl)-1H-benzo[d]imidazole-6-carboxylic acid (Compound 319)

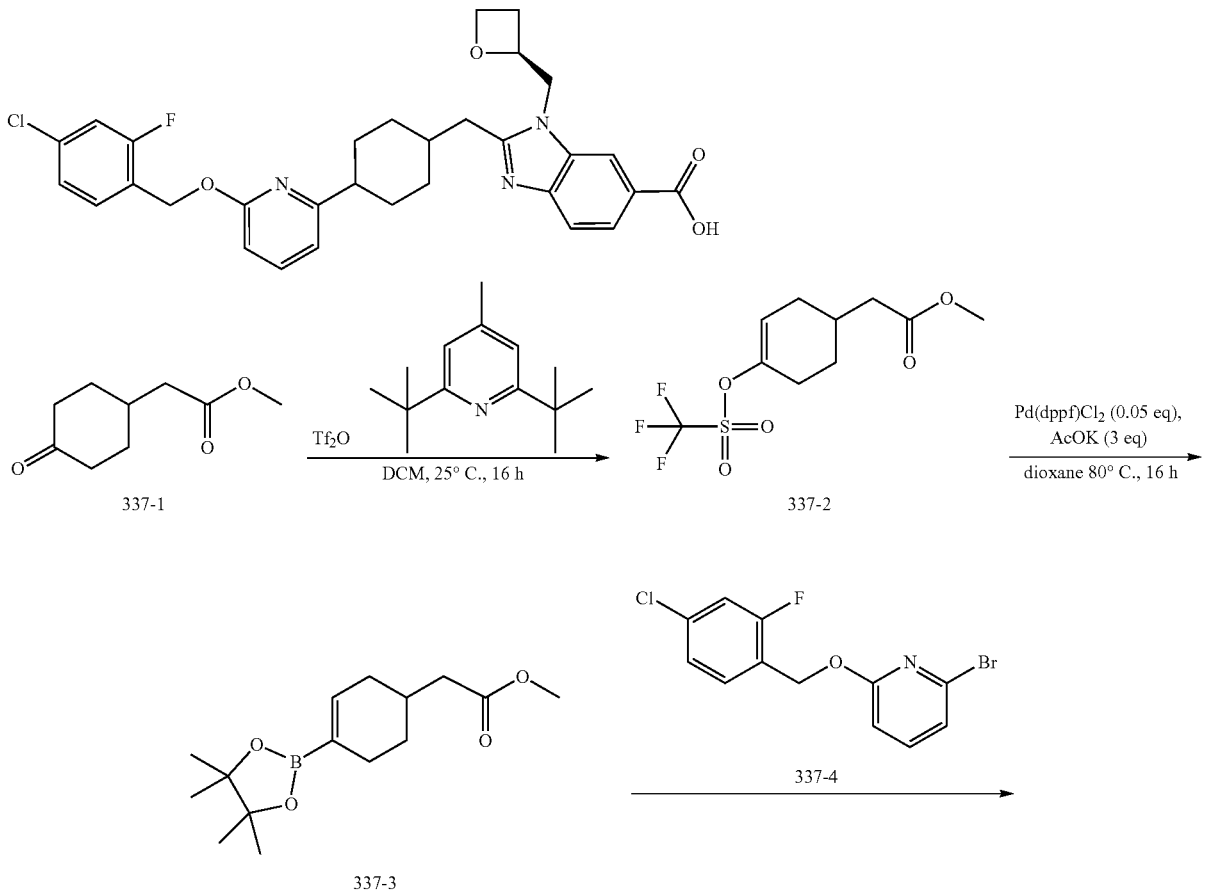

-continued
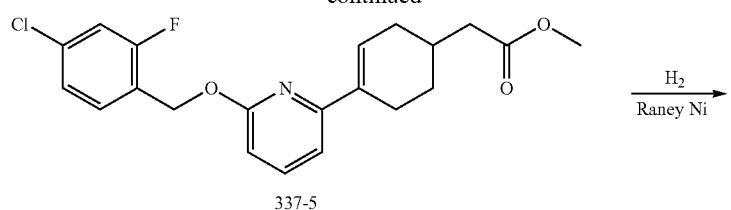
337-5
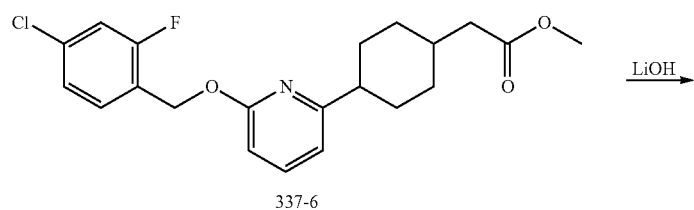
337-6
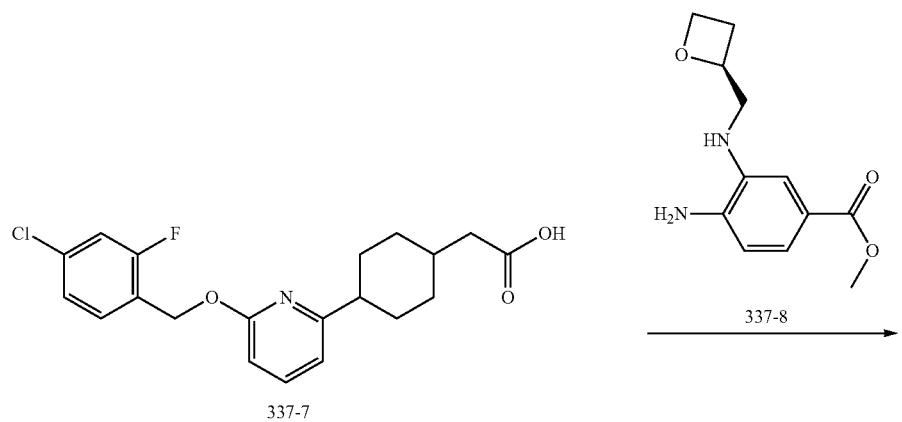
337-7
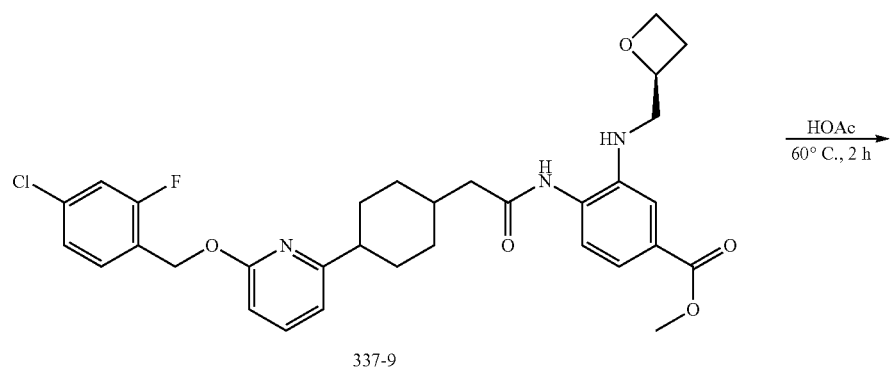
337-9
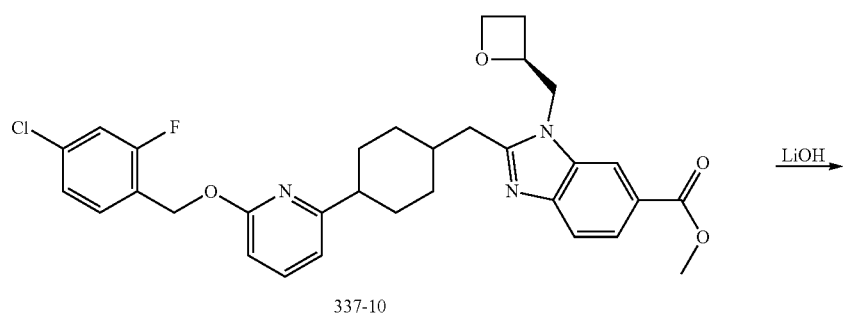
337-10

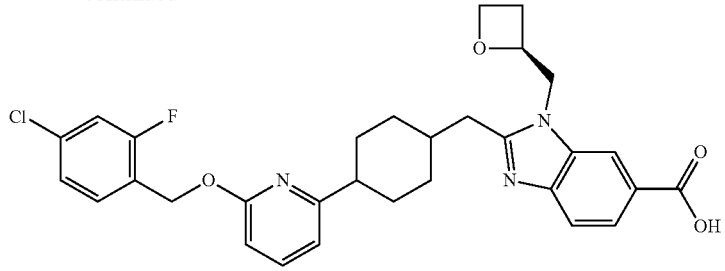

Step 1

Trifluoromethylsulfonyl trifluoromethanesulfonate (2.39 g, 8.46 mmol, 1.42 mL) was added dropwise to a solution of 2,6-ditert-butyl-4-methyl-pyridine (2.17 g, 10.58 mmol) in Dichloromethane (16 mL) followed by the dropwise addition of a solution of methyl 2-(4-oxocyclohexyl)acetate (1.2 g, 7.05 mmol) in Dichloromethane (16 mL). The reaction mixture was allowed to stir at 25° C. for 16 h and then concentrated to give methyl 2-[4(trifluoromethylsulfonyloxy)cyclohex-3-en-1-yl]acetate (1.48 g, 66.1% yield) as a colorless oil. LCMS: [M+H]$^+$=591, Retention time (10 mM NH$_4$HCO$_3$)=2.35 min.

Step 2

A mixture of methyl 2-[4-(trifluoromethylsulfonyloxy)cyclohex-3-en-1-yl]acetate (700 mg, 2.32 mmol), 4,4,5,5-tetramethyl-2-(4,4,5,5-tetramethyl-1,3,2-dioxaborolan-2-yl)-1,3,2-dioxaborolane (646.9 mg, 2.55 mmol), Pd(dppf)Cl$_2$ (94.6 mg, 116 µmol), potassium acetate (681.84 mg, 6.95 mmol), Pd(dppf)Cl$_2$ (64.2 mg, 116 µmol) in Dioxane (1 mL) was exchanged in glove box. The reaction mixture was stirred at 80° C. for 17 h. LCMS indicated the reaction was complete. Silica gel (3 g) was added into the reaction mixture and evaporated to give a dry powder, which was purified through silica gel. Methyl 2-[4-(4,4,5,5-tetramethyl-1,3,2-dioxaborolan-2-yl)cyclohex-3-en-1-yl]acetate (546 mg, 1.85 mmol, 80.0% yield) was obtained as light-yellow solid. LCMS: [M+H]$^+$=280, Retention time (0.01% TFA)=2.16 min.

Step 3

A mixture of [4-(2-methoxy-2-oxo-ethyl)cyclohexen-1-yl]boronic acid (443 mg, 2.13 mmol), 2-bromo-6-[(4-chloro-2-fluoro-phenyl)methoxy]pyridine (672.8 mg, 2.13 mmol), dipotassium carbonate (881.2 mg, 6.38 mmol), Pd(dppf)Cl$_2$ (77.7 mg, 106 µmol) in Dioxane (6 mL) was bubbled with nitrogen for 10 min, and then stirred at 80° C. for 16 h. LCMS indicated the reaction was almost complete. Methyl 2-[4-[6-[(4-chloro-2-fluoro-phenyl)methoxy]-2-pyridyl]cyclohex-3-en-1-yl]acetate (361 mg, 833 µmol, 39.2% yield) was obtained as white solid. LCMS: [M+H]$^+$=390, Retention time (10 mmol NH$_4$HCO$_3$)=2.49 min.

Step 4

To a solution of methyl 2-[4-[6-[(4-chloro-2-fluoro-phenyl)methoxy]-2-pyridyl]cyclohex-3-en-1-yl]acetate (351 mg, 810 µmol) in Methanol (50 mL) was added Raney nickel (0.5 g, 5.84 mmol). The reaction mixture was stirred at 20° C. for 2 h. LCMS indicated the reaction mixture was complete. The reaction mixture was filtered through celite, washed with ethyl acetate. The filtrate was evaporated under reduced pressure to give methyl 2-[4-[6-[(4-chloro-2-fluoro-phenyl)methoxy]-2-pyridyl]cyclohexyl]acetate (331 mg, 718 µmol, 88.6% yield) as white solid. LCMS: [M+H]$^+$=392, Retention time (0.01% TFA)=2.42 min.

Step 5

To a solution of methyl 2-[4-[6-[(4-chloro-2-fluoro-phenyl)methoxy]-2-pyridyl]cyclohexyl]acetate (330 mg, 716 µmol) in THF (3 mL) in ice-bath was added dropwise a solution of Lithium hydroxide hydrate (150.2 mg, 3.58 mmol) in Water (3 mL). The reaction mixture was stirred at 50° C. for 16 h. 2-[4-[6-[(4-chloro-2-fluoro-phenyl)methoxy]-2-pyridyl]cyclohexyl]acetic acid (180 mg, 453 µmol, 63.2% yield) was obtained as light-yellow oil. LCMS: [M+H]$^+$=378; Retention time (0.01% TFA)=2.20 min.

Step 6

To a solution of 2-[4-[6-[(4-chloro-2-fluoro-phenyl)methoxy]-2-pyridyl]cyclohexyl]acetic acid (137 mg, 344 µmol), methyl 4-amino-3-[[(2S)-oxetan-2-yl]methylamino]benzoate (81.38 mg, 344 µmol), 3-hydroxytriazolo[4,5-b]pyridine (56.26 mg, 413 µmol), 3-(ethyliminomethyleneamino)-N,N-dimethyl-propan-1-amine; hydrochloride (79.24 mg, 413 µmol) in DMF (1 mL) was stirred at 25° C. for 1 hr. LCMS indicated the reaction was complete. The reaction mixture was diluted with brine (10 mL) and extracted with ethyl acetate (3×10 mL). The combined organic layers were dried over sodium sulfate and evaporated under reduced pressure to provide a residue, which was purified through silica gel to give tert-butyl 2-[[4-[6-[(4-chloro-2-fluoro-phenyl)methoxy]-2-pyridyl]cyclohexyl]methyl]-3-[[(2S)-oxetan-2-yl]methyl]benzimidazole-5-carboxylate (180 mg, 80.1% yield) as colorless oil. LCMS: [M+H]$^+$=638, Retention time (0.01% TFA)=2.41 min.

Step 7

A solution of tert-butyl 4-[[2-[4-[6-[(4-chloro-2-fluoro-phenyl)methoxy]-2-pyridyl]cyclohexyl]acetyl]amino]-3-[[(2S)-oxetan-2-yl]methylamino]benzoate (175 mg, 261 µmol) in acetic acid (3 mL) was stirred at 60° C. for 2 h. LCMS indicated the reaction was complete. The reaction mixture was flushed slowly with nitrogen until the solvent was removed. Methyl (S)-2-((4-(6-((4-chloro-2-fluorobenzyl)oxy)pyridin-2-yl)cyclohexyl)methyl)-1-(oxetan-2-ylmethyl)-1H-benzo[d]imidazole-6-carboxylate (127 mg, 74.7% yield) was obtained as light-yellow oil. LCMS: [M+H]$^+$=620, Retention time (0.01% TFA)=2.04 min.

Step 8

Methyl (S)-2-((4-(6-((4-chloro-2-fluorobenzyl)oxy)pyridin-2-yl)cyclohexyl)methyl)-1-(oxetan-2-ylmethyl)-1H-benzo[d]imidazole-6-carboxylate (122 mg, 187 μmol) was dissolved in Dichloromethane (2 mL) and 2,2,2-trifluoroacetic acid (21.3 mg, 187 μmol). The reaction mixture was stirred at 25° C. for 0.5 h. LCMS indicated the reaction was complete. The solvents were removed completely. The residue was basified with sat. Ammonium bicarbonate solution until pH=5, extracted with dichloromethane (3×10 mL). The combined organic layers were dried over sodium sulfate and evaporated under reduced pressure. 2-(((1r, 4S)-4-(6-((4-chloro-2-fluorobenzyl)oxy)pyridin-2-yl)cyclohexyl)methyl)-1-(((S)-oxetan-2-yl)methyl)-1H-benzo[d]imidazole-6-carboxylic acid was obtained (60 mg, 54.1% yield) as a brown solid. LCMS: [M+H]$^+$=564, Retention time (0.01% TFA)=1.85 min.

$^1$H NMR (400 MHz, DMSO-D6) δ 8.68 (s, 1H), 8.20 (s, 1H), 7.87 (d, J=41.1 Hz, 2H), 7.61 (s, 1H), 7.47-7.16 (m, 3H), 7.08 (s, 1H), 6.92 (d, J=36.3 Hz, 1H), 5.48 (s, 2H), 5.09 (d, J=49.3 Hz, 2H), 4.87 (s, 1H), 4.47 (s, 2H), 3.37 (s, 1H), 2.87 (s, 1H), 2.46-2.36 (m, 2H), 2.08 (s, 2H), 1.91 (s, 2H), 1.68 (d, J=67.4 Hz, 6H).

(S)-2-((4-(6-((4-cyano-2-fluorobenzyl)oxy)pyridin-2-yl)-2-fluorophenyl) amino)-1-(oxetan-2-ylmethyl)-1H-benzo[d]imidazole-6-carboxylic acid (Compound 320)

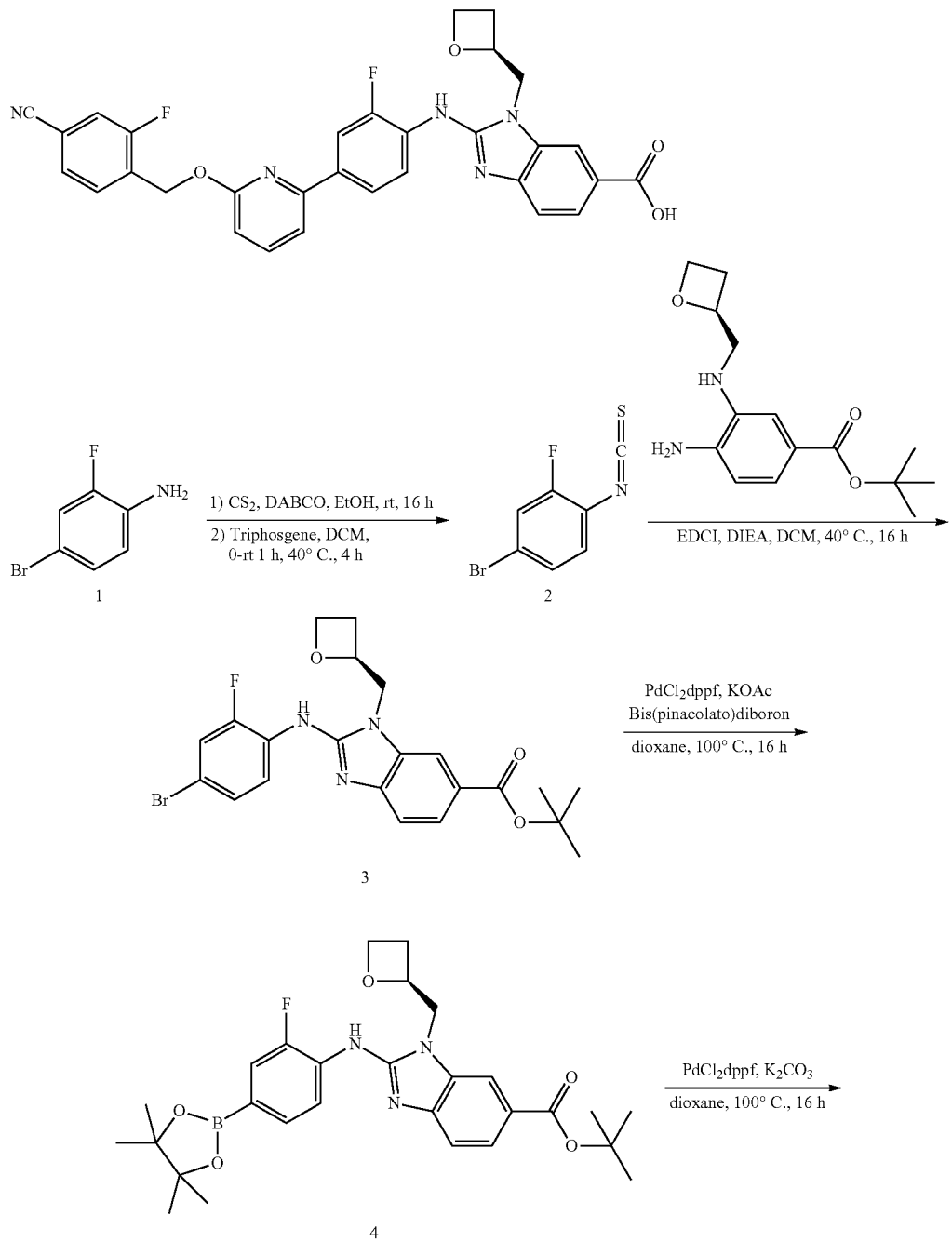

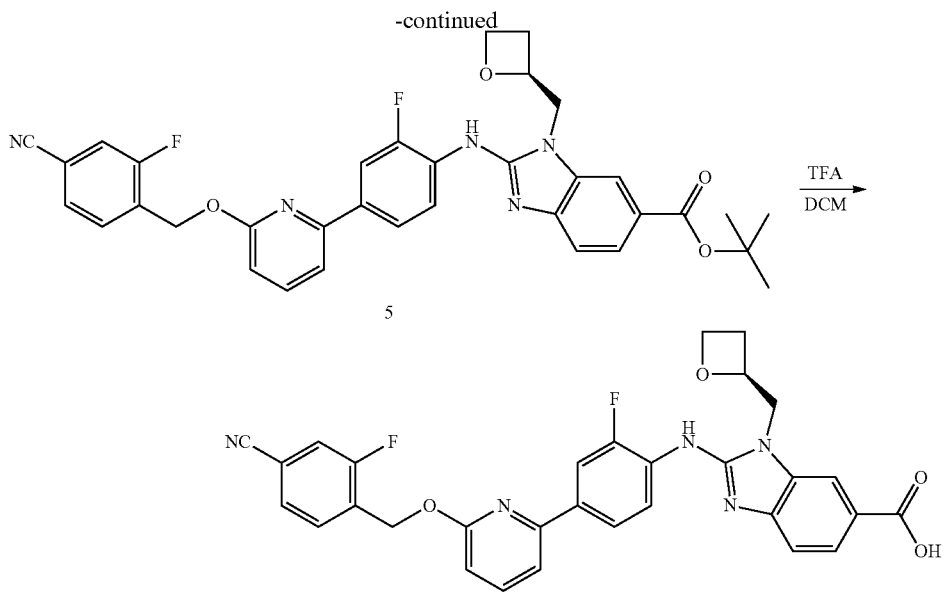

Step 1

To a solution of 4-bromo-2-fluoro-aniline (3.8 g, 20.00 mmol) in ethanol (40 mL) were added $CS_2$ (4.57 g, 60.00 mmol, 3.60 mL) and DABCO (13.46 g, 120.00 mmol). The reaction mixture was stirred at rt overnight. The resulting precipitate was collected by filtration, washed with ice-cold ethanol, and dried to yield a pale yellow solid, which was used in the next step without further characterization and purification. Triphosgene (2.97 g, 10.00 mmol) was added slowly to a solution of the pale yellow solid in DCM (50 mL) at 0° C. The reaction mixture was stirred at this temperature for an additional 1 h and then heated at 40° C. for 4 h; the reaction was quenched with water. The crude was extracted with $CH_2Cl_2$ (3×50 mL) and then dried over $MgSO_4$, concentrated and the residue was purified by flash column chromatograph over silica gel, eluting with petroleum ether to afford 4-bromo-2-fluoro-1-isothiocyanato-benzene (3.6 g, 15.20 mmol, 76.0% yield). Retention time (0.01% TFA)=2.26 min.

Step 2

A suspension of tert-butyl 4-amino-3-[[(2S)-oxetan-2-yl] methylamino]benzoate (115 mg, 413 μmol) in DCM (2 mL) were added 4-bromo-2-fluoro-1-isothiocyanato-benzene (108.4 mg, 467 μmol), EDCI (89.5 mg, 467 μmol) and DIEA (60.3 mg, 467 μmol). The reaction mixture was stirred at 40° C. for 16 h until TLC showed that the reaction was complete. The reaction mixture was evaporated under reduced pressure and the residue was purified by flash column chromatograph over silica gel eluting with $CH_2Cl_2$/MeOH (20:1) to give tert-butyl (S)-2-((4-bromo-2-fluorophenyl)amino)-1-(oxetan-2-ylmethyl)-1H-benzo[d]imidazole-6-carboxylate (99 mg, 50.3% yield) as a pale yellow solid. LCMS: $[M+H]^+$=476, Retention time (0.01% TFA)=2.05 min.

Step 3

A mixture of tert-butyl (S)-2-((4-bromo-2-fluorophenyl) amino)-1-(oxetan-2-ylmethyl)-1H-benzo[d]imidazole-6-carboxylate (100 mg, 210 μmol), potassium acetate (61.8 mg, 630 μmol), Bis(pinacolato)diboron (53.3 mg, 210 μmol), Pd(dppf)Cl$_2$ complex with DCM (8.6 mg, 11 μmol) in anhydrous dioxane (0.5 mL) was stirred at 80° C. for 16 h. The reaction was complete as indicated by LCMS, the reaction mixture was filtered through a pad of celite, washed with ethyl acetate several times and the combined organics were concentrated in vacuo to give crude tert-butyl (S)-2-((2-fluoro-4-(4,4,5,5-tetramethyl-1,3,2-dioxaborolan-2-yl) phenyl)amino)-1-(oxetan-2-ylmethyl)-1H-benzo[d]imidazole-6-carboxylate (109.9 mg, 209.9 mmol, 82% yield) as a black oil which was used for next step directly. LCMS: $[M+H]^+$=524; Retention time (0.01% TFA)=2.10 min.

Step 4

A mixture of tert-butyl (S)-2-((2-fluoro-4-(4,4,5,5-tetramethyl-1,3,2-dioxaborolan-2-yl)phenyl)amino)-1-(oxetan-2-ylmethyl)-1H-benzo[d]imidazole-6-carboxylate (110 mg, 210 μmol), 4-[(6-bromo-2-pyridyl)oxymethyl]-3-fluoro-benzonitrile (64.54 mg, 210 μmol), Pd(dppf)Cl$_2$ complex with DCM (8.6 mg, 11 μmol) and $K_2CO_3$ (87.1 mg, 630 μmol) in dioxane (2 mL) was stirred under $N_2$ at 80° C. for 16 h. The mixture was filtered and concentrated in vacuo to give the crude product tert-butyl (S)-2-((4-(6-((4-cyano-2-fluorobenzyl)oxy)pyridin-2-yl)-2-fluorophenyl)amino)-1-(oxetan-2-ylmethyl)-1H-benzo[d]imidazole-6-carboxylate (120 mg, 91.6% yield) as a black oil. LCMS: $[M+H]^+$= 624.1; Retention time (0.01% TFA)=2.48 min.

Step 5

To a solution of tert-butyl (S)-2-((4-(6-((4-cyano-2-fluorobenzyl)oxy)pyridin-2-yl)-2-fluorophenyl)amino)-1-(oxetan-2-ylmethyl)-1H-benzo[d]imidazole-6-carboxylate (100 mg, 160 μmol) in DCM (1 mL) was added slowly 2,2,2-trifluoroacetic acid (91.4 mg, 801.7 μmol) at 0° C. and stirred for 16 h at room temperature. After completion of the reaction as judged by LCMS, the reaction mixture was filtered and concentrated in vacuo. The crude product was purified by prep-HPLC and lyophilized to afford (S)-2-((4-(6-((4-cyano-2-fluorobenzyl)oxy)pyridin-2-yl)-2-fluorophenyl)amino)-1-(oxetan-2-ylmethyl)-1H-benzo[d]imidazole-6-carboxylic acid (27 mg, 29.7% yield) as a white solid. LCMS: $[M+H]^+$=568.1; Retention time=1.89 min.

$^1$H NMR (400 MHz, DMSO-D6-d6) δ 9.36 (1H, s), 8.47 (1H, d, J=8.4), 8.07 (1H, s), 7.96-7.92 (3H, m), 7.90-7.70 (4H, m), 7.63 (1H, d, J=7.5), 7.49 (1H, d, J=8.2), 6.87 (1H, d, J=8.1), 5.63 (2H, s), 5.23 (1H, s), 4.72-4.44 (4H, m), 2.82-2.65 (1H, m), 2.45-2.31 (1H, s).

(S)-2-(4-(6-((4-cyano-2-fluorobenzyl)oxy)pyridin-2-yl)-2-fluorophenoxy)-1-(oxetan-2-ylmethyl)-1H-benzo[d]imidazole-6-carboxylic acid (Compound 321)
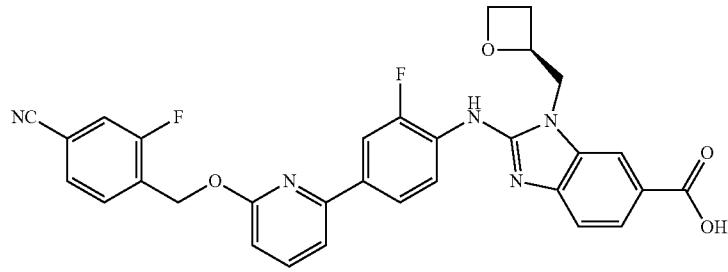
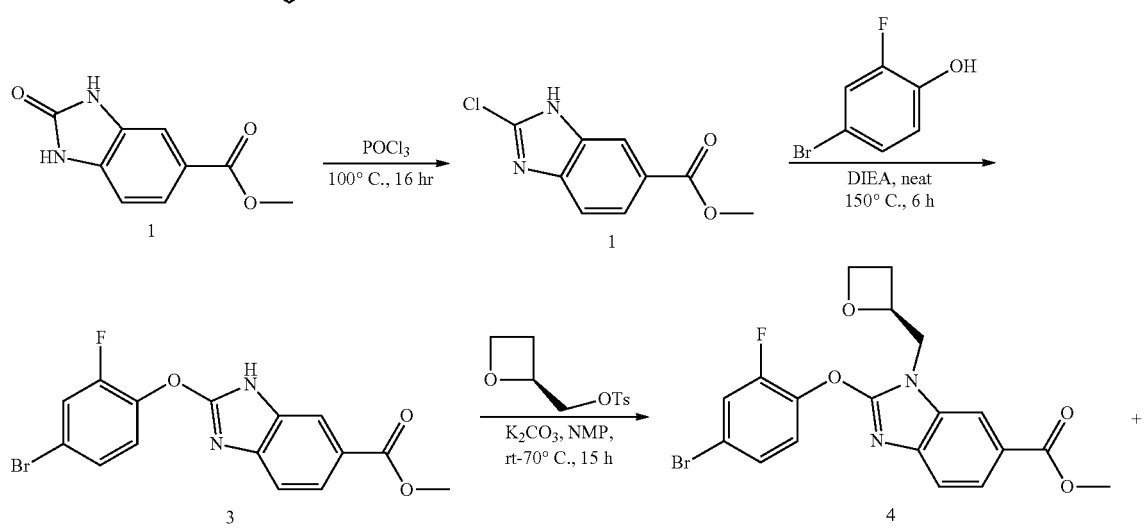
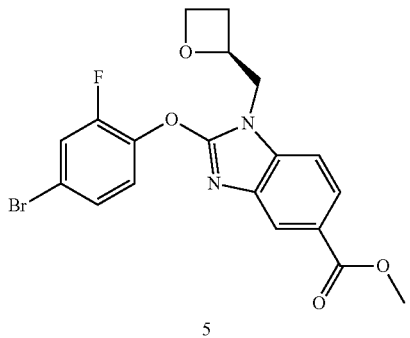
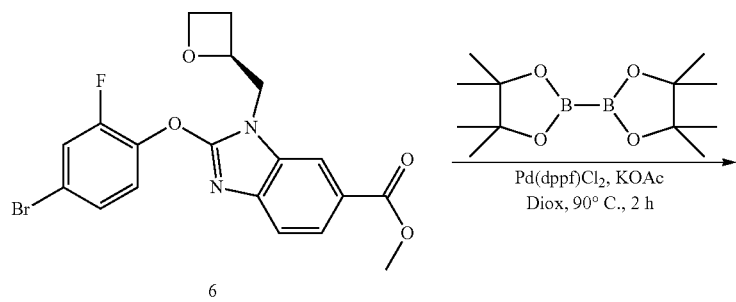

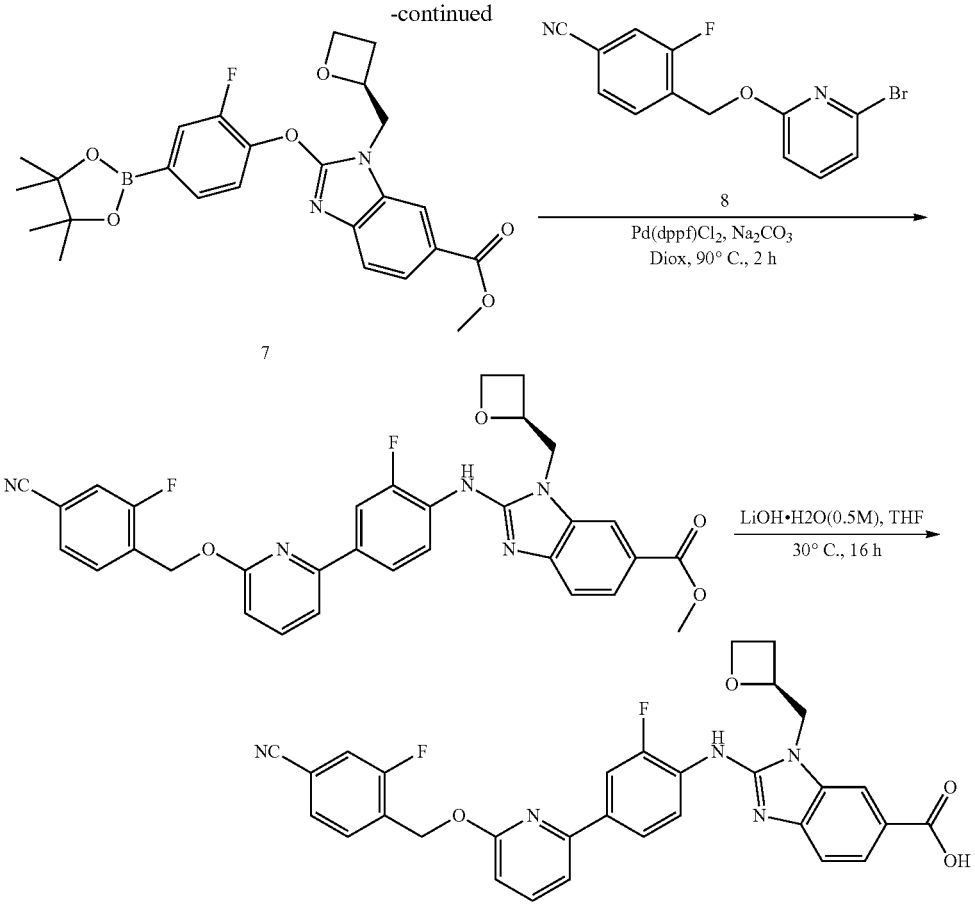

Step 1

A mixture of methyl 2-oxo-1,3-dihydrobenzimidazole-5-carboxylate (1.6 g, 8.33 mmol) and phosphoryl trichloride (25.53 g, 166.52 mmol, 15.47 mL) was stirred for 3 h at 100° C., until the reaction was complete as indicated by LCMS, the reaction mixture was concentrated in vacuo. The residue was cooled to 0° C., and cold, saturated aqueous $NaHCO_3$ (30 mL) was added cautiously. After stirring at rt for 15 min, the mixture was sonicated and the resulting residue was filtered to yield the titled compound methyl 2-chloro-3H-benzimidazole-5-carboxylate (1.3 g, 67.5% yield), which was used in the next step without further purification. LCMS: $[M+H]^+$=211.1; Retention time (0.01% TFA)=1.61 min.

Step 2

A mixture of methyl 2-chloro-3H-benzimidazole-5-carboxylate (1 g, 4.32 mmol), 4-bromo-2-fluoro-phenol (2.48 g, 12.96 mmol, 1.42 mL) and N-ethyl-N-isopropyl-propan-2-amine (1.68 g, 12.96 mmol, 2.26 mL) was stirred for 3 h at 150° C., until the reaction was complete as indicated by LCMS, the reaction mixture was concentrated in vacuo, purified by silica gel chromatography (petroleum ether/EtOAc gradient 0-50%) to give the desired product methyl 2-(4-bromo-2-fluoro-phenoxy)-3H-benzimidazole-5-carboxylate (700 mg, 36.8% yield) as white solid. LCMS: $[M+H]^+$=365.0; Retention time (0.01% TFA)=1.92 min.

Step 3

A mixture of methyl 2-(4-bromo-2-fluoro-phenoxy)-3H-benzimidazole-5-carboxylate (843.4 mg, 1.92 mmol) and dipotassium carbonate (397.4 mg, 2.88 mmol) in NMP (9 mL) was stirred for 1 h at room temperature, then [(2S)-oxetan-2-yl]methyl 4-methylbenzenesulfonate (696.7 mg, 2.88 mmol) was added to the mixture and stirred for 16 h at 80° C. The mixture was purified by Prep-HPLC to afford (product 1) methyl 2-(4-bromo-2-fluoro-phenoxy)-3-[[(2S)-oxetan-2-yl]methyl]benzimidazole-5-carboxylate (4) (135 mg, 307 µmol, 16.0% yield) (NBK0059-76-P2) and (product 2) methyl 2-(4-bromo-2-fluoro-phenoxy)-1-[[(2S)-oxetan-2-yl]methyl]benzimidazole-5-carboxylate (5) (150 mg, 17.6% yield) (NBK0059-76-P1). Product 1: LCMS: $[M+H]^+$= 437.1; Retention time (0.01% TFA)=1.91 min. Product 2: LCMS: $[M+H]^+$=437.1; Retention time (0.01% TFA)=1.89 min.

Step 4

A mixture of methyl 2-(4-bromo-2-fluoro-phenoxy)-3-[[(2S)-oxetan-2-yl]methyl]benzimidazole-5-carboxylate (4) (85 mg, 195 µmol), 4,4,5,5-tetramethyl-2-(4,4,5,5-tetramethyl-1,3,2-dioxaborolan-2-yl)-1,3,2-dioxaborolane (49.6 mg, 195 µmol), potassium acetate (38.3 mg, 391 µmol) and cyclopentyl(diphenyl)phosphane; dichloromethane; dichloropalladium; iron (16.0 mg, 20 µmol) in dioxane (2 mL) was stirred for 2 h at 90° C., until the reaction was complete as indicated by LCMS, the reaction mixture was used in next step without purification. LCMS: $[M+H]^+$=483.3; Retention time=2.11 min; (also observed the hydrolyzed corresponding Boronic acid $[M+H]^+$=401.2; Retention time=1.63 min.

Step 5

Sodium carbonate (62.0 mg, 585 µmol) (2M in water) and cyclopentyl(diphenyl)phosphane; dichloromethane; dichloropalladium; iron (15.92 mg, 20 µmol) were added to the mixture obtained methyl (S)-2-(2-fluoro-4-(4,4,5,5-tetramethyl-1,3,2-dioxaborolan-2-yl)phenoxy)-1-(oxetan-2-ylmethyl)-1H-benzo[d]imidazole-6-carboxylate and the mixture was stirred for 2 h at 90° C., until the reaction was complete as indicated by LCMS, the reaction mixture was filtered through a pad of celite with EtOAc. The combined organics were concentrated in vacuo, purified by silica gel column (petroleum ether/EtOAc gradient 0-50%) to give the desired product methyl (S)-2-(4-(6-((4-cyano-2-fluorobenzyl)oxy)pyridin-2-yl)-2-fluorophenoxy)-1-(oxetan-2-ylmethyl)-1H-benzo[d]imidazole-6-carboxylate (110 mg, 88.2% yield). LCMS: [M+H]$^+$=583.2; Retention time (10 mM NH$_4$HCO$_3$)= 2.12 min.

Step 6

To a stirred solution of methyl 2-[4-[6-[(4-cyano-2-fluoro-phenyl)methoxy]-2-pyridyl]-2-fluoro-phenoxy]-3-[[(2S)-oxetan-2-yl]methyl]benzimidazole-5-carboxylate (100 mg, 156 μmol) in THF (5 mL) was added lithium hydroxide hydrate (0.5 M) (65.6 mg, 1.56 mmol). The reaction mixture was stirred at 30° C. for 16 h and upon completion of the reaction, as judged by LCMS, the mixture was acidified with HOAc until pH~6 and purified by prep-HPLC to afford (S)-2-(4-(6-((4-cyano-2-fluorobenzyl)oxy)pyridin-2-yl)-2-fluorophenoxy)-1-(oxetan-2-ylmethyl)-1H-benzo[d]imidazole-6-carboxylic acid (34.2 mg, 60 μmol, 38.5% yield) as a white solid. LCMS: [M+H]$^+$=669.2.

$^1$H NMR (400 MHz, DMSO-D6) δ 8.20 (d, J=1.2 Hz, 1H), 8.11 (dd, J=12.1, 2.0 Hz, 1H), 8.01 (d, J=8.4 Hz, 1H), 7.97-7.83 (m, 2H), 7.81-7.67 (m, 5H), 7.46 (d, J=8.4 Hz, 1H), 6.96 (d, J=8.2 Hz, 1H), 5.64 (s, 2H), 5.16 (s, 1H), 4.72-4.41 (m, 3H), 4.33 (dt, J=9.0, 6.0 Hz, 1H), 2.87-2.66 (m, 1H), 2.53 (s, 1H).

(S)-2-((6-((4-cyano-2-fluorobenzyl)oxy)-2'-oxo-[2,4'-bipyridin]-1'(2'H)-yl)methyl)-7-fluoro-1-(oxetan-2-ylmethyl)-1H-benzo[d]imidazole-6-carboxylic acid (Compound 322)

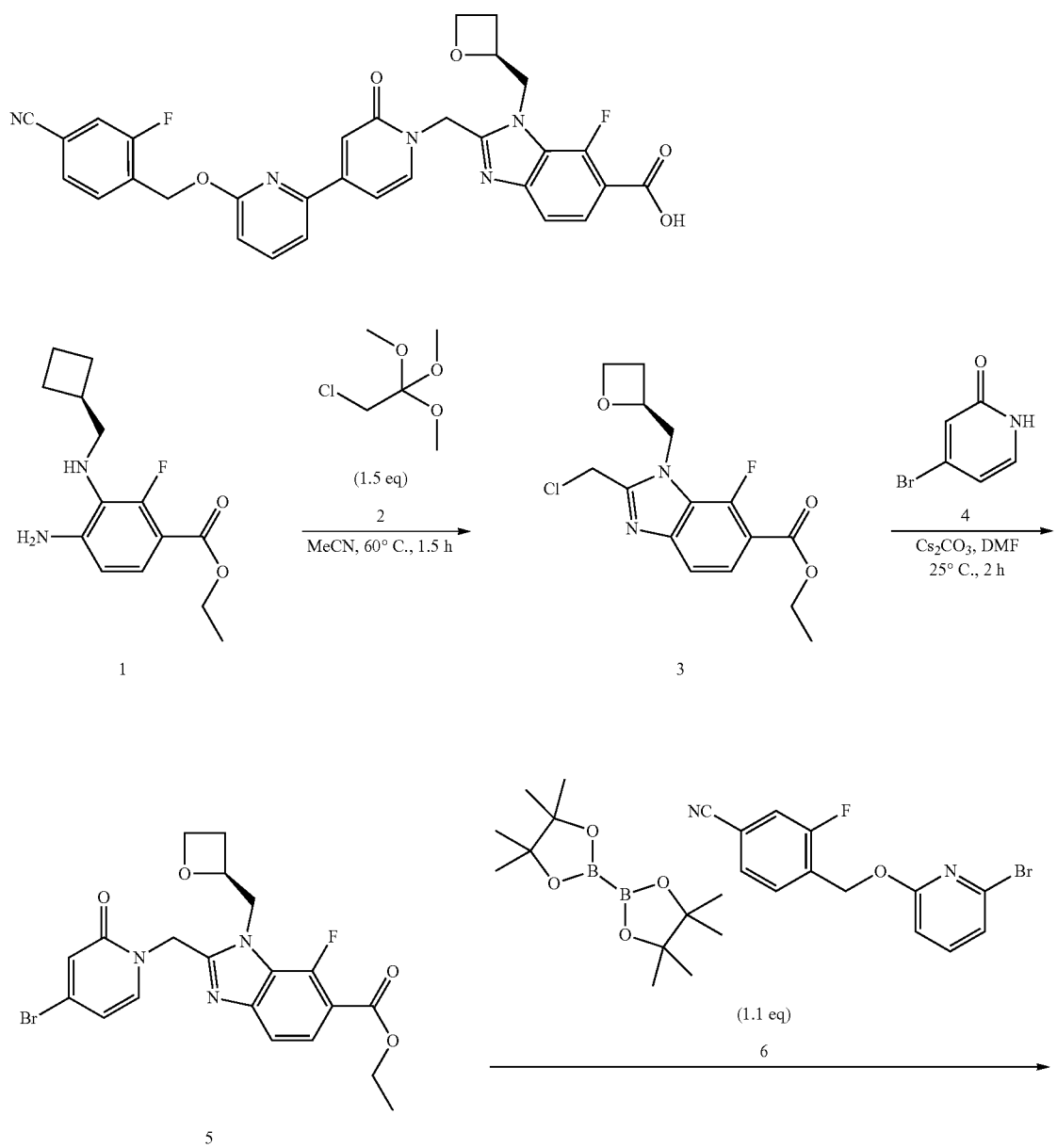

-continued

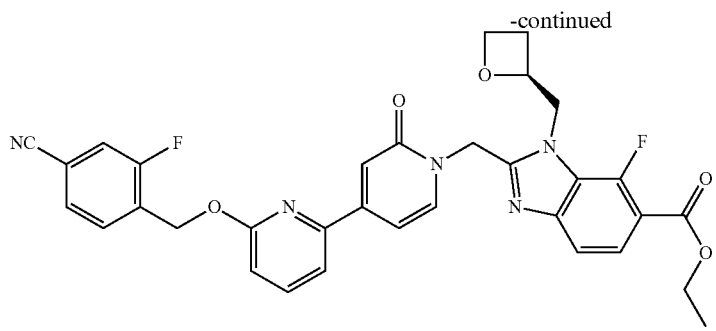

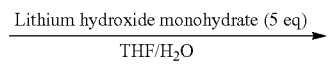

7

30

Step 1

To a solution of ethyl 4-amino-2-fluoro-3-[[(2S)-oxetan-2-yl]methylamino]benzoate (500 mg, 1.77 mmol), 2-chloro-1,1,1-trimethoxy-ethane (288.1 mg, 1.77 mmol) in acetonitrile (5 mL) was added 4-methylbenzenesulfonic acid hydrate (33.7 mg, 177 μmol). The reaction mixture was stirred at 60° C. for 1.5 hr. LCMS indicated the reaction was completed. Silica gel (1 g) was added into the reaction mixture, and the mixture was evaporated under reduced pressure to provide a dry powder, which was purified through silica gel to give ethyl (S)-2-(chloromethyl)-7-fluoro-1-(oxetan-2-ylmethyl)-1H-benzo[d]imidazole-6-carboxylate (600 mg, 98.5% yield) as white solid. LCMS: [M+H]⁺=327; Retention time (10 mM NH₄HCO₃)=1.98 min.

Step 2

A mixture of 4-bromo-1H-pyridin-2-one (124.7 mg, 717 μmol), ethyl 2-(chloromethyl)-4-fluoro-3-[[(2S)-oxetan-2-yl]methyl]benzimidazole-5-carboxylate (239 mg, 717 μmol), cesium carbonate (233.6 mg, 717 μmol) in DMF (3 mL) was stirred at 25° C. for 2 h. LCMS indicated the reaction was complete. The reaction mixture was diluted with saturated ammonium chloride solution, extracted with ethyl acetate (3×4 mL). The combined organic layers were washed with brine (3×4 mL), dried with anhydrous sodium sulfate and evaporated under reduce pressure to provide a residue, which was purified through silica gel (petroleum ether/EtOAc gradient 50%-100%) to give ethyl (S)-2-(chloromethyl)-7-fluoro-1-(oxetan-2-ylmethyl)-1H-benzo[d]imidazole-6-carboxylate (320 mg, 91.3% yield) as light-yellow gum. LCMS: [M+H]⁺=464. Retention time (10 mM NH₄HCO₃)=1.96 min.

Step 3

A mixture of ethyl ethyl (S)-2-(chloromethyl)-7-fluoro-1-(oxetan-2-ylmethyl)-1H-benzo[d]imidazole-6-carboxylate (200 mg, 409 μmol), 4,4,5,5-tetramethyl-2-(4,4,5,5-tetramethyl-1,3,2-dioxaborolan-2-yl)-1,3,2-dioxaborolane (114.3 mg, 450 μmol), potassium acetate (120.5 mg, 1.23 mmol), Bis(triphenylphosphine)palladium(II) chloride (28.7 mg, 41 μmol) in Dioxane (5 mL) was charged under nitrogen in glovebox. The reaction mixture was then stirred at 80° C. for 4 h. LCMS indicated the reaction was complete, and the reaction mixture was cooled down, into which 4-[(6-bromo-2-pyridyl)oxymethyl]-3-fluoro-benzonitrile (132.3 mg, 409 μmol), dipotassium carbonate (169.7 mg, 1.23 mmol), Pd(dppf)Cl₂ (29.9 mg, 41 μmol) were added. The reaction mixture was bubbled with nitrogen for 2 min. The resulting mixture was stirred at 80° C. for 16 h. LCMS indicated the reaction was complete. Silica gel (2 g) was added into the reaction mixture, and the solvent was removed under reduced pressure to provide a dry powder which was purified through silica gel (eluent: petroleum ether/ethyl acetate gradient 33-100%) to give ethyl (S)-2-((6-((4-cyano-2-fluorobenzyl)oxy)-2'-oxo-[2,4'-bipyridin]-1'(2'H)-yl)methyl)-7-fluoro-1-(oxetan-2-ylmethyl)-1H-benzo[d]imidazole-6-carboxylate (220 mg, 323.7 μmol, 79.1% yield, 90% purity) as white solid.

LCMS: [M+H]⁺=612; Retention time (10 mM NH₄HCO₃)=1.98 min.

Step 4

A solution of ethyl (S)-2-((6-((4-cyano-2-fluorobenzyl)oxy)-2'-oxo-[2,4'-bipyridin]-1'(2'H)-yl)methyl)-7-fluoro-1-(oxetan-2-ylmethyl)-1H-benzo[d]imidazole-6-carboxylate (220 mg, 324 μmol) in THF (5 mL) was added a solution of Lithium hydroxide hydrate (67.9 mg, 1.62 mmol) in Water (8 mL). LCMS indicated the reaction mixture was completed. The reaction mixture was acidified with acetic acid until pH=5. Tetrahydrofuran was removed under reduced pressure. The aqueous phase was extracted with ethyl acetate (3×20 mL). The combined organic layers was dried and evaporated under reduced pressure to provide a residue which was purified through prep-HPLC to give (S)-2-((6-((4-cyano-2-fluorobenzyl)oxy)-2'-oxo-[2,4'-bipyridin]-1'(2'H)-yl)methyl)-7-fluoro-1-(oxetan-2-ylmethyl)-1H-benzo

[d]imidazole-6-carboxylic acid (95.5 mg, 49.0% yield). LCMS: [M+H]⁺=584; Retention time (0.01% TFA)=1.84 min.

¹H NMR (400 MHz, DMSO-D6) δ 8.04-7.84 (m, 3H), 7.79-7.68 (m, 3H), 7.67-7.54 (m, 1H), 7.40 (d, J=8.5 Hz, 1H), 7.09 (d, J=1.7 Hz, 1H), 7.03 (d, J=8.2 Hz, 1H), 6.96 (dd, J=7.2, 1.9 Hz, 1H), 5.50 (dd, J=61.4, 17.0 Hz, 4H), 5.11 (d, J=6.8 Hz, 1H), 4.89 (dd, J=15.5, 7.0 Hz, 1H), 4.73 (d, J=12.8 Hz, 1H), 4.58-4.46 (m, 1H), 4.40 (dd, J=6.1, 2.9 Hz, 1H), 2.86-2.70 (m, 1H), 2.44 (d, J=9.1 Hz, 1H).

(S)-2-((6-((4-chloro-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylic acid (Compound 323)

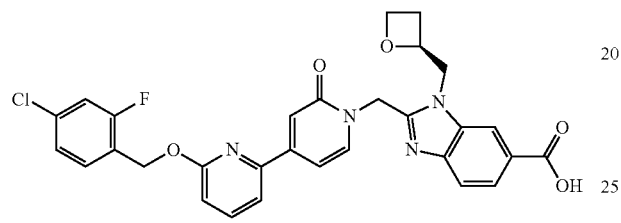

Prepared in analogous manner as for Compound 322. LCMS: [M+H]⁺=575.0; Retention time=1.52 min.

¹H NMR (400 MHz, DMSO-D6) δ 8.28 (s, 1H), 7.98 (d, J=7.2 Hz, 1H), 7.90-7.86 (m, 1H), 7.82-7.79 (m, 1H), 7.70 (d, J=7.4 Hz, 1H), 7.63-7.59 (m, 2H), 7.50 (dd, J=10.0, 2.0 Hz, 1H), 7.33 (dd, J=8.2, 1.7 Hz, 1H), 7.12-7.11 (m, 1H), 7.01-6.98 (m, 2H), 5.60-5.43 (m, 4H), 5.11-5.07 (m, 1H), 4.88-4.83 (m, 1H), 4.74-4.70 (m, 1H), 4.52-4.47 (m, 1H), 4.39-4.34 (m, 1H), 2.75-2.71 (m, 1H), 2.41-2.36 (m, 1H).

(S)-2-((6-((4-cyano-2-fluorobenzyl)oxy)-2'-oxo-[2,4'-bipyridin]-1'(2'H)-yl)methyl)-3-(oxetan-2-ylmethyl)-3H-imidazo[4,5-b]pyridine-5-carboxylic acid (Compound 324)

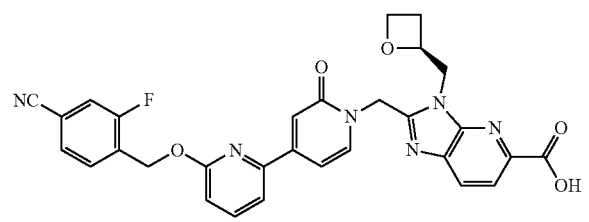 [SMILES: N#Cc1ccc(COc2cccc(-c3ccn(Cc4nc5ccc(C(=O)O)nc5n4C[C@@H]4CCO4)c(=O)c3)n2)c(F)c1]

Prepared in analogous manner as for Compound 322. LCMS: [M+H]⁺=567.0; Retention time=1.40 min.

¹H NMR (400 MHz, DMSO-D6-D6) δ 8.09-8.07 (d, J=8.0 Hz, 1H), 7.98-7.96 (t, J=5.6 Hz, 2H), 7.93-7.87 (m, 2H), 7.77-7.70 (m, 3H), 7.08-7.02 (m, 2H), 6.97-6.94 (dd, J₁=7.2 Hz, J₂=2.0 Hz, 1H), 5.67-5.49 (m, 4H), 5.18-5.12 (m, 1H), 4.87-4.81 (m, 1H), 4.74-4.69 (m, 1H), 4.53-4.47 (m, 1H), 4.39-4.33 (m, 1H), 2.77-2.68 (m, 1H), 2.44-2.36 (m, 1H).

(S)-2-((4-(4-((4-cyano-2-fluorobenzyl)oxy)-5-fluoropyrimidin-2-yl)-2-oxopyridin-1(2H)-yl)methyl)-3-(oxetan-2-ylmethyl)-3H-imidazo[4,5-b]pyridine-5-carboxylic acid (Compound 325)

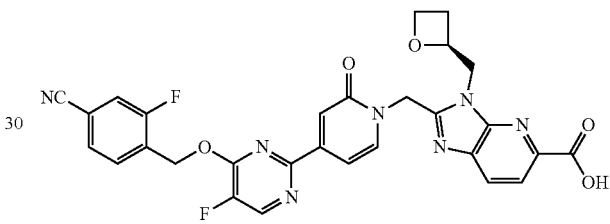

Prepared in analogous manner as for Compound 322. LCMS: [M+H]⁺=586.2; Retention time=1.18 min.

¹H NMR (400 MHz, DMSO-D6) δ 8.85 (d, J=2.8 Hz, 1H), 8.10-7.93 (m, 4H), 7.88-7.73 (m, 2H), 7.29 (d, J=1.8 Hz, 1H), 7.11 (dd, J=7.1, 1.9 Hz, 1H), 5.79 (brs, 2H), 5.68 (d, J=16.1 Hz, 1H), 5.53 (d, J=16.1 Hz, 1H), 5.22-5.09 (m, 1H), 4.84 (dd, J=15.0, 6.2 Hz, 1H), 4.71 (dd, J=15.0, 3.2 Hz, 1H), 4.50 (dd, J=13.8, 7.6 Hz, 1H), 4.36 (dt, J=8.9, 6.0 Hz, 1H), 2.78-2.64 (m, 1H), 2.44-2.31 (m, 1H).

2-(4-(6-(4-chloro-2-fluorobenzyloxy)pyridin-2-yl)-2-fluorobenzyl)-3-(oxetan-2-ylmethyl)-2H-indazole-S-carboxylic acid (Compound 326)

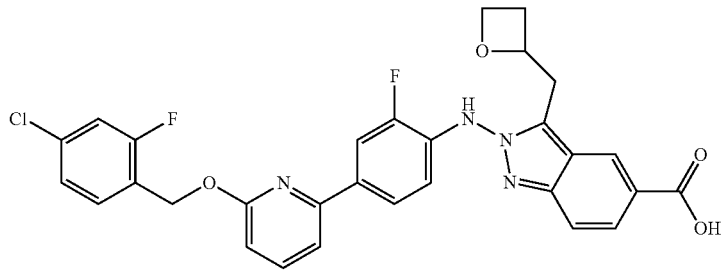

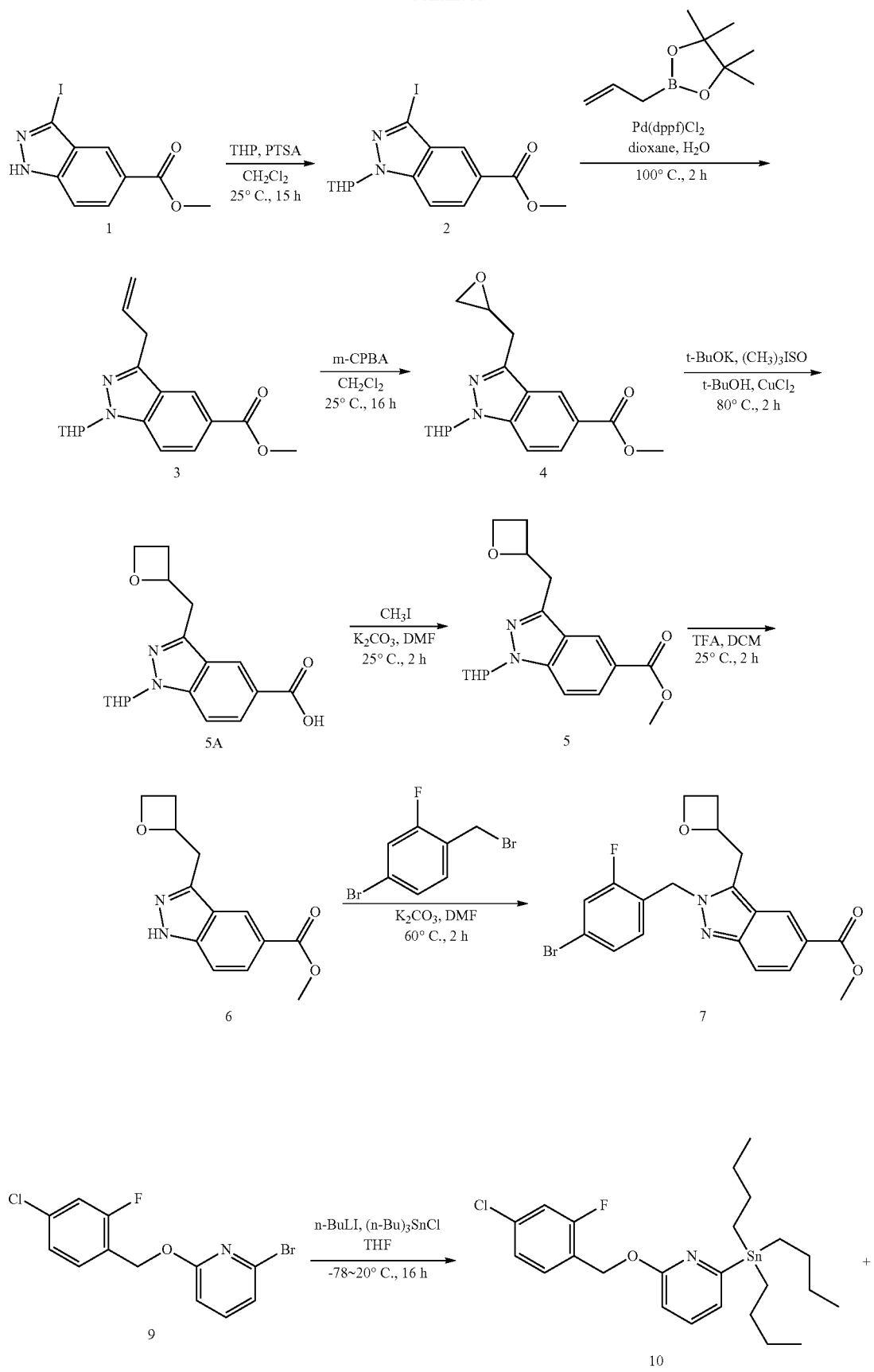

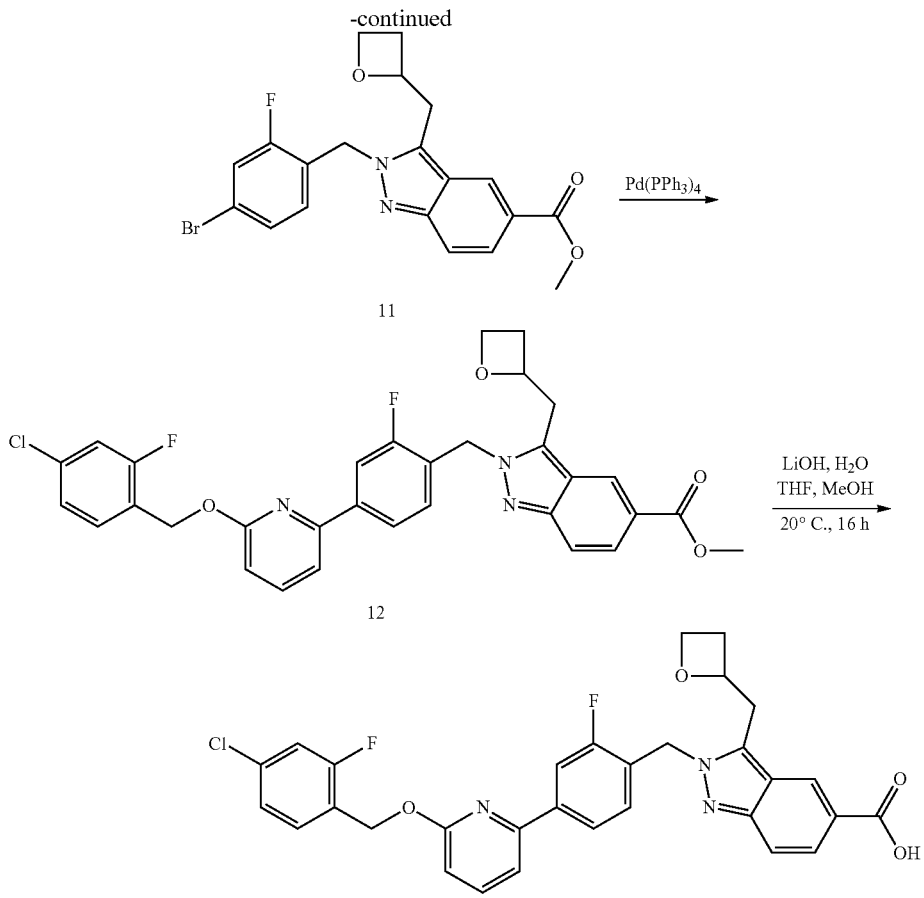

Step 1

A mixture of 3,4-dihydro-2H-pyran (327.19 mg, 3.89 mmol), methyl 3-iodo-3a,7a-dihydro-1H-indazole-5-carboxylate (1.18 g, 3.89 mmol), 4-methylbenzenesulfonic acid hydrate (739.9 mg, 3.89 mmol) in DCM (50 mL) was stirred for 12 h at 30° C. under $N_2$, until the reaction was complete as indicated by LCMS, the reaction mixture was poured into water and extracted with EtOAc, and the combined organics were concentrated in vacuum, purified by silica gel chromatography (Hexanes/EtOAc=10:1) to give the desired product methyl 3-iodo-1-tetrahydropyran-2-yl-3a,7a-dihydroindazole-5-carboxylate (0.9 g, 59.6% yield) as pale yellow solid. LCMS: $[M+H]^+$=387; Retention time=2.00 min.

Step 2

A mixture of 2-allyl-4,4,5,5-tetramethyl-1,3,2-dioxaborolane (300 mg, 1.79 mmol), methyl 3-iodo-1-tetrahydropyran-2-yl-indazole-5-carboxylate (300 mg, 777 μmol), Pd(dppf)Cl$_2$ (10 mg) and sodium carbonate (300.0 mg, 2.83 mmol) in water (1 mL) and dioxane (4 mL) was stirred for 2 h at 100° C. under $N_2$, the reaction mixture was monitored by LCMS. The reaction mixture was filtered through a pad of celite with EtOAc and washed with water, the combined organics were concentrated in vacuum, purified by silica gel chromatography (Hexanes/EtOAc=10:1) to give the desired product methyl 3-allyl-1-tetrahydropyran-2-yl-indazole-5-carboxylate (170 mg, 72.9% yield) as pale yellow solid. LCMS: $[M+H]^+$=301; Retention time=2.14 min.

Step 3

A mixture of 3-chlorobenzenecarboperoxoic acid (2.76 g, 15.98 mmol), methyl 3-allyl-1-tetrahydropyran-2-yl-indazole-5-carboxylate (2.4 g, 7.99 mmol) in DCM (20 mL) was stirred for 16 h at 20° C. under N2, the reaction mixture was monitored by LCMS. The reaction mixture was filtered through a pad of celite with EtOAc, and the combined organics were concentrated in vacuum, purified by silica gel chromatography (Hexanes/EtOAc=5:1) to give the desired product methyl 3-(oxiran-2-ylmethyl)-1-tetrahydropyran-2-yl-indazole-5-carboxylate (1.4 g, 55.4% yield) as pale yellow solid. LCMS: $[M+H]^+$=317; Retention time=1.78 min.

Step 4

A mixture of BLAH methane iodide (3.48 g, 15.81 mmol), potassium 2-methylpropan-2-olate (1.77 g, 15.81 mmol) and methyl 3-(oxiran-2-ylmethyl)-1-tetrahydropyran-2-yl-indazole-5-carboxylate (500 mg, 1.58 mmol, 280.37 mL), dichloro copper (21.3 mg, 158 μmol) in t-BuOH (50 mL) was stirred in an oil bath of 80° C. for 2 h, the reaction was monitored by LCMS. The reaction mixture was adjusted to pH=1 with HCl, the aqueous layer was extracted with DCM, dried over Na$_2$SO$_4$ and concentrated, and purified by prep-HPLC to give the desired product 3-(oxetan-2-ylmethyl)-1-tetrahydropyran-2-yl-indazole-5-carboxylic acid (200 mg, 24.0% yield) as pale yellow solid. LCMS: $[M+H]^+$=317; Retention time=1.47 min.

Step 5

A mixture of 3-(oxetan-2-ylmethyl)-1-tetrahydropyran-2-yl-indazole-5-carboxylic acid (30 mg, 94.8 mol) iodomethane (14.8 mg, 104.3 μmol, 6.5 μL, 100% purity) and dipotassium; carbonate (39.3 mg, 284.5 μmol, 17.2 μL, 100% purity) in DMF (5 mL) was stirred for 1 hr at 25° C.

in a round bottom flask under N2, until the reaction was complete as indicated by LCMS, the reaction mixture was filtered through a pad of Celite with EtOAc, and the combined organics were concentrated in vacuo, purified by silica gel chromatography to give the desired product methyl 3-(oxetan-2-ylmethyl)-1-tetrahydropyran-2-yl-indazole-5-carboxylate (22 mg, 47.8 μmol, 50.4% yield, 71.8% purity) as colorless oil. LCMS [M+H]$^+$=331.1; Retention time (0.01% TFA)=1.82 min.

Step 6

A mixture of methyl 3-(oxetan-2-ylmethyl)-1-tetrahydropyran-2-yl-indazole-5-carboxylate (120 mg, 363 μmol), 2,2,2-trifluoroacetic acid (1.48 g, 12.98 mmol, 1 mL) in DCM (2 mL) was stirred at 20° C. for 2 h, the reaction was monitored by LCMS. The reaction mixture was concentrated to give the desired product methyl 3-(oxetan-2-ylmethyl)-1H-indazole-5-carboxylate (100 mg, 89.4% yield) as pale yellow solid. LCMS: [M+H]$^+$=247; Retention time=1.47 min.

Step 7

A mixture of methyl 3-(oxetan-2-ylmethyl)-1H-indazole-5-carboxylate (100 mg, 406 μmol), 4-bromo-1-(bromomethyl)-2-fluoro-benzene (108.8 mg, 406 μmol) and potassium carbonate (168.4 mg, 1.22 mmol) in DMF (10 mL) was stirred in an oil bath of 60° C. for 2 h, the reaction was monitored by LCMS. The reaction mixture was filtered through a pad of celite with EtOAc, and the combined organics were concentrated in vacuum, purified by silica gel chromatography (Hexanes/EtOAc=5:1) give the desired product methyl 1-[(4-bromo-2-fluoro-phenyl)methyl]-3-(oxetan-2-ylmethyl)indazole-5-carboxylate (80 mg, 45.5% yield) as pale yellow solid. LCMS: [M+H]$^+$=433; Retention time=1.47 min.

Step 8

A mixture of 2-bromo-6-[(4-chloro-2-fluoro-phenyl)methoxy]pyridine (1.6 g, 5.05 mmol), Butyllithium (356.14 mg, 5.56 mmol, 2.5 mL) and tributyl(chloro)stannane (1.97 g, 6.07 mmol, 1.65 mL) in THF (10 mL) was stirred for 16 h at 30° C. under N$_2$, the reaction mixture was monitored by LCMS. The reaction mixture was poured into water and extracted with EtOAc, and the combined organics were concentrated in vacuum, purified by silica gel chromatography (Hexanes/EtOAc=10:1) to give the desired product tributyl-[6-[(4-chloro-2-fluoro-phenyl)methoxy]-2-pyridyl]stannane (300 mg, 18.8% yield) as pale yellow solid. LCMS: [M+H]$^+$=528; Retention time=2.14 min.

Step 9

A mixture of tributyl-[6-[(4-chloro-2-fluoro-phenyl)methoxy]-2-pyridyl]stannane (60.8 mg, 115 mol), methyl 2-[(4-bromo-2-fluoro-phenyl)methyl]-3-(oxetan-2-ylmethyl)indazole-5-carboxylate (50 mg, 115 μmol) and Pd(PPh$_3$)$_4$ (115 μmol) in DMF (1 mL) was stirred for 2 h at 130° C. under N$_2$, the reaction mixture was monitored by LCMS. The reaction mixture was filtered through a pad of celite with EtOAc, and the combined organics were concentrated in vacuum, purified by silica gel chromatography (Hexanes/EtOAc=2:1) to give the desired product methyl 2-[[4-[6-[(4-chloro-2-fluoro-phenyl)methoxy]-2-pyridyl]-2-fluoro-phenyl]methyl]-3-(oxetan-2-ylmethyl)indazole-5-carboxylate (50 mg, 73.4% yield) as pale yellow solid. LCMS: [M+H]$^+$=590; Retention time=1.99 min.

Step 10

A mixture of methyl 2-[[4-[6-[(4-chloro-2-fluoro-phenyl)methoxy]-2-pyridyl]-2-fluoro-phenyl]methyl]-3-(oxetan-2-ylmethyl)indazole-5-carboxylate (50 mg, 84.7 μmol), Lithium hydroxide hydrate (400 mg, 9.53 mmol) in THF (2 mL), Methanol (2 mL) and Water (2 mL) was stirred for 2 h at 25° C. under N$_2$, the reaction mixture was monitored by LCMS. LCMS shows work well. The reaction mixture was adjusted to pH=1 with HCl, extracted with DCM and the combined organics were concentrated in vacuum, after PREP-HPLC purification to give the desired product 1-[[4-[6-[(4-chloro-2-fluoro-phenyl)methoxy]-2-pyridyl]-2-fluoro-phenyl]methyl]-3-(oxetan-2-ylmethyl)indazole-5-carboxylic acid (20.3 mg, 35 μmol, 41.6% yield). LCMS: [M+H]$^+$=576; Retention time=1.50 min.

$^1$H NMR (400 MHz, CDCl$_3$) δ 8.66 (s, 1H), 8.13 (ddd, J=10.3, 7.0, 1.3 Hz, 2H), 7.60 (ddd, J=8.4, 7.1, 2.0 Hz, 1H), 7.45 (dd, J=8.3, 6.6 Hz, 2H), 7.28 (d, J=1.1 Hz, 1H), 7.19-7.00 (m, 3H), 6.90 (ddd, J=7.1, 5.1, 0.9 Hz, 1H), 6.80 (d, J=8.4 Hz, 1H), 5.69 (s, 2H), 5.43 (s, 2H), 5.38-5.24 (m, 1H), 4.74-4.61 (m, 1H), 4.59-4.45 (m, 1H), 3.47 (ddd, J=32.1, 14.5, 6.2 Hz, 2H), 2.72 (d, J=5.6 Hz, 1H), 2.57 (d, J=8.9 Hz, 1H).

2-((6-((4-chloro-2-fluorobenzyl)oxy)-3',6'-dihydro-[2,4'-bipyridin]-1'(2'H)-yl)methyl)-3-(oxazol-4-ylmethyl)imidazo[1,2-a]pyridine-6-carboxylic acid
(Compound 327)

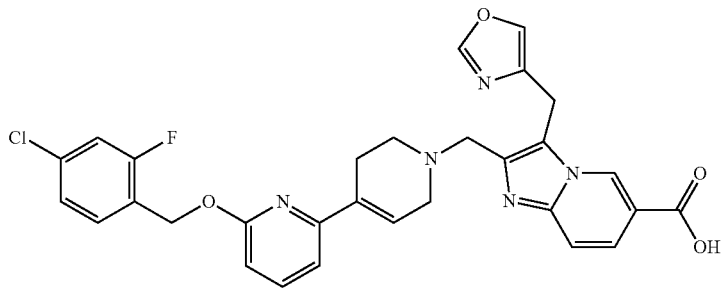

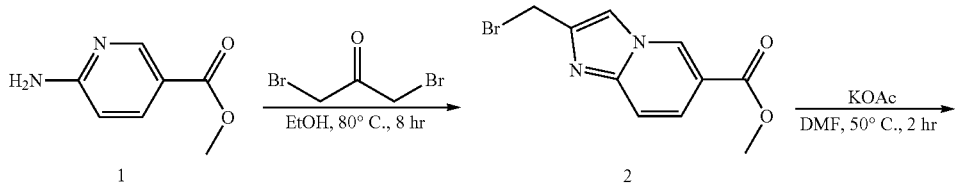

-continued
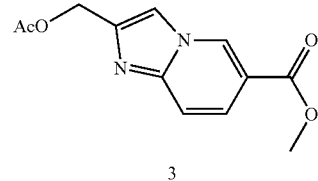 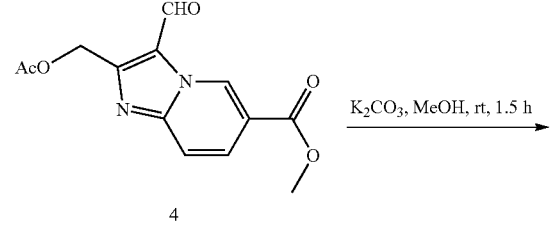
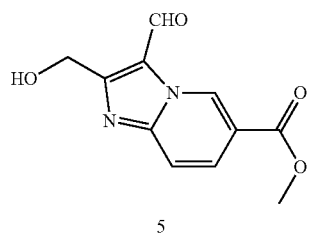 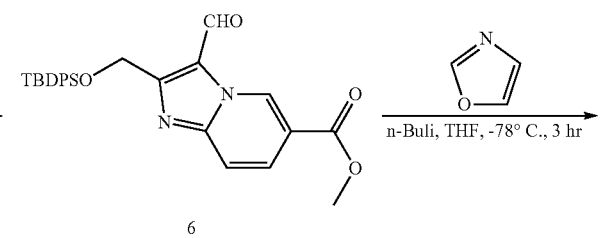
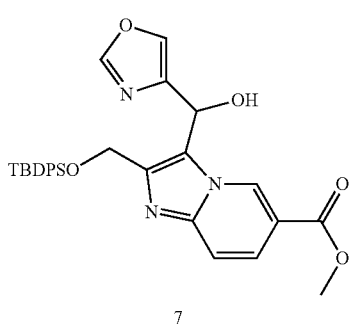 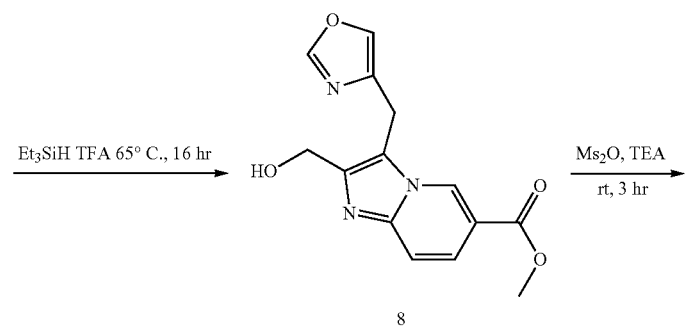
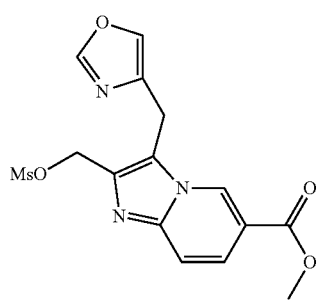 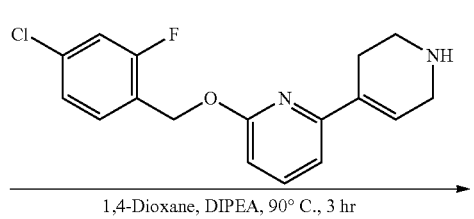

-continued

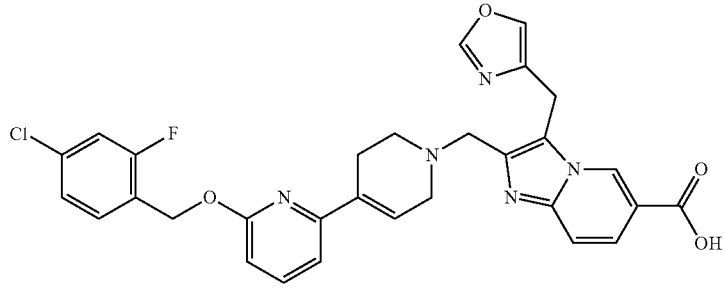

Step 1
A mixture of methyl 6-aminopyridine-3-carboxylate (17.62 g, 115.81 mmol), 1,3-dibromopropan-2-one (25 g, 115.81 mmol) in EtOH (400 mL) was stirred for 12 h at 80° C. under $N_2$, until the reaction was complete as indicated by LCMS, the reaction mixture added was $NaHCO_3$ and filtered through a pad of Celite with EtOAc, and the combined organics were concentrated in vacuo, purified by silica gel chromatography (Hexanes/EtOAc=12:1) to give the desired product methyl 2-(bromomethyl)imidazo[1,2-a]pyridine-6-carboxylate (5.2 g, 16.7% yield) as pale yellow solid.

LCMS: $[M+H]^+$=269.0; Retention time (0.01% TFA)= 0.99 min.

Step 2
A mixture of methyl 2-(bromomethyl)imidazo[1,2-a]pyridine-6-carboxylate (6.9 g, 25.64 mmol) and potassium acetate (7.55 g, 76.92 mmol, 4.81 mL) in DMF (150 mL) was stirred for 2 h at 50° C. under $N_2$, until the reaction was complete as indicated by LCMS, the reaction mixture was filtered through a pad of Celite with EtOAc, and the combined organics were concentrated in vacuo, purified by silica gel chromatography (Hexanes/EtOAc=5:1) to give the desired product methyl 2-(acetoxymethyl)imidazo[1,2-a]pyridine-6-carboxylate (5.8 g, 91.1% yield) as pale yellow solid.

LCMS: $[M+H]^+$=249.1; Retention time (0.01% TFA)= 0.95 min.

Step 3
A mixture of phosphoryl trichloride (11.74 g, 76.54 mmol) in DMF (50 mL) was stirred for 0.5 h at 0° C. under $N_2$, and methyl 2-(acetoxymethyl)imidazo[1,2-a]pyridine-6-carboxylate (3.8 g, 15.31 mmol) was then added and the mixture was stirred for 2 h at rt until the reaction was complete as indicated by LCMS, the reaction mixture was filtered through a pad of Celite with EtOAc, and the combined organics were concentrated in vacuo, purified by silica gel chromatography (Hexanes/EtOAc=6:1) to give the desired product methyl 2-(acetoxymethyl)-3-formyl-imidazo[1,2-a]pyridine-6-carboxylate (2.4 g, 56.78% yield) as pale yellow solid. LCMS: $[M+H]^+$=277.2; Retention time (0.01% TFA)=1.58 min.

Step 4
A mixture of methyl 2-(acetoxymethyl)-3-formyl-imidazo[1,2-a]pyridine-6-carboxylate (2.4 g, 8.69 mmol) and potassium carbonate (1.80 g, 13.03 mmol) in MeOH (50 mL) was stirred for 1.5 h at rt under $N_2$, until the reaction was complete as indicated by LCMS, the reaction mixture was filtered through a pad of Celite with DCM, and the combined organics were concentrated in vacuo, purified by silica gel chromatography (Hexanes/EtOAc=2:1) to give the desired product methyl 3-formyl-2-(hydroxymethyl)imidazo[1,2-a]pyridine-6-carboxylate (2.1 g, 87.7% yield) as pale yellow solid.

LCMS: $[M+H]^+$=235.1; Retention time (0.01% TFA)= 1.08 min.

Step 5
A mixture of methyl 3-formyl-2-(hydroxymethyl)imidazo[1,2-a]pyridine-6-carboxylate (2.1 g, 8.97 mmol), tert-butyl-chloro-diphenyl-silane (2.96 g, 10.76 mmol, 2.76 mL), and imidazole (1.83 g, 26.90 mmol) in DCM (40 mL) was stirred for 2 hr at rt under $N_2$, until the reaction was complete as indicated by LCMS, the reaction mixture was filtered through a pad of Celite with EtOAc, and the combined organics were concentrated in vacuo, purified by silica gel chromatography (Hexanes/EtOAc=8:1) to give the desired product methyl 2-[[tert-butyl(diphenyl)silyl]oxymethyl]-3-formyl-imidazo[1,2-a]pyridine-6-carboxylate (5.8 g, 89.0% yield) as pale yellow solid. LCMS: $[M+H]^+$=473.0; Retention time (0.01% TFA)=2.36 min.

Step 6
A mixture of oxazole (1.46 g, 21.16 mmol) butyllithium (1.08 g, 16.93 mmol) in THF (30 mL) was stirred for 0.5 h at −78° C. under $N_2$, methyl 2-[[tert-butyl(diphenyl)silyl]oxymethyl]-3-formyl-imidazo[1,2-a]pyridine-6-carboxylate (1 g, 2.12 mmol) was then added and the resulting mixture was further stirred for 2 h at −78° C. under $N_2$, until the reaction was complete as indicated by LCMS. The reaction mixture was filtered through a pad of Celite with EtOAc, and the combined organics were concentrated in vacuo, purified by prep-HPLC to give the desired product methyl 2-[[tert-butyl(diphenyl)silyl]oxymethyl]-3-(oxazol-4-ylmethyl)imidazo[1,2-a]pyridine-6-carboxylate (500 mg, 45.0% yield) as pale white solid. LCMS: $[M+H]^+$=542.0; Retention time (0.01% TFA)=1.75 min.

Step 7
A mixture of methyl 2-[[tert-butyl(diphenyl)silyl]oxymethyl]-3-[hydroxy(oxazol-4-yl)methyl]imidazo[1,2-a]pyridine-6-carboxylate (800 mg, 1.48 mmol), triethylsilane (1.72 g, 14.77 mmol, 2.36 mL) in TFA (20 mL) was stirred for 16 h at 65° C. under $N_2$, until the reaction was complete as indicated by LCMS. The reaction mixture was concentrated and neutralized with $NaHCO_3$, and the resulting residue was dissolved in DCM, filtered through a pad of Celite with DCM and MeOH, and the combined organics were concentrated in vacuo to give the desired product methyl 2-(hydroxymethyl)-3-(oxazol-4-ylmethyl)imidazo[1,2-a]pyridine-6-carboxylate (105 mg, 24.8% yield) as pale yellow oil. LCMS: $[M+H]^+$=288.0; Retention time=1.30 min.

Step 8
To a stirred solution of methyl 2-(hydroxymethyl)-3-(oxazol-4-ylmethyl)imidazo[1,2-a]pyridine-6-carboxylate (30 mg, 104 μmol) in DCM (10 mL) solution was added methanesulfonic anhydride (21.8 mg, 125 μmol) TEA (31.7 mg, 313 μmol). The reaction mixture was stirred at rt for 3 h and upon completion of the reaction, as judged by TLC, the mixture was diluted with DCM (50 mL) and warmed to room temperature. The layers were separated, and the aqueous layer was extracted with DCM (2×50 mL). The combined organic phase was washed with brine (50 mL) and dried over anhydrous $Na_2SO_4$, filtered and concentrated in vacuo to afford methyl 2-(methylsulfonyloxymethyl)-3-(oxazol-4-ylmethyl)imidazo[1,2-a]pyridine-6-carboxylate (30 mg, 51.5% yield) as a light-yellow liquid. LCMS: [M+H]$^+$=366.0; Retention time (10 mM $NH_4HCO_3$)=1.38 min.

Step 9

A mixture of methyl 2-(bromomethyl)-3-(oxazol-4-ylmethyl)imidazo[1,2-a]pyridine-6-carboxylate (115.0 mg, 49 μmol), 2-[(4-chloro-2-fluoro-phenyl)methoxy]-6-(1,2,3,6-tetrahydropyridin-4-yl)pyridine (18.8 mg, 59 μmol), N-ethyl-N-isopropyl-propan-2-amine (31.8 mg, 246 μmol) in 1,4-dioxane (12 mL) was stirred for 1.5 hr at 95° C. under $N_2$, until the reaction was complete as indicated by LCMS. The reaction mixture was filtered through a pad of Celite with EtOAc, and the combined organics were concentrated in vacuo, purified by silica gel chromatography (DCM: MeOH=20:1) to give the desired product methyl 2-[[4-[6-[(4-chloro-2-fluoro-phenyl)methoxy]-2-pyridyl]-3,6-dihydro-2H-pyridin-1-yl]methyl]-3-(oxazol-4-ylmethyl)imidazo[1,2-a]pyridine-6-carboxylate (10 mg, 34.5% yield) as pale yellow oil. LCMS: [M+H]$^+$=588.0; Retention time (0.01% TFA)=2.12 min.

Step 10

A mixture of methyl 2-[[4-[6-[(4-chloro-2-fluoro-phenyl)methoxy]-2-pyridyl]-3,6-dihydro-2H-pyridin-1-yl]methyl]-3-(oxazol-4-ylmethyl)imidazo[1,2-a]pyridine-6-carboxylate (10 mg, 17 μmol), lithium hydroxide (1.2 mg, 51 μmol) in MeOH (1 mL), H2O (3 mL) and THF (3 mL) was stirred for 2 h at rt under $N_2$, until the reaction was complete as indicated by LCMS. The reaction mixture was filtered through a pad of Celite with EtOAc, and the combined organics were concentrated in vacuo, purified by prep-HPLC to give the desired product 2-[[4-[6-[(4-chloro-2-fluoro-phenyl)methoxy]-2-pyridyl]-3,6-dihydro-2H-pyridin-1-yl]methyl]-3-(oxazol-4-ylmethyl)imidazo[1,2-a]pyridine-6-carboxylic acid (2 mg, 20.5% yield) as pale white solid. LCMS: [M+H]$^+$=574.1; Retention time=1.56 min.

$^1$H NMR (400 MHz, DMSO-D6) δ 8.79-8.78 (brs, 1H), 8.02 (t, J=11.2 Hz, 1H), 7.74-7.64 (m, 2H), 7.51 (ddd, J=12.8, 12.0, 5.1 Hz, 3H), 7.30 (dd, J=8.2, 1.8 Hz, 1H), 7.09 (d, J=0.7 Hz, 1H), 7.04 (d, J=7.4 Hz, 1H), 6.76-6.62 (m, 2H), 5.39 (s, 2H), 4.76 (s, 2H), 3.82 (s, 2H), 3.18-3.17 (brs, 2H), 2.66 (t, J=5.5 Hz, 2H), 2.40-2.39 (brs, 2H).

(S)-(2-((6-((4-cyano-2-fluorobenzyl)oxy)-3',6'-dihydro-[2,4'-bipyridin]-1'(2'H)-yl)methyl)-1-(oxetan-2-ylmethyl)-1H-benzo[d]imidazol-6-yl)boronic acid (Compound 328)

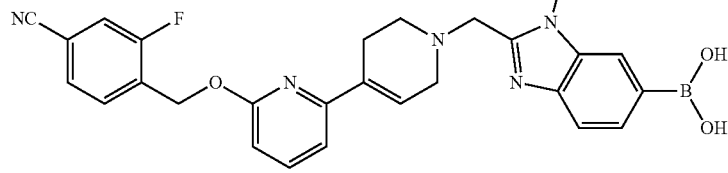

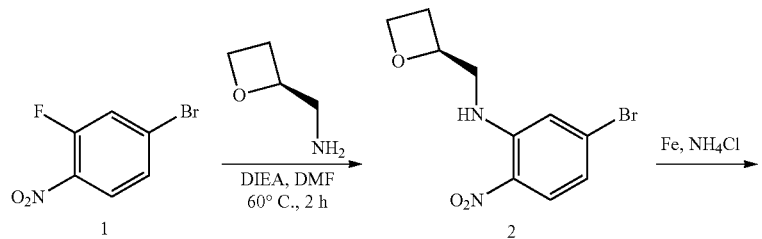

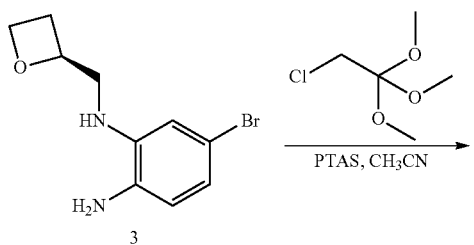

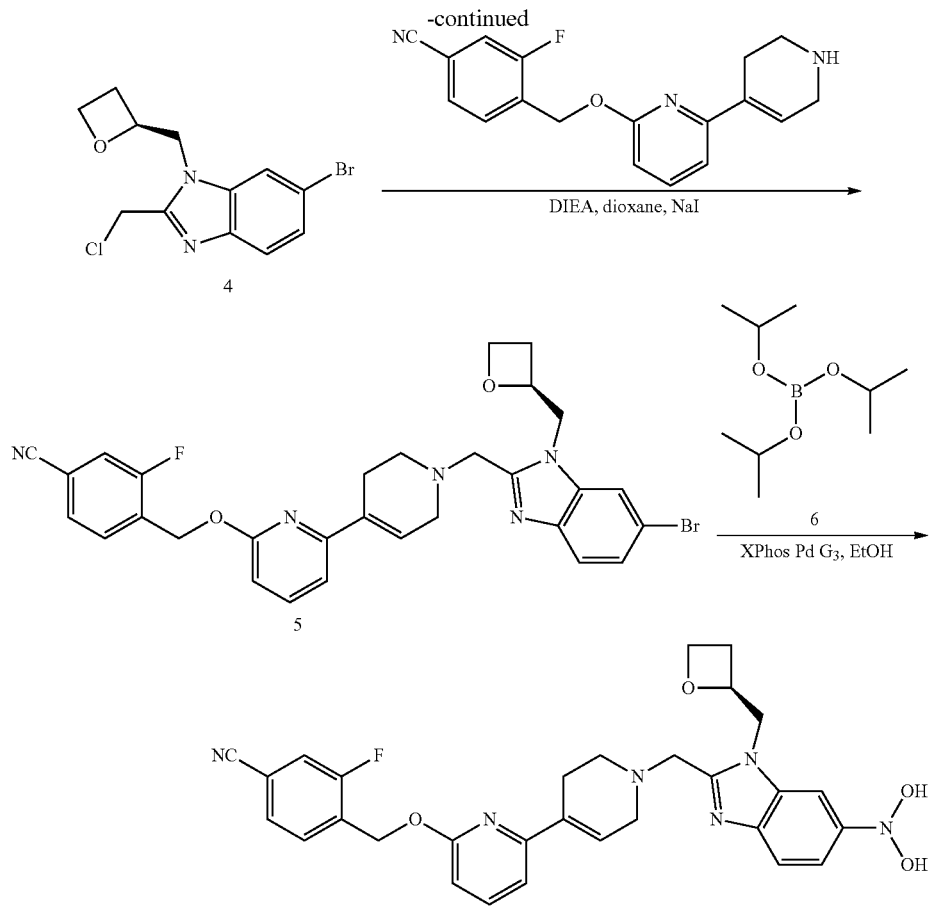

Step 1

A mixture of 4-bromo-2-fluoro-1-nitro-benzene (2 g, 9.09 mmol), 4-methylbenzenesulfonic acid, [(2S)-oxetan-2-yl]methanamine (2.36 g, 9.09 mmol), N,N-diethylethanamine (4.60 g, 45.46 mmol) in DMF (50 mL) was stirred for 2 h at 60° C. under $N_2$ until the reaction was complete as indicated by LCMS. The reaction mixture was filtered through a pad of celite with EtOAc, and the combined organics were concentrated in vacuo, purified by silica gel chromatography to give the desired product 5-bromo-2-nitro-N-[[(2S)-oxetan-2-yl]methyl]aniline (2.42 g, 7.58 mmol, 83.4% yield, 89.8% purity) as yellow solid. LCMS: [M+H]$^+$=289.0; Retention time (0.01% TFA)=1.72 min.

Step 2

A mixture of 5-bromo-2-nitro-N-[[(2S)-oxetan-2-yl]methyl]aniline (2.42 g, 8.44 mmol) Iron (3.77 g, 67.54 mmol) and ammonia hydrochloride (3.61 g, 67.54 mmol) in Ethanol (16 mL) and Water (4 mL) was stirred for 1.5 h at 80° C. in a RBF under $N_2$, until the reaction was completed as indicated by LCMS, the reaction mixture was filtered through a pad of Celite with EtOAc, and the combined organics were concentrated in vacuo, purified by silica gel chromatography to give the desired product 4-bromo-N2-[[(2S)-oxetan-2-yl]methyl]benzene-1,2-diamine (1.44 g, 5.56 mmol, 65.8% yield, 99.5% purity) as brown oil. LCMS: [M+H]$^+$=259.1; Retention time (0.01% TFA)=1.16 min.

Step 3

A mixture of 4-bromo-N2-[[(2S)-oxetan-2-yl]methyl]benzene-1,2-diamine (1.4 g, 5.44 mmol), 2-chloro-1,1,1-trimethoxy-ethane (925.9 mg, 5.99 mmol) and 4-methylbenzenesulfonic acid hydrate (103.6 mg, 544.5 μmol) in ACN (30 mL) was stirred for 1 h at 60° C. under $N_2$ until the reaction was complete as indicated by LCMS, the reaction mixture was filtered through a pad of Celite with EtOAc, and the combined organics were concentrated in vacuo, purified by silica gel chromatography to give the desired product 6-bromo-2-(chloromethyl)-1-[[(2S)-oxetan-2-yl]methyl] benzimidazole (1.04 g, 2.37 mmol, 43.6% yield) as white solid. LCMS: [M+H]$^+$=317.0; Retention time (0.01% TFA)= 1.45 min.

Step 4

A mixture of 6-bromo-2-(chloromethyl)-1-[[(2S)-oxetan-2-yl]methyl]benzimidazole (500 mg, 1.58 mmol), 3-fluoro-4-[[6-(1,2,3,6-tetrahydropyridin-4-yl)-2-pyridyl]oxymethyl]benzonitrile (735.1 mg, 2.38 mmol), N-ethyl-N-isopropyl-propan-2-amine (1.43 g, 11.09 mmol) and sodium iodide dihydrate (28.8 mg, 158.4 μmol) in dioxane (20 mL) was stirred for 16 h at 90° C. in a RBF under $N_2$, until the reaction was completed as indicated by LCMS, the reaction mixture was filtered through a pad of Celite with EtOAc, and the combined organics were concentrated in vacuo, purified by silica gel chromatography to give the desired product 4-[[6-[1-[[6-bromo-1-[[(2S)-oxetan-2-yl]methyl]benzimidazol-2-yl]methyl]-3,6-dihydro-2H-pyridin-4-yl]-2-pyridyl] oxymethyl]-3-fluoro-benzonitrile (800 mg, 869.65 μmol, 54.9% yield) as white solid. LCMS: [M+H]$^+$=588.0; Retention time (10 mM NH$_4$HCO$_3$)=1.82 min.

Step 5

A solution of 4-[[6-[1-[[6-bromo-1-[[(2S)-oxetan-2-yl] methyl]benzimidazol-2-yl]methyl]-3,6-dihydro-2H-pyridin-4-yl]-2-pyridyl]oxymethyl]-3-fluoro-benzonitrile (20 mg, 33.99 µmol) and hypoboric acid (9.1 mg, 102 µmol), dicyclohexyl-[2-(2,4,6-triisopropylphenyl) phenyl]phosphane (0.3 mg, 0.7 µmol), XPhos Pd G$_3$ (0.3 mg, 0.34 µmol) potassium acetate (20 mg, 203.9 µmol) in Ethanol (3 mL) and ethyleneglycol (0.15 mL), and the mixture was stirred at 60° C. for 3 h. The reaction mixture was purified by HPLC to give the desired product [2-[[4-[6-[(4-cyano-2-fluorophenyl)methoxy]-2-pyridyl]-3,6-dihydro-2H-pyridin-1-yl]methyl]-3-[[(2S)-oxetan-2-yl]methyl]benzimidazol-5-yl]boronic acid (2 mg, 2.7 µmol, 8.0% yield) as a white solid. LCMS: [M+H]$^+$=554.1; Retention time (0.01% TFA)=1.72 min.

$^1$H NMR (400 MHz, DMSO-D6) δ 8.16 (s, 2H), 8.01 (s, 1H), 7.89 (d, J=10.4 Hz, 1H), 7.75-7.61 (m, 4H), 7.54 (d, J=8.0 Hz, 1H), 7.10 (d, J=7.4 Hz, 1H), 6.77 (d, J=8.2 Hz, 1H), 6.71 (s, 1H), 5.49 (s, 2H), 5.14-5.03 (m, 1H), 4.71 (dd, J=15.1, 7.1 Hz, 1H), 4.57 (dd, J=15.1, 3.4 Hz, 1H), 4.47 (dd, J=14.1, 7.1 Hz, 1H), 4.38 (dt, J=9.0, 6.0 Hz, 1H), 4.04 (d, J=13.3 Hz, 1H), 3.89 (d, J=13.3 Hz, 1H), 3.22 (d, J=9.2 Hz, 3H), 2.76-2.64 (m, 3H), 2.44-2.30 (m, 2H).

(S)-2-((2-((4-chloro-2-fluorobenzyl)oxy)-3',6'-dihydro-[3,4'-bipyridin]-1'(2'H)-yl)methyl)-1-(oxetan-2-ylmethyl)-1H-benzo[d]imidazole-6-carboxylic acid (Compound 329)

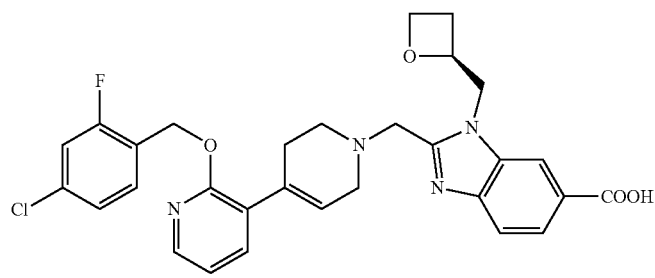

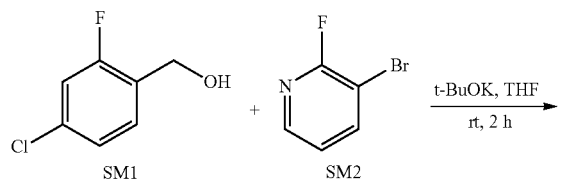

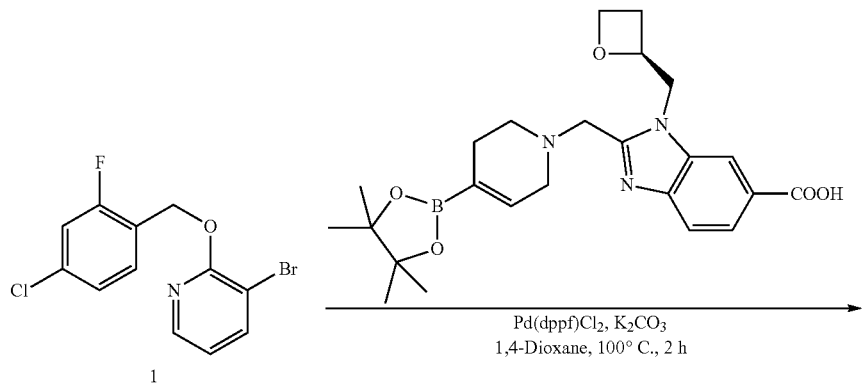

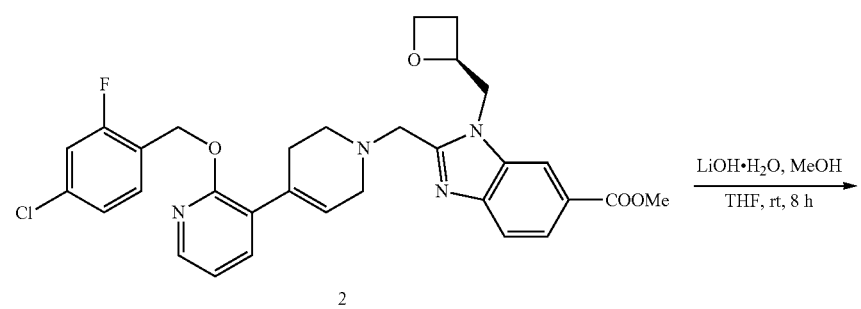

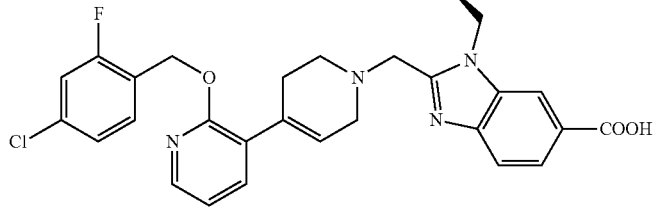

Step 1

A suspension of (4-chloro-2-fluoro-phenyl)methanol (1 g, 6.23 mmol) and potassium 2-methylpropan-2-olate (768.7 mg, 6.85 mmol) in THF (20 mL) was stirred for 0.5 h at 0° C. under $N_2$. Then 3-bromo-2-fluoro-pyridine (1.21 g, 6.85 mmol) was added slowly and stirred for 1 h under $N_2$. After completion of the reaction as judged by LCMS, reaction mixture was quenched with water (20 mL) and extracted with EtOAc (3×20 mL). The organic phase was washed with brine (50 mL) and dried over anhydrous $Na_2SO_4$, filtered and concentrated in vacuo. The crude product was purified by flash chromatography to afford 3-bromo-2-[(4-chloro-2-fluoro-phenyl)methoxy]pyridine (1.4 g, 4.04 mmol, 64.9% yield) as yellow oil. LCMS: $[M+H]^+=315.9$; Retention time (0.01% TFA)=2.30 min.

Step 2

A mixture of 3-bromo-2-[(3-chloro-2-fluoro-phenyl)methoxy]pyridine (184.3 mg, 582 μmol), methyl 3-[[(2S)-oxetan-2-yl]methyl]-2-[[4-(4,4,5,5-tetramethyl-1,3,2-dioxaborolan-2-yl)-3,6-dihydro-2H-pyridin-1-yl]methyl]benzimidazole-5-carboxylate (272.1 mg, 582 μmol), Pd(dppf)Cl₂ (42.6 mg, 58 mol) and $K_2CO_3$ (241.4 mg, 1.75 mmol) in dioxane (10 mL) and Water (2 mL) was stirred for 16 h at 90° C. under $N_2$ until the reaction was complete as indicated by LCMS. The reaction mixture was filtered through a pad of Celite with EtOAc and the combined organics were concentrated in vacuo, purified by silica gel chromatography to give the desired product methyl 2-[[4-[2-(4-chloro-2-fluoro-phenyl)-2-methyl-1,3-benzodioxol-4-yl]-3,6-dihydro-2H-pyridin-1-yl]methyl]-3-[[(2S)-oxetan-2-yl]methyl]benzimidazole-5-carboxylate (200 mg, 227.5 μmol, 39.1% yield, 68.7% purity) as brown oil. LCMS: $[M+H]^+=577.3$; Retention time (0.01% TFA)=1.63 min.

Step 3

A mixture of methyl 2-[[4-[2-[(4-chloro-2-fluoro-phenyl)methoxy]-3-pyridyl]-3,6-dihydro-2H-pyridin-1-yl]methyl]-3-[[(2S)-oxetan-2-yl]methyl]benzimidazole-5-carboxylate (200 mg, 207.96 μmol) and LiOH (43.6 mg, 1.04 mmol) in THF (2.5 mL), Methanol (2.5 mL) and Water (1.5 mL) was stirred for 1.5 h at 25° C. under $N_2$, until the reaction was complete as indicated by LCMS. The reaction mixture was purified by HPLC to give the desired product 2-[[4-[2-[(4-chloro-2-fluoro-phenyl)methoxy]-3-pyridyl]-3,6-dihydro-2H-pyridin-1-yl]methyl]-3-[[(2S)-oxetan-2-yl]methyl]benzimidazole-5-carboxylic acid (12.4 mg, 22.02 μmol, 10.6% yield) as white solid.

LCMS: $[M+H]^+=563.0$; Retention time (10 mM $NH_4HCO_3$)=1.59 min.

$^1$H NMR (400 MHz, MeOD) δ 8.27-8.26 (brs, 1H), 8.05 (dd, J=5.0, 1.8 Hz, 1H), 7.98 (d, J=8.5 Hz, 1H), 7.64 (d, J=8.5 Hz, 1H), 7.58 (dd, J=7.3, 1.8 Hz, 1H), 7.51 (t, J=8.1 Hz, 1H), 7.34-7.16 (m, 2H), 6.97 (dd, J=7.3, 5.0 Hz, 1H), 5.92-5.91 (brs, 1H), 5.43 (s, 2H), 5.24 (d, J=4.9 Hz, 1H), 4.87 (dd, J=15.3, 7.1 Hz, 1H), 4.69 (dd, J=15.4, 2.7 Hz, 1H), 4.60 (dd, J=13.7, 7.9 Hz, 1H), 4.46 (dt, J=9.0, 5.9 Hz, 1H), 4.12 (d, J=13.6 Hz, 1H), 4.00 (d, J=13.6 Hz, 1H), 3.27-3.14 (m, 2H), 2.84-2.68 (m, 3H), 2.60-2.41 (m, 3H).

2-((4-(2-(4-chloro-2-fluorophenyl)-2-methylbenzo[d][1,3]dioxol-4-yl)-5,6-dihydropyridin-1(2H)-yl)methyl)-1-((S)-oxetan-2-ylmethyl)-1H-benzo[d]imidazole-6-carboxylic acid (Compound 330)

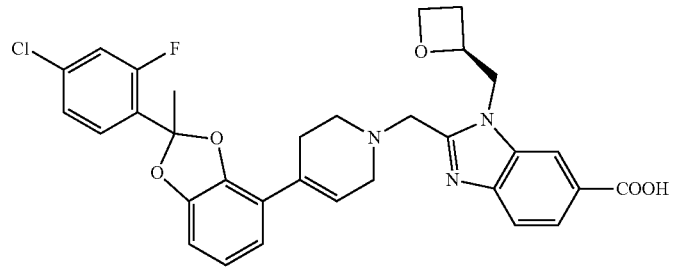

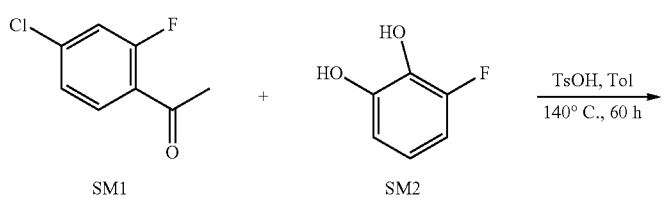

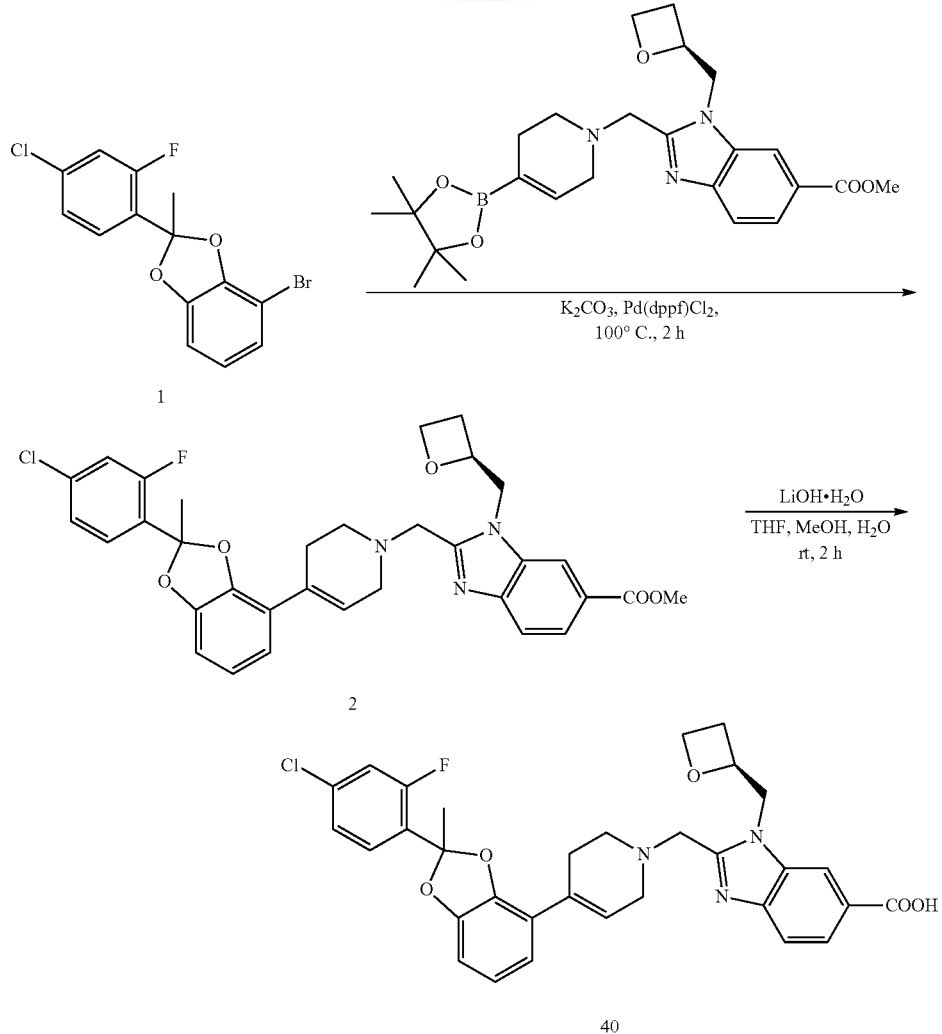

Step 1

To a suspension of 3-bromobenzene-1,2-diol (1.20 g, 6.37 mmol) in toluene (100 mL) were added 1-(4-chloro-2-fluoro-phenyl)ethanone (1 g, 5.79 mmol) and 4-methylbenzenesulfonic acid hydrate (1.10 g, 5.79 mmol). The reaction apparatus was fitted with a Dean-Stark trap, and the reaction mixture was heated at 140° C. for 60 h, whereupon the solution was concentrated in vacuo and purified by flash chromatography to afford 4-bromo-2-(4-chloro-2-fluorophenyl)-2-methyl-1,3-benzodioxole (280 mg, 774.2 µmol, 13.4% yield) as yellow oil.

LCMS [M+H]⁺=343.0; Retention time (0.01% TFA)=2.07 min.

Step 2

To a stirred solution of 4-bromo-2-(4-chloro-2-fluorophenyl)-2-methyl-1,3-benzodioxole (100 mg, 291.06 µmol) in 1,4-Dioxane (10 mL) and water (2 mL) were added methyl 3-[[(2S)-oxetan-2-yl]methyl]-2-[[4-(4,4,5,5-tetramethyl-1,3,2-dioxaborolan-2-yl)-3,6-dihydro-2H-pyridin-1-yl]methyl]benzimidazole-5-carboxylate (142.8 mg, 305 µmol), Pd(dppf)Cl₂ (21.3 mg, 29 µmol) and K₂CO₃ (80.3 mg, 582 µmol). The reaction mixture was stirred at 100° C. for 2 h. Upon completion of the reaction as judged by TLC, the mixture was diluted with EtOAc (100 mL) and warmed to room temperature. The layers were separated, and the aqueous layer was extracted with EtOAc (2×50 mL). The combined organic phase was washed with brine (50 mL) and dried over anhydrous Na₂SO₄, filtered and concentrated in vacuo to afford the crude product methyl 2-[[4-[2-(4-chloro-2-fluoro-phenyl)-2-methyl-1,3-benzodioxol-4-yl]-3,6-dihydro-2H-pyridin-1-yl]methyl]-3-[[(2S)-oxetan-2-yl]methyl] benzimidazole-5-carboxylate (150 mg, 206.2 µmol, 70.9% yield) as a light-yellow liquid which was used directly in the next step. LCMS: [M+H]⁺=604.0, Retention time (10 mM NH₄HCO₃)=2.31 min.

Step 3

To a stirred solution of methyl 2-[[4-[2-(4-chloro-2-fluoro-phenyl)-2-methyl-1,3-benzodioxol-4-yl]-3,6-dihydro-2H-pyridin-1-yl]methyl]-3-[[(2S)-oxetan-2-yl]methyl] benzimidazole-5-carboxylate (150 mg, 206.2 µmol) in THF (3 mL), MeOH (3 mL) and water (3 mL) was added LiOH.H₂O (31.3 mg, 744 µmol). The reaction mixture was stirred at rt for 8 h. Upon completion of the reaction as judged by TLC, the mixture was diluted with EtOAc (100 mL) and warmed to room temperature. The layers were separated, and the aqueous layer was extracted with EtOAc (2×50 mL). The combined organic phase was washed with brine (50 mL) and dried over anhydrous Na₂SO₄, filtered and concentrated in vacuo. The crude product was purified by prep-HPLC to afford 2-[[4-[2-(4-chloro-2-fluoro-phenyl)-2-methyl-1,3-benzodioxol-4-yl]-3,6-dihydro-2H-pyridin-1-yl]methyl]-3-[[(2S)-oxetan-2-yl]methyl]benzimidazole-5-carboxylic acid (53.9 mg, 91 μmol, 44.3% yield) as a white solid. LCMS: [M+H]$^+$=590.0, Retention time (10 mM NH$_4$HCO$_3$)=1.68 min.

$^1$H NMR (400 MHz, MeOD) δ 8.35-8.34 (brs, 1H), 8.00 (dd, J=8.5, 1.4 Hz, 1H), 7.71 (d, J=8.5 Hz, 1H), 7.58 (t, J=8.3 Hz, 1H), 7.30 (dd, J=10.9, 1.9 Hz, 1H), 7.26-7.20 (m, 1H), 6.84 (dt, J=15.4, 7.2 Hz, 2H), 6.80-6.73 (m, 1H), 6.41-6.40 (brs, 1H), 5.26 (d, J=8.1 Hz, 1H), 4.87-4.86 (brs, 1H), 4.74 (d, J=14.0 Hz, 1H), 4.63 (dd, J=14.0, 7.7 Hz, 1H), 4.48 (dd, J=14.7, 5.7 Hz, 1H), 4.19 (d, J=14.0 Hz, 1H), 4.07 (d, J=13.9 Hz, 1H), 3.32-3.25 (m, 2H), 2.88 (d, J=5.7 Hz, 2H), 2.83-2.74 (m, 1H), 2.63-2.62 (brs, 2H), 2.58-2.48 (m, 1H), 2.05 (s, 3H).

(S)-2-((4-(4-(((4-chloro-2-fluorobenzyl)oxy)thiazol-5-yl)-3,6-dihydropyridin-1(2H)-yl)methyl)-1-(oxetan-2-ylmethyl)-1H-benzo[d]imidazole-6-carboxylic acid (Compound 331)

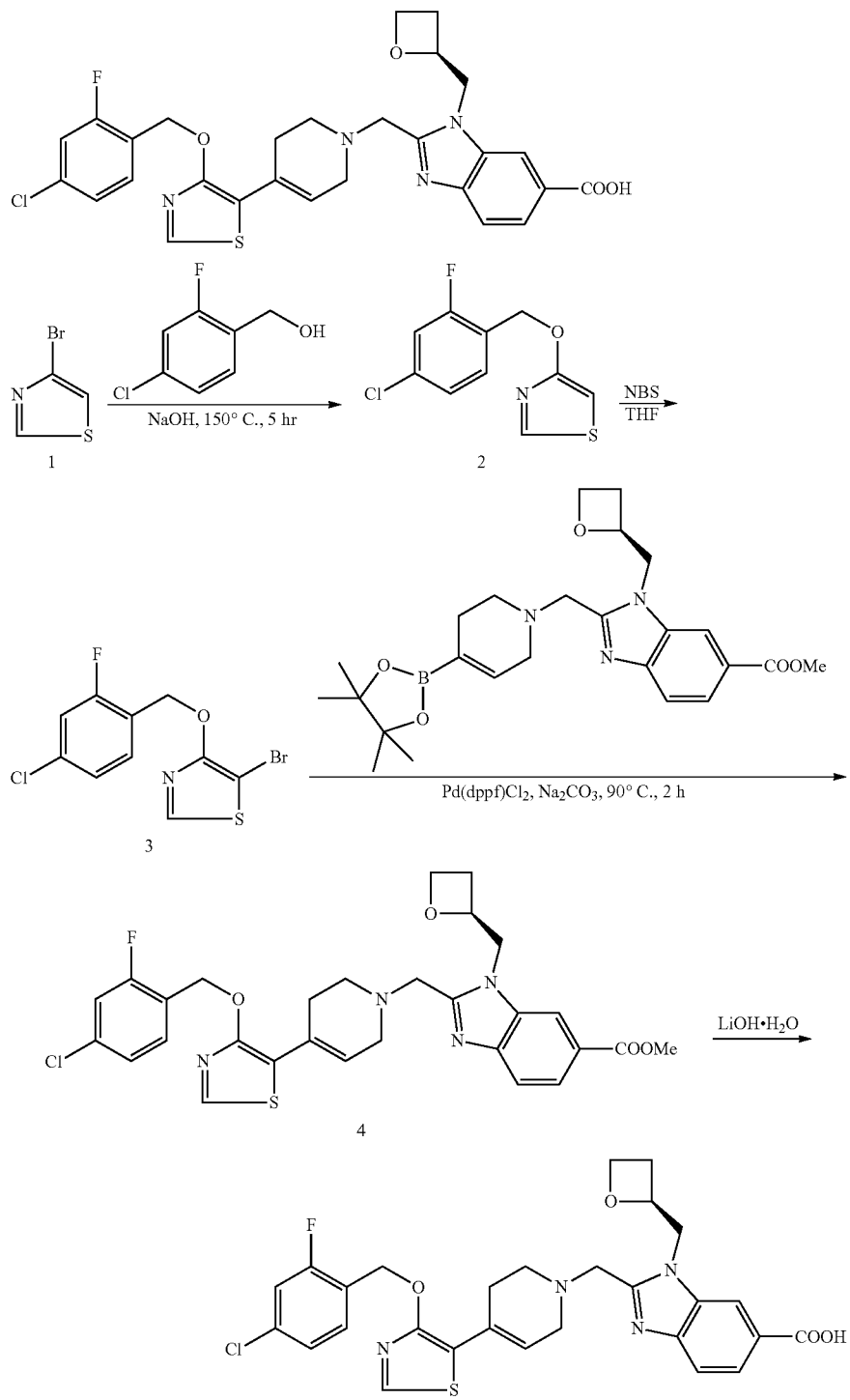

Step 1

To a mixture of 4-bromothiazole (2 g, 12.2 mmol) in 4-bromothiazole (2 g, 12.19 mmol) was added sodium hydroxide (2.93 g, 73.2 mmol). And then the mixture was stirred at 150° C. for 4 h under $N_2$ atmosphere. The reaction mixture was diluted with water and then extracted with EtOAc (3×50 mL), the organic was concentrated to yield the residue which was purified by silica gel chromatography (petroleum ether:EtOAc=95:5) to give the 4-[(4-chloro-2-fluoro-phenyl)methoxy]thiazole (370 mg, 1.52 mmol, 12.5% yield). LCMS: [M+H]$^+$=244.1; Retention time (0.01% TFA)=1.77 min.

Step 2

To a mixture of 4-[(4-chloro-2-fluoro-phenyl)methoxy]thiazole (60 mg, 246 μmol) in THF (5 mL) was added 1-bromopyrrolidine-2,5-dione (65.7 mg, 369.3 μmol). And then the mixture was stirred at rt for 3 h under $N_2$ atmosphere. The reaction mixture was diluted with water and extracted with DCM (3×20 mL) and then concentrated to yield a residue which was purified by silica gel chromatography (petroleum ether:EtOAc=98:2) to give the 5-bromo-4-[(4-chloro-2-fluoro-phenyl)methoxy]thiazole (60 mg, 186.0 μmol, 75.5% yield). LCMS: [M+H]$^+$=322.0; Retention time (0.01% TFA)=1.96 min.

Step 3

To a mixture of 5-bromo-4-[(4-chloro-2-fluoro-phenyl)methoxy]thiazole (30 mg, 93.00 μmol) and methyl 3-[[(2S)-oxetan-2-yl]methyl]-2-[[4-(4,4,5,5-tetramethyl-1,3,2-dioxaborolan-2-yl)-3,6-dihydro-2H-pyridin-1-yl]methyl]benzimidazole-5-carboxylate (52.2 mg, 111.6 μmol) in Water (1 mL) and 1,4-dioxane (5 mL) were added Pd(dppf)Cl$_2$ (6.80 mg, 9.30 μmol), disodium carbonate (19.7 mg, 186.0 μmol). And then the mixture was stirred at 90° C. for 2 h under $N_2$ atmosphere. The reaction mixture was concentrated to yield a residue which was purified by silica gel chromatography (PE:EtOAc=10:1) to give the methyl 2-[[4-[4-[(4-chloro-2-fluoro-phenyl)methoxy]thiazol-5-yl]-3,6-dihydro-2H-pyridin-1-yl]methyl]-3-[[(2S)-oxetan-2-yl]methyl]benzimidazole-5-carboxylate (20 mg, 34.30 μmol, 36.88% yield). LCMS [M+H]$^+$=583.2; Retention time (0.01% TFA)=1.67 min.

Step 4

To a mixture of methyl 2-[[4-[4-[(4-chloro-2-fluoro-phenyl)methoxy]thiazol-5-yl]-3,6-dihydro-2H-pyridin-1-yl]methyl]-3-[[(2S)-oxetan-2-yl]methyl]benzimidazole-5-carboxylate (20 mg, 34.3 μmol) in Water (2 mL) and THF (2 mL) and Methanol (2 mL) was added lithium hydroxide (7.2 mg, 171.5 mol). And then the mixture was stirred at 20° C. for 3 h under $N_2$ atmosphere. The reaction mixture was concentrated to yield a residue which was purified by prep-HPLC to give the 2-[[4-[4-[(4-chloro-2-fluoro-phenyl)methoxy]thiazol-5-yl]-3,6-dihydro-2H-pyridin-1-yl]methyl]-3-[[(2S)-oxetan-2-yl]methyl]benzimidazole-5-carboxylic acid (5 mg, 8.8 μmol, 25.6% yield). LCMS: [M+H]$^+$=568.9; Retention time (10 mM $NH_4HCO_3$)=1.28 min.

$^1$H NMR (400 MHz, DMSO-D6) δ 8.72 (s, 1H), 8.24 (s, 1H), 7.80 (d, J=8.8 Hz, 1H), 7.63 (d, J=8.4 Hz, 1H), 7.55-7.44 (m, 2H), 7.36-7.28 (m, 1H), 6.15 (s, 1H), 5.41 (s, 2H), 5.07-5.01 (m, 1H), 4.77 (dd, J=14.8, 7.2 Hz, 1H), 4.62 (d, J=12.4 Hz, 1H), 4.45 (dd, J=13.2, 8.0 Hz, 1H), 4.34 (dt, J=12.8, 6.0 Hz, 1H), 4.01 (d, J=14.0 Hz, 1H), 3.86 (d, J=13.6 Hz, 1H), 3.14 (s, 2H), 2.74-2.63 (m, 3H), 2.41 (s, 4H).

(S)-2-((4-(3-(4-chloro-2-fluorobenzyloxy)isothiazol-4-yl)-5,6-dihydropyridin-(2H)-yl)methyl)-1-(oxetan-2-ylmethyl)-1H-benzo[d]imidazole-6-carboxylic acid (Compound 332)

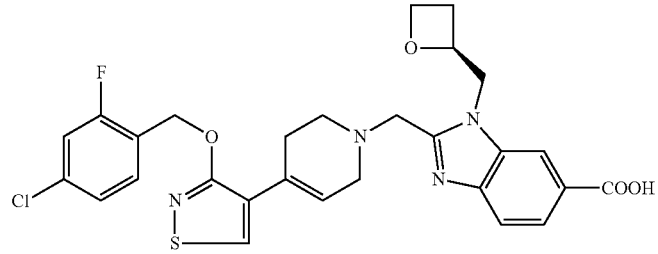

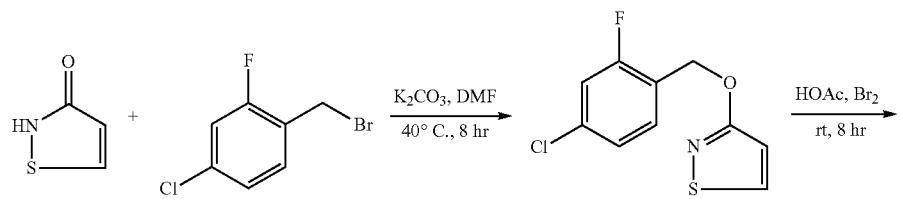

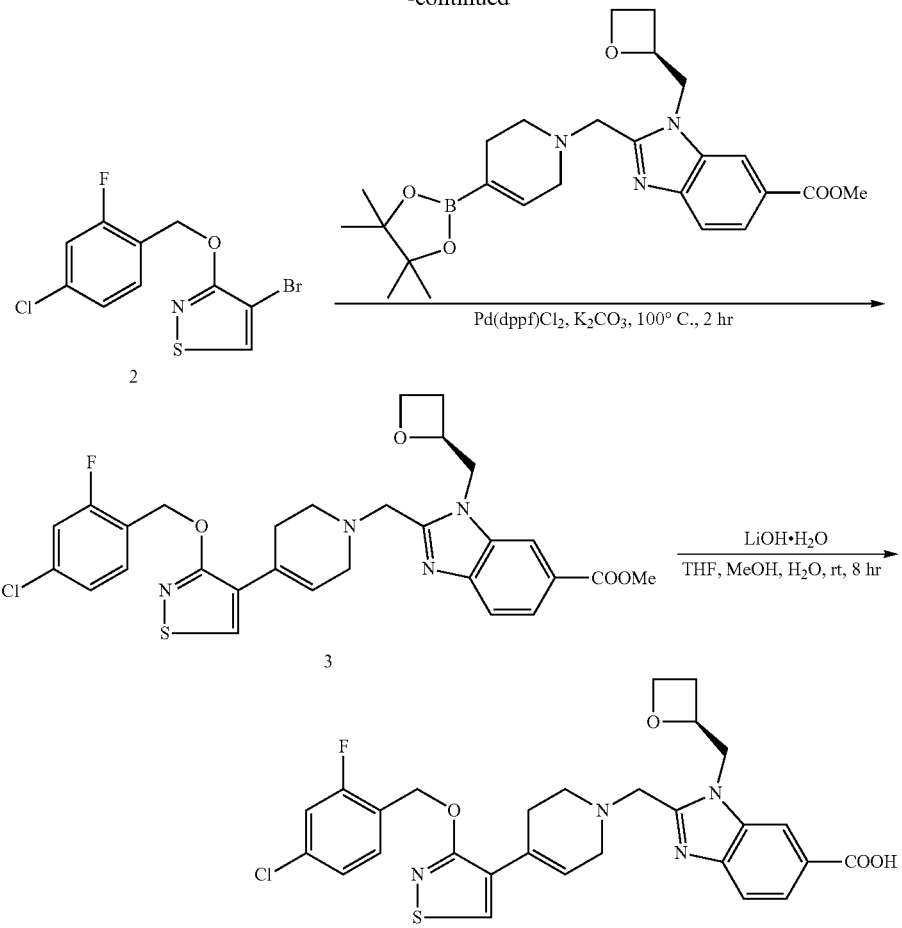

Step 1

To a stirred solution of isothiazol-3-one (1 g, 9.89 mmol) in DMF (20 mL) were added 1-(bromomethyl)-4-chloro-2-fluoro-benzene (2.21 g, 9.89 mmol) and $K_2CO_3$ (4.09 g, 29.67 mmol). The reaction mixture was stirred at 40° C. for 8 h and upon completion of the reaction as judged by TLC, the mixture was diluted with EtOAc (100 mL) and warmed to room temperature. The layers were separated, and the aqueous layer was extracted with EtOAc (2×50 mL). The combined organic phase was washed with brine (50 mL) and dried over anhydrous $Na_2SO_4$, filtered and concentrated in vacuo. The crude product was purified by flash column chromatography ($SiO_2$, hexanes/ethyl acetate 10:1) to afford 3-[(4-chloro-2-fluoro-phenyl)methoxy]isothiazole (1.6 g, 6.57 mmol, 66.4% yield, 100% purity) as a light-yellow liquid. LCMS: $[M+H]^+$=243.9; Retention time (0.1% TFA)= 2.12 min $^1$H NMR (400 MHz, CDCl3) δ 8.52-8.40 (m, 1H), 7.45 (t, J=7.9 Hz, 1H), 7.20-7.10 (m, 2H), 6.70-6.58 (m, 1H), 5.46 (d, J=11.0 Hz, 2H).

Step 2

To a stirred solution of 3-[(4-chloro-2-fluoro-phenyl)methoxy]isothiazole (200 mg, 820.7 μmol) in HOAc (5 mL) was added $Br_2$ (1.05 g, 6.57 mmol). The reaction mixture was stirred at rt for 8 h and upon completion of the reaction as judged by TLC, the mixture was diluted with EtOAc (50 mL) and warmed to room temperature. The layers were separated, and the aqueous layer was extracted with EtOAc (2×50 mL). The combined organic phase was washed with 1 M $NaHCO_3$ (100 mL) and dried over anhydrous $Na_2SO_4$, filtered and concentrated in vacuo. The crude product was purified by Prep-HPLC (0.2% TFA) to afford 4-bromo-3-[(4-chloro-2-fluoro-phenyl)methoxy]isothiazole (80 mg, 244.0 μmol, 29.7% yield, 98.4% purity) as a light-yellow liquid. LCMS: $[M+H]^+$=322.0; Retention time (0.05% TFA)= 1.99 min $^1$H NMR (400 MHz, CDCl3) δ 8.49-8.35 (m, 1H), 7.49 (dd, J=15.0, 7.0 Hz, 1H), 7.15 (ddd, J=11.5, 8.7, 1.9 Hz, 2H), 5.48 (s, 2H).

Step 3

To a stirred solution of 4-bromo-3-[(4-chloro-2-fluoro-phenyl)methoxy]isothiazole (80 mg, 243.98 μmol) in 1,4-Dioxane (10 mL) and water (2 mL) were added methyl 3-[[(2S)-oxetan-2-yl]methyl]-2-[[4-(4,4,5,5-tetramethyl-1,3,2-dioxaborolan-2-yl)-3,6-dihydro-2H-pyridin-1-yl]methyl]benzimidazole-5-carboxylate (125.43 mg, 268.38 μmol), Pd(dppf)Cl$_2$ (17.8 mg, 24.4 μmol) and $K_2CO_3$ (67.3 mg, 488.0 μmol). The reaction mixture was stirred at 100° C. for 2 h and upon completion of the reaction as judged by TLC, the mixture was diluted with EtOAc (100 mL) and warmed to room temperature. The layers were separated, and the aqueous layer was extracted with EtOAc (2×50 mL). The combined organic phase was washed with brine (50 mL) and dried over anhydrous $Na_2SO_4$, filtered and concentrated in vacuo to afford the crude product methyl 2-[[4-[3-[(4-chloro-2-fluoro-phenyl)methoxy]isothiazol-4-yl]-3,6-dihydro-2H-pyridin-1-yl]methyl]-3-[[(2S)-oxetan-2-yl]
methyl]benzimidazole-5-carboxylate (150 mg, 157.6 μmol,
64.6% yield, 61.3% purity) as a brown liquid. LCMS:
[M+H]⁺=583.0; Retention time (10 mM NH₄HCO₃)=1.81
min.

Step 4

To a stirred solution of methyl 2-[[4-[3-[(4-chloro-2-fluoro-phenyl)methoxy]isothiazol-4-yl]-3,6-dihydro-2H-pyridin-1-yl]methyl]-3-[[(2S)-oxetan-2-yl]methyl]benzimidazole-5-carboxylate (150 mg, 157.6 μmol) in THF (3 mL), MeOH (3 mL) and water (3 mL) was added LiOH.H₂O (33.1 mg, 788.1 μmol). The reaction mixture was stirred at rt for 8 h and upon completion of the reaction as judged by TLC, the mixture was diluted with EtOAc (50 mL) and warmed to room temperature. The layers were separated, and the aqueous layer was extracted with EtOAc (2×0 mL). The combined organic phase was washed with brine (50 mL) and dried over anhydrous Na₂SO₄, filtered and concentrated in vacuo. The crude product was purified by prep-HPLC (NH₄HCO₃) to afford 2-[[4-[3-[(4-chloro-2-fluoro-phenyl)methoxy]isothiazol-4-yl]-3,6-dihydro-2H-pyridin-1-yl]methyl]-3-[[(2S)-oxetan-2-yl]methyl]benzimidazole-5-carboxylic acid (46.6 mg, 81.89 μmol, 52.0% yield, 100% purity) as a white solid. LCMS: [M+H]⁺=569.0; Retention time (10 mM NH₄HCO₃)=1.61 min.

¹H NMR (400 MHz, DMSO-D6) δ 8.70 (s, 1H), 8.25 (s, 1H), 7.80 (dd, J=8.5, 1.5 Hz, 1H), 7.65 (d, J=8.4 Hz, 1H), 7.57 (t, J=8.2 Hz, 1H), 7.49 (dd, J=10.0, 2.0 Hz, 1H), 7.32 (dd, J=8.2, 1.8 Hz, 1H), 6.39-6.38 (brs, 1H), 5.46 (s, 2H), 5.04 (d, J=7.2 Hz, 1H), 4.77 (dd, J=15.3, 7.2 Hz, 1H), 4.67-4.58 (m, 1H), 4.45 (dd, J=13.5, 7.9 Hz, 1H), 4.34 (dt, J=8.9, 5.9 Hz, 1H), 4.02 (d, J=13.7 Hz, 1H), 3.87 (d, J=13.6 Hz, 1H), 3.15 (t, J=13.2 Hz, 2H), 2.65 (dd, J=21.6, 12.1 Hz, 3H), 2.43-2.33 (m, 3H).

(S)-2-((4-(2-(4-cyano-2-fluorobenzyloxy)pyridin-3-yl)-5,6-dihydropyridin-1(2H)-yl)methyl)-1-(oxetan-2-ylmethyl)-1H-benzo[d]imidazole-6-carboxylic acid (Compound 333)

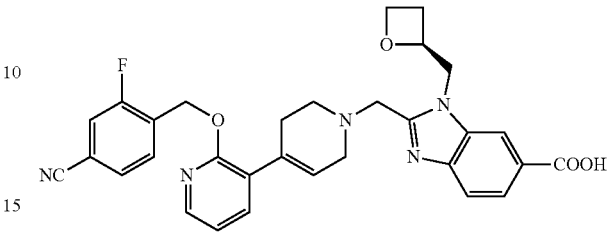

Prepared in analogous manner as for Compound 329. LCMS: [M+H]⁺=554.0; Retention time (10 mM NH₄HCO₃)= 1.22 min.

¹H NMR (400 MHz, DMSO-D6) δ 8.26-8.25 (brs, 1H), 8.05 (dd, J=4.9, 1.8 Hz, 1H), 7.91 (d, J=10.0 Hz, 1H), 7.81 (dd, J=8.5, 1.5 Hz, 1H), 7.72 (dd, J=7.9, 1.4 Hz, 1H), 7.68-7.56 (m, 3H), 7.02 (dd, J=7.3, 4.9 Hz, 1H), 5.98-5.97 (brs, 1H), 5.50 (s, 2H), 5.05 (d, J=7.3 Hz, 1H), 4.77 (dd, J=15.2, 7.2 Hz, 1H), 4.63 (d, J=12.8 Hz, 1H), 4.44 (dd, J=13.8, 7.2 Hz, 1H), 4.34 (dt, J=11.9, 5.9 Hz, 1H), 4.05 (d, J=13.3 Hz, 1H), 3.89 (d, J=13.5 Hz, 1H), 3.14 (d, J=22.7 Hz, 2H), 2.76-2.58 (m, 3H), 2.45-2.31 (m, 3H).

2-((4-(2-(4-cyano-2-fluorophenyl)-2-methylbenzo[d][1,3]dioxol-4-yl)-3,6-dihydropyridin-1(2H)-yl)methyl)-1-(((S)-oxetan-2-yl)methyl)-1H-benzo[d]imidazole-6-carboxylic acid (Compound 334)

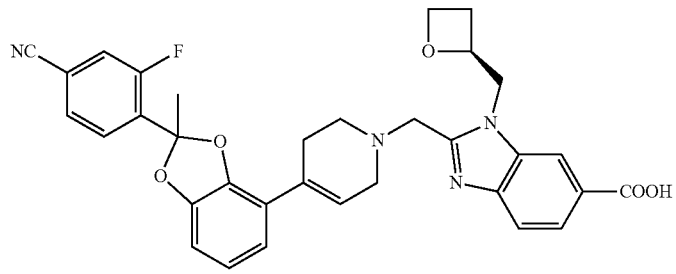

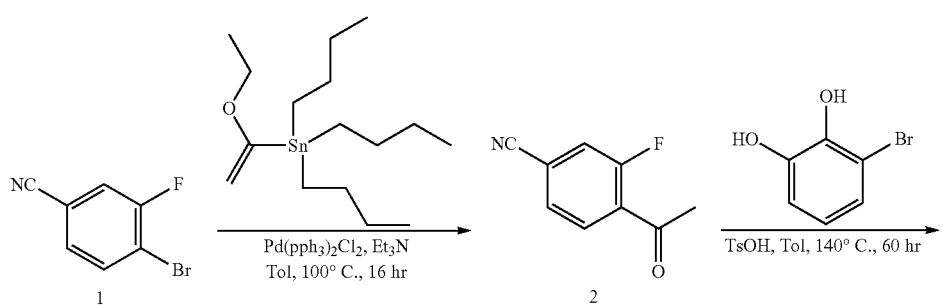

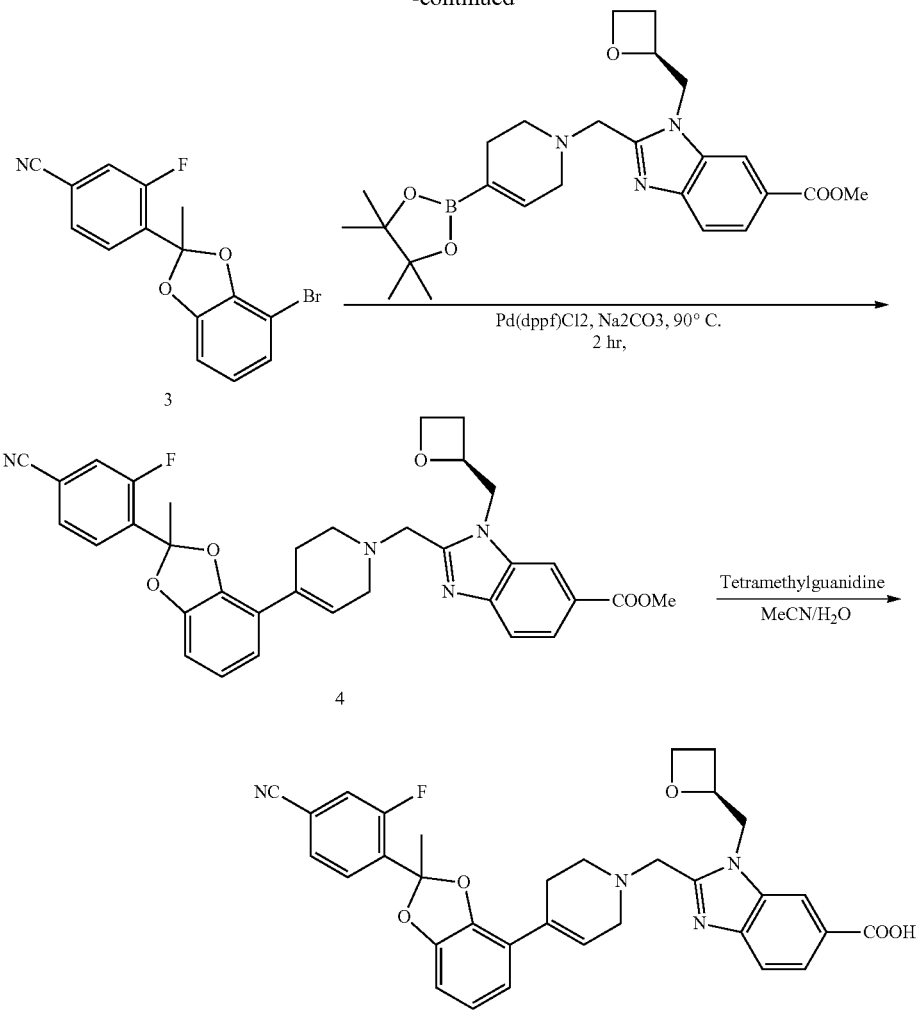

Step 1

To a stirred solution of 4-bromo-3-fluoro-benzonitrile (1 g, 5.00 mmol) in Toluene (20 mL) solution was added tributyl(1-ethoxyvinyl)stannane (2.17 g, 6.00 mmol, 2.03 mL) PdCl$_2$(PPh$_3$)$_2$ (351.0 mg, 500 µmol) TEA (1.52 g, 15.00 mmol). The reaction mixture was stirred at 120° C. for 8 h and upon completion of the reaction as judged by TLC, the mixture was filtered and concentrated in vacuo. The crude was dissolved THF (10 mL) and 4N HCl (10 mL), and the resulting mixture was stirred at rt for 1 h. The mixture was diluted with EtOAc (100 mL) and warmed to room temperature. The layers were separated, and the aqueous layer was extracted with EtOAc (2×50 mL). The combined organic phase was washed with brine (50 mL) and dried over anhydrous Na$_2$SO$_4$, filtered and concentrated in vacuo. The crude product was purified by flash column chromatography (SiO$_2$, hexanes/ethyl acetate=7:1) to afford 4-acetyl-3-fluoro-benzonitrile (800 mg, 4.90 mmol, 98.1% yield, 100% purity) as a light-yellow liquid. LCMS: [M+H]$^+$=164.0; Retention time (0.1% TFA)=1.56 min Step 2

A mixture of 4-acetyl-3-fluoro-benzonitrile (800 mg, 4.90 mmol), 3-bromobenzene-1,2-diol (1.02 g, 5.39 mmol) and 4-methylbenzenesulfonic acid (279.8 mg, 1.47 mmol) in Toluene (100 mL) was stirred for 60 h at 140° C. under N$_2$ until the reaction was complete as indicated by LCMS. The reaction mixture was filtered through a pad of Celite with EtOAc, and the combined organics were concentrated in vacuo, purified by silica gel chromatography (Hexanes/EtOAc=20:1) to give the desired product 4-(4-bromo-2-methyl-1,3-benzodioxol-2-yl)-3-fluoro-benzonitrile (98 mg, 96.8 µmol, 33% purity) as colorless oil. LCMS: [M+H]$^+$=336.1; Retention time (0.01% TFA)=1.93 min.

Step 3

4-(4-bromo-2-methyl-1,3-benzodioxol-2-yl)-3-fluoro-benzonitrile (40 mg, 119.7 µmol), methyl 3-[[(2S)-oxetan-2-yl]methyl]-2-[[4-(3,3,4,4-tetramethyl-1,2,5-bromadioxolan-1-yl)-3,6-dihydro-2H-pyridin-1-yl]methyl]benzimidazole-5-carboxylate (96.3 mg, 179.6 µmol), Pd(dppf)Cl2 (8.8 mg, 11.97 µmol), K$_2$CO$_3$ (33.1 mg, 239.42 µmol) was dissolved in dioxane (3 mL) and Water (1 mL). The reaction was stirred at 90° C. for 2 h under N$_2$. The reaction was concentrated to give a residue which was purified by silica gel chromatography (petroleum ether:EtOAc=3:7) to give methyl 2-[[4-[2-(4-cyano-2-fluoro-phenyl)-2-methyl-1,3-benzodioxol-4-yl]-3,6-dihydro-2H-pyridin-1-yl]methyl]-3-[[(2S)-oxetan-2-yl]methyl]benzimidazole-5-carboxylate (40 mg, 67.27 µmol) as a yellow solid. LCMS: [M+H]$^+$=595.0; Retention time (0.01% TFA)=1.61 min.

Step 4 methyl 2-[[4-[2-(4-cyano-2-fluoro-phenyl)-2-methyl-1,3-benzodioxol-4-yl]-3,6-dihydro-2H-pyridin-1-yl]methyl]-3-[[(2S)-oxetan-2-yl]methyl]benzimidazole-5-carboxylate (40 mg, 67.27 μmol) was dissolved in MeCN (3 mL) and water (1 mL) and 1,1,3,3-tetramethylguanidine (155.0 mg, 1.35 mmol) was then added. The reaction was stirred at 60° C. for 4 h. The mixture was quenched with water (20 mL), adjusted pH to 4-5 with HOAc, then extracted with DCM (3×20 mL). The organic phase was concentrated to give a residue which was purified by prep-HPLC to give 2-[[4-[2-(4-cyano-2-fluoro-phenyl)-2-methyl-1,3-benzodioxol-4-yl]-3,6-dihydro-2H-pyridin-1-yl]methyl]-3-[[(2S)-oxetan-2-yl]methyl] benzimidazole-5-carboxylic acid (12.4 mg, 21.4 μmol, 31.8% yield) as a white solid. LCMS: [M+H]$^+$=581.0; Retention time (10 mM NH$_4$HCO$_3$)=1.29 min.

$^1$H NMR (400 MHz, DMSO-D6) δ 8.26 (s, 1H), 7.99-7.96 (m, 1H), 7.82-7.70 (m, 3H), 7.66-7.64 (m, 1H), 6.89-6.84 (m, 3H), 6.39-6.38 (m, 1H), 5.08-5.06 (m, 1H), 4.78-4.77 (m, 1H), 4.67-4.63 (m, 1H), 4.47-4.34 (m, 2H), 4.08-4.03 (m, 1H), 3.93-3.88 (m, 1H), 3.23-3.21 (m, 2H), 2.76-2.65 (m, 4H), 2.43- 2.32 (m, 2H), 2.05 (s, 3H).

The invention claimed is:

1. A compound or a pharmaceutically acceptable salt thereof; wherein the compound is represented by the following structure:

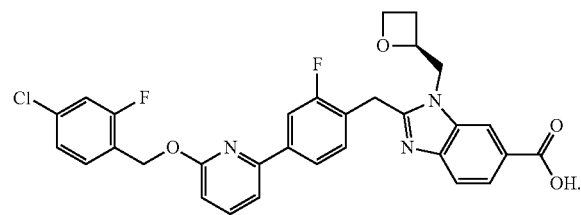 [SMILES: O=C(O)c1ccc2nc(Cc3ccc(-c4cccc(OCc5ccc(Cl)cc5F)n4)cc3F)n(C[C@@H]3CCO3)c2c1]

2. A compound or a pharmaceutically acceptable salt thereof; wherein the compound is represented by the following structure:

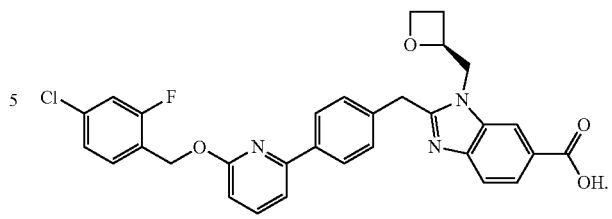

3. A pharmaceutical composition comprising a pharmaceutically acceptable excipient, and a compound represented by the following structure:

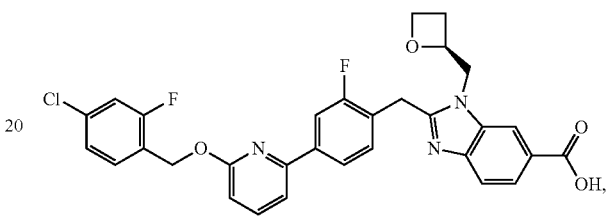

or a pharmaceutically acceptable salt thereof.

4. A pharmaceutical composition comprising a pharmaceutically acceptable excipient, and a compound represented by the following structure:

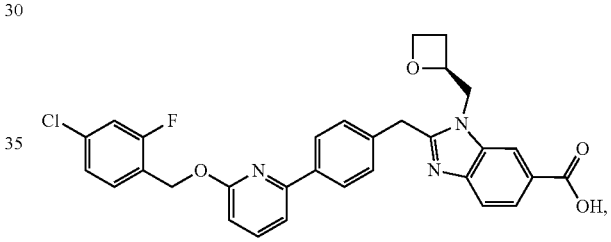

or a pharmaceutically acceptable salt thereof.

* * * * *